US012082565B2

(12) United States Patent
Brydges et al.

(10) Patent No.: US 12,082,565 B2
(45) Date of Patent: **\*Sep. 10, 2024**

(54) NON-HUMAN ANIMALS MODELS OF RETINOSCHISIS

(71) Applicant: Regeneron Pharmaceuticals, Inc., Tarrytown, NY (US)

(72) Inventors: Susannah Brydges, Putnam Valley, NY (US); Yajun Tang, White Plains, NY (US); Yang Liu, Valhalla, NY (US); Jingtai Cao, White Plains, NY (US); Carmelo Romano, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 438 days.

This patent is subject to a terminal disclaimer.

(21) Appl. No.: 17/348,907

(22) Filed: Jun. 16, 2021

(65) Prior Publication Data

US 2021/0307304 A1 Oct. 7, 2021

Related U.S. Application Data

(63) Continuation of application No. 15/905,068, filed on Feb. 26, 2018, now Pat. No. 11,064,685.

(60) Provisional application No. 62/576,256, filed on Oct. 24, 2017, provisional application No. 62/463,872, filed on Feb. 27, 2017.

(51) Int. Cl.
| | |
|---|---|
| *C12N 5/00* | (2006.01) |
| *A01K 67/0276* | (2024.01) |
| *A01K 67/0278* | (2024.01) |
| *C07K 14/47* | (2006.01) |
| *C12N 15/85* | (2006.01) |
| *G01N 33/50* | (2006.01) |
| *G01N 33/68* | (2006.01) |

(52) U.S. Cl.
CPC ...... *A01K 67/0278* (2013.01); *A01K 67/0276* (2013.01); *C07K 14/47* (2013.01); *C12N 15/8509* (2013.01); *G01N 33/5088* (2013.01); *G01N 33/6893* (2013.01); *A01K 2217/054* (2013.01); *A01K 2217/072* (2013.01); *A01K 2217/075* (2013.01); *A01K 2217/15* (2013.01); *A01K 2217/206* (2013.01); *A01K 2227/105* (2013.01); *A01K 2267/0306* (2013.01); *A01K 2267/0393* (2013.01); *C12N 2015/8527* (2013.01); *C12N 2015/8536* (2013.01); *C12N 2510/00* (2013.01); *C12N 2800/30* (2013.01); *C12N 2830/008* (2013.01)

(58) Field of Classification Search
None
See application file for complete search history.

(56) References Cited

U.S. PATENT DOCUMENTS

| | | | |
|---|---|---|---|
| 6,586,251 B2 | 7/2003 | Economides et al. |
| 7,294,754 B2 | 11/2007 | Poueymirou et al. |
| 8,354,389 B2 | 1/2013 | Frendewey et al. |
| 8,518,392 B2 | 8/2013 | Frendewey et al. |
| 8,697,851 B2 | 4/2014 | Frendewey et al. |
| 2004/0261141 A1 | 12/2004 | Heinrich et al. |
| 2014/0235933 A1 | 8/2014 | Lee et al. |
| 2014/0310828 A1 | 10/2014 | Lee et al. |
| 2018/0255754 A1 | 9/2018 | Brydges et al. |

FOREIGN PATENT DOCUMENTS

| | | |
|---|---|---|
| CN | 107287243 A | 10/2017 |
| WO | 2015/021298 A2 | 2/2015 |

OTHER PUBLICATIONS

Apushkin M.A. et al., "Use of Dorzolamide for Patients With X-Linked Retinoschisis", Retina 26:741-745 (2006).
Bradshaw K. et al., "Mutations of the XLRS1 Gene Cause Abnormalities of Photoreceptor as Well as Inner Retinal Responses of the ERG", Documenta Ophthalmologica 98:153-173 (1999).
Bush R.A. et al., "Convergence of Human Genetics and Animal Studies: Gene Therapy for X-Linked Retinoschisis", Cold Spring Harbor Perspective in Medicine 5(8):p. a017368 (Jun. 22, 2015).
Byrne LC et al., "Retinoschisin Gene Therapy in Photoreceptors, Müuller Glia or All Retinal Cells in the Rs1h-/1Mouse", Gene Therapy 21:585-592 (2014).
Dechiara T.M. et al., "Producing Fully ES Cell-Derived Mice from Eight-Cell Stage Embryo Injections", Methods in Enzymology 476:285-294 (2010).
Dechiara T.M. et al., "VelociMouse: Fully ES Cell-Derived F0-Generation Mice Obtained from the Injection of ES Cells into Eight-Cell-Stage Embryos", Gene Knockout Protocols: Second Edition 530:311-324 (2009).
Deutman A.F., The Hereditary Dystrophies of the Posterior Pole of the Eye, Assen, The Netherlands, Van Gorcum, pp. 100-171 (1971).
Devoy A. et al., "Genomically Humanized Mice: Technologies and Promises", Nature Reviews-Genetics 13:14-20 (Jan. 2012).
Dyka F.M. et al., "Coexpression and Interaction of Wild-Type and Missense RS1 Mutants Associated With X-Linked Retinoschisis: Its Relevance to Gene Therapy", IOVS 48(6): 2491-2497 (Jun. 2007).

(Continued)

*Primary Examiner* — Marcia S Noble
(74) *Attorney, Agent, or Firm* — Scully, Scott, Murphy & Presser, P.C.; Shing-Yi Cheng

(57) ABSTRACT

Non-human animals suitable for use as animal models for Retinoschisis are provided. In some embodiments, provided non-human animals are characterized by a disruption in a Retinoschisin-1 locus. In some embodiments, provided non-human animals are characterized by a mutant Retinoschisin-1 gene. The non-human animals may be described, in some embodiments, as having a phenotype that includes the development of one or more symptoms or phenotypes associated with Retinoschisis. Methods of identifying therapeutic candidates that may be used to prevent, delay or treat Retinoschisis or eye-related diseases, disorders or conditions are also provided.

26 Claims, 25 Drawing Sheets
(12 of 25 Drawing Sheet(s) Filed in Color)
Specification includes a Sequence Listing.

(56) References Cited

OTHER PUBLICATIONS

Genead M.A. et al., "Efficacy of Sustained Topical Dorzolamide Therapy for Cystic Mascular Lesions in Patients With X-Linked Retinoschisis", Arch Ophthalmol. 128(2):190-197 (Feb. 2010).
George NDL et al., "X-Linked Retinoschisis", British Journal of Ophthalmology 79:697-702 (1995).
George N.D.L. et al., "Clinical Features in Affected Males With X-Linked Retinoschisis", Arch Ophthalmol. 114:274-280 (Mar. 1996).
Ghajarnia M. et al., "Acetazolamide in the Treatment of X-Linked Retinoschisis Maculopathy", Arch Ophthalmol 125(4):571-573 (2007).
Janssen A. et al., "Effect of Late-Stage Therapy on Disease Progression in AAV-Mediated Rescue of Photoreceptor Cells in the Retinoschisin-Deficient Mouse", Molecular Therapy 16(6):1010-1017 (Jun. 2008).
Kellner U. et al., "X-Linked Congenital Retinoschisis", Graefe's Arch Clin Exp Ophthalmol 228:432-437 (1990).
Khan N.W. et al., "Analysis of Photoreceptor Function and Inner Retinal Activity in Juvenile X-Linked Retinoschisis", Vision Research 41:3931-3942 (2001).
Kim L.S. et al., "Multifocal ERG Findings in Carriers of X-Linked Retinoschisis", Doc Ophthalmol 114:21-26 (2007).
Kim D.Y. et al., "X-Linked Juvenile Retinoschisis (XLRS): A Review of Genotype-Phenotype Relationships", Seminars in Ophthalmology 28(5-6):392-396 (2013).
Kjellstrom S. et al., "Retinoschisin Gene Therapy and Natural History in the Rs1b-KO Mouse: Long-Term Rescue from Retinal Degeneration", Investigative Ophthalmology & Visual Science 48(8):3837-3845 (Aug. 2007).
Lee, MD J J et al., "Infantile Vetreous Hemorrhage as the Initial Presentation of X-Linked Juvenile Retinoschisis", Korean Journal of Ophthalmology 23(2):118-120 (2009).
Lesch B. et al., "Clinical and Genetic Findings in Hungarian Patients With X-Linked Juvenile Retinoschisis", Molecular Vision 14:2321-2332 (2008).
Mattapallilm.J. et al., "The rd8 Mutation of the Crb1 Gene is Present in Vendor Lines of C57BL/6N Mice and Embryonic Stem Cells, and Confounds Ocular Induced Mutant Phenotypes", IOVS Papers in Press., Manuscript iovs. 12-9662 (22 pages) (Mar. 23, 2012).
Mehalow A.K. et al., "CRB1 is Essential for External Limiting Membrane Integrity and Photoreceptor Morphogenesis in the Mammalian Retina", Human Molecular Genetics 12(17):2179-2189 (2003).
Min S.H. et al., "Prolonged Recovery of Retinal Structure/Function After Gene Therapy in an Rs1h-Deficient Mouse Model of X-Linked Juvenile Retinoschisis", Molecular Therapy 12(4):644-651 (Oct. 4, 2005).
Molday R.S. et al., "X-Linked Juvenile Retinoschisis: Clinical Diagnosis, Genetic Analysis, and Molecular Mechanisms", Progress in Retinal and Eye Research 31:195-212 (2012).
Molday L.L et al., "Expression of X-Linked Retinoschisis Protein RS1 in Photoreceptor and Biopolar Cells", Investigative Ophthalmology & Visual Science 42(3):816-825 (Mar. 2001).
Ou J. et al., "Synaptic Pathology and Therapeutic Repair in Adult Retinoschisis Mouse by AAV-RS1 Transfer", The Journal of Clinical Investigation 125(7):2891-2903 (Jul. 2015).
Park TK et al., "Intravitreal Delivery of AAV8 Retinoschisin Results in Cell Type-Specific Gene Expression and Retinal Rescue in the Rs1-KO Mouse", Gene Therapy 16:916-926 (2009).
Poueymirou W.T. et al., "F0 Generation Mice Fully Derived from Gene-Targeted Embryonic Stem Cells Allowing Immediate Phenotypic Analyses", Nature Biotechnology 25(1): 91-99 (Jan. 2007).
Prasad A. et al., "Vitreous Hemorrhage as the Initial Manifestation of X-Linked Retinoschisis in a 9-Month-Old Infant", J Pediatr Ophthalmol Strabismus 43(1):56-58 (Jan./Feb. 2006).
Reid S.N.M. et al., "Retinoschisin, a Photoreceptor-Secreted Protein, and its Interaction With Bipolar and Müller Cells", The Journal of Neuroscience 23(14):6030-6040 (Jul. 9, 2003).
Renner A.B. et al., "ERG Variability in X-Linked Congenital Retinoschisis Patients With Mutations in the RS1 Gene and the Diagnostic Importance of Fundus Autofluorescence and OCT", Doc Ophthalmol 116:97-109 (2008).
Sauer C.G. et al., "Positional Cloning of the Gene Associated With X-Linked Juvenile Retinoschisis", Nature Genetics 17:164-170 (Oct. 1997).
Sergeev Y.Y. et al., "Molecular Modeling of Retinoschisin With Functional Analysis of Pathogenic Mutations from Human X-Linked Retinoschisis", Human Molecular Genetics 19(7):1302-1313 (Jan. 2010).
Sikkink S.K. et al., "X-Linked Retinoschisis: An Update", J. Med Genet 44(4):225-232 (2007).
Takada Y. et al., "Synaptic Pathology in Retinoschisis Knockout (Rs1-/y) Mouse Retina and Modification by rAAV-Rs1 Gene Delivery", Investigative Ophthalmology & Visual Science 49(8):3677-3686 (Aug. 2008).
Takada Y. et al., "Retinoschisin Expression and Localization in Rodent and Human Pineal and Consequences of Mouse RS1 Gene Knockout", Molecular Vision 12:1108-1116 (2006).
Tantri A. et al., "X-Linked Retinoschisis: A Clinical and Molecular Genetic Review", Survey of Ophthalmology 49 (2):214-229 (Mar.-Apr. 2004).
Tong C. et al., "Generating Gene Knockout Rats by Homologous Recombination in Embryonic Stem Cells", Nature Protocols 6(6):827-844 (May 26, 2011).
Tong C. et al., "Production of p53 Gene Knockout Rats by Homologous Recombination in Embryonic Stem Cells", Nature 467:211-215 (Sep. 9, 2010).
Valenzuela D.M. et al., "High-Throughput Engineering of the Mouse Genome Coupled With High-Resolution Expression Analysis", Nature Biotechnology 21(6):652-659 (Jun. 2003).
Vijayasarathy C. et al., "Biology of Retinoschisin", Chapter 64, pp. 513-518 (2012).
Vijayasarathy C. et al., "Molecular Mechanisms Leading to Null-Protein Product from Retinoschisin (RS1) Signal-Sequence Mutants in X-Linked Retinoschisis (XLRS) Disease", Human Mutation 31(11):1251-1260 (2010).
Vijayasarathy C. et al., "Null Retinoschisin-Protein Expression from an RS1 c354del1-ins18 Mutation Causing Progressive and Severe XLRS in a Cross-Sectional Family Study", Investigative Ophthalmology & Visual Science 50 (11):5375-5383 (Nov. 2009).
Vijayasarathy C. et al., "Retinoschisin is a Peripheral Membrane Protein With Affinity for Anionic Phospholipids and Affected by Divalent Cations", Investigative Ophthalmology & Visual Science 48(3):991-1000 (Mar. 2007).
Vijayasarathy C. et al., "Identification and Characterization of Two Mature Isoforms of Retinoschisin in Murine Retina", Biochemical and Biophysical Research Communications 349:99-105 (Jul. 2006).
Wang T. et al., "Intracellular Retention of Mutant Retinoschisin is the Pathological Mechanism Underlying X-Linked Retinoschisis", Human Molecular Genetics 11(24):3097-3105 (2002).
Weber H.F. et al., "Inactivation of the Murine X-Linked Juvenile Retinoschisis Gene, Rs1h, Suggests a Role of Retinoschisin in Retinal Cell Layer Organization and Synaptic Structure", PNAS 99(9):6222-6227 (Apr. 30, 2002).
Wu W W-H, "RS1 Structure-Function Relationships: Roles in Retinal Adhesion and X-Linked Retinoschisis", Thesis—The University of British Columbia (170 pages) (Oct. 2005).
Wu W. W.H. et al., "RS1, a Discoidin Domain-Containing Retinal Cell Adhesion Protein Associated With X-Linked Retinoschisis, Exists as a Novel Disulfide-Linked Octamer", The Journal of Biological Chemistry 280(11):10721-10730 (Mar. 18, 2005).
NCBI Reference Sequence No. XP_001491233.3 (2 pages) (Jan. 23, 2018).
NCBI Reference Sequence No. XP_010820476.1 (1 page) (Jan. 26, 2016).
NCBI Reference Sequence No. XP_011961706.2 (2 pages) (Dec. 17, 2015).
NCBI Reference Sequence No. XP_019679180.1 (1 page) (Dec. 12, 2017).
NCBI Reference Sequence No. XP_013841410.1 (1 page) (Sep. 11, 2015).
Dolatshad H. et al., "A Versatile Transgenic Allele for Mouse Overexpression Studies", *Mamm Genome* 26:598-608 (2015).

(56) References Cited

OTHER PUBLICATIONS

Li R. et al., "Production of Genetically Engineered Golden Syrian Hamsters by Pronuclear Injection of the CRISPR/Cas9 Complex", *J Vis Exp.* 131: (Jan. 9, 2018), abstract only.
NCBI Reference Sequence No. NP_035432.3 (3 pages) (May 27, 2018).
NCBI Reference Sequence No. NP_001098113.1 (2 pages) (May 28, 2018).
NCBI Reference Sequence No. NP_001181840.1 (1 page) (Apr. 1, 2016).
NCBI Reference Sequence No. XM_548882.5 (2 pages) (Sep. 5, 2017).
NCBI Reference Sequence No. XM_001491183.5 (2 pages) (Jan. 23, 2018).
NCBI Reference Sequence No. XM_010822174.1 (2 pages) (Jan. 26, 2016).
NCBI Reference Sequence No. XM_012106316.2 (2 pages) (Dec. 17, 2015).
NCBI Reference Sequence No. XM_019823621.2 (3 pages) (Dec. 12, 2017).
NCBI Reference Sequence No. XM_013985956.1 (2 pages) (Sep. 11, 2015).
NCBI Reference Sequence No. XP_548882.2 (1 page) (Sep. 5, 2017).
Wu W. W.H. et al., "Defective Discoidin Domain Structure, Subunit Assembly, and Endoplasmic Reticulum Processing of Retinoschisin are Primary Mechanisms Responsible for X-Linked Retinoschisis", The Journal of Biological Chemistry 278(30):28139-28146 (Jul. 25, 2003).
Zheng Y. et al., "RS-1 Gene Delivery to an Adult Rs1h Knockout Mouse Model Restores ERG b-Wave With Reversal of the Electronegative Waveform of X-Linked Retinoschisis", *Investigative Ophthalmology & Visual Science* 45(9):3279-3285 (Sep. 2004).
International Search Report and Written Opinion dated May 14, 2018 received in International Patent Application No. PCT/US2018/019721.
NCBI Reference Sequence No. NM_011302.3 (5 pages) (May 27, 2018).
NCBI Reference Sequence No. NM_001104643.1 (3 pages) (May 28, 2018).
NCBI Reference Sequence No. NM_000330.3 (4 pages) (Jun. 24, 2018).
NCBI Reference Sequence No. NM_001109823.1 (1 page) (Jul. 3, 2016).
NCBI Reference Sequence No. NP_001103293.1 (1 page) (Jul. 3, 2016).
NCBI Reference Sequence No. NM_001194911.1 (2 pages) (Apr. 1, 2016).
NCBI Reference Sequence No. NP_000321.1 (3 pages) (Jun. 24, 2018).

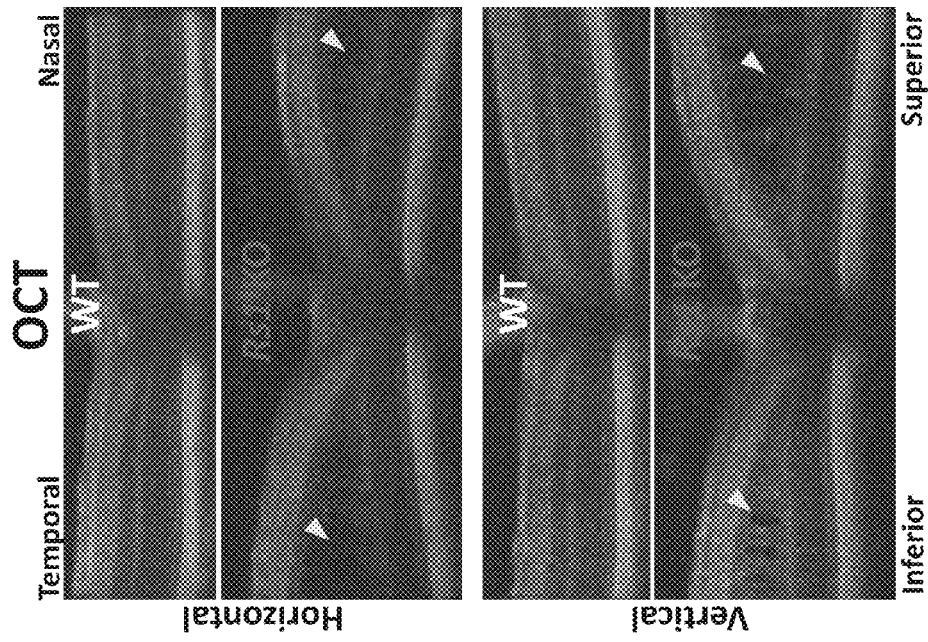
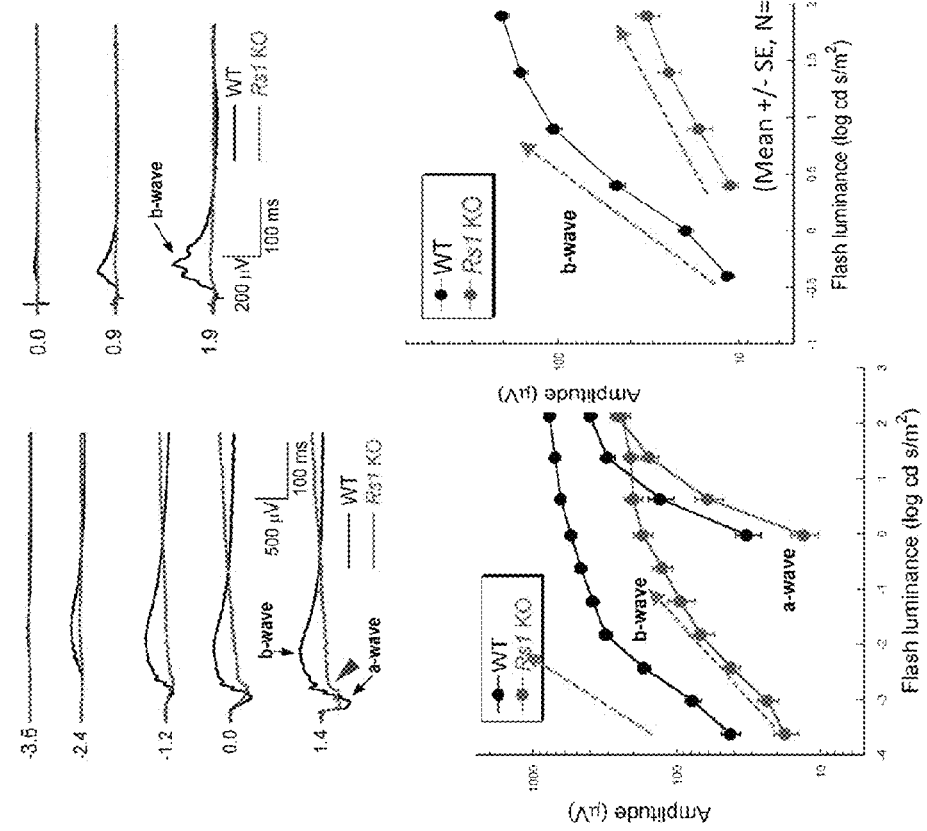
Figures 16A-16C

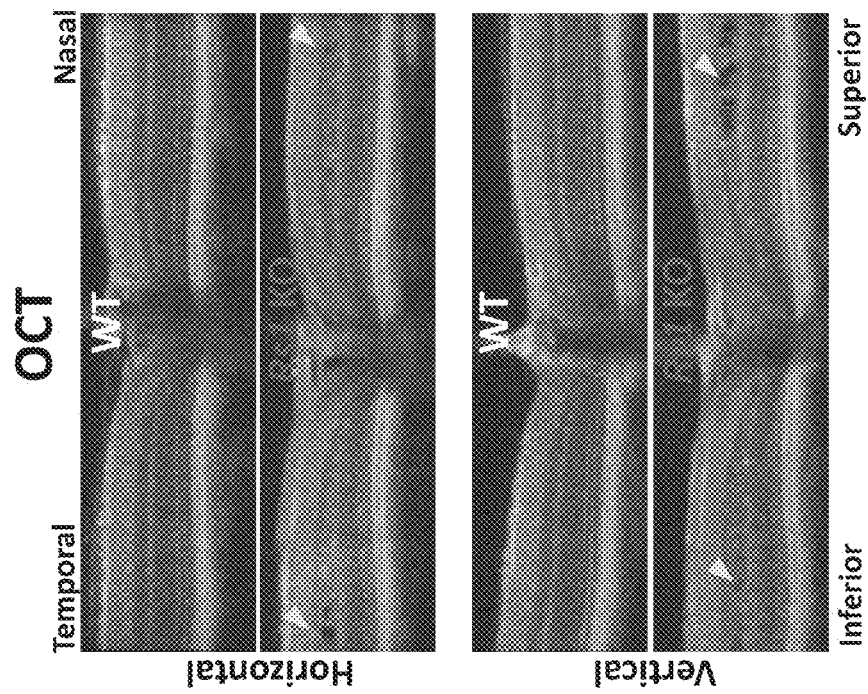
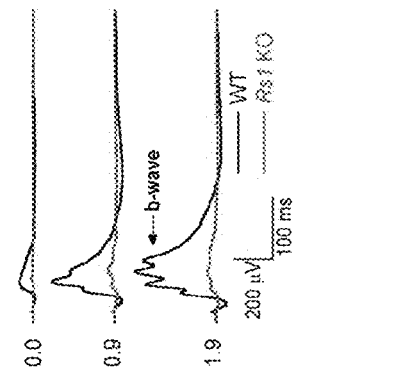
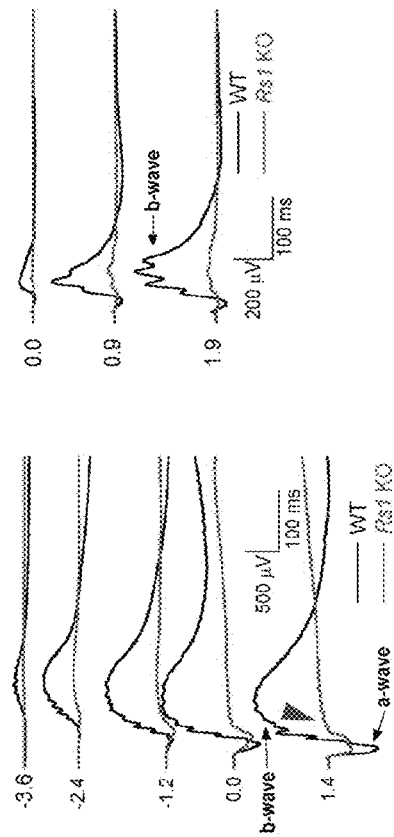
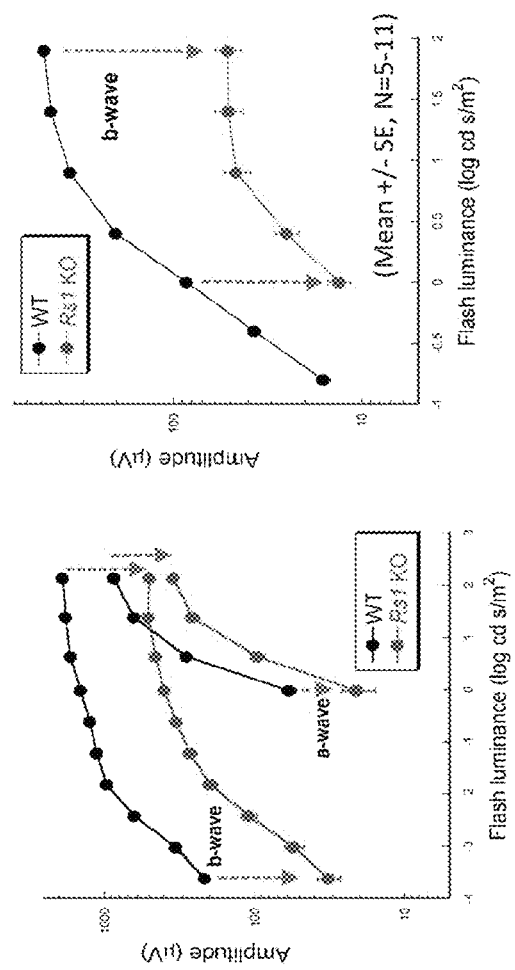
Figures 16D-16F

A. DA-ERG

```
mouse  MPHKIEGFFLLLLFGYEATLGLSSTEDEGEDPWYQKACKCDCQVGANALWSAGATSLDCI  60
rat    MPHKIEGFFLLLLFGYEATLGLSSTEDEGEDPWYQKACKCDCQGGANALWSAGAASLDCI  60
human  MSRKIEGFLLLLLFGYEATLGLSSTEDEGEDPWYQKACKCDCQGGPNALWSAGATSLDCI  60
       * **                                  *            * mouse  PECPYHKPLGFESGEVTPDQITCSNPEQYVGWYSSWTANKARLNSQGFGCAWLSKYQDSS  120
rat    PECPYHKPLGFESGEVTPDQITCSNPEQYVGWYSSWTANKARLNSQGFGCAWLSKYQDSS  120
human  PECPYHKPLGFESGEVTPDQITCSNPEQYVGWYSSWTANKARLNSQGFGCAWLSKFQDSS  120
                                                              * mouse  QWLQIDLKEIKVISGILTQGRCDIDEWVTKYSVQYRTDERLNWIYYKDQTGNNRVFYGNS  180
rat    QWLQIDLKEIKVISGILTQGRCDIDEWMTKYSVQYRTDERLNWIYYKDQTGNNRVFYGNS  180
human  QWLQIDLKEIKVISGILTQGRCDIDEWMTKYSVQYRTDERLNWIYYKDQTGNNRVFYGNS  180
                                  * mouse  DRSSTVQNLLRPPIISRFIRLIPLGWHVRIAIRMELLECASKCA  224
rat    DRSSTVQNLLRPPIISRFIRLIPLGWHVRIAIRMELLECASKCA  224
human  DRTSTVQNLLRPPIISRFIRLIPLGWHVRIAIRMELLECVSKCA  224
         *                                    *
```

Figure 20

SEQUENCE LISTING

<160> NUMBER OF SEQ ID NOS: 59

<210> SEQ ID NO 1
<211> LENGTH: 5855
<212> TYPE: DNA
<213> ORGANISM: Mus musculus

<400> SEQUENCE: 1

```
aacaatacct ccccagactg cttgttgagg caggggacta tgtggcttaa ttggatgggg    60
gctgagtgaa agacctaaga actaaatgaa ataagatgct taagttaatc gcctgctcct   120
atgccagctc tccacttcac ttagatcttg ctgtgaccaa ggacaaggag aaaatgccac   180
acaagattga aggcttcttc ttgttacttc tctttggcta tgaagccaca ttgggattgt   240
catcgacaga ggatgagggt gaggacccct ggtaccagaa agcatgcaag tgtgattgcc   300
aggtaggagc caatgctctg tggtctgctg gagctacctc cttagactgt attccagaat   360
gcccatatca caagcccctg ggtttcgagt caggggaggt cacgccagat cagatcactt   420
gctccaaccc agagcagtat gtgggctggt attcctcatg gacagcaaac aaggcccgac   480
tcaacagtca aggttttggg tgtgcttggc tttccaagta tcaggacagc agccagtggt   540
tacagataga tttgaaggag atcaaggtga tttcggggat cctgacccaa ggacgctgtg   600
acatagacga gtgggtgacc aagtacagtg tgcagtatag gactgatgag cgcctgaact   660
```

```
ggatctacta taaggatcag accggaaaca atcgggtctt ctatggaaac tcagaccgga      720
gttctacagt tcagaactta ctcaggcccc ccatcattc ccgcttcatc cgactgatcc       780
ctctaggctg gcatgtccga attgccatcc ggatggagct gcttgagtgt gccagcaagt      840
gtgcctgatg tctatttcag ctcagttctg tcacttgcag ggagagcttt ggggggaggg      900
caccctgaaa taccactggg atgaatgggg ctatatctta taagcacttt acaatgtaga      960
tctgggtaga gaatatttca cttttaaaa gatagtttca aatttcaaag ggagagagag      1020
agagagagag agagagagag agagagagag agaagctttt aagcttttct tcaactcagg     1080
gccaaagaaa ataagaacaa agaaagtatc tctcaaacca attttcttac acaaacccaa     1140
atagcagggg taatttgctg ctctggctcc ccatcttttt ctctttgtct cagtgacacc     1200
gtcaaaggtg caggcccagg ggaacacaaa gcagctctga taatttgaaa attctttttg     1260
gctcttagca cattcagaag aggagcgtac tctttggcaa agcctcacat gaacacttgc     1320
atgaaatcct cactatagag gcctggtgac aagtacatag gtgtgaagaa agcagaagga     1380
agcctggcgt atggcccacg agtctggagc cagtaaccaa ccaaccaact aaccaactaa     1440
ccaaccagtc aaggcttccc cctccctgga attgcttttg cctggaaggg gtggagctcc     1500
ttgtgcagaa actccattct acagcccttt tggcaatgtg tccttctgtg attgcctgga     1560
gatgaatgca aggggcaggc tatatgtgtg tgtggatagt gaggtttccc ttaaactgag     1620
gaagcccaaa taactagaat acatcacacc ttctttatcc atggctacag tttcccagaa     1680
attgaacagg cttagaaaac agctgagata aaccatatct ctatctactg ggaagagatc     1740
atgctttggg ggaaggggtt aggactccta tcatagagga ctgtacacag atgatctgtc     1800
agtaaagggc ttgctgtaca gcataggaac ttgagattat atttctagaa tgcatgtaaa     1860
aagctaggta tggacaggta tggtggaaca tgccattagt cttagtattt ggaagacaga     1920
ggcaagcaga tctgagttca gggccagcct ggtctacata gcagttccaa gctagccaag     1980
gctacacagt aaggccctgt ttcaagaaaa aaagaccagg catggagggg cacacctgca     2040
aatccaggac taggaggcag gcagagacag gatgatgcct agagcttgtc tgccaatcag     2100
tacactccag gttcatggtc agaccctgtc tcaaaactaa agtgaagagc tattgaggaa     2160
gataccagat gtcaacctct gtccaacatg cacacataca catacactgg taggtttcaa     2220
acctggggca aatggcagag gtgcctagtt aaggttctcc cagcatctct cagcccctac     2280
caggtcctcc tagttggcat accccgcccc ctaccccgaa actcttcagc ccagggggtt     2340
gggcttcttc cctatataat ccaactattt tggtcaccct ttctcttgt accttttgggc    2400 ctcctggttg ctgcatctgg ttcctctgtt ctcccttatc tcttttcctc cctcctctcc     2460
tcacaaggcc cagcttagag tgttcatgtc tattctggac tctctcccgg atgcccctgc     2520
ctctggctat gctctcccac atatctacca taaactctct cctctaccat acctaggaca     2580
agtcatgttc ctttcctttt cctttttgtt tccattcaa acatgtaaat aggaaaaaca     2640
aaatacaaca acaacaaaca aaaataaaac cacaaaagcc ttctctccga gcggcttcct     2700
cccgtcctgc ccacccaaac atgcttactc agacatgaca tttgaaactt ctttcggtag     2760
tcattctctg gcaggaatag ctcatttaat caggagcttt ggagcctgag agaatgacta     2820
ctggtctcta gctcatttcc atctgtagct caagctgggt ttgaggctct tctctgggag     2880
aggctgttaa ctggagtgag ggtcaaaaag gcatgcgggg agaagctgag aatgagaact     2940
gcccagagac aaggtcttgg cctcacacac acacaataca gccttggtta gtacttttct     3000
```

```
ctgagctatt ttctatttcc aggtattaaa ggagattaca tggattcaca ccaaaataac    3060
tttggatggc cagacatggt atcttccatc tttaatccta gcactgggaa aacacagaca    3120
ggtggatctc tgtgagttca aggccaggtt tgcatagcaa gctccagacc agccaaggct    3180
atgtagtgag actgtctcaa aaatcaatcc atcaatcaaa tgatcttgga tgtcacattc    3240
ttctcagtga atagaacaac attttaatag catcaaattt cctacctagt attttggagt    3300
tccacaggtg tgtgtgtatg tgtggcaatg tacaacaata ttcctggtat gactacatat    3360
gtacaaattc attttggata atattcctga cagcagacct ttatttggaa aattgagtta    3420
cctttctcac cacactgagt aattgttaga gaaaaatggc aataacttaa gaatactgat    3480
cagggagaaa aaacccaaa tggtacaagg catgggtaaa tagtcatcaa attaaaaaat    3540
catgccataa atttgttttc taatagtttc attaacttca cataaacagt cctaattcat    3600
ttaaggtgtg taattcaata tagtatattc aaacttgaac aatcatcact acaagtaact    3660
ttagactatt cttatcaccc caagagaat cctctaacaa tgggccatca gccaccacag     3720
ctctagatta ctcgtcatcc attttctatt tgtgtgtgga ttttttttcc attctgggca    3780
tttctccaca caaatggaat cttagaatat atagtagttt atgacttgtt tcttgtactt    3840
atcatagtgt ttttaaagtc catgtgttgg agaagtacat cctccttttt tgttattaac    3900
attctgtgta gggtattgta ttattattta tccatgcatt tgggtggggc tagtatgaat    3960
aatgctgctt catgaaaatt tatatgtaag ttattgcgtg acatgtttt atcttgggca     4020 tactcacact gagaatagag aattgttggg tctcttggga actatttctc caggtggctg    4080
taccatcttc tgttcccacc agcaatgtct aatgcttcca gcctctcatc tttagcaatg    4140
cttcttgtat ttcattagat ctgtcctagt atgtatgaag tagcattcga tgatgaattt    4200
gatttgcatt tctctaataa ccaatgtttt ttgagcatct tttcaagtca ccagtgacat    4260 attttttggag aaagttctat tcagacccctt gcccatataa agatttcatt tcacggattc   4320
attaagagtt ctttgggtgt tctacataca attctcttat gcaaacattt cttccatcct    4380 gttttttcttc ttgtcattgt cttggtttag ttttgcacca ggatttcact atgtagctca    4440
ggctggcctg gaacttgcaa agatccttct gtctctgcct cccaggttct gagattctgg    4500
gtatttgcca ccacacctgg cctttctctg aagcacaaca ataccaaat tttaatgaag     4560 tccaaccttc cggtttcctt ttttggtgta ttatctgaga aactactgtc aaaccatggt    4620
caagaagatt cactcttgtg ttttcttcta aatgttttga aaaaaatttt ttaaaaagtt    4680 ttaaagttttt aactcttact ttgtgaacag ttataaagta agggtgtaat ttcattcttt    4740
ggatatcaat atgcagctgt cttggtagct tgtgttgtct tcaccacagt caatggtctt    4800
tattcttcca aaaacaactg accaagaata ttagagtata tgctaggcct cataattcta    4860
ttaccacata gtcttcatta ctgtagcatt gtagtgagtt gtggaattag gacatataaa    4920
tcttccaatt ctggttatgt ttcaagactg aactaactat tctgggttcc ttaaacttct    4980
aagtaagtat atctgtaaat aagccagcca ggggtctcac aatggaaaat gttttcaatt    5040
tcaaaattaa ataaacaatg agatattaag atctgcaaga tatttatctg tagttaattt    5100
tctttcaata gttaatgaaa atgttagcat tttcttcctt ttgtgttagg atatatatat    5160
aaaagaaacc ctattattaa agtaaacctg aaaagaatc ttcctattaa acaaaaaata     5220
tgtttgcaat attatttctt ttagggggca actaattcaa taagagattat ataatggagg   5280 aaagtcattc ctatccttaac acattttgtt tattttacc actagacttt gggttattaa    5340
ggattttatt ttttatggtt ttgaggacat aacccaggtt tttcatacat ggtaggcaaa    5400
```

-continued

```
tactcttcaa ttgagttctc tctgcagcct gcagatcaaa acaaaacaaa acattatggt    5460
aaagcataac aatttacata cttttagtta actgtgaagc attaaataat gatattaaga    5520
aaaaaatgga agtaatcctg gtagttgatg tgggaggtta tatagtgtgg tggtttggat    5580
atgcttggcc tattaggagg tgtggctttg ttggagtagg tgtggccttg ttggaagaag    5640
tacatcattg tgggagtggg ctttgacacc ctcctcctcg ctgcccgaaa gacagtattc    5700
tggctacctt tggatcaaga tatagaactc ttggctcctt ctccagcacc atgtctgcct    5760
gcatgctgtt ggctaggatg ataattgact aaacatctga aactgtaagc cagccccaat    5820
taaatgttgt ctttctaaga aaaaaaaaaa aaaa                                5855
```

<210> SEQ ID NO 2
<211> LENGTH: 224
<212> TYPE: PRT
<213> ORGANISM: Mus musculus

<400> SEQUENCE: 2

```
Met Pro His Lys Ile Glu Gly Phe Phe Leu Leu Leu Phe Gly Tyr
1               5                   10                  15

Glu Ala Thr Leu Gly Leu Ser Ser Thr Glu Asp Glu Gly Glu Asp Pro
                20                  25                  30

Trp Tyr Gln Lys Ala Cys Lys Cys Asp Cys Gln Val Gly Ala Asn Ala
            35                  40                  45

Leu Trp Ser Ala Gly Ala Thr Ser Leu Asp Cys Ile Pro Glu Cys Pro
        50                  55                  60

Tyr His Lys Pro Leu Gly Phe Glu Ser Gly Glu Val Thr Pro Asp Gln
65                  70                  75                  80

Ile Thr Cys Ser Asn Pro Glu Gln Tyr Val Gly Trp Tyr Ser Ser Trp
                85                  90                  95

Thr Ala Asn Lys Ala Arg Leu Asn Ser Gln Gly Phe Gly Cys Ala Trp
            100                 105                 110

Leu Ser Lys Tyr Gln Asp Ser Ser Gln Trp Leu Gln Ile Asp Leu Lys
        115                 120                 125

Glu Ile Lys Val Ile Ser Gly Ile Leu Thr Gln Gly Arg Cys Asp Ile
    130                 135                 140

Asp Glu Trp Val Thr Lys Tyr Ser Val Gln Tyr Arg Thr Asp Glu Arg
145                 150                 155                 160

Leu Asn Trp Ile Tyr Tyr Lys Asp Gln Thr Gly Asn Asn Arg Val Phe
                165                 170                 175

Tyr Gly Asn Ser Asp Arg Ser Ser Thr Val Gln Asn Leu Leu Arg Pro
            180                 185                 190

Pro Ile Ile Ser Arg Phe Ile Arg Leu Ile Pro Leu Gly Trp His Val
        195                 200                 205

Arg Ile Ala Ile Arg Met Glu Leu Leu Glu Cys Ala Ser Lys Cys Ala
    210                 215                 220
```

<210> SEQ ID NO 3
<211> LENGTH: 675
<212> TYPE: DNA
<213> ORGANISM: Rattus norvegicus

<400> SEQUENCE: 3

```
atgccacaca agattgaagg cttcttctta ttgcttctct ttggctatga agccacattg    60
ggattgtctt cgacagagga tgagggtgag gacccttggt accagaaagc gtgcaagtgt    120
```

```
gattgccagg gaggagccaa tgctctgtgg tctgctggag ccgcctcctt agactgtatt      180
ccagaatgcc catatcacaa gcccctgggt tcgagtcag gggaagtcac accagatcag       240
atcacttgct ccaacccaga gcagtatgtg gctggtatt cctcatggac tgcaaacaag       300
gcccggctca acagtcaagg ttttgggtgt gcttggcttt ccaagtatca ggacagtagc      360
cagtggttac agatagattt gaaggagatc aaggtgattt cggggatcct tacccaagga     420
cgctgtgaca tagatgagtg gatgaccaag tacagtgtgc aatataggac tgatgaacgc      480
ctgaactgga tttactataa ggatcagact ggaaacaatc gggtcttcta tggaaactcc     540
gaccggagtt ctacagtcca gaacttactg aggccccca ttatttcccg cttcatccga      600
ctgatccctc taggctggca tgtccgaatt gccatccgga tggagctgct tgagtgtgcc     660
agcaagtgtg cctga                                                       675
```

```
<210> SEQ ID NO 4
<211> LENGTH: 224
<212> TYPE: PRT
<213> ORGANISM: Rattus norvegicus

<400> SEQUENCE: 4
```

Met Pro His Lys Ile Glu Gly Phe Phe Leu Leu Leu Leu Phe Gly Tyr
1               5                   10                  15

Glu Ala Thr Leu Gly Leu Ser Ser Thr Glu Asp Glu Gly Glu Asp Pro
            20                  25                  30

Trp Tyr Gln Lys Ala Cys Lys Cys Asp Cys Gln Gly Gly Ala Asn Ala
        35                  40                  45

Leu Trp Ser Ala Gly Ala Ala Ser Leu Asp Cys Ile Pro Glu Cys Pro
    50                  55                  60

Tyr His Lys Pro Leu Gly Phe Glu Ser Gly Glu Val Thr Pro Asp Gln
65                  70                  75                  80

Ile Thr Cys Ser Asn Pro Glu Gln Tyr Val Gly Trp Tyr Ser Ser Trp
                85                  90                  95

Thr Ala Asn Lys Ala Arg Leu Asn Ser Gln Gly Phe Gly Cys Ala Trp
            100                 105                 110

Leu Ser Lys Tyr Gln Asp Ser Ser Gln Trp Leu Gln Ile Asp Leu Lys
        115                 120                 125

Glu Ile Lys Val Ile Ser Gly Ile Leu Thr Gln Gly Arg Cys Asp Ile
    130                 135                 140

Asp Glu Trp Met Thr Lys Tyr Ser Val Gln Tyr Arg Thr Asp Glu Arg
145                 150                 155                 160

Leu Asn Trp Ile Tyr Tyr Lys Asp Gln Thr Gly Asn Asn Arg Val Phe
                165                 170                 175

Tyr Gly Asn Ser Asp Arg Ser Ser Thr Val Gln Asn Leu Leu Arg Pro
            180                 185                 190

Pro Ile Ile Ser Arg Phe Ile Arg Leu Ile Pro Leu Gly Trp His Val
        195                 200                 205

Arg Ile Ala Ile Arg Met Glu Leu Leu Glu Cys Ala Ser Lys Cys Ala
    210                 215                 220

```
<210> SEQ ID NO 5
<211> LENGTH: 994
<212> TYPE: DNA
<213> ORGANISM: Macaca mulatta
```

<400> SEQUENCE: 5

```
cagttcagta aggtagagct tcggccgagg acgaggggaa gatgtcacgc aagatagaag      60
gcttttgct attacttctc tttggctatg aagccacatt gggattatcg tctaccgagg      120
atgaaggcga ggaccctgg taccaaaaag catgcaagtg tgattgccaa ggaggaccca      180
atgctctgtg gtctgcaggt gccacctcct tggactgcat accagaatgc ccatatcaca      240
agcccctggg tttcgagtca ggggaggtca caccagacca gatcacctgc tctaacccgg      300
agcagtatgt gggctggtat tcctcgtgga ctgcaaacaa ggcccggctc aacagtcaag      360
gctttgggtg cgcctggctc tccaagttcc aggacagtag ccagtggtta cagatagatc      420
tgaaggagat caaggtgatt tcagggatcc ttacccaggg gcgctgtgac atcgatgagt      480
ggatgaccaa gtacagcgtg cagtacagga ccgatgagcg cctgaactgg atttactata      540
aggaccagac tggaaataac cgggtcttct atggcaactc ggaccgcacc tccacggttc      600
agaacctgct gcggccccc atcatctccc gcttcattcg cctcatcccg ctgggctggc      660
acgtccgcat tgccatccgg atggagctgc tggagtgcgt cagcaagtgt gcctgatgcc      720
tgcctcagct tggcgcctgc tggggggtga ccggcgcaga gcggggccgt aggggaccc      780
ctcacatacc actgggatgg acagggctat atttcgcaaa gcaaattta actgcagtgc      840
tgggtagata cttttttttt tttttttttt aagatatagc tttctgattt caatgaaata      900
aaaatgaact tattccccac tcagggccag agaaagtcag aacaaagaaa atgtcccgaa      960
aaccaatttt cttacaaaag cctaagcagc aggg                                  994
```

<210> SEQ ID NO 6  
<211> LENGTH: 224  
<212> TYPE: PRT  
<213> ORGANISM: Macaca mulatta

<400> SEQUENCE: 6

```
Met Ser Arg Lys Ile Glu Gly Phe Leu Leu Leu Leu Phe Gly Tyr
1               5                   10                  15

Glu Ala Thr Leu Gly Leu Ser Ser Thr Glu Asp Glu Gly Glu Asp Pro
            20                  25                  30

Trp Tyr Gln Lys Ala Cys Lys Cys Asp Cys Gln Gly Gly Pro Asn Ala
        35                  40                  45

Leu Trp Ser Ala Gly Ala Thr Ser Leu Asp Cys Ile Pro Glu Cys Pro
    50                  55                  60

Tyr His Lys Pro Leu Gly Phe Glu Ser Gly Glu Val Thr Pro Asp Gln
65                  70                  75                  80

Ile Thr Cys Ser Asn Pro Glu Gln Tyr Val Gly Trp Tyr Ser Ser Trp
                85                  90                  95

Thr Ala Asn Lys Ala Arg Leu Asn Ser Gln Gly Phe Gly Cys Ala Trp
            100                 105                 110

Leu Ser Lys Phe Gln Asp Ser Ser Gln Trp Leu Gln Ile Asp Leu Lys
        115                 120                 125

Glu Ile Lys Val Ile Ser Gly Ile Leu Thr Gln Gly Arg Cys Asp Ile
    130                 135                 140

Asp Glu Trp Met Thr Lys Tyr Ser Val Gln Tyr Arg Thr Asp Glu Arg
145                 150                 155                 160

Leu Asn Trp Ile Tyr Tyr Lys Asp Gln Thr Gly Asn Asn Arg Val Phe
                165                 170                 175
```

```
Tyr Gly Asn Ser Asp Arg Thr Ser Thr Val Gln Asn Leu Leu Arg Pro
            180                 185                 190

Pro Ile Ile Ser Arg Phe Ile Arg Leu Ile Pro Leu Gly Trp His Val
        195                 200                 205

Arg Ile Ala Ile Arg Met Glu Leu Leu Glu Cys Val Ser Lys Cys Ala
    210                 215                 220

<210> SEQ ID NO 7
<211> LENGTH: 3039
<212> TYPE: DNA
<213> ORGANISM: Homo sapiens

<400> SEQUENCE: 7
agtaaggtag agctttggcc gaggacgagg ggaagatgtc acgcaagata gaaggctttt      60
tgttattact tctctttggc tatgaagcca cattgggatt atcgtctacc gaggatgaag     120
gcgaggaccc ctggtaccaa aaagcatgca agtgcgattg ccaaggagga cccaatgctc     180
tgtggtctgc aggtgccacc tccttggact gtataccaga atgcccatat cacaagcctc     240
tgggtttcga gtcaggggag gtcacaccgg accagatcac ctgctctaac ccggagcagt     300
atgtgggctg gtattcttcg tggactgcaa acaaggcccg gctcaacagt caaggctttg     360
ggtgtgcctg gctctccaag ttccaggaca gtagccagtg gttacagata gatctgaagg     420
agatcaaagt gatttcaggg atcctcaccc aggggcgctg tgacatcgat gagtggatga     480
ccaagtacag cgtgcagtac aggaccgatg agcgcctgaa ctggatttac tacaaggacc     540
agactggaaa caaccgggtc ttctatggca actcggaccg cacctccacg gttcagaacc     600
tgctgcggcc cccatcatc tcccgcttca tccgctcat cccgctgggc tggcacgtcc     660
gcattgccat ccgatggag ctgctggagt gcgtcagcaa gtgtgcctga tgcctgcctc     720
agctcggcgc ctgccagggg gtgactggca cagagcgggc cgtagggac cccctcacac     780 accaccgaga tggacagggc tatatttcgc aaagcaattg taactgcagt gctgggtaga     840 taatttttt tttttaaga tatagctttc tgatttcaat gaaataaaaa tgaacttatt     900
ccccactcag ggccagagaa agtcagaaca aagaaaatgt ccccgaaacg aattttctta     960
caaaagccta agtagcaggg gtaattttct gctcattttt tgtctcagtg atactgtgaa    1020
aggtgcagtc tcaggggaac acaaagcagc cctgataatt tgaaaattca tttgctttac    1080
cacattcaag acagaaacat acagtttcct aaagcctggc tttgaatgca gaagggagca    1140
gctcctccta gttaagtttc cactaaatca tcgccaaaga ggacttcaga gccctgggga    1200
ggcagctgag ggtctcaagg gtgactgggt ggcagggatg agtgcggtgg gtgagaatcc    1260
cggtgccctg agaggctata cgtgacaaat gaccaaaagc ccaaggtagg ggagtttcct    1320
ctgctcacag ttcttacctt caaggcggat ctgggcttcc accctcatga acacagggat    1380
tggggaggga ccagagcgcc caatacacac agctccatta tgcaatccat tccagcaaat    1440
tccccgtgtc tgtggtcacc atttaggtga tcatacagga caggctgcac atctcagtat    1500
atgtagggac cccaaatgac cacaacacag tacaattgcc ctttacctag ggctaccatt    1560
tcctagcaaa ccaaacatag ttcgagaaca gctggcccag gagctaccac tggctactca    1620
gaggaggctc attagctggc tacatgcttc gcaggaagtg ggaaggactc acatcataaa    1680
aaggaccatg tagcttttc cctgaaagct tctcacccct caccctctgc cttgcaatac    1740
gcaaactgcg cctgctcctg aaaagctctc tgggaaggaa tgggcctggc tttccgttcc    1800
tggaggcggc gccttagatt gggaggcctc attggccact tagagcgcag cctgagtttc    1860
```

```
caggcccctt cctgggagag gctgttaaca cggggagggg gcaggagagg gatatggaga    1920
gcaggtggtg gaatcagagg acgaggctgc tctaaagact gttctggccc cagacacagg    1980
gtagtctttg ctagcagctc atttccgagt tacttttcat tttcaaatgc caaggcaagt    2040
gactagactc gcgctaatac agtgctggac aacacattca ccttttctgt gaacaggcag    2100
ccttctaaaa gccccaaaca tccttcttga tgctttgggg gctcaattat tttatatcca    2160
acccagcatc tttctagtcc ctatgctgta tgcttgaact cggaaaatgc ttttccccgc    2220
ccaatcttct ctcaaatata aacacatcac acagggtgtt gggggtgggg gggggggtg    2280 gggggactta tccctggcct taggacacag gacaaatcta ttttggatag aaatgcctga    2340
acagagaccc ttatttggaa aggtgaatta actttggtca cgacatggac tgtcagacaa    2400
aatggcagta tcctaagagt taaggcacat caaacacagg agtcgagaga gtgcagttca    2460
gggaaaaagg agaggaggaa acagtgaggc agggagaaag gctttccaaa taagagttca    2520
tgttggaaac ttttgtcacg gctttattga gattaagttc acatacaatt tgtatccatt    2580
taaagtgtac aatttgatga cttttggtat attcagagtt gtgcaaccat tatcactaga    2640
tcaattttag aaagtttatc accccaaaga gaaatcctgc acccatcagc caacactccc    2700
caacccatcg gccaccccaa gccctctgca accacgaatc gactgtctct gtagattggc    2760
cttctggacg ttctacataa atgaaatcat atagtatgtg gtatttcgtg actggcttct    2820
ttcacttagc atagtgtttt aaagttcatc cacgttataa catgtgtatc actatgtcac    2880
ttgtcactcc ttttattgc tgaacatcat tgttcagtat catgtcaaga gcacattgtt    2940
atttatccat tcatccattg atggatattt gggtttccac tctttagcta ttatgaataa    3000
tgctgctatg aacatttgtg tataaaaaaa aaaaaaaaa                          3039
```

<210> SEQ ID NO 8
<211> LENGTH: 224
<212> TYPE: PRT
<213> ORGANISM: Homo sapiens

<400> SEQUENCE: 8

```
Met Ser Arg Lys Ile Glu Gly Phe Leu Leu Leu Leu Phe Gly Tyr
1               5                   10                  15

Glu Ala Thr Leu Gly Leu Ser Ser Thr Glu Asp Glu Gly Asp Pro
                20                  25                  30

Trp Tyr Gln Lys Ala Cys Lys Cys Asp Cys Gln Gly Pro Asn Ala
                35                  40                  45

Leu Trp Ser Ala Gly Ala Thr Ser Leu Asp Cys Ile Pro Glu Cys Pro
50                  55                  60

Tyr His Lys Pro Leu Gly Phe Glu Ser Gly Glu Val Thr Pro Asp Gln
65                  70                  75                  80

Ile Thr Cys Ser Asn Pro Glu Gln Tyr Val Gly Trp Tyr Ser Ser Trp
                85                  90                  95

Thr Ala Asn Lys Ala Arg Leu Asn Ser Gln Gly Phe Gly Cys Ala Trp
                100                 105                 110

Leu Ser Lys Phe Gln Asp Ser Ser Gln Trp Leu Gln Ile Asp Leu Lys
                115                 120                 125

Glu Ile Lys Val Ile Ser Gly Ile Leu Thr Gln Gly Arg Cys Asp Ile
                130                 135                 140

Asp Glu Trp Met Thr Lys Tyr Ser Val Gln Tyr Arg Thr Asp Glu Arg
145                 150                 155                 160
```

| Leu | Asn | Trp | Ile | Tyr | Tyr | Lys | Asp | Gln | Thr | Gly | Asn | Asn | Arg | Val | Phe |
|---|---|---|---|---|---|---|---|---|---|---|---|---|---|---|---|
| | | | | 165 | | | | 170 | | | | | 175 | | |

| Tyr | Gly | Asn | Ser | Asp | Arg | Thr | Ser | Thr | Val | Gln | Asn | Leu | Leu | Arg | Pro |
|---|---|---|---|---|---|---|---|---|---|---|---|---|---|---|---|
| | | | 180 | | | | | 185 | | | | | 190 | | |

| Pro | Ile | Ile | Ser | Arg | Phe | Ile | Arg | Leu | Ile | Pro | Leu | Gly | Trp | His | Val |
|---|---|---|---|---|---|---|---|---|---|---|---|---|---|---|---|
| | | | | 195 | | | | | 200 | | | | | 205 | |

| Arg | Ile | Ala | Ile | Arg | Met | Glu | Leu | Leu | Glu | Cys | Val | Ser | Lys | Cys | Ala |
|---|---|---|---|---|---|---|---|---|---|---|---|---|---|---|---|
| | | 210 | | | | | 215 | | | | | 220 | | | |

<210> SEQ ID NO 9
<211> LENGTH: 2061
<212> TYPE: DNA
<213> ORGANISM: Canis lupus

<400> SEQUENCE: 9

```
aatgaggcca gcgctcaagt taagcccctg ctcctggaga agctctccac ttggataagg    60
tagagctgcg gccaaggaca agggagaat gccccgcaag atagaaggct tcttgttttt   120
acttctcttc ggctatgaag ccacactggg attatcgtct actgaggatg agagtgagga   180
cccctggtac cagaaagcat gcaaatgtga ctgccaaggc agtcccaatg gcctctggtc   240
ggctggtgcc acctccttag attgcatacc agaatgcccg tatcataagc ccctgggttt   300
cgagtcagga gaggttacac cagaccagat cacttgctcc aacctggatc agtatgtggg   360
ctggtattcc tcatggacag ctaacaaggc ccggctcaac agtcaaggct ttgggtgcgc   420
ctggctctcc aagtaccagg acagcagcca gtggttacag atcgatctga aggaggtcaa   480
ggtgatttca ggaatcctca cccagggggcg ctgtgacatc gacgagtgga tgaccaagta   540
cagcgtgcag tacaggacgg atgagaacct gaactggatt tactataagg accagacagg   600
aaacaatcgg gtcttctatg gaaattcaga ccgaacctcc acagtccaga accttctgcg   660
gccccccatc atttcccgct tcattcggct gatcccgctg ggctggcatg tccgcattgc   720
catccggatg gagctgctgg aatgcgtcag caagtgtgcc tgaggcctcc ttcagctcca   780
cacctgccct ggggtggggg tgggggggtag ataggggtgg agggctcaga gcagcctgca   840
ggggaacccct gacagggttc caacagggtg acaaacgcag ctgtatttta caagctcttt   900
tcaatgcaga gcctggcaga ataatttct ttaaaaaac aagtttccca tttcaatcaa    960
agagaaagga aaacgagcgt atttcccact cactgccaaa gaaataagaa acaaagaaaa  1020
cgtccctaaa actagttttc atctaaaagc ctaagtagca ggggtaattt tgctgctttt  1080
tcttttggt tttggtctga cagtgtgaaa ggtgtggtcc cagggaacac aaaagagccc  1140
agataattta aaaactcttt tgctttacca cactaaaaac aggaacatag aggttttct  1200
tttcttttct tttcttttct tttcttttct tttcttttct tttcttttct tttcttttct  1260
tttctttccg gaacacagag tttcataaaa ccttgatttg attgcaaatg gggagcaagc  1320
ttgcggtttc tccttttaag ttttcagtga atcatggcct tttaggactt ttagagcacc  1380
cggcatgcag ggggcaaggt tttgggtgac tggttgtcag atgagtag agcagttggg  1440
agcctgtgtc ctggtgtcct gagagctgtg cacaaccaat cccccaggt aagagggctt  1500
cctctgctct gagcttcac ccccacgcac acaaggatag ggaggggtg gttgcagagc  1560
tctcattaca tacagatcta ttctagcaaa ttttccagc ctgtggtcac tatctgggtg  1620
aatacatggg acaggctgca catgtaagca gcagttctct atatttagga aagccaaatg  1680
accagagctc accagaattt ccccttatct agggctacca ttttcaaca agcttaacat  1740
tttaaaaaca gctggcccag gagctatcac tggctacaca gaggaagccc attagctaac  1800
```

-continued

```
tgcatgcttt gcaggaagtg gtcagaccct atgtcctaag aagggccatg tggctgtgtc    1860
tctcacgacc caactgttta acctctcccc cttgccctag aacacacaac catgcctact    1920
cctgaggctg aaatggcctt gggagggacg gggctaggaa tgggcctggc cttccgaggg    1980
gagtgcataa agcagggact tttcagggac cacagcctaa gcctcctctg tcatttatag    2040
ctcagcctga gttttcaggc t                                              2061
```

<210> SEQ ID NO 10
<211> LENGTH: 224
<212> TYPE: PRT
<213> ORGANISM: Canis lupus

<400> SEQUENCE: 10

```
Met Pro Arg Lys Ile Glu Gly Phe Leu Phe Leu Leu Phe Gly Tyr
1               5                   10                  15

Glu Ala Thr Leu Gly Leu Ser Ser Thr Glu Asp Glu Ser Glu Asp Pro
            20                  25                  30

Trp Tyr Gln Lys Ala Cys Lys Cys Asp Cys Gln Gly Ser Pro Asn Gly
        35                  40                  45

Leu Trp Ser Ala Gly Ala Thr Ser Leu Asp Cys Ile Pro Glu Cys Pro
    50                  55                  60

Tyr His Lys Pro Leu Gly Phe Glu Ser Gly Glu Val Thr Pro Asp Gln
65                  70                  75                  80

Ile Thr Cys Ser Asn Leu Asp Gln Tyr Val Gly Trp Tyr Ser Ser Trp
                85                  90                  95

Thr Ala Asn Lys Ala Arg Leu Asn Ser Gln Gly Phe Gly Cys Ala Trp
            100                 105                 110

Leu Ser Lys Tyr Gln Asp Ser Ser Gln Trp Leu Gln Ile Asp Leu Lys
        115                 120                 125

Glu Val Lys Val Ile Ser Gly Ile Leu Thr Gln Gly Arg Cys Asp Ile
    130                 135                 140

Asp Glu Trp Met Thr Lys Tyr Ser Val Gln Tyr Arg Thr Asp Glu Asn
145                 150                 155                 160

Leu Asn Trp Ile Tyr Tyr Lys Asp Gln Thr Gly Asn Asn Arg Val Phe
                165                 170                 175

Tyr Gly Asn Ser Asp Arg Thr Ser Thr Val Gln Asn Leu Leu Arg Pro
            180                 185                 190

Pro Ile Ile Ser Arg Phe Ile Arg Leu Ile Pro Leu Gly Trp His Val
        195                 200                 205

Arg Ile Ala Ile Arg Met Glu Leu Leu Glu Cys Val Ser Lys Cys Ala
    210                 215                 220
```

<210> SEQ ID NO 11
<211> LENGTH: 1772
<212> TYPE: DNA
<213> ORGANISM: Sus scrofa

<400> SEQUENCE: 11

```
ccgggtcttc tgattccagt ttctattttc ctccactgct tcccttacat ttaaagatag      60
aataaagcca gtagcttcct tgctaaacc gacctcagtt gacatcggct tcttctcaga     120
gacttccttg ttgaggcagg taacgacgtg ggttaacttg tcggggctca gccaaagccc     180
taagagctaa atggaataag atgcttaatg aggccagtgc tcaagttaag ctcctgttcc     240
tagggaagct ctccacttcg ataaggaaga gcagcagcca aggacaaggg gagaatgcca     300
```

-continued

```
cgcaagatag aaggcttctt gttttactt ctctttggct atgaagccac cctgggatta    360
tcgtctacgg aggatgaggg tgaggacccc tggtacaaca aagcgtgcaa gtgtgactgc    420
caaggaggcg ccaatgccct gtggtctgcg ggcaccaccc ccttagactg cataccggaa    480
tgcccgtatc ataagcccct ggggttcgag tcaggagagg ttacaccaga ccagattacc    540
tgctccaacc tggagcagta cgtgggctgg tattcctcgt ggactgccaa caaggcccgg    600
ctcaacagtc aaggctttgg gtgcgcctgg ctctccaagt tccaggacag cagccagtgg    660
ttacagatag atctgaagga ggtcaaggtg atttcaggga cctcacccca gggccgctgt    720
gacatcgatg agtggatgac caagtacagc gtgcagtaca ggaccgatga gagcctgaac    780
tggatttact ataaggacca gactggaaac aaccgggttt tctatggaaa ctcagaccga    840
acctccacag tccagaacct gctacggccc cccatcattt cccgcttcat ccggctcatc    900
ccgctgggct ggcacgtgcg cattgccatc cggatggagt tgctggagtg cgtcagcaag    960
tgtacctgac ggggtgcccg ccagggtgcg cagggcacgg agcagccggg cgactgctga   1020
tctaccgctg tgaccaacaa ggctgtatct tacaggctct actcaatgca gagctgggca   1080
gagaagacat ctttctttct ttggttttct tcctttcttt ttttttaaat atagtttgca   1140
tttcaataaa caaaccgaat taaatcttca ctcagggcca agaaaataa gaacaaagaa    1200
aatgtcccta aaaacaattt tcatgcaaaa gcaaagcagg agtaatttgc tgctctctgg   1260
agttttttgt tttcgctttt ttttttttt ttttttttga ttgtttgctt tttggtctca   1320
gtgacactgt gcaaggtgcc ctcccaggag aatgcaaagc agccctaata atctgaaaat   1380
tcttttgctt taccacattc aaaacaagaa cacagagttt cataaagcct cactttgaaa   1440
gcaaagaggg agcaagcttg tgggttctcc tagcttcgtt ttcattaaat catggccttt   1500
tagaacttga gagcactggg tatgcagggt aaaaggttct ggagtgacta ggagggtggg   1560
agcccatttt acggtcccct gagagccagg taggagggcc tccctgctc agagtttcac    1620
ccccagtcag tgcaatttat cctagtctgt ggtcactact taggtgaata atggacaggc   1680
tgcacatgta tgtagccaag tctccctata tttaggaacc tcaaatgacc agaacacacc   1740
agaatttcct tttatctagg gtaaccattt aa                                 1772
```

<210> SEQ ID NO 12
<211> LENGTH: 224
<212> TYPE: PRT
<213> ORGANISM: Sus scrofa

<400> SEQUENCE: 12

```
Met Pro Arg Lys Ile Glu Gly Phe Leu Phe Leu Leu Phe Gly Tyr
1               5                   10                  15

Glu Ala Thr Leu Gly Leu Ser Ser Thr Glu Asp Glu Gly Glu Asp Pro
                20                  25                  30

Trp Tyr Asn Lys Ala Cys Lys Cys Asp Cys Gln Gly Gly Ala Asn Ala
            35                  40                  45

Leu Trp Ser Ala Gly Thr Thr Pro Leu Asp Cys Ile Pro Glu Cys Pro
        50                  55                  60

Tyr His Lys Pro Leu Gly Phe Glu Ser Gly Glu Val Thr Pro Asp Gln
65                  70                  75                  80

Ile Thr Cys Ser Asn Leu Glu Gln Tyr Val Gly Trp Tyr Ser Ser Trp
                85                  90                  95

Thr Ala Asn Lys Ala Arg Leu Asn Ser Gln Gly Phe Gly Cys Ala Trp
            100                 105                 110
```

Leu Ser Lys Phe Gln Asp Ser Ser Gln Trp Leu Gln Ile Asp Leu Lys
            115                 120                 125

Glu Val Lys Val Ile Ser Gly Ile Leu Thr Gln Gly Arg Cys Asp Ile
        130                 135                 140

Asp Glu Trp Met Thr Lys Tyr Ser Val Gln Tyr Arg Thr Asp Glu Ser
145                 150                 155                 160

Leu Asn Trp Ile Tyr Tyr Lys Asp Gln Thr Gly Asn Asn Arg Val Phe
                165                 170                 175

Tyr Gly Asn Ser Asp Arg Thr Ser Thr Val Gln Asn Leu Leu Arg Pro
            180                 185                 190

Pro Ile Ile Ser Arg Phe Ile Arg Leu Ile Pro Leu Gly Trp His Val
        195                 200                 205

Arg Ile Ala Ile Arg Met Glu Leu Leu Glu Cys Val Ser Lys Cys Thr
    210                 215                 220

<210> SEQ ID NO 13
<211> LENGTH: 899
<212> TYPE: DNA
<213> ORGANISM: Bos taurus

<400> SEQUENCE: 13
ctccactttg ataaggaaga gcagcagcca aggacaaggg gagaatgcca cgcaagatag      60
aaaacttctt gttttttactt ctcttcggct atgaagccac actgggatta tcatctactg    120
aggatgaggg tgaagatccc tggtaccaca aagcgtgcaa gtgcgattgc caaggaggtg    180
ccaatgccct gtggtctgca ggtcccaccc ccttggactg cataccggaa tgcccatacc    240
ataagcccct gggtttcgag tcaggagagg ttacaccaga ccagatcacc tgctccaacg    300
tggagcagta cgtgggctgg tattcttcct ggactgccaa caaggcccgg cttaacagtc    360
aaggctttgg gtgtgcctgg ctctccaagt tccaggacag cagccagtgg ttacagatag    420
atctgaagga ggtcaaggtg atttcgggga tcctcaccca ggggcgctgt gacatcgatg    480
agtggatgac caagtacagt gtgcagtaca ggaccgatga gagtctgaac tggatttact    540
ataaagacca gaccggaaac aaccgggttt tctatggaaa ttcggaccga acctccacag    600
tccagaacct gctgcggccc cccatcatct cccgcttcat ccggctcata ccgctaggct    660
ggcatgttcg cattgccatc cggatggagc tgctggagtg cgtcagcaag tgtacctgat    720
gttgcctcgg ctcataccctg cagtgggtga agggtgcaga gcggcccatg ggggaacgct    780
gacttatcac tgtgaccagc agggctggat tttacaggct cttttcagcg cagggctggg    840
cagagaatac tatctttttt gcatagtttc caatttcagt gagagaaaat gaaaatgaa       899

<210> SEQ ID NO 14
<211> LENGTH: 224
<212> TYPE: PRT
<213> ORGANISM: Bos taurus

<400> SEQUENCE: 14

Met Pro Arg Lys Ile Glu Asn Phe Leu Phe Leu Leu Leu Phe Gly Tyr
1               5                   10                  15

Glu Ala Thr Leu Gly Leu Ser Ser Thr Glu Asp Glu Gly Glu Asp Pro
            20                  25                  30

Trp Tyr His Lys Ala Cys Lys Cys Asp Cys Gln Gly Gly Ala Asn Ala
        35                  40                  45

Leu Trp Ser Ala Gly Pro Thr Pro Leu Asp Cys Ile Pro Glu Cys Pro
    50                  55                  60

| | | | | | | | | | | | | |
|---|---|---|---|---|---|---|---|---|---|---|---|---|
|Tyr|His|Lys|Pro|Leu|Gly|Phe|Glu|Ser|Gly|Glu|Val|Thr|Pro|Asp|Gln|
|65| | | |70| | | |75| | | |80|

Ile Thr Cys Ser Asn Val Glu Gln Tyr Val Gly Trp Tyr Ser Ser Trp
            85                  90                  95

Thr Ala Asn Lys Ala Arg Leu Asn Ser Gln Gly Phe Gly Cys Ala Trp
            100                 105                 110

Leu Ser Lys Phe Gln Asp Ser Ser Gln Trp Leu Gln Ile Asp Leu Lys
            115                 120                 125

Glu Val Lys Val Ile Ser Gly Ile Leu Thr Gln Gly Arg Cys Asp Ile
            130                 135                 140

Asp Glu Trp Met Thr Lys Tyr Ser Val Gln Tyr Arg Thr Asp Glu Ser
145                 150                 155                 160

Leu Asn Trp Ile Tyr Tyr Lys Asp Gln Thr Gly Asn Asn Arg Val Phe
            165                 170                 175

Tyr Gly Asn Ser Asp Arg Thr Ser Thr Val Gln Asn Leu Leu Arg Pro
            180                 185                 190

Pro Ile Ile Ser Arg Phe Ile Arg Leu Ile Pro Leu Gly Trp His Val
            195                 200                 205

Arg Ile Ala Ile Arg Met Glu Leu Leu Glu Cys Val Ser Lys Cys Thr
210                 215                 220

<210> SEQ ID NO 15
<211> LENGTH: 1604
<212> TYPE: DNA
<213> ORGANISM: Ovis aries

<400> SEQUENCE: 15
actttgactt cttccagaag gggccttgtt aacttttat gtgactatta tcactttgct    60
tttccgtgta atgagtcatt tgttgaattt ttctttcttg ttttaacttg attttttcctc   120
tcttgtcctt tgctcagcc acactgggat tatcatctac tgaggtatgt tacagtaaga   180
aggctggaat tcatacggat actgttttg aacattttca tagccaaaaa caatgtatag   240
gattatcact tctttaaaaa tgtattttta acatatatt ttttctggtg gtggaaatag   300
catgttttat ctggacaaag ttcaagactg attcagataa atgagacaat gcaagtgaac   360
caggtcttat gtcagatggc agaatcttga attcagtccc ttttaaaact ggatccccag   420
aagggccctg cagatgtgag gagcctgact ggaagatcac tacaatgggg tggacacggc   480
tctctacata ggtgtgtctg tgaagttttt agctggtcat ccacagtgac aaacatttgt   540
ctatttagac tcaaagatga gtggtgactg tgtgttaaac tgggttcata agtcagttgc   600
actgctgtag agtgaaagct gccctagaca ataggaacta aatgagtgag gtttgtgaat   660
gcaagctttt ccagtagttc tgaccacagt tgcctttgac tatggctttt ctgaagttcc   720
tgccccctga tttccgcag gatgagggtg aggatccctg gtaccacaaa gcatgcaagt   780
gtgattgcca aggaggtgcc aatgccctgt ggtctgcagg ttccacccc ttggactgca   840
taccggaatg cccataccat aagccctgg gtttcgagtc aggagaggtt acaccagacc   900
agatcacctg ctccaacgtg gagcagtacg tgggctggta ttcttcctgg actgccaaca   960
aggcccggct caacagtcaa ggctttgggt gcgcttggct ctccaagttc caggacagca  1020
gccagtggtt acagatagat ctgaaggagg tcaaggtgat ttcggggatc ctcacccagg  1080
ggcgctgtga catcgatgag tggatgacca agtacagtgt gcagtacagg accgatgaga  1140
gcctgaactg gatttactat aaagaccaga ctggaaacaa ccgggtttc tatggaaatt  1200
cggaccgaac ctccacagtc cagaacctgc tgcggccccc catcatctcc cgcttcatcc  1260

```
ggctcatccc actaggctgg catgtccgca ttgccatccg gatggagctg ctggagtgcg    1320
tcagcaagtg tacctgatgc tgcctcggct catgcctgca gtgggtgaag ggcgcagagt    1380
ggcccatggg ggaactctga cttatcactg tgaccaacag ggctggattt tacaggctct    1440
tttcagtgca gggctgggca gagaatacta tcttttttgc atagtttcca atttcagtaa    1500
gagaaaatga aaataaacgt atttcccatt cagggtcaaa gaaaataaga acaaagaaaa    1560
tgtctctaaa aacaatttcc atgcagaaag cctaagtagc agga                     1604
```

<210> SEQ ID NO 16
<211> LENGTH: 211
<212> TYPE: PRT
<213> ORGANISM: Ovis aries

<400> SEQUENCE: 16

```
Met Ala Phe Leu Lys Phe Leu Pro Pro Asp Phe Pro Gln Asp Glu Gly
1               5                   10                  15

Glu Asp Pro Trp Tyr His Lys Ala Cys Lys Cys Asp Cys Gln Gly Gly
                20                  25                  30

Ala Asn Ala Leu Trp Ser Ala Gly Ser Thr Pro Leu Asp Cys Ile Pro
            35                  40                  45

Glu Cys Pro Tyr His Lys Pro Leu Gly Phe Glu Ser Gly Glu Val Thr
        50                  55                  60

Pro Asp Gln Ile Thr Cys Ser Asn Val Glu Gln Tyr Val Gly Trp Tyr
65                  70                  75                  80

Ser Ser Trp Thr Ala Asn Lys Ala Arg Leu Asn Ser Gln Gly Phe Gly
                85                  90                  95

Cys Ala Trp Leu Ser Lys Phe Gln Asp Ser Ser Gln Trp Leu Gln Ile
                100                 105                 110

Asp Leu Lys Glu Val Lys Val Ile Ser Gly Ile Leu Thr Gln Gly Arg
            115                 120                 125

Cys Asp Ile Asp Glu Trp Met Thr Lys Tyr Ser Val Gln Tyr Arg Thr
        130                 135                 140

Asp Glu Ser Leu Asn Trp Ile Tyr Tyr Lys Asp Gln Thr Gly Asn Asn
145                 150                 155                 160

Arg Val Phe Tyr Gly Asn Ser Asp Arg Thr Ser Thr Val Gln Asn Leu
                165                 170                 175

Leu Arg Pro Pro Ile Ile Ser Arg Phe Ile Arg Leu Ile Pro Leu Gly
                180                 185                 190

Trp His Val Arg Ile Ala Ile Arg Met Glu Leu Leu Glu Cys Val Ser
            195                 200                 205

Lys Cys Thr
    210
```

<210> SEQ ID NO 17
<211> LENGTH: 4553
<212> TYPE: DNA
<213> ORGANISM: Felis catus

<400> SEQUENCE: 17

```
cttctgagga aaccctccac tcggataagg tagagctaca gccaaggaca aggggagaat      60
gccacgcaag atagaaggtt tcttgttctt acttctcttt ggctacgaag ccacactggg     120
actgtcgtct actgaggatg agggtgagga cccctggtac cacaaagcat gcaaatgcga     180
ttgccaagga ggtgccaatg ccctctggtc tgctggcgcc acctccttag actgcattcc     240
```

-continued

```
ggaatgccca tatcataagc ccctgggttt cgaatcggga gaagttacac cagaccagat    300
cacctgctcc aacctggagc agtacgtggg ctggtattcc tcgtggaccg ctaacaaggc    360
ccggctcaac agtcaaggct ttgggtgcgc ctggctgtcc aagtaccagg acagcagcca    420
gtggctagag atagatctga aggaggtcaa ggtgatttca gggatcctca cccaggggcg    480
ctgtgacatt gatgagtgga tgaccaagta cagcgtgcag tacaggaccg atgagaacct    540
gaactggatt tactataagg accagacagg aaacaaccgg gtcttctacg caactcaga    600 ccgaacctcc acggtccaga acctcctgcg gccccccatc atttcccgct tcatccggct    660
gatcccactg ggctggcacg tccgcattgc catccggatg gagctgttgg agtgcgtcag    720
caagtgtgcg tgacgcctcc ttcagctcgg cacctgccag gtggggtgga gggcgcagag    780
cagcctgtag gggaaaattg acgcgaccag ggcttgaaca gggtgacaaa cagggctgaa    840
ttttacaagc tcttttcaat gcagagctgg gcagaaataa tttctttttt ttaagacgta    900
gtttccaatg tcaatgagag agaaagaaaa atgaactcat tccccactca gggccaaaga    960
aaataagaac aaagaaaatg tccctaaaga caatgttcat caaaagccta agtagcaggg   1020
gtaattttct gctcttgggt ttttgtgttt ggcctgacag tgtgaaaggt gtggtctcag   1080
ggaacacaaa ggagcccaga taatttaaaa accccttttgc ttcaccaccc tgaaaacagg   1140
aacagaagtt tcataaaacc ttgatttgaa cgcaaatggg tagcaggctt gcggtctctc   1200
cggcgttttc accaaattag ggcctctcac aactttagag caccgtgtat gcagacggaa   1260
aggatttggg gtgactgggg ggccgaaagg catagtcggg agcctgtgtc ctggtctcct   1320
ggaggctggc accatcaccc caggcaggag ggcctcccct gctctgcgcc ttcacccca   1380 cgcacacaag gactgtggag ccacaaaagc tctcatcaca tacagatcca ttctagcaaa   1440
gttttccagt ctgtggtcac tatttgggta aatacatggg acgggctgca tgtgtaagta   1500
gcaaagtttc tctgtattta ggaaccccac atgaccgaag cacaccagaa tttcccttca   1560
tctagggcta ccatttttca acaggattca cattttaaaa ccagttggca caggagctag   1620
atcactggct acacggagga ggcccatcag ctaaccacat gctttgcagg aagtgggcag   1680
accgcaagtc ctaagaaggg atgtggatac gtttcttgtg acccacggtt aaacttcacc   1740
ccttgccttg caacacacaa aacaggcctg ctcctgaggt tgaaacctcc ttgagaagga   1800
ccgggcctgg catgggcctg gccttccccc tcctggagga gctcatgaag ctgggacctt   1860
tcgggaagag tctcagtctc ctgagttttc aggcccttcc ctggggagag gctgatgaca   1920
tggggagtgg gcaggagagg tatatgaaag taggagctga gaggggtga aactggggga   1980 tgagggccct ctgacaagac tggggaatcc gagactgtcc tggccctgac acagcacagc   2040
ctctactaga ggctttctcc tgagttactt tctgttttca aatgccaagc cgagtgaaga   2100
ctcacactaa catgatcctg gacatcacat tcaccttctc tgtgaggggg aagcctccta   2160
aaaaccccaa atctcttccc tggtgttttg ggcttagaac agctctatat ttaacccacc   2220 atccttttt ttttttttt tttttttttt aacgtttatt ttgaaagaga gaggagagag   2280
agagagggag agagcatgca tacgcacgcg agcaagcaga gaagggtcag atagagaggg   2340
agacagagga tctgaagcgg gctctgcacg gtcagcagtg agcctgatgt ggggccgaac   2400
ttgtgacctg tgagatcatg acctgagctg aagtcggacg cttaaccgac tgagccgccc   2460
aggtgcccct aacccaccat ctttttaatc ccccaactgt atacttggac ctggaaaaat   2520
gcttcccttg ctcagtattc tctcaaatac aaacatatca aattcaaggt ggggaaaaaa   2580
aaatccttct ctggactttg gacacatgaa taaatccatt tagagcaggc gcctcatcag   2640
```

```
agcccttag tgaaaagctg aatgaacttt catcatgaca cggattgtca gagaaaatgg    2700
tggtagccta agagctcagg tcctctacag tggtcacatc agacacagga ggcgagtacg    2760
gttaagagga aagaagaaaa gaatgaaact gtgaggcagt gataaaggtt ctccaactaa    2820
ttgttcatgt tagaaatgtt tgctttgtaa aggtttaatg agataaagtc ataccgta     2880 caaatttcaa ccatttcaag tgtacaattc aatgactttt agtagactca gagttgagga    2940
accattatca caattttaga aaaatttcat caccccacag agaaaccctg cacccattaa    3000
ccatcacctc ccaacctact cgtccccgca gccctaggca accactgatg gactttctgt    3060
ctcagtagat tgcctattc tggacatttc atataaatgg gatcattttc tgcctggctt     3120
cttttgctta gcatagtgtt tttccaagtt tcattcaggt tgcagcatgc acttaattcc    3180
ttcttatagc tgaacatcat tccgttatat ggataggtca cattgtattt atccgttcat    3240
ctgttgatgg acatttgggt tgtttctaca ttttttggcta tcgtgaataa tgctgctata    3300
aacacctgtg tacaagtttt tgtttggaca tatgttttta tttatcttgg gcatatacct    3360
aggagtggaa tgctggggtc atatggtaac tctacgtcta accttttag gaactgtcag    3420 acaattttcc aaaggggcca caccattatg cattcccacc agcaacatat gagagtttca    3480
ggttctctac atttgttatt atcttttga ttagagccgt cctggtgtgt atgaagtagc    3540
atcactctgg tttttgattt gcatttccct aggactaatg atgctaagca tcttttttat    3600
gtgttcactg gccttttgaa taacttcttt ggagaaatgt cttttccgat cctttgccca    3660
tttaaaaatc aggtggcctt tttattaacg aattgtaaga gctctttaat attctagata    3720
caaccccctt aggagatacg tgacttgcaa atactttctc ctattcggta ggttatcttc    3780
ttactctctt gatggagtcc tttgaaacac atttttaaat tttgataaag tccaatttat    3840
tcttttttgt tgcatgtgtt tttggtgtca tatctgaggt accattgcca aatcccgatc    3900
atgaagattt actcctatgt ttcaagagtt ttatagtttt acttcttaca tttagacctt    3960
tgatctattt ggggttattt tgtatatggt atgaggtagg ggtccaactt cagtatctgc    4020
acgtggacat ccagttgtcc cagcaccatt tgttgaaaag acttttccc cactgaatgg    4080 tcttggcatc cttttgaga aatcaattaa ccataaaggt gagaatttgt ttctggatcc    4140
tcaattctat tccattatag gtctatcttt ataccagtac cacacagttg tcattactgt    4200
agccttttta gtaagttttg aaattggaac aggttaactc tccaacttg ttcttcttca    4260 aggctgtctg ggctgctgag tcctttgaat gtccatatga attttagaat cactgtgtca    4320
atttctgcaa agaagccagc tgagatttca catcggaaat cgctccatac ttgagaattt    4380
aatcaacaat gagatactga gatccataat acgttaatct gtaggtaacc tgtgtataac    4440
agcatattaa ttatttactt catttaattt agaacagaaa gtataaaaac aaaactttta    4500
ttgaggggca tctgcagcct aacagaatct tgctattaaa cacatgaact gtg           4553
```

<210> SEQ ID NO 18
<211> LENGTH: 224
<212> TYPE: PRT
<213> ORGANISM: Felis catus

<400> SEQUENCE: 18

Met Pro Arg Lys Ile Glu Gly Phe Leu Phe Leu Leu Leu Phe Gly Tyr
1               5                   10                  15

Glu Ala Thr Leu Gly Leu Ser Ser Thr Glu Asp Glu Gly Glu Asp Pro
            20                  25                  30

```
Trp Tyr His Lys Ala Cys Lys Cys Asp Cys Gln Gly Ala Asn Ala
         35                  40                  45

Leu Trp Ser Ala Gly Ala Thr Ser Leu Asp Cys Ile Pro Glu Cys Pro
 50                  55                  60

Tyr His Lys Pro Leu Gly Phe Glu Ser Gly Glu Val Thr Pro Asp Gln
 65                  70                  75                  80

Ile Thr Cys Ser Asn Leu Glu Gln Tyr Val Gly Trp Tyr Ser Ser Trp
                 85                  90                  95

Thr Ala Asn Lys Ala Arg Leu Asn Ser Gln Gly Phe Gly Cys Ala Trp
            100                 105                 110

Leu Ser Lys Tyr Gln Asp Ser Ser Gln Trp Leu Glu Ile Asp Leu Lys
        115                 120                 125

Glu Val Lys Val Ile Ser Gly Ile Leu Thr Gln Gly Arg Cys Asp Ile
130                 135                 140

Asp Glu Trp Met Thr Lys Tyr Ser Val Gln Tyr Arg Thr Asp Glu Asn
145                 150                 155                 160

Leu Asn Trp Ile Tyr Tyr Lys Asp Gln Thr Gly Asn Asn Arg Val Phe
                165                 170                 175

Tyr Gly Asn Ser Asp Arg Thr Ser Thr Val Gln Asn Leu Leu Arg Pro
            180                 185                 190

Pro Ile Ile Ser Arg Phe Ile Arg Leu Ile Pro Leu Gly Trp His Val
        195                 200                 205

Arg Ile Ala Ile Arg Met Glu Leu Leu Glu Cys Val Ser Lys Cys Ala
210                 215                 220

<210> SEQ ID NO 19
<211> LENGTH: 1193
<212> TYPE: DNA
<213> ORGANISM: Equus caballus

<400> SEQUENCE: 19
atgccacaca aaatagaagg cttcttgttt ttacttctct ttggctatga agccacactg       60
ggattatcgt ctactgagga tgagggcgag acccctggt accacaaagc gtgcaagtgc      120
gattgccaag gaggcaccaa caccctgtgg tctgtgggtg ccacctcctt agactgcata      180
ccggaatgcc ataccataa gccctgggt ttcgagtcag gagaggtgac cccagagcag      240
atcacctgct ccaaccccgga gcagtacgtg ggctggtact cctcgtggac cgccaacaag      300
gcccggctca cagtcaagg ctttgggtgc gcctggctct ccaaattcca ggacagcagc      360
cagtggttac agatagacct gaaggaggtc aaggtgattt cagggatcct cacccagggg      420
cgctgtgaca tcgacgagtg gatgaccaag tacagcgtgc agtacaggac tgatgagagc      480
ctgaactgga tttactataa ggaccagacc ggaaataacc gggtcttcta tggaaactca      540
gaccgaacct ccacagtcca gaacctgctg cggcccccaa ttatttcccg cttcatccgg      600
ctgatcccac tgggctggca cgtccgcatc gccatccga tggagctgct ggagtgtgtc      660
agcaagtgtc cctgacgcct cctgcctcag cctcggccct cggggggagg cgcagaggg      720 cctgggggac cctgatgccg cactgtgaca acaaggccg tattttacaa gctgctctcg      780
ggtttttttt gtctccatga tgctgtgaaa ggtgcagtcc caggggaaca cgaagcagcc      840
ctgatcattc gagaattctt gtgctttacc acgttcaaaa caggaacaga gagtttcata      900
aaccctcact tgaatgcaa aggggagca agcttgcagt ttctcctagc taggttttcg      960
ttaaatcagg gcctcttagg actttagagc accgggtagg cagagtgaaa gttttggggc     1020
tgactgggtg gcggcgttga gtatggtgga tgggagcctg tgtcctggtc tcctgagagc     1080
```
catacacgtc caaacgcctc acgtaggatg gcctccoctg ccccgggctc tcgtctcctg     1140
cacacagaga ttgtgcatgg gcccatgctg cagcccattt caggccaact gtc           1193

<210> SEQ ID NO 20
<211> LENGTH: 224
<212> TYPE: PRT
<213> ORGANISM: Equus caballus

<400> SEQUENCE: 20

Met Pro His Lys Ile Glu Gly Phe Leu Phe Leu Leu Leu Phe Gly Tyr
1               5                   10                  15

Glu Ala Thr Leu Gly Leu Ser Ser Thr Glu Asp Glu Gly Glu Asp Pro
            20                  25                  30

Trp Tyr His Lys Ala Cys Lys Cys Asp Cys Gln Gly Gly Thr Asn Thr
        35                  40                  45

Leu Trp Ser Val Gly Ala Thr Ser Leu Asp Cys Ile Pro Glu Cys Pro
    50                  55                  60

Tyr His Lys Pro Leu Gly Phe Glu Ser Gly Glu Val Thr Pro Glu Gln
65                  70                  75                  80

Ile Thr Cys Ser Asn Pro Glu Gln Tyr Val Gly Trp Tyr Ser Ser Trp
                85                  90                  95

Thr Ala Asn Lys Ala Arg Leu Asn Ser Gln Gly Phe Gly Cys Ala Trp
            100                 105                 110

Leu Ser Lys Phe Gln Asp Ser Ser Gln Trp Leu Gln Ile Asp Leu Lys
        115                 120                 125

Glu Val Lys Val Ile Ser Gly Ile Leu Thr Gln Gly Arg Cys Asp Ile
    130                 135                 140

Asp Glu Trp Met Thr Lys Tyr Ser Val Gln Tyr Arg Thr Asp Glu Ser
145                 150                 155                 160

Leu Asn Trp Ile Tyr Tyr Lys Asp Gln Thr Gly Asn Asn Arg Val Phe
                165                 170                 175

Tyr Gly Asn Ser Asp Arg Thr Ser Thr Val Gln Asn Leu Leu Arg Pro
            180                 185                 190

Pro Ile Ile Ser Arg Phe Ile Arg Leu Ile Pro Leu Gly Trp His Val
        195                 200                 205

Arg Ile Ala Ile Arg Met Glu Leu Leu Glu Cys Val Ser Lys Cys Pro
    210                 215                 220

<210> SEQ ID NO 21
<211> LENGTH: 675
<212> TYPE: DNA
<213> ORGANISM: Oryctolagus cuniculus

<400> SEQUENCE: 21
atgctacgca agatggaagg cttcttgttc ttacttctct ttggctatga agccacactg      60
ggattatcgt ctactgagga tgagagtgag gacccgtggt accacaaagc gtgcaagtgc     120
gactgccaag gaggagccaa tgccctgtgg aatgcaggtg ccacctcctt agactgcata     180
ccagaatgcc cgtatcacaa gcccctgggt ttcgagtcag gggaagtgac agcagaccag     240
atcacctgct ccaatccgga gcagtatgtg gctggtatt cctcgtggac cgcaaacaag      300
gcccggctca atagtcaagg ctttgggtgc gcttggctct ccaagttcca ggacagcagc     360
cagtggttac agatagacct gaaggagatc aaggtgattt cgggcatcct cacccaagga     420
cgctgtgaca tcgatgagtg gatgaccaag tacagtgtgc agtacaggac cgatgagcgc     480

```
ctgaactgga tttactacaa ggaccagacc ggaaacaacc gggtcttcta tggcaactcg        540
gaccgaagct ccacagtcca gaacctgctg cggccaccga tcatctcccg cttcatccgg        600
ctgatcccgc tgggctggca cgtccgcatt gccatccgga tggagctgct ggagtgtgtc        660
agcaagtgtg cctga                                                          675
```

```
<210> SEQ ID NO 22
<211> LENGTH: 224
<212> TYPE: PRT
<213> ORGANISM: Oryctolagus cuniculus

<400> SEQUENCE: 22
```

```
Met Leu Arg Lys Met Glu Gly Phe Leu Phe Leu Leu Phe Gly Tyr
1               5                   10                  15

Glu Ala Thr Leu Gly Leu Ser Ser Thr Glu Asp Glu Ser Glu Asp Pro
            20                  25                  30

Trp Tyr His Lys Ala Cys Lys Cys Asp Cys Gln Gly Gly Ala Asn Ala
        35                  40                  45

Leu Trp Asn Ala Gly Ala Thr Ser Leu Asp Cys Ile Pro Glu Cys Pro
    50                  55                  60

Tyr His Lys Pro Leu Gly Phe Glu Ser Gly Glu Val Thr Ala Asp Gln
65                  70                  75                  80

Ile Thr Cys Ser Asn Pro Glu Gln Tyr Val Gly Trp Tyr Ser Ser Trp
                85                  90                  95

Thr Ala Asn Lys Ala Arg Leu Asn Ser Gln Gly Phe Gly Cys Ala Trp
            100                 105                 110

Leu Ser Lys Phe Gln Asp Ser Ser Gln Trp Leu Gln Ile Asp Leu Lys
        115                 120                 125

Glu Ile Lys Val Ile Ser Gly Ile Leu Thr Gln Gly Arg Cys Asp Ile
    130                 135                 140

Asp Glu Trp Met Thr Lys Tyr Ser Val Gln Tyr Arg Thr Asp Glu Arg
145                 150                 155                 160

Leu Asn Trp Ile Tyr Tyr Lys Asp Gln Thr Gly Asn Asn Arg Val Phe
                165                 170                 175

Tyr Gly Asn Ser Asp Arg Ser Ser Thr Val Gln Asn Leu Leu Arg Pro
            180                 185                 190

Pro Ile Ile Ser Arg Phe Ile Arg Leu Ile Pro Leu Gly Trp His Val
        195                 200                 205

Arg Ile Ala Ile Arg Met Glu Leu Leu Glu Cys Val Ser Lys Cys Ala
    210                 215                 220
```

```
<210> SEQ ID NO 23
<211> LENGTH: 8202
<212> TYPE: DNA
<213> ORGANISM: Artificial Sequence
<220> FEATURE:
<223> OTHER INFORMATION: recombinant or synthetic polynucleotide

<400> SEQUENCE: 23
```

```
ggtaccgatt taaatgatcc agtggtcctg cagaggagag attgggagaa tcccggtgtg         60
acacagctga acagactagc cgcccaccct cctttgctt cttggagaaa cagtgaggaa        120
gctaggacag acagaccaag ccagcaactc agatctttga cggggagtg gagatttgcc        180 tggtttccgg caccgaaagc ggtgccggaa agctggctgg agtgcgatct tcctgaggcc        240
gatactgtcg tcgtccccct caaactggcag atgcacggtt acgatgcgcc catctacacc        300
aacgtgacct atcccattac ggtcaatccg ccgtttgttc ccacggagaa tccgacgggt        360
```

```
tgttactcgc tcacatttaa tgttgatgaa agctggctac aggaaggcca gacgcgaatt      420
atttttgatg gcgttaactc ggcgtttcat ctgtggtgca acgggcgctg ggtcggttac      480
ggccaggaca gtcgtttgcc gtctgaattt gacctgagcg cattttttacg cgccggagaa    540 aaccgcctcg cggtgatggt gctgcgctgg agtgacggca gttatctgga agatcaggat     600
atgtggcgga tgagcggcat tttccgtgac gtctcgttgc tgcataaacc gactacacaa     660
atcagcgatt ccatgttgc cactcgcttt aatgatgatt tcagccgcgc tgtactggag      720
gctgaagttc agatgtgcgg cgagttgcgt gactacctac gggtaacagt ttctttatgg     780
cagggtgaaa cgcaggtcgc cagcggcacc gcgccttttcg gcggtgaaat tatcgatgag    840
cgtggtggtt atgccgatcg cgtcacacta cgtctgaacg tcgaaaaccc gaaactgtgg     900
agcgccgaaa tcccgaatct ctatcgtgcg gtggttgaac tgcacaccgc cgacggcacg    960
ctgattgaag cagaagcctg cgatgtcggt ttccgcgagg tgcggattga aaatggtctg    1020
ctgctgctga acggcaagcc gttgctgatt cgaggcgtta accgtcacga gcatcatcct    1080
ctgcatggtc aggtcatgga tgagcagacg atggtgcagg atatcctgct gatgaagcag    1140
aacaacttta cgccgtgcg ctgttcgcat tatccgaacc atccgctgtg gtacacgctg      1200
tgcgaccgct acggcctgta tgtggtggat gaagccaata ttgaaaccca cggcatggtg    1260
ccaatgaatc gtctgaccga tgatccgcgc tggctaccgg cgatgagcga acgcgtaacg    1320
cgaatggtgc agcgcgatcg taatcacccg agtgtgatca tctggtcgct ggggaatgaa    1380
tcaggccacg cgctaatca cgacgcgctg tatcgctgga tcaaatctgt cgatccttcc     1440
cgcccggtgc agtatgaagg cggcggagcc gacaccacgg ccaccgatat tatttgcccg    1500
atgtacgcgc gcgtggatga agaccagccc ttcccggctg tgccgaaatg gtccatcaaa    1560
aaatggcttt cgctacctgg agagacgcgc ccgctgatcc tttgcgaata cgcccacgcg    1620
atgggtaaca gtcttggcgg tttcgctaaa tactggcagg cgtttcgtca gtatccccgt    1680
ttacagggcg gcttcgtctg ggactgggtg atcagtcgc tgattaaata tgatgaaaac     1740
ggcaacccgt ggtcggctta cggcggtgat tttggcgata cgccgaacga tcgccagttc    1800
tgtatgaacg gtctggtctt tgccgaccgc acgccgcatc cagcgctgac ggaagcaaaa    1860
caccagcagc agttttttcca gttccgttta tccgggcaaa ccatcgaagt gaccagcgaa    1920
tacctgttcc gtcatagcga taacgagctc ctgcactgga tggtggcgct ggatggtaag    1980
ccgctggcaa gcggtgaagt gcctctggat gtcgctccac aaggtaaaca gttgattgaa    2040
ctgcctgaac taccgcagcc gggagagcgcc gggcaactct ggctcacagt acgcgtagtg    2100
caaccgaacg cgaccgcatg gtcagaagcc gggcacatca gcgcctggca gcagtggcgt    2160
ctggcggaaa acctcagtgt gacgctcccc gccgcgtccc acgccatccc gcatctgacc    2220
accagcgaaa tggattttttg catcgagctg gtaataagc gttggcaatt taaccgccag    2280
tcaggctttc tttcacagat gtggattggc gataaaaaac aactgctgac gccgctcgc    2340 gatcagttca cccgtgcacc gctggataac gacattggcg taagtgaagc gacccgcatt    2400
gaccctaacg cctgggtcga acgctggaag gcggcgggcc attaccaggc cgaagcagcg    2460
ttgttgcagt gcacggcaga tacacttgct gatgcggtgc tgattacgac cgctcacgcg    2520
tggcagcatc agggggaaaac cttatttatc agccggaaaa cctaccggat tgatggtagt    2580
ggtcaaatgg cgattaccgt tgatgttgaa gtggcgagcg atacaccgca tccggcgcgc    2640
attggcctga actgccagct ggcgcaggta gcagagcggg taaactggct cggattaggg    2700
```

```
ccgcaagaaa actatcccga ccgccttact gccgcctgtt ttgaccgctg ggatctgcca      2760
ttgtcagaca tgtataccc gtacgtcttc ccgagcgaaa acggtctgcg ctgcgggacg       2820
cgcgaattga attatggccc acaccagtgg cgcggcgact tccagttcaa catcagccgc      2880
tacagtcaac agcaactgat ggaaaccagc catcgccatc tgctgcacgc ggaagaaggc      2940
acatggctga atatcgacgg tttccatatg gggattggtg gcgacgactc ctggagcccg      3000
tcagtatcgg cggaattcca gctgagcgcc ggtcgctacc attaccagtt ggtctggtgt      3060
caaaaataat aataaccggg caggggggat ctaagctcta gataagtaat gatcataatc      3120
agccatatca catctgtaga ggttttactt gctttaaaaa acctcccaca cctcccctg      3180 aacctgaaac ataaaatgaa tgcaattgtt gttgttaact tgtttattgc agcttataat      3240
ggttacaaat aaagcaatag catcacaaat ttcacaaata aagcattttt ttcactgcat      3300
tctagttgtg gtttgtccaa actcatcaat gtatcttatc atgtctggat cccccggcta     3360
gagtttaaac actagaacta gtggatcccc gggctcgata actataacgg tcctaaggta     3420
gcgactcgac ataacttcgt ataatgtatg ctatacgaag ttatatgcat gccagtagca     3480
gcacccacgt ccaccttctg tctagtaatg tccaacacct ccctcagtcc aaacactgct     3540
ctgcatccat gtggctccca tttatacctg aagcacttga tggggcctca atgtttact     3600 agagcccacc cccctgcaac tctgagaccc tctggatttg tctgtcagtg cctcactggg     3660
gcgttggata atttcttaaa aggtcaagtt ccctcagcag cattctctga gcagtctgaa     3720
gatgtgtgct tttcacagtt caaatccatg tggctgtttc acccacctgc ctggccttgg     3780
gttatctatc aggacctagc ctagaagcag gtgtgtggca cttaacacct aagctgagtg     3840
actaactgaa cactcaagtg gatgccatct ttgtcacttc ttgactgtga cacaagcaac     3900
tcctgatgcc aaagccctgc ccaccctct catgcccata tttggacatg gtacaggtcc      3960
tcactggcca tggtctgtga ggtcctggtc ctctttgact tcataattcc tagggccac      4020 tagtatctat aagaggaaga gggtgctggc tcccaggcca cagcccacaa aattccacct     4080
gctcacaggt tggctggctc gacccaggtg gtgtcccctg ctctgagcca gctcccggcc     4140
aagccagcac catgggaacc cccaagaaga agaggaaggt gcgtaccgat ttaaattcca     4200
atttactgac cgtacaccaa aatttgcctg cattaccggt cgatgcaacg agtgatgagg     4260
ttcgcaagaa cctgatggac atgttcaggg atcgccaggc gttttctgag catacctgga     4320
aaatgcttct gtccgtttgc cggtcgtggg cggcatggtg caagttgaat aaccggaaat     4380
ggtttcccgc agaacctgaa gatgttcgcg attatcttct atatcttcag gcgcgcggtc     4440
tggcagtaaa aactatccag caacatttgg gccagctaaa catgcttcat cgtcggtccg     4500
ggctgccacg accaagtgac agcaatgctg tttcactggt tatgcggcgg atccgaaaag     4560
aaaacgttga tgccggtgaa cgtgcaaaac aggtaaatat aaaattttta agtgtataat     4620
gatgttaaac tactgattct aattgtttgt gtattttagg ctctagcgtt cgaacgcact     4680
gatttcgacc aggttcgttc actcatggaa aatagcgatc gctgccagga tatacgtaat     4740
ctggcatttc tggggattgc ttataacacc ctgttacgta gccgaaat tgccaggatc     4800 agggttaaag atatctcacg tactgacggt gggagaatgt taatccatat tggcagaacg     4860
aaaacgctgg ttagcaccgc aggtgtagag aaggcactta gcctgggggt aactaaactg     4920
gtcgagcgat ggatttccgt ctctggtgta gctgatgatc cgaataacta cctgttttgc     4980
cgggtcagaa aaaatggtgt tgccgcgcca tctgccacca gccagctatc aactcgcgcc     5040
ctggaaggga ttttttgaagc aactcatcga ttgatttacg gcgctaagga tgactctggt     5100
```

```
cagagatacc tggcctggtc tggacacagt gcccgtgtcg gagccgcgcg agatatggcc    5160
cgcgctggag tttcaatacc ggagatcatg caagctggtg gctggaccaa tgtaaatatt    5220
gtcatgaact atatccgtaa cctggatagt gaaacagggg caatggtgcg cctgctggaa    5280
gatggcgatt aggcggccgg ccgctaatca gccataccac atttgtagag gttttacttg    5340
ctttaaaaaa cctcccacac ctcccsctga acctgaaaca taaaatgaat gcaattgttg    5400
ttgttaactt gtttattgca gcttataatg gttacaaata aagcaatagc atcacaaatt    5460
tcacaaataa agcattttt tcactgcatt ctagttgtgg tttgtccaaa ctcatcaatg    5520
tatcttatca tgtctggatc ccccggctag agtttaaaca ctagaactag tggatccccc    5580
gggatcatgg cctccgcgcc gggttttggc gcctcccgcg gcgcccccc tcctcacggc    5640 gagcgctgcc acgtcagacg aagggcgcag cgagcgtcct gatccttccg cccgacgct    5700 caggacagcg gcccgctgct cataagactc ggccttagaa ccccagtatc agcagaagga    5760 catttagga cgggacttgg gtgactctag ggcactggtt ttctttccag agagcggaac    5820
aggcgaggaa aagtagtccc ttctcggcga ttctgcggag ggatctccgt ggggcggtga    5880
acgccgatga ttatataagg acgcgccggg tgtggcacag ctagttccgt cgcagccggg    5940
atttgggtcg cggttcttgt ttgtggatcg ctgtgatcgt cacttggtga gtagcgggct    6000
gctgggctgg ccggggcttt cgtggccgcc gggccgctcg gtgggacgga agcgtgtgga    6060
gagaccgcca agggctgtag tctgggtccg cgagcaaggt tgccctgaac tgggggttgg    6120
ggggagcgca gcaaaatggc ggctgttccc gagtcttgaa tggaagacgc ttgtgaggcg    6180
ggctgtgagg tcgttgaaac aaggtggggg gcatggtggg cggcaagaac ccaaggtctt    6240
gaggccttcg ctaatgcggg aaagctctta ttcgggtgag atgggctggg gcaccatctg    6300
gggaccctga cgtgaagttt gtcactgact ggagaactcg gtttgtcgtc tgttgcgggg    6360
gcggcagtta tggcggtgcc gttgggcagt gcacccgtac cttttgggagc gcgcgccctc    6420 gtcgtgtcgt gacgtcaccc gttctgttgg cttataatgc agggtggggc cacctgccgg    6480
taggtgtgcg gtaggctttt ctccgtcgca ggacgcaggg ttcgggccta gggtaggctc    6540
tcctgaatcg acaggcgccg gacctctggt gaggggaggg ataagtgagg cgtcagtttc    6600
tttggtcggt tttatgtacc tatcttctta agtagctgaa gctccggttt gaactatgc    6660 gctcggggtt ggcgagtgtg ttttgtgaag tttttaggc acctttgaa atgtaatcat    6720 ttgggtcaat atgtaatttt cagtgttaga ctagtaaatt gtccgctaaa ttctggccgt    6780
ttttggcttt tttgttagac gtgttgacaa ttaatcatcg gcatagtata tcggcatagt    6840
ataatacgac aaggtgagga actaaaccat gggatcggcc attgaacaag atggattgca    6900
cgcaggttct ccgccgcttg ggtggagag gctattcggc tatgactggg cacaacagac    6960
aatcggctgc tctgatgccg ccgtgttccg gctgtcagcg caggggcgcc cggttctttt    7020
tgtcaagacc gacctgtccg gtgccctgaa tgaactgcag gacgaggcag cgcggctatc    7080
gtggctggcc acgacgggcg ttccttgcgc agctgtgctc gacgttgtca ctgaagcggg    7140
aagggactgg ctgctattgg gcgaagtgcc ggggcaggat ctcctgtcat ctcaccttgc    7200
tcctgccgag aaagtatcca tcatggctga tgcaatgcgg cggctgcata cgcttgatcc    7260
ggctacctgc ccattcgacc accaagcgaa acatcgcatc gagcgagcac gtactcggat    7320
ggaagccggt cttgtcgatc aggatgatct ggacgaagag catcagggc tcgcgccagc    7380 cgaactgttc gccaggctca aggcgcgcat gcccgacggc gatgatctcg tcgtgaccca    7440
```

| | |
|---|---|
| tggcgatgcc tgcttgccga atatcatggt ggaaaatggc cgcttttctg gattcatcga | 7500 |
| ctgtggccgg ctgggtgtgg cggaccgcta tcaggacata gcgttggcta cccgtgatat | 7560 |
| tgctgaagag cttggcggcg aatgggctga ccgcttcctc gtgctttacg gtatcgccgc | 7620 |
| tcccgattcg cagcgcatcg ccttctatcg ccttcttgac gagttcttct gagggggatcc | 7680 |
| gctgtaagtc tgcagaaatt gatgatctat aaacaataa agatgtccac taaaatggaa | 7740 |
| gttttccctg tcatactttg ttaagaaggg tgagaacaga gtacctacat tttgaatgga | 7800 |
| aggattggag ctacggggt ggggtgggg tgggattaga taaatgcctg ctctttactg | 7860 |
| aaggctcttt actattgctt tatgataatg tttcatagtt ggatatcata atttaaacaa | 7920 |
| gcaaaaccaa attaagggcc agctcattcc tcccactcat gatctataga tctatagatc | 7980 |
| tctcgtggga tcattgtttt tctcttgatt cccactttgt ggttctaagt actgtggttt | 8040 |
| ccaaatgtgt cagtttcata gcctgaagaa cgagatcagc agcctctgtt ccacatacac | 8100 |
| ttcattctca gtattgtttt gccaagttct aattccatca gacctcgacc tgcagcccct | 8160 |
| agataacttc gtataatgta tgctatacga agttatgcta gc | 8202 |

```
<210> SEQ ID NO 24
<211> LENGTH: 13716
<212> TYPE: DNA
<213> ORGANISM: Artificial Sequence
<220> FEATURE:
<223> OTHER INFORMATION: recombinant or synthetic polynucleotide

<400> SEQUENCE: 24
```

| | |
|---|---|
| ccacacaaga ttgaaggctt cttcttgtta cttctctttg gctatgaagg tatgtactat | 60 |
| tctactattg gcatttatta atgtatttaa taatgtgatt taatatagaa atatatagaa | 120 |
| aatagttgat aaatagaaat gcaacctgag taataaaaat tgttggatga caacatgcca | 180 |
| attagttcac aggttattaa tttaaaaggt cactgttgtg tggctctttg tcactgtctt | 240 |
| gctcctggct tcctggtttc atgaggaacc ttctaaagtt caaatgatat tgaaactcaa | 300 |
| cagaaagaag gaagggcctc agagtttcta taaaaacaac tttaaattgc aacaattaat | 360 |
| gagaagtcat gtttcttgga aattttagga ggcaaagttg aagcaattgt agaatttaat | 420 |
| attgtaagcc ggactattac tgagggttaa ggatgaagct attaatagct ctgctgggac | 480 |
| aagtgtaaat gaggactgtc ccaggcaaat caggacaaag ggtcacccta gtttaaatat | 540 |
| ggattagcat aaggccaagc accactgcag tctaatagaa gtctaataaa ataatccaaa | 600 |
| gaaagtcaat aaaccctaaa gactcaatat attccatcac ttttaaactt ctaaatgtgg | 660 |
| ccctggcagg cataatatgc ttaaataagg acagattaaa gctaaatctc taaaatgtca | 720 |
| atcaaataaa ctttaaatct cttttccatct tagacataat actctctcat gcctctctta | 780 |
| cctctctagt gcccatcaat tcagaattcc ttttaaagtt tatactttca aatattaaaa | 840 |
| attggttgaa gggttgggga tgtggctcag tggtacagcc cctgcccagc cttcatgagt | 900 |
| ccctgagtta aattcccaga agcagtataa gacaaacaaa caaaaaccttt acttcatcca | 960 |
| ttttctggca tagctacaca tacctgcaat cctagttctg gacaaattca agcaggagca | 1020 |
| ttcaatgcca acctcagcta cttaggtttg ggctatctga gaccctgtct taacattggg | 1080 |
| ggagagccta ggctaggctg agctatacag taagcctctg tctgggaagg agggaaaaag | 1140 |
| gaaggaaaga cattggttga atgacttgtg ggtgacactg tatgtttaga gtgttcaggg | 1200 |
| aaaaggaggc ctctctgctc tgcaaatgac ctgccactca gataagacga atacacacaa | 1260 |
| gagtcagaat tcctctgttt cttctatatt catgaaccag cagtcttgtg tcttttatta | 1320 |

```
tctaataata tttctagtgt ctggaaagcc ttgtgaaaat aaaatctcaa ggtcatacgg    1380
caaacacaaa gaaacaggtt ttttttttctt tttttttcttt tttttttttt atacatattt    1440
gttttattta tttatttatt atatgtacgt acactgtagc tgtcttcaga cactccagaa    1500
gagggcatca gatctcgtta cggatggttg tgagccacca tgtggttgct gggatttgaa    1560
cttcagacct tcggaagagc agtcgggtgc tcttacccac tgagccatct caccagcccc    1620
aggttttttt ttcttagtt gttattatta ttgttattct tttgagacag gatcccacac    1680
tgaaactcag gctagccttc aatttcctat ggatttgacc tcatagcagt cagccagttt    1740
ccaccttctg agtgctaaga tttcaagcct gagccaccac acccaattcc taagatatgt    1800
ttttaagcaa ggttattggc attacacctt aacccttgc aatgacgtgt caggaatttg    1860
cacctttttt tttttttccag ttgtcaggcc tggcaatgga gcccagggcc ctgtgcttgc    1920
taaacgatgg ctctacccct aagttatata tacccagctt atcccaggat ctttctcaga    1980
ctttctgatg tttgctatcg atgttgcttc tctttggttc cttgctcttt tctcacaaaa    2040
agatctaagc aagaacccctt gtctggagtc agagagatag cttagtctgg aaagtgctta    2100
tagcttacac acagaaacttt gagttcgatc cccagaactt ttcttgttta aaaacaaac    2160 aaacaaacaa acaaaaacta ggcatgacag ctggagaggt ggcttcgcaa ttaacagcac    2220
ttgttaaaga ggacctcagc ttggttccca gggctctata actccagttc cagggcctca    2280
gacagcctcc tgtagcctct tcatgcatca gacatggtcc atatgcatgc aggtcaaaca    2340
ctcatacaca ttaaatgaaa aataaaagtc taaaaaaagg tcaaacatag tgatgcatgc    2400
tataatccca gtgctaggga ggcaaatgtc tggaccttgt cggtcggcca gtcagtcagc    2460
cagccagtca gtctagccta gcatagccta ctaggtgtgc tccagcccaa tgagagacct    2520
tgtctctaaa aaaagggta gaaagaaaag acaaatgga tgtctcctga ggaatgatac    2580
ccacggatac ccacaattgt cctctggtct ccgtgtgcaa tacaaaccca tgtctgaata    2640
tttgcaacag ggtaaacatt agagtttgat gttcagaatt agactagatt ccctcatcta    2700
gtaaagctgt gctttggccc tcccatctgt cttattttttc tactggtgtg ctaaggcacc    2760
atgaccaagg caacttagag aagaagaaac agtttattga gggtttatag ttatagaggg    2820
taaggcaagg acttggtagc aggcaggcag gcaggcatgg tactggtgta gtagctggga    2880
gcttgtatct tgagacacgg ttacaaagct gagagatagc taagtgggcc tggtgtgagc    2940
ttttgaaacc tcaaagctgt ccccagtgaa atgcctccat caacaaggcc acacctaacc    3000
cttcccaaac agttctacca actgggaacc aagcattcat atgagcctca ggggagcagt    3060
ctcattcaag taagtactca gtacactgcc ccatgggcag aagtcctcta acggttact    3120 aatgtgtgtg tgtatatccc tcaccatact tagaaggaaa caagccatcc caaaatggat    3180
agcatgactc agaaagttcc tgtgtacttc acccagagca aatgtggata cggtgggaaa    3240
cagaggacag tgataggaca caaaggctgt gctgtctcag tttctagttc agatggagac    3300
ataaaccaac acacatagga aagatacact ccactggaca gtgggagccc atgcacaaag    3360
gttctttggc tcatttagtc tatgctgttt ctattcttcg atgacagcag tttcttatta    3420
ttgggaaata agatcagtag atgagctttg tttctgccct gggtgagagt ttatttagga    3480
acacacatgt gatcacacta agacaaccac tgatggccta gaacaaagtc agagcactgt    3540
gcgttgtgga tcttaggcca ttcatgatga ttaaagcatc catcctatta aaatgtgtta    3600
gtccattttt gggggttatgt ttactataca aaggtggaag gggttatctg gccccatctt    3660
```

-continued

```
acaggtaact gtgtcccttt tgtggatata aaaaccatca gatactgcaa tttattttt    3720 gtaaaaagca actgttttt tttaagactt atttattt tgattatgtg tctgagggag      3780
cagtatgcac atctgcatgc aggtgcctgt ggaagcctgt ggagacatca gatcacctga   3840
agctggagtt tcaggcagtt ttatgccacc agacactggt gctgagaata gagtctcctg   3900
caaaagcagt atatttatt aatctgtgag ccatctctcc agccaaaagc aacctttaaa    3960
agctgtggtt tatgtgccat ttaattcatc cacttagagg gtacacttca atagtttttt   4020
ttaaaaatat gcttacagat ctgtgggcac atatgatcca atttagaac ccttttagca    4080 ctacagatat taaatactta ctccctattc tccccagccc ccagctccag tccctggcat   4140
ccacaaatcc ccttcctgcc atctatagat tcacctcttc tagactttac actgaaatgg   4200
tattacacaa catgtggtct tttgtctttt gcttgccgtg tgtctgtgag gttcatctgt   4260
gttgagcatg aaaggataac agatttaccc atgaatatgc ctgtcgccta aaatagcaac   4320
actttcacac tagaagcaat ttccttcttt cttcttccca agagggacat tattgcagcc   4380
tgctagtttt ctcctgtgtc tttttcgtg tttctcaagt agatgaaggg actggttact    4440
tttatttttt taatcattca tacttttata cttttctccc ctgctttgtc agtttcctaa   4500
atgagtgaat actgtatttg gtgatcccca atcagaaaga ccaaataat ttaaaataat    4560 ctcgtctcta tatcactaag gtatcctttt ccacttgggc catgcagaga ataagcatg    4620 ccttgattga ccccacccca ccccaacccc cagtggtgac aaggacctcc ccagcggctc   4680
aaccatttga ataaaaagga cacttgagcc cattttgcac aaatctaaga tgagcaagtg   4740
gcagtgtcac ctgtaaacat gtgcctggag cacggaacga cctgagtagg cagaaaaagg   4800
tggaagtaat ttatgatttt tcttttaaag gttgccattt ccccacctt tctcactttc     4860 caacaatatt atattctggt gtgatatgtt gtagacaaaa aaagctttaa gctttattc     4920 cccagttgtt ttggtgatta aatcattttg ggggaactgc aacagtgact ctcattcact   4980
gctcccttgg tgacagtgtt ttttctgt aaaaagcgcc tgctgttccc tctgtctctg     5040
ctcattttca taggaatctg gcaccttaga atcccaggct gcctgcagtc aaatgcttgc   5100
tagggagggg agccagtggg tggggaacc tgcaagaaat caactccaaa tttaatagga    5160
ctaagctcct acaccatgcc tgattagcag ctaggtctca tccttacccc tccaggaata   5220
aggaaggttg cagaagtccc tgaaaggtat ttgctgagcc tcttgtgaac cgtgggttgg   5280
ctcacctgaa ctttagtaga tattctttag cgacatattt gggctttggt cctctctctt   5340
ttatctctcc acaaaagtct tggcaaactg atgtttatgc aaccagtaag gcctctgggg   5400
ctgagggggt gggaagccag tgggtggcgg aacctgcaag aaatccgccc caaatttaag   5460
gaagcatagg aataagctcc tacccctatgt ctgccttgtg gctaggtcct tagttcattg   5520
tctcttaggt atcccagatt ctcttgagag tagaaggtgg aacatagtac ctcctgatta   5580
acaaatccga gaggtgctaa tctcatgaat tctcccggac tatggttata tatagctcag   5640
tgatctcatg tagcttaggc tggctggaag ctagttttga gctcactatg aagcaaagga   5700
tgaccctgaa cttcttggtt ttcctgcttt catcttccaa gtgctgcgat tacaagaatg   5760
aatgctgcca tgtctagttc atgtggtgct agggatcaac cctgaggctt tgtgcatgtt   5820
aagacaagca ctctactaac tgagctctag ctctagccct gaccctgact caaaagaata   5880
gggggggagg aaggaaggaa ggaaggaagg aagggaggga gggagggagg gaggagggga   5940
gggagggagg gaggaaggat gttgagaaca aaagccaagg ccaacaggtg agttgggatt   6000
aggaaaagtc cttttcatag caaagggggat gtggaagaag agaagttgac aggtaagtag   6060
```

```
ggaaatttga gacaaagaaa aaagaaaaaa atctgtggac cagggcatgg caagaaacgc    6120
agagagcaaa tgttcataaa gagaggtggg caggaggcag accatggtct caagactcat    6180
cagagagata aggcaatatc ctgaggagca cccatctgag gggcgttgag caagtgggtt    6240
tcatttctct gcattcacag atggaggata gatgtgtgca actatcttta gcagtgaggc    6300
atgctgggta gtgctaagag cgggcggggt ctgtggaatg gagaggagaa accactcctt    6360
attaccacgt cattttactt ttgattatct tcattgtgat ttagtgttct agtttgtgaa    6420
tttatcacta tgtatcttgc ctcttgacgg tcacacaagt acttccagtt gaagagtagg    6480
cattacaagg tctgcttcca tgaatattct agggcacatt tttattccag gaaaaaatat    6540
atgaaagcat ttctaattat gaatggaatt ggtggtttat ggggaacaca tatgctcagc    6600 cttgaataa attaccaaaa ccaaagaggc tagactccct tctaccgatc aacagaagca    6660
tataagagtt ggcactgttc tctactctac caacttgtgg ttgggtcctg tttagaataa    6720
taagaggcat ctacatgtag agctctagga agccattcaa tgcaggatct aaaccttggc    6780
tttagcaatg tctgtgcggt acttggagta agctaagctc tcaaagaaaa ccaagattta    6840
tcggaatggt ggacactgaa agtagacagg aaaggctgac aatacctagt gtgcagtgtg    6900
cagatggaag ggcagtgctg gggagaatcc attgcatttg gaaagaagaa gccctctgcg    6960
atttcttttg ctaatgcagg ccttttcact gtagtacttg cttgtggtgg tttgaatgaa    7020
aatggtcccc acaggctatt tttgaaaact tgatcccag ttggtgaaac tgtttggaaa    7080
ggattaggaa gtgtggcctt gctggatgag gtctgtcaat ggcggaaggc tttgaagttt    7140
cccagtgtgc ctctctctgt ctcctactta ttgattgaaa aatgagcttt cagctgtcat    7200
gcctttgctc tgccatccag aattctaatc acccaaaacc atatagccta attaaatact    7260
gtttttataa gttaccttgg tcatggtact ttaggatatc aatagttaag aaactaagac    7320
attggttcac ttgctcaact taaccaaaac accacagacg ggcttgcata tgacaacagt    7380
tctagaggat caaatgtccc tgatcaaatg ccctagcagg ttctgtgtct gatgagggct    7440
gctggttcat gggtggtgct ttttctcagt gtccttacag gtggaaggta tccagctttc    7500 ttggaccta tattaaagca cgcattccat tgatgtgagt agatagctta gtcagagccc    7560
caaagtgatt taagcacctc caaaaccctc cgtctccgga tgctccccca ttggtgaaca    7620
gatttcaaca tagcaattga gcaggaggaa aggaagccaa attatttgat cacagccagt    7680
actttggtga acacccaaac ccagcatgga gctgaatatc tgtaatctca gtatccagca    7740
ggtggatatt ggggaattaa gacttcaagg ccagacttgg ctacatagta agtttgatgc    7800
catcctgggc tatatgagat cctgttccca aaacccccaa atagaaacaa taaaaaaatg    7860
gcagtccttc atgttcactg ctaccctaga aggtcagttt tgcttgtaac agatgactaa    7920
cagaggaaca aggtcccgga agagctacca gtatgctggc tgccaatgaa gctgctgaag    7980
tcttagtaga tttaggagct atggtcctga cttccatcac agcccagca ccaccatggg    8040 cactgcccag cagtctatct tctttaggt cttcaggtgt ccctgggtag agaacaaggc    8100
ttctgcttgc atagggctga tgcccagta cagtgacagt ctcacaatga gtgcagcaat    8160
gtggccacag aacggggaaa tgtgtgttct ttaactagta gcttttataa tcatgataaa    8220
aagataagtg tctactctca agctgaaagc ttttcacagg catctgattc tcttgctaaa    8280
tgacaaagtg gttagaggag ggacctcacag ctttcattgt ctacactcag gtttcttttg    8340 agaatttac agtaggtatg tattgttttc tagtcaacac agaaataaaa ggatttgttt    8400
```

```
tgttgaaaag aagtgggggt tttggtactg atgaggggaa attgatttat gttacttatt    8460
cattctcagg ttcatggctg agactcctta tgacaaatga tagattaata aaagcatgca    8520
aatgctggag ctctgctggc ggagtacctg atatgcaagg atgaagatct ctgttcaatc    8580
cccagaaatc aaataaaaaa gctgggcata gtgaggaaga ggagatggga ggattcctgt    8640
ggctggctgg acagctaacc tagcctattc atctatttcc aggccactaa gggatggtac    8700
cttaaaaaat aacaataata ataaaaaata acaataataa taaataaaaa aggtagctgg    8760
ttcctgagga gcatctaagg atatccttta actccacgtg cacatacact gtatacacag    8820
gaacacatac aagcatgcag atttacctat caagttttac caaaaaaaaa aaaaaaaaaa    8880
aaaagaaaca ctttattcac tgttggtggg tatgtaaact ggcatatgta gccactatga    8940
aaatcagcac agaggttccc ttcccactcc aacaaaacaa aacaaaacaa aacaaaacaa    9000
aacaaaacaa aacaaaacaa aaccctctag aactagaact agaactactg cacgatccag    9060
gtttaccact cctaggtatt tactcaaagg actctatacg tcaacctgtg acagaggcat    9120
catatacaag cagggagtgg tggcacctgc ctttaatccc accctcagg aggcagagtc    9180 aggtagatct ctgtgagttc gaggccagtt tggtctacat agtgagttct agtacagcca    9240
taagaccata tagccatatg gagggggat tgtgagcata gagtatgaat gttcttgaga    9300
gaattattaa atgaattgga attattatac actgtcttct ttcataggaa aaatgaacag    9360
aaagggagag atctttgggt ggggctaaca gcatacatga catgaaagca aaggggatt    9420 agttattgga aggcagggag ggacccagga ggatgaaggg aagagaatgc aagggaaagg    9480
agtaaaggag gaggaggtag aggtacacac tattaattcc agcacttgtg aggaggggac    9540
agagctctgt gagttcaagg tcagccccct ctgcatagtc agttccagga tagccaatgg    9600
ctacataatg agaccctgtg tcagagaagg tggccggcga gggatattga tgcttacagt    9660
ttactttagc caccacacag ctgaatgagt taaacctgtt cctgctactt ttgcactttc    9720
aatgctccca gattacttac atggaattta tattttattg tggtttaata gctcctgtac    9780
atcatagaca aacctcaaga aaaattttca accaatagtc caggcaaaaa taacctcttt    9840
ttctttcttt ctttctttct tttttttttt ttttttttgg ttttttgaaa cagggtttct    9900
ctgtatagcc ctggctgtcc tggaactcac tttgtacacc aggctggcct cgaactcaga    9960
aatccacctg cctctgcctc ccgagtgctg ggattaaagg cgtgcaccac caccgtcccg   10020
caaaaaataa cctgttttg ttgttttaat tattttaag attttatgtg tatgggtgtc     10080
tgtctgtatg tatgtctgtg taccacttgt atgcttggtg cccaagaagg acagaacaga   10140
tcatagggtt tcctgggata agagttatag gagttataga tgactgtaag ccaccaagtg   10200
gacgctggga attgaacctt ggttagctgg aagagtgtcc agtatttta attccagtcc    10260 ccgttgtttg tctatgaaga ttttgcttgg tagtccagtc tggctttaag aaacagggtc    10320
tcatgcatcc ctggcttgct cagacttcca tgcagctgag gatggcttta gagtaacaac    10380
cctcctgcct tttcctcgta gagtgctgag attacagtcc tgtgccacca gcagacttct    10440
cctaacaaga atgtggcaca gggaggcaac tgggaatcaa acaggaagga ggagtaaaag   10500
gaaggggagg aaggagagga gaagtggcag gaggagaaga aaaaggaggc ggagaaaagg   10560
tggtagtggt ggaggaagag gaggaggagg aggaggagga ggaggggac ttaatcagta    10620 aaggaaaaag gctgagctca gtccttggaa cctacatggt aggagagaat gagacttctg   10680 caaagttcc tctgatcccc acactggagc aatggtgcca tcacatcact ctcccacttc     10740
acccaactcc tcacaaaaat aaaaacaaa aacaaaacaa cagacaaaca aatacataaa    10800
```

```
taaatgtagt ttaaaaaaga aagctgtagc cgggcgtggt ggcacacact tttaatcccg   10860
gcacttggga ggcagaggca agcggatttc tgagttcgag gccagcttgg tctacaaagt   10920
gagttccagg acagccaggg ctacacagag aaaccctgtc ttgaaaaacc aaaagaaaaa   10980
aagaaagctg tactgcaccc tgctttgcta tattaatata ttttccataa ttctataaga   11040
aaaaacaaca gtcattgcca tccttttcct ccctccagaa tgagctcctt aatctctatg   11100
gcattgtttt cattttgcct tctttccttt cttaatttca ttttttccct ctcttgttct   11160
tttgctcagc cacattggga ttgtcatcga cagaggtatg ttacagtaag aagggtggaa   11220
ttttcatcgg tgttgctttt gaagtaaaac taatatatga gtctagcact attgggggga   11280
agagtgctga gggtgaagcc aagggccttg gcatgctag gcacgtgatt cacactgata    11340
ccctactcct gaagcctgag agcctttttc aaatgtctgt tgttttagtt gggtgttggg   11400
tgtgggcatg agtggaaagg caggtcttcc tattgttcta tccctccttg ccttaattca   11460
ggctctctca ctaaactgga agcttgcttt tgtggttagg tgggctggcc atgagttacc   11520
caaatcaccc ttctctatcc cctccccccc taaactatgg ccacatcaag cagccatgcc   11580
cagctttctg cctgggctct ggagatttga gctcaggtgc tcatatttgc acagcaaagg   11640
ctcttaccca cttagccatc tccccagccc cttttcaaatg ttttttttttt taagttttac   11700
actgaactta ggcctatcac tccagcatgc agtaaactga ggcactcaag tctagttatc   11760
ctgggctaca aagtgagaca ttgactaaaa ggaaaaagag aaaaggaagg aagggaggga   11820
gggaggaaga aaggaaggaa ggaaggaagg aaggaaggaa ggaaggaagg aaggaaggaa   11880
gggagggagg gagggaggga gggagggaga aaggagagag agagaaagag gacaaagaag   11940
gagggaaaga tggatggatg gagggaggga gggagggagg gagagaaaga gggggagtt    12000
cagtggagaa gctagggata tggctcagtt ggcagagtgc ttatctagca tacatgatag   12060
tgaatgccta taatctcaga actctagagg catcattcca aggttttact ttgactccat   12120
agagtttaag gccagcttgg gacacaagag actgtgtctc aaaacaagga aataaaaaca   12180
aaaatctaaa aaacacccac ccagacctat tttaggcacc tttttgtcc atgctaggca   12240
agtgatttaa cacttagctg catccatagg aagcttgctg gacttctttg tttttgggac   12300
aggagttttg tatgtagccc agataccaga cccagttaca ttggcatttg ttttgctatt   12360
gttattgctt tttgatgtca ttgttgcttt tttttttttt tttttttttt ttttttggc   12420
aagttctcct gtagcccagg cttgcctgga actctggaac ttgataggta gctgatgata   12480
actttgtact cttgatcctc ctatccctat cttccaagtg ctgggattac agtcacgtac   12540
tactctagtt ttaaaattgg atgccttaga taggatcctc cagggagcat aaagagtcca   12600
atcttgtact ggaactccat ctccaagaag gtaaacatta tccttgtgta cataggtagc   12660
cctaggaata atcagttggt gcctatagtg agaagcattt ttttttttat ttagatgagc   12720
agggcatggt ggaacatgtc tttaattcta gcatttggga catagaggca ggaggatcaa   12780
aaggctcaag gccattcttg gctacacaga gagttggagg ttagccagcc tgtgctgaat   12840
gagacccagc ctgaaacaaa aaggggggagg tgggagatag aaggatggct cctgtggtaa   12900
atccagagac tcataaaaaa tgctgggcat ggtggcagga gtttgtaatc ccagtgtcgg   12960
ggaggtgaag acaagagaat ccccagggca tgctggccaa ctaactagtc tagcctaatt   13020
ggtgagctcc aggacagtaa gatacccctgc ttcaaagaag gcacatggga ttcctgagga   13080
tgccacccaa aggtgtcctc tagcatcctc acatgagcat gcaagaacat gtgcacctga   13140
```

| | |
|---|---:|
| atgtaacatg tgcgcacaca cacacacaca cacacacaca cacacacaca cacacacatt | 13200 |
| tttaaaaagt aatatagagc tggagtgtac ctttgttgat agaacacttg tttaggattc | 13260 |
| gtgaaggtct tgatttgatc ctaagcacca tgtaaactgg gcacccatct agaagcccag | 13320 |
| cactcagagg tggagacagg aggtcaggag ttcaacaagg tcattctctg ctacacagtg | 13380 |
| agtttaaaat cggcctggga tacacgagag agaccctgtg taagagcagt agcagcagca | 13440 |
| agaactcaag ctgaaaagga acatgcagtg taagacaaag gccactgtg tgcatagagc | 13500 |
| cagcaacctc acactgtaat gaacgggtct gacctttgca agtaagcttc ttgtgatgct | 13560 |
| ctggttgagc ctttgactac gacttttgtg acttgtgctc ctctggatgc ttgcaggatg | 13620 |
| agggtgagga cccctggtac cagaaagcat gcaagtgtga ttgccaggta ggagccaatg | 13680 |
| ctctgtggtc tgctggagct acctccttag actgta | 13716 |

<210> SEQ ID NO 25
<211> LENGTH: 3670
<212> TYPE: DNA
<213> ORGANISM: Artificial Sequence
<220> FEATURE:
<223> OTHER INFORMATION: recombinant or synthetic polynucleotide

<400> SEQUENCE: 25

| | |
|---|---:|
| aagaactaaa tgaaataaga tgcttaagtt aatcgcctgc tcctatgcca gctctccact | 60 |
| tcacttagat cttgctgtga ccaaggacaa ggagaaaatg ggtaccgatt taatgatcc | 120 |
| agtggtcctg cagaggagag attgggagaa tcccggtgtg acacagctga acagactagc | 180 |
| cgcccaccct cccctttgctt cttggagaaa cagtgaggaa gctaggacag acagaccaag | 240 |
| ccagcaactc agatctttga acggggagtg gagatttgcc tggtttccgg caccagaagc | 300 |
| ggtgccggaa agctggctgg agtgcgatct tcctgaggcc gatactgtcg tcgtcccctc | 360 |
| aaactggcag atgcacggtt acgatgcgcc catctacacc aacgtgacct atcccattac | 420 |
| ggtcaatccg ccgtttgttc ccacggagaa tccgacgggt tgttactcgc tcacatttaa | 480 |
| tgttgatgaa agctggctac aggaaggcca gacgcgaatt ttttttgatg cgttaactc | 540 |
| ggcgtttcat ctgtgtgca acgggcgctg ggtcggttac ggccaggaca gtcgtttgcc | 600 |
| gtctgaattt gacctgagcg catttttacg cgccggagaa aaccgcctcg cggtgatggt | 660 |
| gctgcgctgg agtgacggca gttatctgga agatcaggat atgtggcgga tgagcggcat | 720 |
| tttccgtgac gtctcgttgc tgcataaacc gactacacaa atcagcgatt ccatgttgc | 780 |
| cactcgcttt aatgatgatt tcagccgcgc tgtactggag gctgaagttc agatgtgcgg | 840 |
| cgagttgcgt gactacctac gggtaacagt ttctttatgg cagggtgaaa cgcaggtcgc | 900 |
| cagcggcacc gcgcctttcg gcggtgaaat tatcgatgag cgtggtggtt atgccgatcg | 960 |
| cgtcacacta cgtctgaacg tcgaaaaccc gaaactgtgg agcgccgaaa tcccgaatct | 1020 |
| ctatcgtgcg gtggttgaac tgcacaccgc cgacggcacg ctgattgaag cagaagcctg | 1080 |
| cgatgtcggt ttccgcgagg tgcggattga aaatggtctg ctgctgctga acggcaagcc | 1140 |
| gttgctgatt cgaggcgtta accgtcacga gcatcatcct ctgcatggtc aggtcatgga | 1200 |
| tgagcagacg atggtgcagg atatcctgct gatgaagcag aacaacttta cgcgcgtgcg | 1260 |
| ctgttcgcat tatccgaacc atccgctgtg gtacacgctg tgcgaccgct acggcctgta | 1320 |
| tgtggtggat gaagccaata ttgaaaccca cggcatggtg ccaatgaatc gtctgaccga | 1380 |
| tgatccgcgc tggctaccgg cgatgagcga acgcgtaacg cgaatggtgc agcgcgatcg | 1440 |
| taatcacccg agtgtgatca tctggtcgct ggggaatgaa tcaggccacg gcgctaatca | 1500 |

```
cgacgcgctg tatcgctgga tcaaatctgt cgatccttcc cgcccggtgc agtatgaagg    1560
cggcggagcc gacaccacgg ccaccgatat tatttgcccg atgtacgcgc gcgtggatga    1620
agaccagccc ttcccggctg tgccgaaatg gtccatcaaa aaatggcttt cgctacctgg    1680
agagacgcgc ccgctgatcc tttgcgaata cgcccacgcg atgggtaaca gtcttggcgg    1740
tttcgctaaa tactggcagg cgtttcgtca gtatccccgt ttacagggcg gcttcgtctg    1800
ggactgggtg gatcagtcgc tgattaaata tgatgaaaac ggcaaccgt ggtcggctta     1860 cggcggtgat tttggcgata cgccgaacga tcgccagttc tgtatgaacg gtctggtctt    1920
tgccgaccgc acgccgcatc cagcgctgac ggaagcaaaa caccagcagc agttttcca    1980 gttccgttta tccgggcaaa ccatcgaagt gaccagcgaa tacctgttcc gtcatagcga    2040
taacgagctc ctgcactgga tggtggcgct ggatggtaag ccgctggcaa gcggtgaagt    2100
gcctctggat gtcgctccac aaggtaaaca gttgattgaa ctgcctgaac taccgcagcc    2160
ggagagcgcc gggcaactct ggctcacagt acgcgtagtg caaccgaacg cgaccgcatg    2220
gtcagaagcc gggcacatca gcgcctggca gcagtggcgt ctggcggaaa acctcagtgt    2280
gacgctcccc gccgcgtccc acgccatccc gcatctgacc accagcgaaa tggattttg    2340 catcgagctg gtaataagc gttggcaatt taaccgccag tcaggctttc tttcacagat     2400
gtggattggc gataaaaaac aactgctgac gccgctgcgc gatcagttca cccgtgcacc    2460
gctggataac gacattggcg taagtgaagc gacccgcatt gaccctaacg cctgggtcga    2520
acgctggaag gcggcgggcc attaccagcc gaagcagcg ttgttgcagt gcacggcaga     2580
tacacttgct gatgcggtgc tgattacgac cgctcacgcg tggcagcatc aggggaaaac    2640
cttatttatc agccggaaaa cctaccggat tgatggtagt ggtcaaatgg cgattaccgt    2700
tgatgttgaa gtggcgagcg atacaccgca tccggcgcgg attggcctga actgccagct    2760
ggcgcaggta gcagagcggg taaactggct cggattaggg ccgcaagaaa actatcccga    2820
ccgccttact gccgcctgtt tgaccgctg ggatctgcca ttgtcagaca tgtataccc      2880 gtacgtcttc ccgagcgaaa acggtctgcg ctgcgggacg cgcgaattga attatggccc    2940
acaccagtgg cgcggcgact tccagttcaa catcagccgc tacagtcaac agcaactgat    3000
ggaaaccagc catcgccatc tgctgcacgc ggaagaaggc acatggctga atatcgacgg    3060
tttccatatg gggattggtg cgacgactc ctggagcccg tcagtatcgg cggaattcca     3120
gctgagcgcc ggtcgctacc attaccagtt ggtctggtgt caaaataat aataaccggg     3180 cagggggat ctaagctcta gataagtaat gatcataatc agccatatca catctgtaga    3240
ggttttactt gctttaaaaa acctcccaca cctcccctg aacctgaaac ataaatgaa      3300 tgcaattgtt gttgttaact tgtttattgc agcttataat ggttacaaat aaagcaatag    3360
catcacaaat ttcacaaata aagcattttt ttcactgcat tctagttgtg gtttgtccaa    3420
actcatcaat gtatcttatc atgtctggat ccccgggcta gagtttaaac actagaacta    3480
gtggatcccc gggctcgata actataacgg tcctaaggta gcgactcgac ataacttcgt    3540
ataatgtatg ctatacgaag ttatgctagc ttccaggtga gtggctcaac gccctagcat    3600
tcctccttcc aactcttaat ccctctgctt tctctcaagt tggcttgtga gcttcacatc    3660
tcaccgtggc                                                          3670
```

<210> SEQ ID NO 26
<211> LENGTH: 5987
<212> TYPE: DNA

<213> ORGANISM: Artificial Sequence
<220> FEATURE:
<223> OTHER INFORMATION: recombinant or synthetic polynucleotide

<400> SEQUENCE: 26

```
gcatgcaaga acatgtgcac ctgaatgtaa catgtgcgca cacacacaca cacacacaca       60
cacacacaca cacacacaca cattttttaaa aagtaatata gagctggagt gtacctttgt     120
tgatagaaca cttgtttagg attcgtgaag gtaaactggg cacccatcta gaagcccagc     180
actcagaggt ggagacagga ggtcaggagt tcaacaaggt cattctctgc tacacagtga     240
gtttaaaatc ggcctgggat acacgagaga daccctgtgt aagagcagta gcagcagcaa     300
gaactcaagc tgaaaaggaa catgcagtgt aagacaaagg gccactgtgt gcatagagcc     360
agcaacctca cactgtaatg aacgggtctg acctttgcaa gtaagcttct tgtgatgctc     420
tggttgagcc tttgactacg acttttgtga cttgtgctcc tctggatgct tgcaggatga     480
gggtgaggac ccctggtacc agaaagcatg caagtgtgat tgccaggtag gagccaatgc     540
tctgtggtct gctggagcta cctccttaga cagtattcca ggtgagtggc tcaacgccct     600
agcattcctc cttccaactc ttaatccctc tgctttctct caagttggct tgtgagcttc     660
acatctcacc gtggccactg ctccaacatt ctgttcatta tcaagtgcca ggctctctcc     720
ctccctggct tgcctgagat ggtcaggtaa daccctcga gataacttcg tataatgtat     780
gctatacgaa gttatatgca tgccagtagc agcacccacg tccaccttct gtctagtaat     840
gtccaacacc tccctcagtc caaacactgc tctgcatcca tgtggctccc atttatacct     900
gaagcacttg atggggcctc aatgttttac tagagcccac cccctgcaa ctctgagacc      960
ctctggattt gtctgtcagt gcctcactgg ggcgttggat aatttcttaa aaggtcaagt    1020
tccctcagca gcattctctg agcagtctga agatgtgtgc ttttcacagt tcaaatccat    1080
gtggctgttt cacccacctg cctggccttg ggttatctat caggacctag cctagaagca    1140
ggtgtgtggc acttaacacc taagctgagt gactaactga acactcaagt ggatgccatc    1200
tttgtcactt cttgactgtg acacaagcaa ctcctgatgc caaagccctg cccaccctc     1260
tcatgcccat atttggacat ggtacaggtc ctcactggcc atggtctgtg aggtcctggt    1320
cctctttgac ttcataattc ctaggggcca ctagtatcta aagaggaag agggtgctgg     1380
ctcccaggcc acagcccaca aaattccacc tgctcacagg ttggctggct cgacccaggt    1440
ggtgtcccct gctctgagcc agctcccggc caagccagca ccatgggaac ccccaagaag    1500
aagaggaagg tgcgtaccga tttaaattcc aatttactga ccgtacacca aaatttgcct    1560
gcattaccgg tcgatgcaac gagtgatgag gttcgcaaga acctgatgga catgttcagg    1620
gatcgccagc cgttttctga gcatacctgg aaaatgcttc tgtccgtttg ccggtcgtgg    1680
gcggcatggt gcaagttgaa taaccggaaa tggtttcccg cagaacctga agatgttcgc    1740
gattatcttc tatatcttca ggcgcgcggt ctggcagtaa aaactatcca gcaacatttg    1800
ggccagctaa acatgcttca tcgtcggtcc gggctgccac gaccaagtga cagcaatgct    1860
gtttcactgg ttatgcggcg gatccgaaaa gaaaacgttg atgccggtga acgtgcaaaa    1920
caggtaaata taaaatttt aagtgtataa tgatgttaaa ctactgattc taattgttg     1980
tgtatttag gctctagcgt tcgaacgcac tgatttcgac caggttcgtt cactcatgga    2040
aaatagcgat cgctgccagg atatacgtaa tctggcattt ctggggattg cttataacac    2100
cctgttacgt atagccgaaa ttgccaggat cagggttaaa gatatctcac gtactgacgg    2160
tgggagaatg ttaatccata ttggcagaac gaaaacgctg gttagcaccg caggtgtaga    2220
```

-continued

```
gaaggcactt agcctggggg taactaaact ggtcgagcga tggatttccg tctctggtgt    2280
agctgatgat ccgaataact acctgttttg ccgggtcaga aaaaatggtg ttgccgcgcc    2340
atctgccacc agccagctat caactcgcgc cctggaaggg attttttgaag caactcatcg   2400 attgatttac ggcgctaagg atgactctgg tcagagatac ctggcctggt ctggacacag    2460
tgcccgtgtc ggagccgcgc gagatatggc ccgcgctgga gtttcaatac cggagatcat    2520
gcaagctggt ggctggacca atgtaaatat tgtcatgaac tatatccgta acctggatag    2580
tgaaacaggg gcaatggtgc gcctgctgga agatggcgat taggcggccg gccgctaatc    2640
agccatacca catttgtaga ggttttactt gctttaaaaa acctcccaca cctcccctg     2700 aacctgaaac ataaaatgaa tgcaattgtt gttgttaact tgtttattgc agcttataat    2760
ggttacaaat aaagcaatag catcacaaat ttcacaaata aagcattttt ttcactgcat    2820
tctagttgtg gtttgtccaa actcatcaat gtatcttatc atgtctggat ccccggcta    2880 gagtttaaac actagaacta gtggatcccc cgggatcatg gcctccgcgc gggttttgg    2940 cgcctcccgc gggcgccccc ctcctcacgg cgagcgctgc cacgtcagac gaagggcgca    3000
gcgagcgtcc tgatccttcc gcccggacgc tcaggacagc ggcccgctgc tcataagact    3060
cggccttaga accccagtat cagcagaagg acattttagg acgggacttg ggtgactcta    3120
gggcactggt tttcttttcca gagagcggaa caggcgagga aaagtagtcc cttctcggcg    3180
attctgcgga gggatctccg tggggcggtg aacgccgatg attatataag gacgcgccgg    3240
gtgtggcaca gctagttccg tcgcagccgg gatttgggtc gcggttcttg tttgtggatc    3300
gctgtgatcg tcacttggtg agtagcgggc tgctgggctg gccggggctt tcgtggccgc    3360
cgggccgctc ggtgggacgg aagcgtgtgg agagaccgcc aagggctgta gtctgggtcc    3420
gcgagcaagg ttgccctgaa ctgggggttg ggggagcgc agcaaaatgg cggctgttcc    3480
cgagtcttga atgaagacg cttgtgaggc gggctgtgag gtcgttgaaa caaggtgggg    3540
ggcatggtgg gcggcaagaa cccaaggtct tgaggccttc gctaatgcgg gaaagctctt    3600
attcgggtga gatgggctgg ggcaccatct ggggaccctg acgtgaagtt tgtcactgac    3660
tggagaactc ggtttgtcgt ctgttgcggg ggcggcagtt atggcggtgc cgttgggcag    3720
tgcacccgta cctttgggag cgcgcgccct cgtcgtgtcg tgacgtcacc cgttctgttg    3780
gcttataatg cagggtgggg ccacctgccg gtaggtgtgc ggtaggcttt tctccgtcgc    3840
aggacgcagg gttcgggcct agggtaggct ctcctgaatc gacaggcgcc ggacctctgg    3900
tgaggggagg gataagtgag gcgtcagttt ctttggtcgg ttttatgtac ctatcttctt    3960
aagtagctga agctccggtt ttgaactatg cgctcggggt tggcgagtgt gttttgtgaa    4020
gttttttagg caccttttga aatgtaatca tttgggtcaa tatgtaattt tcagtgttag    4080
actagtaaat tgtccgctaa attctggccg ttttttggctt ttttgttaga cgtgttgaca    4140
attaatcatc ggcatagtat atcggcatag tataatacga caaggtgagg aactaaacca    4200
tgaaaaagcc tgaactcacc gcgacgtctg tcgagaagtt tctgatcgaa aagttcgaca    4260
gcgtgtccga cctgatgcag ctctcggagg gcgaagaatc tcgtgctttc agcttcgatg    4320
taggagggcg tggatatgtc ctgcgggtaa atagctgcgc cgatggtttc tacaaagatc    4380
gttatgttta tcggcacttt gcatcggccg cgctcccgat tccggaagtg cttgacattg    4440
gggaattcag cgagagcctg acctattgca tctcccgccg tgcacagggt gtcacgttgc    4500
aagacctgcc tgaaaccgaa ctgcccgctg ttctgcagcc ggtcgcggag gccatggatg    4560
```

| | |
|---|---:|
| cgattgctgc ggccgatctt agccagacga gcgggttcgg cccattcgga ccgcaaggaa | 4620 |
| tcggtcaata cactacatgg cgtgatttca tatgcgcgat tgctgatccc catgtgtatc | 4680 |
| actggcaaac tgtgatggac gacaccgtca gtgcgtccgt cgcgcaggct ctcgatgagc | 4740 |
| tgatgctttg ggccgaggac tgccccgaag tccggcacct cgtgcacgcg gatttcggct | 4800 |
| ccaacaatgt cctgacggac aatggccgca taacagcggt cattgactgg agcgaggcga | 4860 |
| tgttcgggga ttcccaatac gaggtcgcca acatcttctt ctggaggccg tggttggctt | 4920 |
| gtatggagca gcagacgcgc tacttcgagc ggaggcatcc ggagcttgca ggatcgccgc | 4980 |
| ggctccgggc gtatatgctc cgcattggtc ttgaccaact ctatcagagc ttggttgacg | 5040 |
| gcaatttcga tgatgcagct tgggcgcagg tcgatgcga cgcaatcgtc cgatccggag | 5100 |
| ccgggactgt cgggcgtaca caaatcgccc gcagaagcgc ggccgtctgg accgatggct | 5160 |
| gtgtagaagt actcgccgat agtggaaacc gacgccccag cactcgtccg agggcaaagg | 5220 |
| aataggggga tccgctgtaa gtctgcagaa attgatgatc tattaaacaa taaagatgtc | 5280 |
| cactaaaatg gaagtttttc ctgtcatact ttgttaagaa gggtgagaac agagtaccta | 5340 |
| cattttgaat ggaaggattg gagctacggg ggtgggggtg gggtgggatt agataaatgc | 5400 |
| ctgctcttta ctgaaggctc tttactattg ctttatgata atgtttcata gttggatatc | 5460 |
| ataatttaaa caagcaaaac caaattaagg gccagctcat tcctcccact catgatctat | 5520 |
| agatctatag atctctcgtg ggatcattgt ttttctcttg attcccactt tgtggttcta | 5580 |
| agtactgtgg tttccaaatg tgtcagtttc atagcctgaa gaacgagatc agcagcctct | 5640 |
| gttccacata cacttcattc tcagtattgt tttgccaagt tctaattcca tcagacctcg | 5700 |
| acctgcagcc cctagataac ttcgtataat gtatgctata cgaagttatg ctaggtaact | 5760 |
| ataacgtcc taaggtagcg agctagcagc gtgagggaag tcccttcctc ttaggtatca | 5820 |
| gaggaaatgt gtgtgtgtgt gtgtgtgt gtgtttctat atcctgtgga gtcatgctgt | 5880 |
| ctctaaatca gtaatgagga tatggagggc aagaatttag taaaacaagt cgcttctaga | 5940 |
| agctaaatta ctgtcatttc atggattggc agaaaactgg gcaccca | 5987 |

<210> SEQ ID NO 27
<211> LENGTH: 1033
<212> TYPE: DNA
<213> ORGANISM: Artificial Sequence
<220> FEATURE:
<223> OTHER INFORMATION: recombinant or synthetic polynucleotide

<400> SEQUENCE: 27

| | |
|---|---:|
| gcatgcaaga acatgtgcac ctgaatgtaa catgtgcgca cacacacaca cacacacaca | 60 |
| cacacacaca cacacacaca cattttttaaa aagtaatata gagctggagt gtacctttgt | 120 |
| tgatagaaca cttgtttagg attcgtgaag gtaaactggg cacccatcta gaagcccagc | 180 |
| actcagaggt ggagacagga ggtcaggagt tcaacaaggt cattctctgc tacacagtga | 240 |
| gtttaaaatc ggcctgggat acacgagaga gaccctgtgt aagagcagta gcagcagcaa | 300 |
| gaactcaagc tgaaaaggaa catgcagtgt aagacaaagg ccactgtgt gcatagagcc | 360 |
| agcaacctca cactgtaatg aacgggtctg acctttgcaa gtaagcttct tgtgatgctc | 420 |
| tggttgagcc tttgactacg acttttgtga cttgtgctcc tctggatgct tgcaggatga | 480 |
| gggtgaggac ccctggtacc agaaagcatg caagtgtgat tgccaggtag gagccaatgc | 540 |
| tctgtggtct gctggagcta cctccttaga cagtattcca ggtgagtggc tcaacgcccc | 600 |
| agcattcctc cttccaactc ttaatccctc tgctttctct caagttggct tgtgagcttc | 660 |

| | |
|---|---|
| acatctcacc gtggccactg ctccaacatt ctgttcatta tcaagtgcca ggctctctcc | 720 |
| ctccctggct tgcctgagat ggtcaggtaa gaccccctcga gataacttcg tataatgtat | 780 |
| gctatacgaa gttatgctag gtaactataa cggtcctaag gtagcgagct agcagcgtga | 840 |
| gggaagtccc ttcctcttag gtatcagagg aaatgtgtgt gtgtgtgtgt gtgtgtgtgt | 900 |
| ttctatatcc tgtggagtca tgctgtctct aaatcagtaa tgaggatatg gagggcaaga | 960 |
| atttagtaaa acaagtcgct tctagaagct aaattactgt catttcatgg attggcagaa | 1020 |
| aactgggcac cca | 1033 |

<210> SEQ ID NO 28
<211> LENGTH: 5629
<212> TYPE: DNA
<213> ORGANISM: Artificial Sequence
<220> FEATURE:
<223> OTHER INFORMATION: recombinant or synthetic polynucleotide

<400> SEQUENCE: 28

| | |
|---|---|
| aagagctcat ttgttaaaca tgccagggaa gtctttccta aggaaaagaa ttaagagtcg | 60 |
| ggctatgtct gaaggcccag atacctcttg atgctaggta acccttcaaa actcagcacc | 120 |
| tgttggcttt ttacagacat agataagagg atggctcctg gtaatttggt gtgttcctgg | 180 |
| caggtgtgct tggcttttcca agtatcagga cagcagccag tggttacaga tagatttgaa | 240 |
| ggagatcaag gtgatttcgg ggatcctgac ccaaggatgc tgtgacatag acgagtgggt | 300 |
| gaccaagtac agtgtgcagt ataggactga tgagcgcctg aactggatct actataagga | 360 |
| tcagaccgga aacaatcggg taagtggggg tcactccgag tcagcttcag ctcacactgc | 420 |
| ggagacacac tccatcccta tgttcctgct gtccgcgtct gtctgagcat tgaccccctct | 480 |
| acatgctggg tcatctgctc gagataactt cgtataatgt atgctatacg aagttatatg | 540 |
| catgccagta gcagcaccca cgtccacctt ctgtctagta atgtccaaca cctccctcag | 600 |
| tccaaacact gctctgcatc catgtggctc ccatttatac ctgaagcact tgatggggcc | 660 |
| tcaatgtttt actagagccc accccccctgc aactctgaga ccctctggat ttgtctgtca | 720 |
| gtgcctcact ggggcgttgg ataatttctt aaaaggtcaa gttccctcag cagcattctc | 780 |
| tgagcagtct gaagatgtgt gcttttcaca gttcaaatcc atgtggctgt ttcacccacc | 840 |
| tgcctggcct tgggttatct atcaggacct agcctagaag caggtgtgtg gcacttaaca | 900 |
| cctaagctga gtgactaact gaacactcaa gtggatgcca tctttgtcac ttcttgactg | 960 |
| tgacacaagc aactcctgat gccaaagccc tgcccacccc tctcatgccc atatttggac | 1020 |
| atggtacagg tcctcactgg ccatggtctg tgaggtcctg gtcctctttg acttcataat | 1080 |
| tcctagggc cactagtatc tataagagga agagggtgct ggctcccagg ccacagccca | 1140 |
| caaaattcca cctgctcaca ggttggctgg ctcgacccag gtggtgtccc ctgctctgag | 1200 |
| ccagctcccg gccaagccag caccatggga accccaaga agaagaggaa ggtgcgtacc | 1260 |
| gatttaaatt ccaatttact gaccgtacac caaaatttgc ctgcattacc ggtcgatgca | 1320 |
| acgagtgatg aggttcgcaa gaacctgatg gacatgttca gggatcgcca ggcgttttct | 1380 |
| gagcatacct ggaaaatgct tctgtccgtt tgccggtcgt gggcggcatg gtgcaagttg | 1440 |
| aataaccgga aatggtttcc cgcagaacct gaagatgttc gcgattatct tctatatctt | 1500 |
| caggcgcgcg gtctggcagt aaaaactatc cagcaacatt tgggccagct aaacatgctt | 1560 |
| catcgtcggt ccgggctgcc acgaccaagt gacagcaatg ctgtttcact ggttatgcgg | 1620 |

```
cggatccgaa aagaaaacgt tgatgccggt gaacgtgcaa acaggtaaa  tataaaattt    1680 ttaagtgtat aatgatgtta aactactgat tctaattgtt tgtgtatttt aggctctagc    1740
gttcgaacgc actgatttcg accaggttcg ttcactcatg gaaaatagcg atcgctgcca    1800
ggatatacgt aatctggcat ttctggggat tgcttataac accctgttac gtatagccga    1860
aattgccagg atcagggtta aagatatctc acgtactgac ggtgggagaa tgttaatcca    1920
tattggcaga acgaaaacgc tggttagcac cgcaggtgta gagaaggcac ttagcctggg    1980
ggtaactaaa ctggtcgagc gatggatttc cgtctctggt gtagctgatg atccgaataa    2040
ctacctgttt tgccgggtca gaaaaaatgg tgttgccgcg ccatctgcca ccagccagct    2100
atcaactcgc gccctggaag ggattttga  agcaactcat cgattgattt acggcgctaa    2160
ggatgactct ggtcagagat acctggcctg tctggacac  agtgcccgtg tcggagccgc    2220
gcgagatatg gcccgcgctg gagtttcaat accggagatc atgcaagctg gtggctggac    2280
caatgtaaat attgtcatga actatatccg taacctggat agtgaaacag ggcaatggt     2340 gcgcctgctg gaagatggcg attaggcggc cggccgctaa tcagccatac cacatttgta    2400
gaggttttac ttgctttaaa aaacctccca cacctccccc tgaacctgaa acataaaatg    2460
aatgcaattg ttgttgttaa cttgtttatt gcagcttata atggttacaa ataaagcaat    2520
agcatcacaa atttcacaaa taaagcattt ttttcactgc attctagttg tggtttgtcc    2580
aaactcatca atgtatctta tcatgtctgg atcccccggc tagagtttaa acactagaac    2640
tagtggatcc cccgggatca tggcctccgc gccgggtttt ggcgcctccc gcgggcgccc    2700
ccctcctcac ggcgagcgct gccacgtcag acgaagggcg cagcgagcgt cctgatcctt    2760
ccgcccggac gctcaggaca gcggcccgct gctcataaga ctcggcctta gaaccccagt    2820
atcagcagaa ggacatttta ggacgggact tgggtgactc tagggcactg gttttctttc    2880
cagagagcgg aacaggcgag gaaaagtagt cccttctcgg cgattctgcg gagggatctc    2940
cgtggggcgg tgaacgccga tgattatata aggacgcgcc gggtgtggca cagctagttc    3000
cgtcgcagcc gggatttggg tcgcggttct tgtttgtgga tcgctgtgat cgtcacttgg    3060
tgagtagcgg gctgctgggc tggccggggc tttcgtggcc gccggccgc  tcggtgggac    3120 ggaagcgtgt ggagagaccg ccaagggctg tagtctgggt ccgcgagcaa ggttgccctg    3180
aactgggggt tgggggagc  gcagcaaaat ggcggctgtt cccgagtctt gaatggaaga    3240
cgcttgtgag gcgggctgtg aggtcgttga acaaggtgg  ggggcatggt gggcggcaag    3300
aacccaaggt cttgaggcct tcgctaatgc gggaaagctc ttattcgggt gagatgggct    3360
ggggcaccat ctggggaccc tgacgtgaag tttgtcactg actggagaac tcggtttgtc    3420
gtctgttgcg ggggcggcag ttatggcggt gccgttgggc agtgcacccg tacctttggg    3480
agcgcgcgcc ctcgtcgtgt cgtgacgtca cccgttctgt tggcttataa tgcagggtgg    3540
ggccacctgc cggtaggtgt gcggtaggct tttctccgtc gcaggacgca gggttcgggc    3600
ctagggtagg ctctcctgaa tcgacaggcg ccggacctct ggtgagggga gggataagtg    3660
aggcgtcagt ttctttggtc ggttttatgt acctatcttc ttaagtagct gaagctccgg    3720
ttttgaacta tgcgctcggg gttggcgagt gtgttttgtg aagttttta  ggcacctttt    3780 gaaatgtaat catttgggtc aatatgtaat tttcagtgtt agactagtaa attgtccgct    3840
aaattctggc cgttttggct ttttttgtta gacgtgttga caattaatca tcggcatagt    3900
atatcggcat agtataatac gacaaggtga ggaactaaac catgaaaaag cctgaactca    3960
ccgcgacgtc tgtcgagaag tttctgatcg aaaagttcga cagcgtgtcc gacctgatgc    4020
```

```
agctctcgga gggcgaagaa tctcgtgctt tcagcttcga gtgtaggagg cgtggatatg    4080
tcctgcgggt aaatagctgc gccgatggtt tctacaaaga tcgttatgtt tatcggcact    4140
ttgcatcggc cgcgctcccg attccggaag tgcttgacat tggggaattc agcgagagcc    4200
tgacctattg catctcccgc cgtgcacagg gtgtcacgtt gcaagacctg cctgaaaccg    4260
aactgcccgc tgttctgcag ccggtcgcgg aggccatgga tgcgattgct gcggccgatc    4320
ttagccagac gagcgggttc ggcccattcg gaccgcaagg aatcggtcaa tacactacat    4380
ggcgtgattt catatgcgcg attgctgatc cccatgtgta tcactggcaa actgtgatgg    4440
acgacaccgt cagtgcgtcc gtcgcgcagg ctctcgatga gctgatgctt tgggccgagg    4500
actgccccga gtccggcac ctcgtgcacg cggatttcgg ctccaacaat gtcctgacgg    4560
acaatggccg cataacagcg gtcattgact ggagcgaggc gatgttcggg gattcccaat    4620
acgaggtcgc caacatcttc ttctggaggc cgtggttggc ttgtatggag cagcagacgc    4680
gctacttcga gcggaggcat ccggagcttg caggatcgcc gcggctccgg gcgtatatgc    4740
tccgcattgg tcttgaccaa ctctatcaga gcttggttga cggcaatttc gatgatgcag    4800
cttgggcgca gggtcgatgc gacgcaatcg tccgatccgg agccgggact gtcgggcgta    4860
cacaaatcgc ccgcagaagc gcggccgtct ggaccgatgg ctgtgtagaa gtactcgccg    4920
atagtggaaa ccgacgcccc agcactcgtc gagggcaaa ggaataggg gatccgctgt    4980 aagtctgcag aaattgatga tctattaaac aataaagatg tccactaaaa tggaagtttt    5040
tcctgtcata ctttgttaag aagggtgaga acagagtacc tacattttga atggaaggat    5100
tggagctacg ggggtggggg tggggtggga ttagataaat gcctgctctt tactgaaggc    5160
tctttactat tgctttatga taatgtttca tagttggata tcataattta aacaagcaaa    5220
accaaattaa gggccagctc attcctccca ctcatgatct atagatctat agatctctcg    5280
tgggatcatt gttttctct tgattccac tttgtggttc taagtactgt ggtttccaaa    5340
tgtgtcagtt tcatagcctg aagaacgaga tcagcagcct ctgttccaca tacacttcat    5400
tctcagtatt gttttgccaa gttctaattc catcagacct cgacctgcag cccctagata    5460
acttcgtata atgtatgcta tacgaagtta tgctaggtaa ctataacggt cctaaggtag    5520
cgagctagct tttccagatg tgatctggga gactagcagt ttgtaaatga atgtgggtct    5580
tttttgaaaa aaaggaaaaa aaagtaattt tctagttctc actatcagc              5629
```

<210> SEQ ID NO 29
<211> LENGTH: 675
<212> TYPE: DNA
<213> ORGANISM: Artificial Sequence
<220> FEATURE:
<223> OTHER INFORMATION: recombinant or synthetic polynucleotide

<400> SEQUENCE: 29

```
aagagctcat tgttaaaca tgccagggaa gtctttccta aggaaaagaa ttaagagtcg      60
ggctatgtct gaaggcccag atacctcttg atgctaggta acccttcaaa actcagcacc    120
tgttggcttt ttacagacat agataagagg atggctcctg gtaatttggt gtgttcctgg    180
caggtgtgct tggctttcca agtatcagga cagcagccag tggttacaga tagatttgaa    240
ggagatcaag gtgatttcgg ggatcctgac ccaaggatgc tgtgacatag acgagtgggt    300
gaccaagtac agtgtgcagt ataggactga tgagcgcctg aactggatct actataagga    360
tcagaccgga aacaatcggg taagtggggg tcactccgag tcagcttcag ctcacactgc    420
```

```
ggagacacac tccatcccta tgttcctgct gtccgcgtct gtctgagcat tgacccctct    480
acatgctggg tcatctgctc gagataactt cgtataatgt atgctatacg aagttatgct    540
aggtaactat aacggtccta aggtagcgag ctagcttttc cagatgtgat ctgggagact    600
agcagtttgt aaatgaatgt gggtcttttt tgaaaaaaag gaaaaaaaag taattttcta    660
gttctcacta tcagc                                                     675

<210> SEQ ID NO 30
<211> LENGTH: 680
<212> TYPE: DNA
<213> ORGANISM: Artificial Sequence
<220> FEATURE:
<223> OTHER INFORMATION: recombinant or synthetic polynucleotide

<400> SEQUENCE: 30
ccagtagcag cacccacgtc caccttctgt ctagtaatgt ccaacacctc cctcagtcca     60
aacactgctc tgcatccatg tggctcccat ttatacctga agcacttgat ggggcctcaa    120
tgttttacta gagcccaccc ccctgcaact ctgagaccct ctggatttgt ctgtcagtgc    180
ctcactgggg cgttggataa tttcttaaaa ggtcaagttc cctcagcagc attctctgag    240
cagtctgaag atgtgtgctt tcacagttc aaatccatgt ggctgtttca cccacctgcc     300
tggccttggg ttatctatca ggacctagcc tagaagcagg tgtgtggcac ttaacaccta    360
agctgagtga ctaactgaac actcaagtgg atgccatctt tgtcacttct tgactgtgac    420
acaagcaact cctgatgcca aagccctgcc caccoctctc atgcccatat ttggacatgg    480
tacaggtcct cactggccat ggtctgtgag gtcctggtcc tctttgactt cataattcct    540
aggggccact agtatctata agaggaagag ggtgctggct cccaggccac agcccacaaa    600
attccacctg ctcacaggtt ggctggctcg acccaggtgg tgtcccctgc tctgagccag    660
ctcccggcca agccagcacc                                                680

<210> SEQ ID NO 31
<211> LENGTH: 1052
<212> TYPE: DNA
<213> ORGANISM: Artificial Sequence
<220> FEATURE:
<223> OTHER INFORMATION: recombinant or synthetic polynucleotide

<400> SEQUENCE: 31
tgccatcatc acaggatgtc cttccttctc cagaagacag actggggctg aaggaaaagc     60
cggccaggct cagaacgagc cccactaatt actgcctcca acagctttcc actcactgcc    120
cccagcccaa catccccttt ttaactggga agcattccta ctctccattg tacgcacacg    180
ctcggaagcc tggctgtggg tttgggcatg agaggcaggg acaacaaaac cagtatatat    240
gattataact ttttcctgtt tccctatttc caaatggtcg aaaggaggaa gttaggtcta    300
cctaagctga atgtattcag ttagcaggag aaatgaaatc ctatacgttt aatactagag    360
gagaaccgcc ttagaatatt tatttcattg gcaatgactc caggactaca cagcgaaatt    420
gtattgcatg tgctgccaaa atactttagc tctttccttc gaagtacgtc ggatcctgta    480
attgagacac cgagtttagg tgactagggt tttcttttga ggaggagtcc cccacccgc    540 cccgctctgc cgcgacagga agctagcgat ccggaggact tagaatacaa tcgtagtgtg    600
ggtaaacatg gagggcaagc gcctgcaaag ggaagtaaga agattcccag tccttgttga    660
aatccatttg caaacagagg aagctgccgc gggtcgcagt cggtgggggg aagccctgaa    720
ccccacgctg cacggctggg ctggccaggt gcggccacgc cccatcgcg gcggctggta    780
```

```
ggagtgaatc agaccgtcag tattggtaaa gaagtctgcg gcagggcagg gagggggaag      840
agtagtcagt cgctcgctca ctcgctcgct cgcacagaca ctgctgcagt gacactcggc      900
cctccagtgt cgcggagacg caagagcagc gcgcagcacc tgtccgcccg gagcgagccc      960
ggcccgcggc cgtagaaaag gagggaccgc cgaggtgcgc gtcagtactg ctcagcccgg     1020
cagggacgcg ggaggatgtg gactgggtgg ac                                   1052
```

<210> SEQ ID NO 32
<211> LENGTH: 2008
<212> TYPE: DNA
<213> ORGANISM: Artificial Sequence
<220> FEATURE:
<223> OTHER INFORMATION: recombinant or synthetic polynucleotide

<400> SEQUENCE: 32

```
gtggtgctga ctcagcatcg gttaataaac cctctgcagg aggctggatt tcttttgttt       60
aattatcact tggacctttc tgagaactct taagaattgt tcattcgggt ttttttgttt      120
tgttttggtt tggttttttt gggttttttt tttttttttt ttttggtttt ttggagacag      180
ggtttctctg tatatagccc tggcacaaga gcaagctaac agcctgtttc ttcttggtgc      240
tagcgccccc tctggcagaa aatgaaataa caggtggacc tacaaccccc cccccccccc      300
ccagtgtatt ctactcttgt ccccggtata aatttgattg ttccgaacta cataaattgt      360
agaaggattt tttagatgca catatcattt tctgtgatac cttccacaca cccctccccc      420
ccaaaaaaat ttttctggga aagtttcttg aaaggaaaac agaagaacaa gcctgtcttt      480
atgattgagt tgggcttttg ttttgctgtg tttcatttct tcctgtaaac aaatactcaa      540
atgtccactt cattgtatga ctaagttggt atcattaggt tgggtctggg tgtgtgaatg      600
tgggtgtgga tctggatgtg ggtgggtgtg tatgccccgt gtgtttagaa tactagaaaa      660
gataccacat cgtaaacttt tgggagagat gattttaaaa aatggggtg ggggtgaggg      720 gaacctgcga tgaggcaagc aagataaggg gaagacttga gtttctgtga tctaaaaagt      780
cgctgtgatg ggatgctggc tataaatggg ccccttagcag cattgtttct gtgaattgga      840
ggatccctgc tgaaggcaaa agaccattga aggaagtacc gcatctggtt tgttttgtaa      900
tgagaagcag gaatgcaagg tccacgctct taataataaa caaacaggac attgtatgcc      960
atcatcacag gatgtccttc cttctccaga agacagactg gggctgaagg aaaagccggc     1020
caggctcaga acgagcccca ctaattactg cctccaacag cttccactc actgcccca      1080 gcccaacatc ccctttttaa ctgggaagca ttcctactct ccattgtacg cacacgctcg     1140
gaagcctggc tgtgggtttg ggcatgagag gcagggacaa caaaaccagt atatatgatt     1200
ataacttttt cctgtttccc tatttccaaa tggtcgaaag gaggaagtta ggtctaccta     1260
agctgaatgt attcagttag caggagaaat gaaatcctat acgtttaata ctagaggaga     1320
accgccttag aatatttatt tcattggcaa tgactccagg actacacagc gaaattgtat     1380
tgcatgtgct gccaaaatac tttagctctt tccttcgaag tacgtcggat cctgtaattg     1440
agacaccgag tttaggtgac tagggttttc ttttgaggag gagtccccca ccccgccccg     1500
ctctgccgcg acaggaagct agcgatccgg aggacttaga atacaatcgt agtgtgggta     1560
aacatggagg gcaagcgcct gcaaagggaa gtaagaagat tcccagtcct tgttgaaatc     1620
catttgcaaa cagaggaagc tgccgcgggt cgcagtcggt gggggaagc cctgaacccc     1680 acgctgcacg gctgggctgg ccaggtgcgg ccacgccccc atcgcggcgg ctggtaggag     1740
```

```
tgaatcagac cgtcagtatt ggtaaagaag tctgcggcag ggcagggagg gggaagagta    1800
gtcagtcgct cgctcactcg ctcgctcgca cagacactgc tgcagtgaca ctcggccctc    1860
cagtgtcgcg gagacgcaag agcagcgcgc agcacctgtc cgcccggagc gagcccggcc    1920
cgcggccgta gaaaggagg gaccgccgag gtgcgcgtca gtactgctca gcccggcagg     1980
gacgcgggag gatgtggact gggtggac                                       2008

<210> SEQ ID NO 33
<211> LENGTH: 100
<212> TYPE: DNA
<213> ORGANISM: Artificial Sequence
<220> FEATURE:
<223> OTHER INFORMATION: recombinant or synthetic polynucleotide

<400> SEQUENCE: 33
gctctccact tcacttagat cttgctgtga ccaaggacaa ggagaaaatg ggtaccgatt      60
taaatgatcc agtggtcctg cagaggagag attgggagaa                          100

<210> SEQ ID NO 34
<211> LENGTH: 100
<212> TYPE: DNA
<213> ORGANISM: Artificial Sequence
<220> FEATURE:
<223> OTHER INFORMATION: recombinant or synthetic polynucleotide

<400> SEQUENCE: 34
cagcccctag ataacttcgt ataatgtatg ctatacgaag ttatgctagc ttccaggtga      60
gtggctcaac gccctagcat tcctccttcc aactcttaat                          100

<210> SEQ ID NO 35
<211> LENGTH: 172
<212> TYPE: DNA
<213> ORGANISM: Artificial Sequence
<220> FEATURE:
<223> OTHER INFORMATION: recombinant or synthetic polynucleotide

<400> SEQUENCE: 35
atcccccggc tagagtttaa acactagaac tagtggatcc ccgggctcga taactataac      60
ggtcctaagg tagcgactcg acataacttc gtataatgta tgctatacga agttatgcta    120
gcttccaggt gagtggctca acgccctagc attcctcctt ccaactctta at             172

<210> SEQ ID NO 36
<211> LENGTH: 714
<212> TYPE: DNA
<213> ORGANISM: Artificial Sequence
<220> FEATURE:
<223> OTHER INFORMATION: recombinant or synthetic polynucleotide

<400> SEQUENCE: 36
ctggagtgta cctttgttga tagaacactt gtttaggatt cgtgaaggta aactgggcac      60
ccatctagaa gcccagcact cagaggtgga gacaggaggt caggagttca acaaggtcat    120
tctctgctac acagtgagtt taaaatcggc ctgggataca cgagagagac cctgtgtaag    180
agcagtagca gcagcaagaa ctcaagctga aaaggaacat gcagtgtaag acaaagggcc    240
actgtgtgca tagagccagc aacctcacac tgtaatgaac gggtctgacc tttgcaagta    300
agcttcttgt gatgctctgg ttgagccttt gactacgact tttgtgactt gtgctcctct    360
ggatgcttgc aggatgaggg tgaggacccc tggtaccaga aagcatgcaa gtgtgattgc    420
caggtaggag ccaatgctct gtggtctgct ggagctacct ccttagacag tattccaggt    480
```

```
gagtggctca acgccctagc attcctcctt ccaactctta atccctctgc tttctctcaa    540
gttggcttgt gagcttcaca tctcaccgtg gccactgctc caacattctg ttcattatca    600
agtgccaggc tctctccctc cctggcttgc ctgagatggt caggtaagac ccctcgagat    660
aacttcgtat aatgtatgct atacgaagtt atatgcatgc cagtagcagc accc          714

<210> SEQ ID NO 37
<211> LENGTH: 132
<212> TYPE: DNA
<213> ORGANISM: Artificial Sequence
<220> FEATURE:
<223> OTHER INFORMATION: recombinant or synthetic polynucleotide

<400> SEQUENCE: 37
ttccatcaga cctcgacctg cagccctag ataacttcgt ataatgtatg ctatacgaag     60
ttatgctagg taactataac ggtcctaagg tagcgagcta gcagcgtgag ggaagtccct    120
tcctcttagg ta                                                        132

<210> SEQ ID NO 38
<211> LENGTH: 760
<212> TYPE: DNA
<213> ORGANISM: Artificial Sequence
<220> FEATURE:
<223> OTHER INFORMATION: recombinant or synthetic polynucleotide

<400> SEQUENCE: 38
ctggagtgta cctttgttga tagaacactt gtttaggatt cgtgaaggta aactgggcac    60
ccatctagaa gcccagcact cagaggtgga gacaggaggt caggagttca acaaggtcat    120
tctctgctac acagtgagtt taaaatcggc ctgggataca cgagagagac cctgtgtaag    180
agcagtagca gcagcaagaa ctcaagctga aaaggaacat gcagtgtaag acaaagggcc    240
actgtgtgca tagagccagc aacctcacac tgtaatgaac gggtctgacc tttgcaagta    300
agcttcttgt gatgctctgg ttgagccttt gactacgact tttgtgactt gtgctcctct    360
ggatgcttgc aggatgaggg tgaggacccc tggtaccaga aagcatgcaa gtgtgattgc    420
caggtaggag ccaatgctct gtggtctgct ggagctacct ccttagacag tattccaggt    480
gagtggctca acgccctagc attcctcctt ccaactctta atccctctgc tttctctcaa    540
gttggcttgt gagcttcaca tctcaccgtg gccactgctc caacattctg ttcattatca    600
agtgccaggc tctctccctc cctggcttgc ctgagatggt caggtaagac ccctcgagat    660
aacttcgtat aatgtatgct atacgaagtt atgctaggta actataacgg tcctaaggta    720
gcgagctagc agcgtgaggg aagtcccttc tcttaggta                           760

<210> SEQ ID NO 39
<211> LENGTH: 528
<212> TYPE: DNA
<213> ORGANISM: Artificial Sequence
<220> FEATURE:
<223> OTHER INFORMATION: recombinant or synthetic polynucleotide

<400> SEQUENCE: 39
tctttcctaa ggaaaagaat taagagtcgg gctatgtctg aaggcccaga tacctcttga    60
tgctaggtaa cccttcaaaa ctcagcacct gttggctttt tacagacata gataagagga    120
tggctcctgg taatttggtg tgttcctggc aggtgtgctt ggctttccaa gtatcaggac    180
agcagccagt ggttacagat agatttgaag gagatcaagg tgatttcggg gatcctgacc    240
```

```
caaggatgct gtgacataga cgagtgggtg accaagtaca gtgtgcagta taggactgat    300
gagcgcctga actggatcta ctataaggat cagaccggaa acaatcgggt aagtggggt    360 cactccgagt cagcttcagc tcacactgcg gagacacact ccatccctat gttcctgctg    420
tccgcgtctg tctgagcatt gacccctcta catgctgggt catctgctcg agataacttc    480
gtataatgta tgctatacga agttatatgc atgccagtag cagcaccc                 528
```

<210> SEQ ID NO 40
<211> LENGTH: 30
<212> TYPE: DNA
<213> ORGANISM: Artificial Sequence
<220> FEATURE:
<223> OTHER INFORMATION: recombinant or synthetic polynucleotide

<400> SEQUENCE: 40

```
ttttccagat gtgatctggg agactagcag                                      30
```

<210> SEQ ID NO 41
<211> LENGTH: 574
<212> TYPE: DNA
<213> ORGANISM: Artificial Sequence
<220> FEATURE:
<223> OTHER INFORMATION: recombinant or synthetic polynucleotide

<400> SEQUENCE: 41

```
tctttcctaa ggaaaagaat taagagtcgg gctatgtctg aaggcccaga tacctcttga     60
tgctaggtaa cccttcaaaa ctcagcacct gttggctttt tacagacata gataagagga    120
tggctcctgg taatttggtg tgttcctggc aggtgtgctt ggctttccaa gtatcaggac    180
agcagccagt ggttacagat agatttgaag gagatcaagg tgatttcggg gatcctgacc    240
caaggatgct gtgacataga cgagtgggtg accaagtaca gtgtgcagta taggactgat    300
gagcgcctga actggatcta ctataaggat cagaccggaa acaatcgggt aagtggggt    360 cactccgagt cagcttcagc tcacactgcg gagacacact ccatccctat gttcctgctg    420
tccgcgtctg tctgagcatt gacccctcta catgctgggt catctgctcg agataacttc    480
gtataatgta tgctatacga agttatgcta ggtaactata acggtcctaa ggtagcgagc    540
tagcttttcc agatgtgatc tgggagacta gcag                                574
```

<210> SEQ ID NO 42
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 42

```
tgggacaagt gtaaatgagg ac                                              22
```

<210> SEQ ID NO 43
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 43

```
agtggtgctt ggccttatgc                                                 20
```

<210> SEQ ID NO 44
<211> LENGTH: 26

<212> TYPE: DNA
<213> ORGANISM: Artificial Sequence
<220> FEATURE:
<223> OTHER INFORMATION: synthetic oligonucleotide

<400> SEQUENCE: 44
tcccaggcaa atcaggacaa agggtc                                    26

<210> SEQ ID NO 45
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 45
gagccagcaa cctcacac                                             18

<210> SEQ ID NO 46
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 46
gcatccagag gagcacaagt c                                         21

<210> SEQ ID NO 47
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 47
tgtaatgaac gggtctgacc tttgcaa                                   27

<210> SEQ ID NO 48
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 48
tcgtgaaggt cttgatttga tcct                                      24

<210> SEQ ID NO 49
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 49
acctcctgtc tccacctctg                                           20

<210> SEQ ID NO 50
<211> LENGTH: 24
<212> TYPE: DNA
<213> ORGANISM: Artificial Sequence
<220> FEATURE:
<223> OTHER INFORMATION: synthetic oligonucleotide

```
<400> SEQUENCE: 50
aagcaccatg taaactgggc accc                                        24

<210> SEQ ID NO 51
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 51
ccctggcttg cctgagatg                                              19

<210> SEQ ID NO 52
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 52
ggacttccct cacgctgagt t                                           21

<210> SEQ ID NO 53
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 53
tcaggtaaga cccaattgtc aatgca                                      26

<210> SEQ ID NO 54
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 54
gagtcgggct atgtctgaag g                                           21

<210> SEQ ID NO 55
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 55
gccaacaggt gctgagttt                                              19

<210> SEQ ID NO 56
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 56
ccagatttgg gatgatacct cttgatgc                                    28

<210> SEQ ID NO 57
```

```
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 57
cctctacatg ctgggtcatc tg                                              22

<210> SEQ ID NO 58
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 58
ggacttccct cacgctgagt t                                               21

<210> SEQ ID NO 59
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 59
gacccacatt catttacaaa ctgc                                            24
```

NON-HUMAN ANIMALS MODELS OF RETINOSCHISIS

CROSS REFERENCE TO RELATED APPLICATIONS

This application is a continuation application of U.S. patent application Ser. No. 15/905,068, filed Feb. 26, 2018, now U.S. Pat. No. 11,064,685 B2, which claims the benefit of priority from U.S. Provisional Application No. 62/463,872, filed Feb. 27, 2017, and U.S. Provisional Application No. 62/576,256, filed Oct. 24, 2017, the entire contents of both of which are incorporated herein by reference.

INCORPORATION BY REFERENCE OF SEQUENCE LISTING

The Sequence Listing in the ASCII text file, named as 35518Z_10328US02_SequenceListing.txt of 117 KB, created on Jun. 8, 2021, and submitted to the United States Patent and Trademark Office via EFS-Web, is incorporated herein by reference.

BACKGROUND

The World Health Organization (WHO) estimates that about 180 million people worldwide are visually disabled, of which almost 6 million account for all causes of childhood blindness (Blindness: Vision 2020, The Global Initiative for the Elimination of Avoidable Blindness, Fact Sheet No. 213, The World Health Organization, revised 2000). X-linked juvenile Retinoschisis (XLRS), caused by mutations in the Retinoschisin-1 (Rs1) gene, is an early-onset macular degeneration in male children characterized by a splitting of the inner layers of the retina resulting in severe loss of vision. Current treatment options are limited to low vision aids such as optical (e.g., magnifier), non-optical (e.g., task lighting, reading stands, etc.) and electronic devices.

SUMMARY

The present disclosure encompasses the recognition that it is desirable to engineer non-human animals to provide improved in vivo systems for identifying and developing new therapeutics and, in some embodiments, therapeutic regimens, which can be used for the treatment and/or prevention of Retinoschisis (e.g., X-linked Retinoschisis). In some embodiments, in vivo systems described herein can be used for identifying and developing new therapeutics for treating eye-related diseases, disorders and/or conditions. In some embodiments, provided in vivo systems can also be used for identifying and developing new therapeutics for treating diseases, disorders, and/or conditions associated with vision loss. Provided non-human animals, in some embodiments, comprise a disruption in an Rs1 gene and/or otherwise functionally silenced Rs1 gene, such that a host RS1 polypeptide is not expressed or produced, and are desirable, for example, for use in identifying and developing therapeutics that restore and/or improve retinal structure and/or function. Non-human animals are also provided that comprise an engineered, variant or mutant Rs1 gene such that a variant or mutant RS1 polypeptide is produced from the engineered, variant or mutant Rs1 gene, and are desirable, for example, for use in identifying and developing therapeutics that restore and/or improve retinal structure and/or function. In some embodiments, non-human animals described herein provide improved in vivo systems (or models) for Retinoschisis. In some embodiments, non-human animals described herein provide improved in vivo systems (or models) for eye-related diseases, disorders, and/or conditions.

In some embodiments, non-human animals desirable for use as animal models for Retinoschisis are provided.

In various embodiments, provided non-human animals are characterized by a disruption (e.g., a deletion of a coding region, in whole or in part) or mutation (e.g., one or more point mutations in a coding sequence) in an Rs1 gene. In some embodiments, a disruption or mutation in an Rs1 gene affects one or more retinas of a non-human animal comprising the disruption or mutation. In some embodiments, a disruption or mutation in an Rs1 gene of a non-human animal as described herein results in the formation, development or emergence of one or more of the following phenotypes in the non-human animal: Retinoschisis-like phenotype (e.g., splitting of inner retinal layers, retinal degeneration, and decrease of visual acuity); schisis of the macula or retina; deterioration of visual acuity; retinal fibrosis; and retinal pigmentation; and in certain embodiments, the phenotypes include the development of cystic structures within the inner retina, and reduced ERG b- and a-wave responses as compared to wild type non-human animals, followed by a loss of photoreceptor cells. In some embodiments, a disruption or mutation in an Rs1 gene of a non-human animal as described herein results in early-onset (for example, at or by postnatal day 15, 18, 21, 24 or 27) functional and morphological phenotypes of the retina in the non-human animal. In some embodiments, the early-onset functional defects of the retina may be reflected by (i) reduced b-wave relative to a-wave (resulting in negative ERG) in dark-adapted and light-adapted ERG analyses; (ii) decreased maximum response and sensitivity values of ERG b-waves; (iii) decreased maximum response values of ERG a-waves; or (iv) a combination of (i)-(iii), as compared to wild type non-human animals. In some embodiments, early-onset morphological defects of the retina may be reflected by schisis, a broader ellipsoid zone (EZ), thinner outer retina, or a combination thereof, as compared to wild type non-human animals.

In some embodiments, a disruption (e.g., a deletion) or a mutation in a non-human Rs1 gene is a disruption or mutation of an endogenous Rs1 gene at an endogenous Rs1 locus. In some embodiments, a disruption (e.g., a deletion) in a non-human Rs1 gene results from an insertion of a nucleic acid sequence into an endogenous Rs1 gene at an endogenous Rs1 locus that, in some certain embodiments, comprises a reporter gene. In some embodiments, a disruption is or comprises a deletion, in whole or in part, of an endogenous Rs1 gene that eliminates expression or production of the gene product (e.g., mRNA or polypeptide). In some embodiments, a mutation (e.g., a point mutation) in a non-human Rs1 gene results from an insertion of a nucleic acid sequence into an endogenous Rs1 gene at an endogenous Rs1 locus that, in some certain embodiments, comprises a synthetic exon (e.g., a synthetic exon comprising a point mutation). In some embodiments, a mutation is or comprises one or more point mutations in an Rs1 gene that results in the expression of a variant RS1 polypeptide that has reduced or altered function as compared to a wild-type RS1 polypeptide; in some certain embodiments, the level of a variant RS1 polypeptide in a non-human animal is less than the level of a wild-type RS1 polypeptide in a wild type non-human animal. In some embodiments, a variant RS1 polypeptide as described herein includes one or more amino acid substitutions as compared to a wild type RS1 polypeptide.

In some embodiments, provided non-human animals have a genome comprising an engineered Rs1 gene. In some embodiments, the engineered Rs1 gene is located at an endogenous Rs1 locus; and in other embodiments, the engineered Rs1 gene is located at a different locus. In some embodiments, an engineered Rs1 gene is or comprises a heterologous Rs1 gene (e.g., a human Rs1 gene). In some embodiments, an engineered Rs1 gene includes genetic material that encodes a heterologous RS1 polypeptide, in whole or in part. In some embodiments, an engineered Rs1 gene includes genetic material that encodes a discoidin domain of a heterologous polypeptide, which discoidin domain contains an amino acid substitution as compared to a wild-type or parental heterologous RS1 polypeptide. In some embodiments, an engineered Rs1 gene includes one or more mutations as compared to a wild-type or parental Rs1 gene (e.g., endogenous or homolog) that results in the expression of a variant RS1 polypeptide. In some embodiments, an engineered Rs1 gene includes genetic material that encodes a discoidin domain of a rodent RS1 polypeptide, which discoidin domain contains an amino acid substitution as compared to a wild-type or parental rodent RS1 polypeptide. In some embodiments, an engineered Rs1 gene includes genetic material that encodes a discoidin domain of a heterologous RS1 polypeptide, which discoidin domain contains an amino acid substitution as compared to a wild-type or parental heterologous RS1 polypeptide; for example, an engineered Rs1 gene includes a nucleotide sequence that encodes a discoidin domain of a human RS1 polypeptide, which discoidin domain contains an amino acid substitution as compared to a wild-type human RS1 polypeptide. In some embodiments, a discoidin domain of an RS1 polypeptide encoded by an engineered Rs1 gene as described herein includes one or more amino acid substitutions as compared to a wild-type or parental RS1 polypeptide. Thus, in some embodiments, an engineered Rs1 gene of a non-human animal as described herein encodes an RS1 polypeptide characterized by a discoidin domain that includes an amino acid substitution (e.g., a variant RS1 polypeptide).

In some embodiments, a non-human animal comprising in its genome a deletion, in whole or in part, of the coding sequence of an endogenous Rs1 gene at an endogenous Rs1 locus is provided. In some embodiments, a deletion results in the lack of a functional RS1 polypeptide made from an Rs1 locus. In some embodiments, a deletion is of at least exons 2-3. In some certain embodiments, a deletion is of at least a portion of exon 1 and exons 2-3. In some embodiments, a deletion is or comprises the nucleotides of an endogenous Rs1 gene spanning immediately 3' of the start (ATG) codon to the last six nucleotides of exon three, inclusive. In some embodiments, an Rs1 locus comprising a deletion further comprises a reporter gene. In some embodiments, a reporter gene is operably linked to an Rs1 promoter. In some embodiments, an Rs1 promoter is an endogenous Rs1 promoter (e.g., the endogenous Rs1 promoter at the Rs1 locus comprising a deletion). In some embodiments, an Rs1 promoter is a heterologous Rs1 promoter.

In some embodiments, an Rs1 locus lacks (or includes a deletion of) a portion of exon 1 and exons 2-3, e.g., lacks the nucleotides from immediately 3' of the start (ATG) codon through exon 2 to the last six nucleotides of exon 3, and comprises a reporter gene coding sequence that is fused in-frame to the start (ATG) codon of the Rs1 locus. In some certain embodiments, a reporter gene coding sequence (e.g., the coding sequence of a lacZ gene) is operably linked to (or under the transcriptional control of) an endogenous Rs1 promoter at the Rs1 locus.

In some embodiments, a reporter gene is a lacZ gene. In some embodiments, a reporter is selected from the group consisting of luciferase, green fluorescent protein (GFP), enhanced GFP (eGFP), cyan fluorescent protein (CFP), yellow fluorescent protein (YFP), enhanced yellow fluorescent protein (eYFP), blue fluorescent protein (BFP), enhanced blue fluorescent protein (eBFP), DsRed, and MmGFP. In some embodiments, expression pattern of a reporter gene resembles the expression pattern of an Rs1 gene (e.g., a wild-type Rs1 gene at an Rs1 locus). In some embodiments, expression of a reporter gene resembles the expression pattern of a wild-type or parental RS1 polypeptide.

In some embodiments, a non-human animal is provided whose genome comprises an engineered Rs1 gene, which engineered Rs1 gene comprises one or more point mutations in an exon and encodes an RS1 polypeptide having one or more amino acid substitutions as compared to a wild type RS1 polypeptide. An RS1 polypeptide having one or more amino acid substitutions as compared to a wild type RS1 polypeptide is also referred to herein as a variant or mutant RS1 polypeptide.

In some embodiments, the amino acid substitutions described herein result in elimination or significant reduction in the level of functional RS1 polypeptide produced in a non-human animal due to, for example, protein misfolding which may result in the aggregation of variant (or mutant) RS1 polypeptide localized in the endoplasmic reticulum of a non-human animal as described herein, defective disulfide-linked subunit assembly, and inability of RS1 polypeptide to be inserted into the membrane of the ER as part of the protein secretion process.

In some embodiments, a variant RS1 polypeptide includes an amino acid substitution in the signal sequence, for example, a substitution of a hydrophobic residue with proline or with a hydrophilic or charged residue.

In some embodiments, a variant RS1 polypeptide includes an amino acid substitution in the regions flanking the discoidin domain, i.e., in the RS1 region and the C-terminal segment of an RS1 polypeptide. In some embodiments, a variant RS1 polypeptide includes a substitution of a cysteine at a position selected from the group consisting of 38, 40, 59 and 223. In some embodiments, a variant RS1 polypeptide includes a C59S substitution.

In some embodiments, a variant RS1 polypeptide includes an amino acid substitution in the discoidin domain. In some embodiments, a variant RS1 polypeptide includes a substitution of a cysteine at a position selected from the group consisting of 63, 83, 110, 142 and 219 with a non-cysteine residue. In other embodiments, a variant RS1 polypeptide includes a substitution of a non-cysteine residue in the discoidin domain with cysteine. In specific embodiments, the substitution is an R141C substitution. In some embodiments, a variant RS1 polypeptide includes a substitution in the discoidin domain of a charged residue with a non-charged residue, a non-charged residue with a charged residue, or a charged residue with a reversely charged residue. In other embodiments, a variant RS1 polypeptide includes a substitution in the discoidin domain by insertion or removal of proline (i.e., replacing a proline residue with another residue, or vice versa). In still other embodiments, a variant RS1 polypeptide includes a substitution in the discoidin domain by insertion or removal of a polar residue (i.e., replacing a polar residue with a non-polar residue, or vice versa).

In some embodiments, a non-human animal is provided that expresses an RS1 polypeptide that includes an amino acid substitution; in some certain embodiments, a C59S or R141C substitution. In some embodiments, an engineered Rs1 gene comprises a point mutation in exon three and encodes an RS1 polypeptide having a C59S substitution; in some certain embodiments, a point mutation in exon three is or comprise a codon change of TGT to AGT. In some embodiments, an engineered Rs1 gene comprises a point mutation in exon five and encodes an RS1 polypeptide having a R141C substitution; in some certain embodiments, a point mutation in exon five is or comprises a codon change of CGC to TGC.

In some embodiments, a non-human animal disclosed herein is a male animal. A male animal comprising a disruption or mutation in an Rs1 gene at an endogenous Rs1 locus on the X chromosome is also understood to be hemizygous for the disruption or mutation.

In some embodiments, a provided non-human animal is a female animal. In some embodiments, a female non-human animal is homozygous or heterozygous for a deletion in an Rs1 gene at an endogenous Rs1 locus as described herein. In some embodiments, a female non-human animal is homozygous or heterozygous for an engineered (or mutant) Rs1 gene as described herein which, in some embodiments, is at an endogenous Rs1 locus.

In some embodiments, an engineered Rs1 gene further comprises one or more selection markers. In some embodiments, an engineered Rs1 gene further comprises one or more site-specific recombinase recognition sites. In some embodiments, an engineered Rs1 gene further comprises a recombinase gene and a selection marker flanked by the one or more site-specific recombinase recognition sites, which site-specific recombinase recognition sites are oriented to direct an excision.

In some embodiments, one or more site-specific recombinase recognition sites include loxP, lox511, lox2272, lox2372, lox66, lox71, loxM2, lox5171, FRT, FRT11, FRT71, attp, att, FRT, Dre, rox, or a combination thereof. In some embodiments, a recombinase gene is selected from the group consisting of Cre, Flp (e.g., Flpe, Flpo) and Dre. In some certain embodiments, one or more site-specific recombinase recognition sites are lox (e.g., loxP) sites, and a recombinase gene encodes a Cre recombinase.

In some embodiments, a recombinase gene is operably linked to a promoter that drives expression of the recombinase gene in differentiated cells and does not drive expression of the recombinase gene in undifferentiated cells. In some embodiments, a recombinase gene is operably linked to a promoter that is transcriptionally competent and developmentally regulated.

In some embodiments of a recombinase gene operably linked to a promoter, the promoter is selected from the group consisting of protamine (Prot; e.g., Prot1 or Prot5), Blimp1, Blimp1 (1 kb fragment), Blimp1 (2 kb fragment), Gata6, Gata4, Igf2, Lhx2, Lhx5, and Pax3. In some embodiments of a recombinase gene operably linked to a promoter, the promoter is or comprises SEQ ID NO:30, SEQ ID NO:31, or SEQ ID NO:32. In some embodiments of a recombinase gene operably linked to a promoter, the promoter is or comprises SEQ ID NO:30.

In some embodiments, a selectable marker is selected from group consisting of neomycin phosphotransferase ($neo^R$), hygromycin B phosphotransferase ($hyg^R$), puromycin-N-acetyltransferase ($puro^R$), blasticidin S deaminase ($bsr^R$), xanthine/guanine phosphoribosyl transferase (gpt), and Herpes simplex virus thymidine kinase (HSV-tk). In some embodiments, a selectable marker is under the transcriptional control of a promoter selected from the group consisting of an UbC promoter, Ubi promoter, hCMV promoter, mCMV promoter, CAGGS promoter, EF1 promoter, pgk1 promoter, beta-actin promoter, and a ROSA26 promoter. In some certain embodiments, a selectable marker is $neo^R$ or $hyg^R$ and is under the transcriptional control of a Ubi promoter.

In some embodiments, a provided non-human animal develops one or more signs, symptoms and/or conditions of (or associated with) Retinoschisis.

In some embodiments, an isolated non-human cell or tissue is provided whose genome comprises (i) a deletion, in whole or in part, of the coding sequence in an endogenous Rs1 gene at an endogenous Rs1 locus, or (ii) an engineered Rs1 gene comprising one or more point mutations in an exon and encodes an RS1 polypeptide having one or more amino acid substitutions wherein the engineered Rs1 gene is in some embodiments at an endogenous Rs1 locus. In some embodiments, a cell is a lymphocyte. In some embodiments, a cell is selected from a B cell, dendritic cell, macrophage, monocyte, and a T cell. In some embodiments, a cell is derived from or related to a cell type of the eye or retina. In some certain embodiments, a cell is an eye ganglion cell, bipolar cell, amacrine cell, horizontal cell, cone cell, rod cell or retinal pigment epithelial cell. In some embodiments, a tissue is selected from adipose, bladder, brain, breast, bone marrow, eye, heart, intestine, kidney, liver, lung, lymph node, muscle, pancreas, plasma, serum, skin, spleen, stomach, thymus, testis, ovum, and a combination thereof. In some certain embodiments, eye tissue is selected from the sclera, choroid or retina.

In some embodiments, an immortalized cell made, generated, produced or obtained from an isolated non-human cell or tissue as described herein is provided.

In some embodiments, a non-human embryonic stem cell is provided, whose genome comprises (i) a deletion, in whole or in part, of the coding sequence in an endogenous Rs1 gene at an Rs1 locus, or (ii) an engineered Rs1 gene comprising one or more point mutations in an exon and encodes an RS1 polypeptide having one or more amino acid substitutions wherein the engineered Rs1 gene is in some embodiments at an endogenous Rs1 locus. In some embodiments, a non-human embryonic stem cell is a rodent embryonic stem cell. In some certain embodiments, a rodent embryonic stem cell is a mouse embryonic stem cell and is from a 129 strain, C57BL strain, or a mixture thereof. In some certain embodiments, a rodent embryonic stem cell is a mouse embryonic stem cell and is a mixture of 129 and C57BL strains. In some certain embodiments, a rodent embryonic stem cell is a mouse embryonic stem cell and is from a C57BL strain whose genome lacks a $Crb1^{rd8}$ mutation (i.e., whose genome comprises a wild-type Crbs1 gene). In some embodiments, a non-human ES cell as described herein comprises any one of SEQ ID NO:23, SEQ ID NO:26 and SEQ ID NO:28. In some embodiments, a non-human ES cell as described herein comprises any one of SEQ ID NO:33, SEQ ID NO:34, SEQ ID NO:36, SEQ ID NO:37, SEQ ID NO:39 and SEQ ID NO:40.

In some embodiments, use of a non-human embryonic stem cell as described herein to make a non-human animal is provided. In some certain embodiments, a non-human ES cell is a mouse ES cell and is used to make a mouse comprising (i) a deletion, in whole or in part, of the coding sequence in an endogenous Rs1 gene at an Rs1 locus, or (ii) an engineered Rs1 gene comprising one or more point mutations in an exon and encodes an RS1 polypeptide having one or more amino acid substitutions as described herein wherein the engineered Rs1 gene is in some embodiments at an endogenous Rs1 locus. In some certain embodiments, a non-human ES cell is a rat ES cell and is used to make a rat comprising (i) a deletion, in whole or in part, of the coding sequence in an endogenous Rs1 gene at an Rs1 locus, or (ii) an engineered Rs1 gene comprising one or more point mutations in an exon and encodes an RS1 polypeptide having one or more amino acid substitutions as described herein wherein the engineered Rs1 gene is in some embodiments at an endogenous Rs1 locus.

In some embodiments, a non-human embryo made, produced, generated, or obtained from a non-human ES cell as described herein is provided. In some certain embodiments, a non-human embryo is a rodent embryo; in some embodiments, a mouse embryo; in some embodiments, a rat embryo. In some certain embodiments, a provided non-human embryo comprises SEQ ID NO:25, SEQ ID NO:27 or SEQ ID NO:29. In some certain embodiments, a provided non-human embryo comprises SEQ ID NO:35, SEQ ID NO:38 or SEQ ID NO:41.

In some embodiments, use of a non-human embryo described herein to make a non-human animal is provided. In some certain embodiments, a non-human embryo is a mouse embryo and is used to make a mouse comprising (i) a deletion, in whole or in part, of the coding sequence in an endogenous Rs1 gene at an Rs1 locus, or (ii) an engineered Rs1 gene comprising one or more point mutations in an exon and encodes an RS1 polypeptide having one or more amino acid substitutions as described herein wherein the engineered Rs1 gene is in some embodiments at an endogenous Rs1 locus. In some certain embodiments, a non-human embryo is a rat embryo and is used to make a rat comprising (i) a deletion, in whole or in part, of the coding sequence in an endogenous Rs1 gene at an Rs1 locus, or (ii) an engineered Rs1 gene comprising one or more point mutations in an exon and encodes an RS1 polypeptide having one or more amino acid substitutions as described herein wherein the engineered Rs1 gene is in some embodiments at an endogenous Rs1 locus.

In some embodiments, a kit comprising a non-human animal, an isolated non-human cell or tissue, an immortalized cell, a non-human ES cell, or a non-human embryo as described herein is provided. In some embodiments, a kit as described herein for use in the manufacture and/or development of a drug (e.g., an antibody or antigen-binding fragment thereof) for therapy or diagnosis is provided. In some embodiments, a kit as described herein for use in the manufacture and/or development of a drug (e.g., an antibody or antigen-binding fragment thereof) for the treatment, prevention or amelioration of a disease, disorder or condition is provided.

In some embodiments, a nucleic acid construct or targeting vector as described herein is provided. In some certain embodiments, a provided nucleic acid construct or targeting vector comprises an Rs1 gene (or locus), in whole or in part, as described herein. In some certain embodiments, a provided nucleic acid construct or targeting vector comprises a DNA fragment that includes an Rs1 gene (or locus), in whole or in part, as described herein. In some embodiments, a nucleic acid construct is provided that comprises a nucleic acid sequence to be integrated into a rodent Rs1 gene at a rodent Rs1 locus, flanked by a 5' nucleotide sequence and a 3' nucleotide sequence that are homologous to nucleotide sequences at the rodent Rs1 locus, wherein integration of the nucleic acid sequence into the rodent Rs1 gene results in (i) a deletion, in whole or in part, of the coding sequence of the rodent Rs1 gene, or (ii) an engineered Rs1 gene that encodes an RS1 polypeptide having an amino acid substitution. In some embodiments, the nucleic acid sequence to be integrated comprises a reporter gene and the integration of the nucleic acid sequence results in a deletion of a portion of exon 1 and exons 2-3. In some embodiments, the nucleic acid sequence to be integrated comprises a mutant Rs1 exon such that integration of the nucleic acid sequence into a rodent Rs1 gene results in an engineered Rs1 gene that encodes an RS1 polypeptide having an amino acid substitution. In some certain embodiments, a provided nucleic acid construct or targeting vector comprises any one of SEQ ID NO:23, SEQ ID NO:26 and SEQ ID NO:28. In some certain embodiments, a provided nucleic acid construct or targeting vector comprises SEQ ID NO:33 and SEQ ID NO:35, SEQ ID NO:36 and SEQ ID NO:37, or SEQ ID NO:39 and SEQ ID NO:40. In some certain embodiments, a provided nucleic acid construct or targeting vector comprises one or more selection markers. In some certain embodiments, a provided nucleic acid construct or targeting vector comprises one or more site-specific recombination sites (e.g., loxP, Frt, or combinations thereof). In some certain embodiments, a provided nucleic acid construct or targeting vector is depicted in the Drawings.

In some embodiments, use of a nucleic acid construct or targeting vector as described herein to make a non-human ES cell, non-human cell, non-human embryo and/or non-human animal is provided.

In some embodiments, a method of making a non-human animal is provided, the method comprising (a) introducing a nucleic acid sequence into the genome of a non-human embryonic stem cell so that (i) the coding sequence of an endogenous Rs1 gene at an Rs1 locus is deleted, in whole or in part, or (ii) an exon of an endogenous Rs1 gene at an Rs1 locus is mutated to encode an RS1 polypeptide that includes an amino acid substitution; which nucleic acid sequence comprises a polynucleotide that is homologous to a sequence at the Rs1 locus; (b) obtaining a genetically modified non-human embryonic stem cell from (a); and (c) creating a non-human animal using the genetically modified non-human embryonic stem cell of (b).

In some embodiments of a method of making a non-human animal, an exon three of an Rs1 gene is mutated to encode an RS1 polypeptide that includes a C59S substitution. In some certain embodiments of a method of making a non-human animal, an exon three of an Rs1 gene is mutated to encode an RS1 polypeptide that includes a C59S substitution, a 25 bp deletion is made in intron two of an Rs1 gene and a 28 bp deletion is made in intron three of an Rs1 gene. In some embodiments of a method of making a non-human animal, an exon five of an Rs1 gene is mutated to encode an RS1 polypeptide that includes an R141C substitution. In some embodiments of a method of making a non-human animal, an exon five of an Rs1 gene is mutated to encode an RS1 polypeptide that includes an R141C substitution, a 10 bp deletion is made in intron four of an Rs1 gene and a 29 bp deletion is made in intron five of an Rs1 gene. In some embodiments of a method of making a non-human animal, a portion of exon 1 and exons 2-3 of the coding sequence in an Rs1 locus are deleted. In some certain embodiments of a method of making a non-human animal, 13,716 bp of an Rs1 gene at an Rs1 locus are deleted.

In some embodiments of a method of making a non-human animal, a nucleic acid sequence further comprises one or more selection markers. In some embodiments of a method of making a non-human animal, a nucleic acid sequence further comprises one or more site-specific recombinase recognition sites. In some embodiments of a method of making a non-human animal, a nucleic acid sequence further comprises a recombinase gene and a selection marker flanked by the one or more site-specific recombinase recognition sites, which site-specific recombinase recognition sites are oriented to direct an excision. In some embodiments of a method of making a non-human animal, a nucleic acid sequence further comprises a reporter gene that is downstream of the selection marker.

In some embodiments of a method of making a non-human animal, a recombinase gene is operably linked to a promoter that drives expression of the recombinase gene in differentiated cells and does not drive expression of the recombinase gene in undifferentiated cells. In some embodiments of a method of making a non-human animal, a recombinase gene is operably linked to a promoter that is transcriptionally competent and developmentally regulated.

In some embodiments of a method of making a non-human animal, the method further comprises a step of breeding the non-human animal generated in (c) so that a non-human animal homozygous for the deletion, or homozygous for the or mutant (or engineered) Rs1 gene, is created.

In some embodiments, a method of making a non-human animal is provided, the method comprising modifying a non-human animal genome so that the modified genome comprises (i) a deletion, in whole or in part, of the coding sequence of an endogenous Rs1 gene at an endogenous Rs1 locus, or (ii) an engineered Rs1 gene that encodes an RS1 polypeptide having an amino acid substitution wherein the engineered Rs1 gene is in some embodiments at an endogenous Rs1 locus; and making a non-human animal comprising the modified genome. In some embodiments, a non-human animal genome is modified by utilizing embryonic stem (ES) cells; i.e., the genome of an ES cell is modified, and the ES cell with a modified genome is used to make a non-human animal comprising the modified genome. In some embodiments of a method of making a non-human animal, the genome is modified so that it comprises an engineered Rs1 gene that encodes an RS1 polypeptide having a C59S or R141C substitution. In some embodiments of a method of making a non-human animal, the genome is modified so that it comprises a deletion of at least a portion of exon 1 and exons 2-3 of the coding sequence in the Rs1 locus; in some certain embodiments, so that it comprises a deletion of 13,716 bp in the Rs1 gene at an Rs1 locus.

In some embodiments, a non-human animal made, generated, produced, obtained or obtainable from a method as described herein is provided.

In some embodiments, a method of identifying a therapeutic agent for the treatment of Retinoschisis (or a disease, disorder or condition associated with the eye) in non-human animal, the method comprising (a) administering one or more agents to a non-human animal whose genome comprises (i) a deletion, in whole or in part, of the coding sequence of an endogenous Rs1 gene at an Rs1 locus, or (ii) an engineered Rs1 gene that encodes an RS1 polypeptide having an amino acid substitution wherein the engineered Rs1 gene is in some embodiments at an endogenous Rs1 locus; (b) performing one or more assays to determine if the one or more agents has an effect on one or more signs, symptoms and/or conditions associated with Retinoschisis (or a disease, disorder or condition associated with the eye); and (c) identifying the one or more agents that has an effect on the one or more signs, symptoms and/or conditions associated with Retinoschisis (or a disease, disorder or condition associated with the eye) as the therapeutic agent.

In some embodiments, a non-human animal is provided whose genome comprises a reporter gene operably linked to the start (ATG) codon of an Rs1 gene, wherein the reporter gene is located in the place of a portion of exon 1 and exons 2-3 of the Rs1 gene resulting in the deletion of 13,716 bp of the Rs1 gene sequence.

In some embodiments, a non-human animal is provided whose genome comprises an engineered Rs1 gene characterized by the presence of a point mutation in exon three of TGT to AGT, a 25 bp deletion in intron two, and a 28 bp deletion in intron three, which engineered Rs1 gene encodes an RS1 polypeptide having a C59S substitution.

In some embodiments, a non-human animal is provided whose genome comprises an engineered Rs1 gene characterized by the presence of a point mutation in exon five of CGC to TGC, a 10 bp deletion in intron four, and a 29 bp deletion in intron five, which engineered Rs1 gene encodes an RS1 polypeptide having a R141C substitution.

In some embodiments, a non-human animal model of Retinoschisis is provided, which non-human animal expresses or produces an RS1 polypeptide having an amino acid substitution as described herein.

In some embodiments, a non-human animal model of Retinoschisis is provided, which non-human animal has a genome comprising an engineered Rs1 gene as described herein.

In some embodiments, a non-human animal model of Retinoschisis is provided, which non-human animal has a genome comprising a deletion, in whole or in part, of the coding sequence in an Rs1 gene (or locus) as described herein.

In some embodiments, a non-human animal model of Retinoschisis is provided, obtained by providing a non-human animal, which non-human animal (i) has a genome comprising an engineered Rs1 gene as described herein, (ii) has a genome comprising a deletion, in whole or in part, of the coding sequence in an Rs1 gene (or locus) as described herein, or (iii) expresses an RS1 polypeptide having an amino acid substitution as described herein; thereby providing said non-human animal model of Retinoschisis.

In some embodiments, a non-human animal or cell as described herein is provided for use in the manufacture and/or development of a drug for therapy or diagnosis.

In some embodiments, a non-human animal or cell as described herein is provided for use in the manufacture of a medicament for the treatment, prevention or amelioration of a disease, disorder or condition.

In some embodiments, use of a non-human animal or cell as described herein in the manufacture and/or development of a drug or vaccine for use in medicine, such as use as a medicament, is provided.

In some embodiments, use of a non-human animal or cell as described herein in the manufacture and/or development of gene therapy drug for Retinoschisis is provided.

In some embodiments, a disease, disorder or condition is Retinoschisis. In some embodiments, a disease, disorder or condition is an eye-related disease, disorder or condition or results from deletion of Rs1 function and/or activity.

In various embodiments, one or more phenotypes as described herein is or are as compared to a reference or control. In some embodiments, a reference or control includes a non-human animal having a modification as described herein, a modification that is different than a modification as described herein, or no modification (e.g., a wild type non-human animal).

In various embodiments, a non-human animal as described herein is a rodent; in some embodiments, a mouse; in some embodiments, a rat. In some embodiments, a mouse as described herein is selected from the group consisting of a 129 strain, a BALB/C strain, a C57BL/6 strain, and a mixed 129×C57BL/6 strain; in some certain embodiments, a C57BL/6 strain.

BRIEF DESCRIPTION OF THE DRAWING

The patent or application file contains at least one drawing executed in color. Copies of this patent or patent application publication with color drawing(s) will be provided by the Office upon request and payment of the necessary fee.

The Drawing included herein, which is composed of the following Figures, is for illustration purposes only and not for limitation.

FIGS. 16A-16F illustrate early-onset phenotypes of $Rs1^{KO}$ mice in ERG and OCT analysis. Outer retinal function was evaluated by dark-adapted (DA-)(A and D) and light-adapted (LA-) (B and E) full-field ERGs, which show reduced b-wave relative to a-wave, resulting in negative ERG (quantification data not shown) in all time points. Retinoschisis phenotype was present throughout the observation time course (P15-P24) (C and F, indicated by yellow triangles).

FIG. 20 show the alignment of mouse, rat and human RS1 polypeptides (SEQ ID NO: 2, SEQ ID NO: 4, and SEQ ID NO: 8, respectively). The signal sequence is underlined. The positions where the sequences differ are identified by "*".

DEFINITIONS

Figure 1:
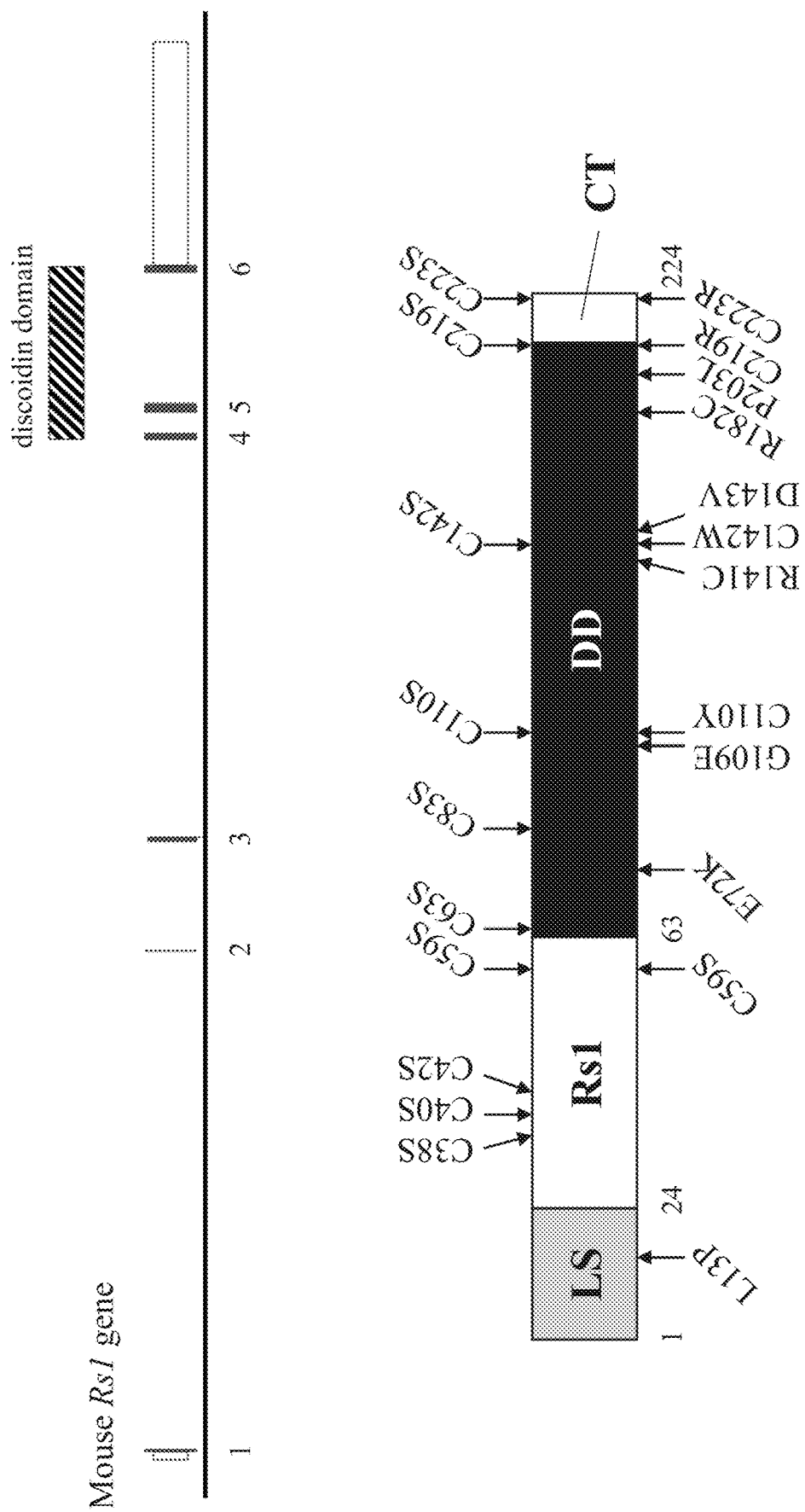
FIG. 1 shows a diagram, not to scale, of the organization of a non-human (e.g., mouse) retinoschisin-1 (Rs1) gene (top) and gene product (bottom). Top: exons are numbered below each exon, untranslated regions (open boxes) and coding sequences (vertical slashes) are also indicated. Bottom: leader sequence (LS), Rs1 domain (Rs1), discoidin domain (DD) and C-terminal region (CT) are indicated along with the location of selected cysteine and disease-linked missense mutations (adapted from FIG. 1 of Wu, W. W. H. et al., 2003, J. Biol. Chem. 278(30):28139-146).

Disruption: In some embodiments, a disruption may achieve or represent an insertion, deletion, substitution, replacement, missense mutation, or a frame-shift of a DNA sequence(s), or any combination thereof. Insertions may include the insertion of entire genes or fragments of genes, e.g., exons, which may be of an origin other than the endogenous sequence (e.g., a heterologous sequence). In some embodiments, a disruption may increase expression and/or activity of a gene or gene product (e.g., of a protein encoded by a gene). In some embodiments, a disruption may decrease expression and/or activity of a gene or gene product. In some embodiments, a disruption may alter sequence of a gene or an encoded gene product (e.g., an encoded polypeptide). In some embodiments, a disruption may truncate or fragment a gene or an encoded gene product (e.g., an encoded protein). In some embodiments, a disruption may extend a gene or an encoded gene product. In some such embodiments, a disruption may achieve assembly of a fusion polypeptide. In some embodiments, a disruption may affect level, but not activity, of a gene or gene product. In some embodiments, a disruption may affect activity, but not level, of a gene or gene product. In some embodiments, a disruption may have no significant effect on level of a gene or gene product. In some embodiments, a disruption may have no significant effect on activity of a gene or gene product. In some embodiments, a disruption may have no significant effect on either level or activity of a gene or gene product.

Non-human animal: as used herein, refers to any vertebrate organism that is not a human. In some embodiments, a non-human animal is a cyclostome, a bony fish, a cartilaginous fish (e.g., a shark or a ray), an amphibian, a reptile, a mammal, and a bird. In some embodiments, a non-human animal is a mammal. In some embodiments, a non-human mammal is a primate, a goat, a sheep, a pig, a dog, a cow, or a rodent. In some embodiments, a non-human animal is a rodent such as a rat or a mouse.

Substantial homology: as used herein, refers to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues with appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution. Typical amino acid categorizations are summarized below.

| | | | | | |
|---|---|---|---|---|---|
| Alanine | Ala | A | Nonpolar | Neutral | 1.8 |
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

| Ambiguous Amino Acids | 3-Letter | 1-Letter |
|---|---|---|
| Asparagine or aspartic acid | Asx | B |
| Glutamine or glutamic acid | Glx | Z |
| Leucine or Isoleucine | Xle | J |
| Unspecified or unknown amino acid | Xaa | X |

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, S. F. et al., 1990, J. Mol. Biol., 215(3): 403-410; Altschul, S. F. et al., 1997, Methods in Enzymology; Altschul, S. F. et al., 1997, Nucleic Acids Res., 25:3389-3402; Baxevanis, A. D., and B. F. F. Ouellette (eds.) Bioinformatics: A Practical Guide to the Analysis of Genes and Proteins, Wiley, 1998; and Misener et al. (eds.) Bioinformatics Methods and Protocols (Methods in Molecular Biology, Vol. 132), Humana Press, 1998. In addition to identifying homologous sequences, the programs mentioned above typically provide an indication of the degree of homology. In some embodiments, two sequences are considered to be substantially homologous if at least 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 9, 10, 11, 12, 13, 14, 15, 16, 17 or more residues. In some embodiments, the relevant stretch includes contiguous residues along a complete sequence. In some embodiments, the relevant stretch includes discontinuous residues along a complete sequence, for example, non-contiguous residues brought together by the folded conformation of a polypeptide or a portion thereof. In some embodiments, the relevant stretch is at least 10, 15, 20, 25, 30, 35, 40, 45, 50, or more residues.

Substantial identity: as used herein, refers to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, S. F. et al., 1990, J. Mol. Biol., 215(3): 403-10; Altschul, S. F. et al., 1996, Meth. Enzymol. 266:460-80; Altschul, S. F. et al., 1997, Nucleic Acids Res., 25:3389-402; Baxevanis, A. D. and B. F. F. Ouellette (eds.) Bioinformatics: A Practical Guide to the Analysis of Genes and Proteins, Wiley, 1998; and Misener et al. (eds.) Bioinformatics Methods and Protocols, Methods in Molecular Biology, Vol. 132, Humana Press, 1998. In addition to identifying identical sequences, the programs mentioned above typically provide an indication of the degree of identity. In some embodiments, two sequences are considered to be substantially identical if at least 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, or more residues.

Targeting vector or targeting construct: as used herein, refers to a polynucleotide molecule that comprises a targeting region. A targeting region comprises a sequence that is identical or substantially identical to a sequence in a target cell, tissue or animal and provides for integration of the targeting construct (and/or a sequence contained therein) into a position within the genome of the cell, tissue or animal via homologous recombination. Targeting regions that target into a position of the cell, tissue or animal via recombinase-mediated cassette exchange using site-specific recombinase recognition sites (e.g., loxP or Frt sites) are also included. In some embodiments, a targeting construct as described herein further comprises a nucleic acid sequence or gene (e.g., a reporter gene, homologous gene, heterologous gene, or mutant gene) of particular interest, a selectable marker, control and/or regulatory sequences, and other nucleic acid sequences that encode a recombinase or recombinogenic polypeptide. In some embodiments, a targeting construct may comprise a gene of interest in whole or in part, wherein the gene of interest encodes a polypeptide, in whole or in part, that has a similar function as a protein encoded by an endogenous sequence. In some embodiments, a targeting construct may comprise a mutant gene of interest, in whole or in part, wherein the mutant gene of interest encodes a variant polypeptide, in whole or in part, that has a similar function as a polypeptide encoded by an endogenous sequence. In some embodiments, a targeting construct may comprise a reporter gene, in whole or in part, wherein the reporter gene encodes a polypeptide that is easily identified and/or measured using techniques known in the art.

Variant: as used herein, refers to an entity that shows significant structural identity with a reference entity, but differs structurally from the reference entity in the presence or level of one or more chemical moieties as compared with the reference entity. In some embodiments, a "variant" also differs functionally from its reference entity. For example, a "variant polypeptide" may differ from a reference polypeptide as a result of one or more differences in amino acid sequence and/or one or more differences in chemical moieties (e.g., carbohydrates, lipids, etc.) covalently attached to the polypeptide backbone. In some embodiments, a "variant polypeptide" shows an overall sequence identity with a reference polypeptide that is at least 85%, 86%, 87%, 88%, 89%, 90%, 91%, 92%, 93%, 94%, 95%, 96%, 97%, or 99%. Alternatively, or additionally, in some embodiments, a "variant polypeptide" does not share at least one characteristic sequence element with a reference polypeptide. In some embodiments, the reference polypeptide has one or more biological activities. In some embodiments, a "variant polypeptide" shares one or more of the biological activities of the reference polypeptide. In some embodiments, a "variant polypeptide" lacks one or more of the biological activities of the reference polypeptide. In some embodiments, a "variant polypeptide" shows a reduced level of one or more biological activities as compared with the reference polypeptide. In some embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 15%, 10%, 9%, 8%, 7%, 6%, 5%, 4%, 3%, or 2% of the residues in the variant are substituted as compared with the parent. In some embodiments, a "variant" has 10, 9, 8, 7, 6, 5, 4, 3, 2, or 1 substituted residue(s) as compared with a parent. Often, a "variant" has a very small number (e.g., fewer than 5, 4, 3, 2, or 1) number of substituted functional residues (i.e., residues that participate in a particular biological activity). Furthermore, a "variant" typically has not more than 5, 4, 3, 2, or 1 additions or deletions, and often has no additions or deletions, as compared with the parent. Moreover, any additions or deletions are typically fewer than about 10, about 9, about 8, about 7, about 6, and commonly are fewer than about 5, about 4, about 3, or about 2 residues. In some embodiments, a parent or reference polypeptide is one found in nature. As will be understood by those of ordinary skill in the art, a plurality of variants of a particular polypeptide of interest may commonly be found in nature, particularly when the polypeptide of interest is an infectious agent polypeptide.

DETAILED DESCRIPTION OF CERTAIN EMBODIMENTS

Non-human animals such as rodents (e.g., mice or rats) are provided having disruption or mutation(s) in the genetic material encoding a Retinoschisin-1 (RS1) polypeptide. In particular, non-human animals having a deletion, in whole or in part, of the coding sequence of an Rs1 gene that results in a mutant Rs1 gene that fails to produce an RS1 polypeptide in the non-human animal are provided. Also provided are non-human animals having one or more mutations in a coding sequence of an Rs1 gene that results in a mutant Rs1 gene encoding a variant or mutant RS1 polypeptide that includes one or more amino acid substitutions as compared to a wild type RS1 polypeptide (i.e., the RS1 polypeptide encoded by the Rs1 gene without the mutations). Such one or more amino acid substitutions, as described herein, result in elimination or significant reduction in functional RS1 polypeptide produced and the formation of pathological and functional features associated with Retinoschisis (e.g., X-linked Retinoschisis, XLRS) in the non-human animals. Therefore, the non-human animals disclosed herein are particularly useful for the development and identification of therapeutic candidates for the treatment and/or amelioration of Retinoschisis. Such non-human animals provide a source of cells for identifying and developing therapeutics (e.g., gene therapies) for the treatment and/or amelioration of Retinoschisis. Further, such non-human animals provide the capacity for a useful animal model system for the development of therapeutics for the treatment of eye-related diseases, disorders and conditions related thereto.

In some embodiments, non-human animals described herein are male animals. In some embodiments, non-human animals described herein are female animals. In some embodiments, non-human animals described herein are female animals heterozygous for a disruption or mutation(s) in an Rs1 gene as described herein. In some embodiments, non-human animals described herein are female animals homozygous for a disruption or mutation(s) in an Rs1 gene as described herein.

Various aspects of the present disclosure are described in detail in the following sections. The use of such sections is not intended to be limiting. Each section can apply to one or more embodiments described herein. In this application, use of "or" means "and/or" unless stated otherwise.

Retinoschisin-1 and Retinoschisis

Retinoschisin-1 is a small gene that is about 32.4 kb long containing six exons and five introns located on chromosome Xp22.2, and encodes a 3.1 kb mRNA that is translated into a 224-amino acid precursor polypeptide termed Retinoschisin. Retinoschisin is expressed as a monomer containing four different domains: N-terminal signal sequence (23 amino acids) directing protein translocation to the exterior of the cell; a unique Rs1 domain (a long/highly conserved sequence motif 39 amino acids in length); a discoidin domain (157 amino acids), contributing to the adhesive function of RS1 to preserve the retinal cell architecture and to establish proper synaptic connectivity; and a C-terminal segment (5 amino acids).

Retinoschisin is assembled in the endoplasmic reticulum and secreted as functional disulfide-linked homo-octamer (eight subunits joined together by Cys59-Cys223 disulfide bonds. Subunits within the octamer are further organized into dimers mediated by Cys(40)-Cys(40) disulfide bonds. RS1 is bound by ionic forces to the outer leaflet of the photoreceptor inner segment plasma membrane, and function in cell-cell interactions and cell adhesion. RS1 is expressed in the retina, prominently by the rod and cone inner segments, and bipolar cells, and pineal gland. Immunostaining in the retina localizes Retinoschisin to the inner segments of photoreceptors, bipolar cells and the inner and outer plexiform layers. High sequence homology exists in human, mouse, rat and rabbit (96% identity and 97.8% similarity between mouse and human; see, also, FIG. 20).

Retinoschisis is a severe eye disease classified into degenerative, hereditary, tractional and exudative forms. In particular, X-linked juvenile Retinoschisis (XLRS), a hereditary form of Retinoschisis, is an early onset macular degeneration characterized by loss in visual acuity, abnormal splitting of the neurosensory layers of the retina and a reduction of the b-wave in an electroretinogram (ERG). XLRS is caused by mutations in the Retinoschisin-1 (RS1) gene and is transmitted in an X-linked recessive pattern that causes disease only in males. Mutations in the RS1 gene product result in the complete absence of an RS1 polypeptide, or the production of a defective RS1 polypeptide having reduced or no function. Almost 200 mutations of the RS1 gene have been reported to be associated with XLRS, and manifests in a phenotype that is highly variable across individuals (e.g., reviewed in Kim, D. Y. and S. Mukai, 2013, Sem. Ophthalmol. 28(5-6):392-6). Of the almost 200 mutations reported, about 40% of the disease-causing mutations are nonsense or frame shift mutations, which are predicted to result in the absence of a full-length polypeptide. About 50% (100/191) of disease causing mutations, however, are missense mutation, which allow for production of full-length mutant polypeptide (Molday, R. S. et al., 2012, Prog. Retin. Eye Res. 31:195-212). Most of these mutations (85/191) are found in the discoidin domain and result in a functionally incompetent misfolded polypeptide.

There is a spectrum of phenotypes for XLRS. Cyctic Macular Lesions involving the fovea are characteristic clinical features of XRLS. In particular, foveal schisis with "cartwheel" or "spoke-wheel" pattern is a characteristic finding on fundus exam, presenting in nearly 100% of cases, and schisis may occur peripherally in up to 50% of patients or retinal detachments. Peripheral schisis can lead to holes and tears of the inner leaf with potential for hemorrhage from unsupported crossing vessels. Additional peripheral changes include pigmentation resembling retinitis pigmentosa, retinal fibrosis and white flecks, and vitreo-retinal dystrophy. ERGs show marked b-wave reduction, and abnormal a-wave in some patients, but in many, a-wave remains normal.

The clinical presentation of XLRS and course of disease is variable presenting as early as at birth to later at school age with only mild visual symptoms. These variations and clinical severity do not appear to correlate with genotype, and female carriers are asymptomatic. Currently, spectral domain OCT (SD-OCT) is the major diagnostic technique for this disease, while existing management options are limited to low vision aids. Carbonic anhydrase inhibitors (CAIs, topical and oral, approved for use in glaucoma) have shown improvement in visual acuity in about 50% of eyes treated in small studies reported.

Non-Human Animals Having a Mutant or Engineered Rs1 Gene

Although significant progress in the understanding of XLRS has been achieved, much of the precise mechanisms of XLRS remains unknown. The present disclosure is based on the creation of improved in vivo systems for generating and developing treatments for XLRS that rely on unique genetic structures not currently present in established systems. Thus, the present disclosure is based on the recognition that improved in vivo systems for generating and developing treatments for XLRS can be provided by generating genetic alterations in an endogenous Rs1 locus in a non-human animal such as a rodent (e.g., a mouse). As described herein, the present disclosure specifically demonstrates, among other things, exemplary strategies of creating Rs1-deficient and Rs1-engineered (e.g., mutant Rs1) non-human animals (e.g., rodent animals such as a mouse) that recapitulate a human XLRS disease phenotype. Without wishing to be bound by any particular theory, the strategies described herein can be employed to create other Rs1-deficient and/or Rs1-engineered non-human animals as desired. For example, Rs1-engineered non-human animals may be created to contain engineered Rs1 genes containing mutations, or combinations of mutations, other than those described in the Examples section below. Examples of mutations that can be engineered into an endogenous Rs1 gene can be found in the X-linked Retinoschisis sequence variation database (RETINOSCHISISDB©).

In some embodiments, the non-human animals disclosed herein have a deletion in the genome, in whole or in part, of the coding sequence of the Rs1 gene at an endogenous Rs1 locus that results in the lack of a functional RS1 polypeptide being produced in the non-human animals. In some embodiments, the deletion includes at least exons 2-3 of the Rs1 gene. Exon 2 encodes amino acids 18-26 of the RS1 polypeptide (with amino acids 18-23 being the last 5 amino acids of the signal sequence). Exon 3 encodes amino acids 27-61 of the RS1 polypeptide. In some embodiments, the deletion includes at least a portion of exon 1 and exons 2-3 of the Rs1 gene. For example, the portion of exon 1 that begins from immediately 3' of the ATG start codon to the 3' end of exon 1 and encodes amino acids 2-17 of the RS1 polypeptide can be included in the deletion. In specific embodiments, the deletion is of a contiguous genomic fragment beginning immediately after the ATG start codon in exon 1, through exon 2, to the 3' end of exon 3 or to the six nucleotides at the 3' end of exon 3 of the Rs1 gene.

In some of the embodiments where the Rs1 locus has a deletion, in whole or in part, of the coding sequence of the Rs1 gene, the Rs1 locus includes a reporter gene. In some embodiments, the reporter gene is operably linked to an Rs1 promoter, e.g., the endogenous Rs1 promoter at the Rs1 locus that has a deletion, in whole or in part, of the coding sequence of the Rs1 gene. In some embodiments, the Rs1 locus has a deletion of a contiguous genomic fragment beginning immediately after the ATG start codon in exon 1 to the 3' end of exon 3 (or to the six nucleotides at the 3' end of exon 3) of the Rs1 gene, and the coding sequence of the reporter gene is fused in frame to the ATG start codon of the Rs1 gene. As a result of an operable linkage to the endogenous Rs1 promoter at the Rs1 locus, the expression of the reporter gene resembles the expression pattern of the Rs1 gene. Reporter genes suitable for use herein include, for example, lacZ, and genes encoding a reporter protein such as luciferase, green fluorescent protein (GFP), enhanced GFP (eGFP), cyan fluorescent protein (CFP), yellow fluorescent protein (YFP), enhanced yellow fluorescent protein (eYFP), blue fluorescent protein (BFP), enhanced blue fluorescent protein (eBFP), DsRed, and MmGFP.

In other embodiments, the non-human animals disclosed herein have one or more point mutations in the coding sequence of an Rs1 gene (e.g., an endogenous Rs1 gene or a heterologous Rs1 gene) that results in a variant RS1 polypeptide that includes one or more amino acid substitutions relative to the wild type RS1 polypeptide (encoded by the Rs1 gene without the point mutations); for example, a variant rodent (e.g., mouse or rat) RS1 polypeptide that includes one or more amino acid substitutions relative to the wild type rodent RS1 polypeptide, or a variant human RS1 polypeptide includes one or more amino acid substitutions relative to the wild type human RS1 polypeptide.

The amino acid substitutions described herein result in elimination or significant reduction in the level of functional RS1 polypeptide produced from an Rs1 mutant allele (i.e., an Rs1 gene having a deletion or a point mutation). Amino acid substitutions can lead to elimination or significant reduction in the level of functional RS1 polypeptide produced as a result of, for example, misfolding of a polypeptide, defective subunit or oligomer assembly, and inability of a polypeptide to be inserted into the membrane of the ER as part of the protein secretion process.

In some embodiments, an amino acid substitution is in the signal sequence that results in an inability of a variant RS1 polypeptide having the amino acid substitution to be inserted into the membrane of the ER for secretion. For example, substitution of hydrophobic residues in the signal sequence with proline or with hydrophilic/charged residues may prevent the signal sequence from adopting an α-helix secondary structure required for insertion into the ER membrane. In specific embodiments, the amino acid substitution is a substitution of L13 (e.g., L13P).

In some embodiments, an amino acid substitution is in the regions flanking the discoidin domain, i.e., the Rs1 region composed of amino acids 24-62 and the C-terminal segment (composed of amino acids 220-224). In specific embodiments, the substitution is a substitution of cysteine at position 38, 40, 42, 59 or 223 with a non-cysteine residue, e.g., Ser, Arg. Trp. Tyr or Gly. C40 is responsible for forming C40-C40 disulfide-linked dimers, and C59 and C223 form intermolecular disulfide bonds to permit assembly of RS1 dimers into octamer. Thus, substitution of Cys at 40, 59 or 223 may have only a limited effect on protein folding and secretion, yet still result in inability of a mutant RS1 polypeptide comprising such substitution to function as a cell adhesion protein. In some embodiments, cysteine at position 40, 59 or 223 has been substituted with Ser, Arg. Trp. Tyr or Gly. Specific examples of substitution include C38S, C40S, C42S, C59S, C223S, C223R and C223Y.

In other embodiments, an amino acid substitution is in the discoidin domain of the RS1 polypeptide, which is composed of amino acids 63-219.

In some embodiments, a substitution in the discoidin domain is a substitution of one of the five Cys residues in the discoidin domain: C63, C83, C110, C142, and C219. Cys63 and Cys219, and Cys110-Cys142, form two intramolecular disulfide bonds that are important for protein folding. In some embodiments, cysteine at one of positions 63, 83, 110, 142 or 219 has been substituted with a non-cysteine residue, e.g., Ser, Arg, Trp, Tyr or Gly. Specific examples of substitution include C63S, C83S, C110S, C110Y, C142S, C142R, C142W, C219S, C219R, C219W and C219G.

In some embodiments, a substitution in the discoidin domain is a substitution of an amino acid residue not directly involved in formation of disulfide bonds but important for protein folding, formation or stability of the discoidin domain, and/or intermolecular interactions among adjacent subunits. Examples of such residues include highly conserved, solvent inaccessible core residues such as E72, G109, E146, R182, and P203, as well as R141 and D143. In some specific embodiments, a substitution is one that replaces a non-cysteine residue with cysteine, which may affect thiol exchange; for example, W92C. W96C, R141C. R182C, R200C, P203C, and R209C. In some other specific embodiments, a substitution is one that affects protein charge by eliminating or reversing the charge of amino acid residues or by replacing a non-charged residue with a charged residue without affect thiol residues; for example, E72K, W96R, R102W, R102Q, G109E, G109R, R141H, D143V, N179D and R213W. In other embodiments, a substitution is one that may affect conformation stability by insertion or removal of Pro residues; for example, S73P, L127P, P192S, P192T, P193S and P203L. In still other embodiments, a substitution is one that may affect hydrophobic core by insertion or removal of polar residues (i.e., replacing a hydrophobic residue with a polar residue or replacing a polar residue with a hydrophobic residue); for example, I136T and N163Y.

In some embodiments, the non-human animals described herein comprise one or more point mutations in an Rs1 gene resulting in a substitution of cysteine [Cys, C] with serine [Ser, S], or substitution of arginine [Arg, R] with cysteine [Cys, C]) in the encoded RS1 polypeptide. In some certain embodiments, the substitution is a C59S substitution. In some certain embodiments, the substitution is a R141C substitution.

In some embodiments, non-human animals as described herein that comprise a disruption or mutation in an endogenous Rs1 gene or an engineered Rs1 gene further comprise genetic material from a heterologous species (e.g., a human). In some embodiments, non-human animals as described herein comprise an engineered Rs1 gene that is a mutant human Rs1 gene, wherein the mutant human Rs1 gene encodes a human RS1 polypeptide that includes a substitution described herein above, e.g., a C59S substitution or an R141C substitution. In some certain embodiments, non-human animals as described herein comprise a mutant human Rs1 gene that is randomly inserted into the genome of the non-human animal such that a human RS1 polypeptide is expressed that includes a substitution described herein above, e.g., a C59S substitution or an R141C substitution.

Retinoschisin-1 Sequences

Exemplary human and non-human Rs1 sequences are set forth in SEQ ID NOS: 1-22 and summarized in Table 1.

An exemplary self-deleting cassette employed for the disruption of a non-human (e.g., mouse) Rs1 allele including a lacZ reporter gene, a Cre recombinase gene under the transcriptional control of a mouse protamine 1 promoter and a neomycin resistance gene flanked by loxP sites under the transcriptional control of a ubiquitin promoter is set forth in SEQ ID NO: 23 (8,202 bp).

An exemplary deletion of a non-human (e.g., mouse) Rs1 allele (sequence of exons 1-3 deleted from an endogenous rodent Rs1 locus) is set forth in SEQ ID NO: 24 (13,716 bp).

An exemplary portion of a disrupted *Mus musculus* Rs1 allele after recombinase-mediated excision of a selection cassette is set forth in SEQ ID NO: 25.

An exemplary portion of a mutant non-human (e.g., mouse) Rs1 allele encoding a C59S amino acid substitution including a self-deleting hygromycin selection cassette is set forth in SEQ ID NO: 26.

An exemplary portion of a mutant non-human (e.g., mouse) Rs1 allele encoding a C59S amino acid substitution after recombinase-mediated excision of a selection cassette is set forth in SEQ ID NO: 27.

An exemplary portion of a mutant non-human (e.g., mouse) Rs1 allele encoding a R141C amino acid substitution including a self-deleting hygromycin selection cassette is set forth in SEQ ID NO: 28:

An exemplary portion of a mutant non-human (e.g., mouse) Rs1 allele encoding a R141C amino acid substitution after recombinase-mediated excision of a selection cassette is set forth in SEQ ID NO: 29.

TABLE 1

| SEQ ID NO | Description | Features |
|---|---|---|
| 1 | *Mus musculus* Rs1 mRNA (NCBI ref. seq. NM_011302) | Length: 5855 nt<br>Coding region: nt. 174-848<br>Exons 1-6: nt 1-225, 226-251, 252-357, 358-499, 500-695, 696-5840. |
| 2 | *Mus musculus* Rs1 amino acid (NCBI ref. seq. NP_035432) | Length: 224 aa<br>Signal sequence: aa 1-23 |
| 3 | *Rattus norvegicus* Rs1 mRNA (NCBI ref. seq. NM_001104643) | Length: 675 nt<br>Coding region: nt 1-675 |
| 4 | *Rattus norvegicus* Rs1 amino acid (NCBI ref. seq. NP_001098113) | Length: 224 aa<br>Signal sequence: aa 1-21 |
| 5 | *Macaca mulatta* RS1 mRNA (NCBI ref. seq. NM_001194911) | Length: 994 nt<br>Coding region: nt. 42-716 |
| 6 | *Macaca mulatta* RS1 amino acid (NCBI ref. seq. NP_001181840) | Length: 224 aa<br>Signal sequence: aa 1-21 |
| 7 | *Homo sapiens* RS1 mRNA (NCBI ref. seq. NM_000330) | Length: 3039 nt<br>Coding region: 36-710<br>Exons 1-6: 1-87, 88-113, 114-219, 220-360, 361-557, 558-3025. |
| 8 | *Homo sapiens* RS1 amino acid (NCBI ref. seq. NP_000321) | Length: 224 aa<br>Signal sequence: aa 1-23 |
| 9 | *Canis lupus familiaris* Rs1 mRNA (NCBI ref. seq. XM_548882) | Length: 2061 nt<br>Coding region: nt 89-763 |

TABLE 1-continued

| SEQ ID NO | Description | Features |
|---|---|---|
| 10 | *Canis lupus familiaris* Rs1 amino acid (NCBI ref. seq. XP_548882) | Length: 224 aa |
| 11 | *Sus scrofa* Rs1 mRNA (NCBI ref. seq. XM_013985956) | Length: 1772 nt<br>Coding region: nt 295-969 |
| 12 | *Sus scrofa* Rs1 amino acid (NCBI ref. seq. XP_013841410) | Length: 224 aa |
| 13 | *Bos taurus* Rs1 mRNA (NCBI ref. seq. XM_010822174) | Length: 899 nt<br>Coding region: nt. 45-719 |
| 14 | *Bos taurus* Rs1 amino acid (NCBI ref. seq. XP_010820476) | Length: 224 aa |
| 15 | *Ovis aries* RS1 mRNA (NCBI ref. seq. XM_012106316) | Length: 1604 nt<br>Coding region: nt 702-1337 |
| 16 | *Ovis aries* (sheep) RS1 amino acid (NCBI ref. seq. XP_011961706) | Length: 211 aa |
| 17 | *Felis catus* (cat) RS1 mRNA (NCBI ref. seq. XM_019823621) | Length: 4553 nt<br>Coding region: nt. 59-733 |
| 18 | *Felis catus* (cat) RS1 amino acid (NCBI ref. seq. XP_019679180) | Length: 224 aa |
| 19 | *Equus caballus* RS1 mRNA (NCBI ref. seq. XM_001491183) | Length: 1193 nt<br>Coding region: nt. 1-675 |
| 20 | *Equus caballus* RS1 amino acid (NCBI ref. seq. XP_001491233) | Length: 224 aa |
| 21 | *Oryctolagus cuniculus* RS1 mRNA (NCBI ref. seq. NM_001109823) | Length: 675 nt<br>Coding region: nt. 1-675 |
| 22 | *Oryctolagus cuniculus* RS1 amino acid (NCBI ref. seq. NP_001103293) | Length: 224 aa<br>Signal sequence: aa 1-21 |
| 23 | An exemplary self-deleting cassette employed for the disruption of a non-human (e.g., mouse) Rs1 allele including a lacZ reporter gene, a Cre recombinase gene under the transcriptional control of a mouse protamine 1 promoter and a neomycin resistance gene flanked by loxP sites under the transcriptional control of a ubiquitin promoter. | Length: 8,202 bp<br>loxP sites: nt. 3431-3464 and 8163-8196 |
| 24 | Exemplary deletion of a mouse Rs1 allele (comprising exon 1 in part and exons 2-3) | Length: 13,716 bp |
| 25 | Exemplary portion of a disrupted *Mus musculus* Rs1 allele after recombinase-mediated excision of a selection cassette. | Length: 3670 nt<br>Mouse sequences: nt 1-100 and 3571-3670<br>lacZ and remaining cloning sites: nt. 101-3570<br>loxP sequence: nt. 3531-3564 |
| 26 | Exemplary portion of a mutant mouse Rs1 allele encoding a C59S amino acid substitution including a self-deleting hygromycin selection cassette | Length: 5987 nt<br>Mouse sequences: nt. 1-755 and 5788-5987<br>Mutated codon: nt. 572-574<br>Exon 3: nt. 476-581<br>Targeting vector sequence: nt. 756-5787 |
| 27 | Exemplary portion of a mutant mouse Rs1 allele encoding a C59S amino acid substitution after recombinase-mediated excision of a selection cassette | Length: nt 1033 nt<br>Mouse sequences: nt. 1-755 and 834-1033<br>Mutated codon: nt. 572-574<br>Exon 3: nt. 476-581<br>Targeting vector sequence: nt. 756-833 |

TABLE 1-continued

| SEQ ID NO | Description | Features |
|---|---|---|
| 28 | Exemplary portion of a mutant mouse Rs1 allele encoding a R141C amino acid substitution including a self-deleting hygromycin selection cassette | Length: 5629 nt<br>Mouse sequences: nt. 1-497 and 5530-5629<br>Mutated codon: nt. 278-280<br>Exon 5: nt. 184-379<br>Targeting vector sequence: nt. 498-5529. |
| 29 | Exemplary portion of a mouse Rs1 allele encoding a R141C amino acid substitution after recombinase-mediated excision of a selection cassette | Length: 675 nt<br>Mouse sequences: nt. 1-497<br>Mutated codon: nt. 278-280<br>Exon 5: nt. 184-379<br>Targeting vector sequence: nt. 498-675. |
| 30 | Protamine 1 (Prm1) promoter | |
| 31 | Blimp1 promoter 1 kb | |
| 32 | Blimp1 promoter 2 kb | |
| 33-41 | Junction sequences in mutant Rs1 alleles described in Example 1 | |
| 42-59 | Primer and probe sequences described in Example 1 | |

Production of Non-Human Animals

Provided herein are DNA constructs, targeting vectors and methods for the production of non-human animals having a disruption or mutation(s) in an Rs1 gene as described herein.

DNA sequences can be used to prepare targeting vectors for knockout animals (e.g., an Rs1$^{KO}$). Typically, a polynucleotide molecule (e.g., an insert nucleic acid) encoding a reporter gene or a mutant (or engineered) Rs1 gene, in whole or in part, is inserted into a vector, preferably a DNA vector, in order to replicate the polynucleotide molecule in a suitable host cell.

A polynucleotide molecule (or insert nucleic acid) comprises a segment of DNA that one desires to integrate into a target locus or gene. In some embodiments, an insert nucleic acid comprises one or more polynucleotides of interest. In some embodiments, an insert nucleic acid comprises one or more expression cassettes. In some certain embodiments, an expression cassette comprises a polynucleotide of interest, a polynucleotide encoding a selection marker and/or a reporter gene along with, in some certain embodiments, various regulatory components that influence expression (e.g., promoter, enhancer, etc.). Virtually any polynucleotide of interest may be contained within an insert nucleic acid and thereby integrated at a target genomic locus. Methods disclosed herein provide for at least 1, 2, 3, 4, 5, 6 or more polynucleotides of interest to be integrated into a targeted Rs1 gene (or locus).

In some embodiments, a polynucleotide of interest contained in an insert nucleic acid encodes a reporter. In some embodiments, a polynucleotide of interest contained in an insert nucleic acid encodes a heterologous, variant or heterologous variant RS1 polypeptide. In some embodiments, a polynucleotide of interest contained in an insert nucleic acid encodes a selectable marker and/or a recombinase.

In some embodiments, a polynucleotide of interest is flanked by or comprises site-specific recombination sites (e.g., loxP. Frt, etc.). In some certain embodiments, site-specific recombination sites flank a DNA segment that encodes a reporter, a DNA segment that encodes a selectable marker, a DNA segment that encodes a recombinase, and combinations thereof. Exemplary polynucleotides of interest, including selection markers, reporter genes and recombinase genes that can be included within insert nucleic acids are described herein.

Depending on size, an Rs1 gene or RS1-encoding sequence as can be cloned directly from cDNA sources available from commercial suppliers or designed in silico based on published sequences available from GenBank (see above). Alternatively, bacterial artificial chromosome (BAC) libraries can provide Rs1 sequences from genes of interest (e.g., rodent or heterologous Rs1 genes). BAC libraries contain an average insert size of 100-150 kb and are capable of harboring inserts as large as 300 kb (Shizuya, H. et al., 1992, Proc. Natl. Acad. Sci., U.S.A. 89:8794-7; Swiatek, P. J. and T. Gridley, 1993, Genes Dev. 7:2071-84; Kim, U. J. et al., 1996, Genomics 34:213-8; herein incorporated by reference). For example, human and mouse genomic BAC libraries have been constructed and are commercially available (e.g., Invitrogen, Carlsbad, CA). Genomic BAC libraries can also serve as a source of rodent or heterologous Rs1 sequences as well as transcriptional control regions.

Alternatively, rodent or heterologous Rs1 sequences may be isolated, cloned and/or transferred from yeast artificial chromosomes (YACs). An entire rodent or heterologous Rs1 gene can be cloned and contained within one or a few YACs. If multiple YACs are employed and contain regions of overlapping homology, they can be recombined within yeast host strains to produce a single construct representing the entire locus. YAC arms can be additionally modified with mammalian selection cassettes by retrofitting to assist in introducing the constructs into embryonic stems cells or embryos by methods known in the art and/or described herein.

DNA constructs or targeting vectors containing Rs1 sequences as described herein, in some embodiments, comprise rodent Rs1 genomic sequences encoding a rodent RS1 polypeptide that includes one or more amino acid substitutions as compared to a wild-type or parent rodent RS1 polypeptide operably linked to non-human regulatory sequences (e.g., a rodent promoter) for expression in a genetically modified non-human animal. In some embodiments, DNA constructs or targeting vectors containing Rs1 sequences as described herein comprise rodent Rs1 genomic sequences encoding a variant rodent RS1 polypeptide that includes an amino acid substitution (e.g., C59S or R141C) as compared to a wild-type or parent rodent RS1 polypeptide operably linked to a rodent Rs1 promoter. Examples of desired amino acid substitutions are described herein. Rodent and/or heterologous sequences included in DNA constructs described herein may be identical or substantially identical with rodent and/or heterologous sequences found in nature (e.g., genomic). Alternatively, such sequences may be artificial (e.g., synthetic) or may be engineered by the hand of man. In some embodiments, Rs1 sequences are synthetic in origin and include a sequence or sequences that are found in a rodent or heterologous Rs1 gene found in nature. In some embodiments, Rs1 sequences comprise a sequence naturally associated with a rodent or heterologous Rs1 gene. In some embodiments, Rs1 sequences comprise a sequence that is not naturally associated with a rodent or heterologous Rs1 gene. In some embodiments, Rs1 sequences comprise a sequence that is optimized for expression in a non-human animal. If additional sequences are useful in optimizing expression of a mutant (or variant) Rs1 gene described herein, such sequences can be cloned using existing sequences as probes. Additional sequences necessary for maximizing expression of a mutant Rs1 gene or RS1-encoding sequence can be obtained from genomic sequences or other sources depending on the desired outcome.

DNA constructs or targeting vectors can be prepared using methods known in the art. For example, a DNA construct can be prepared as part of a larger plasmid. Such preparation allows for cloning and selection of the correct constructions in an efficient manner as known in the art. DNA fragments containing sequences as described herein can be located between convenient restriction sites on the plasmid so that they can be easily isolated from the remaining plasmid sequences for incorporation into the desired animal. Various methods employed in preparation of plasmids, DNA constructs and/or targeting vectors and transformation of host organisms are known in the art. For other suitable expression systems for both prokaryotic and eukaryotic cells, as well as general recombinant procedures, see Molecular Cloning: A Laboratory Manual, 2nd Ed., ed. by Sambrook, J. et al., Cold Spring Harbor Laboratory Press: 1989.

Figure 2:
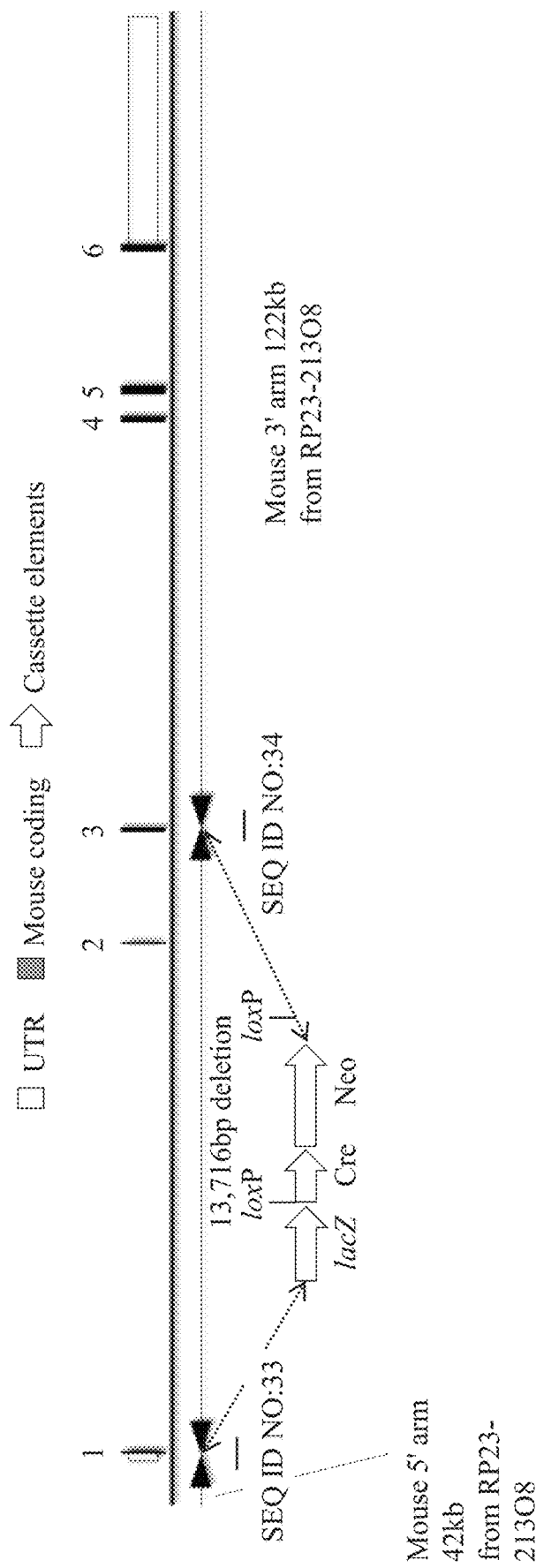
FIG. 2 shows a diagram, not to scale, of a targeting vector for creating a deletion in a Rs1 gene in a rodent as described in Example 1. A lacZ reporter gene is inserted in operable linkage to a mouse Rs1 start (ATG) codon in exon one and deletes the remaining portion of exon 1 to the last 6 nucleotides of exon 3 of the mouse Rs1 locus (13,716 bp deletion). The Rs1-lacZ-SDC targeting vector contains a self-deleting drug selection cassette (e.g., a neomycin resistance gene flanked by loxP sequences; see U.S. Pat. Nos. 8,697,851, 8,518,392 and 8,354,389, all of which are incorporated herein by reference). Upon homologous recombination, the sequence contained in the targeting vector is inserted in the place of exons 1-3 of an endogenous murine Rs1 locus as shown. The drug selection cassette is removed in a development-dependent manner, i.e., progeny derived from mice whose germ line cells containing a disruption in an Rs1 locus as described above will shed the selectable marker from differentiated cells during development. Con-secutive exons (vertical slashes) are indicated by number above each exon, and untranslated regions (open box) and coding sequence (closed slashes) are also indicated. lacZ: β-galactosidase gene; Cre: Cre recombinase gene; Neo: neomycin resistance gene.
Figure 3:
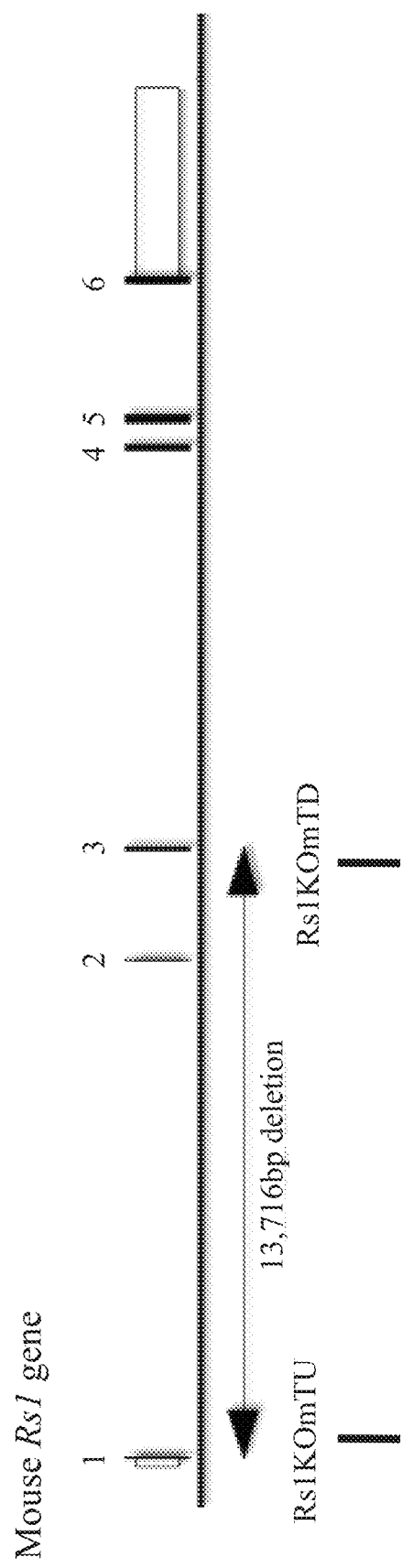
FIG. 3 shows a diagram, not to scale, of the genomic organization of a murine Rs1 gene illustrating an exemplary disruption (e.g., a 13,716 bp deletion of exons 1-3) as described in Example 1. Exons (closed slashes) are numbered above each exon, and untranslated regions (open boxes) are also indicated. Approximate locations of probes (i.e., Rs1KOmTU, Rs1KOmTD) employed in a screening assay described in Example 1 are indicated by thick vertical slashes.
Figure 4:
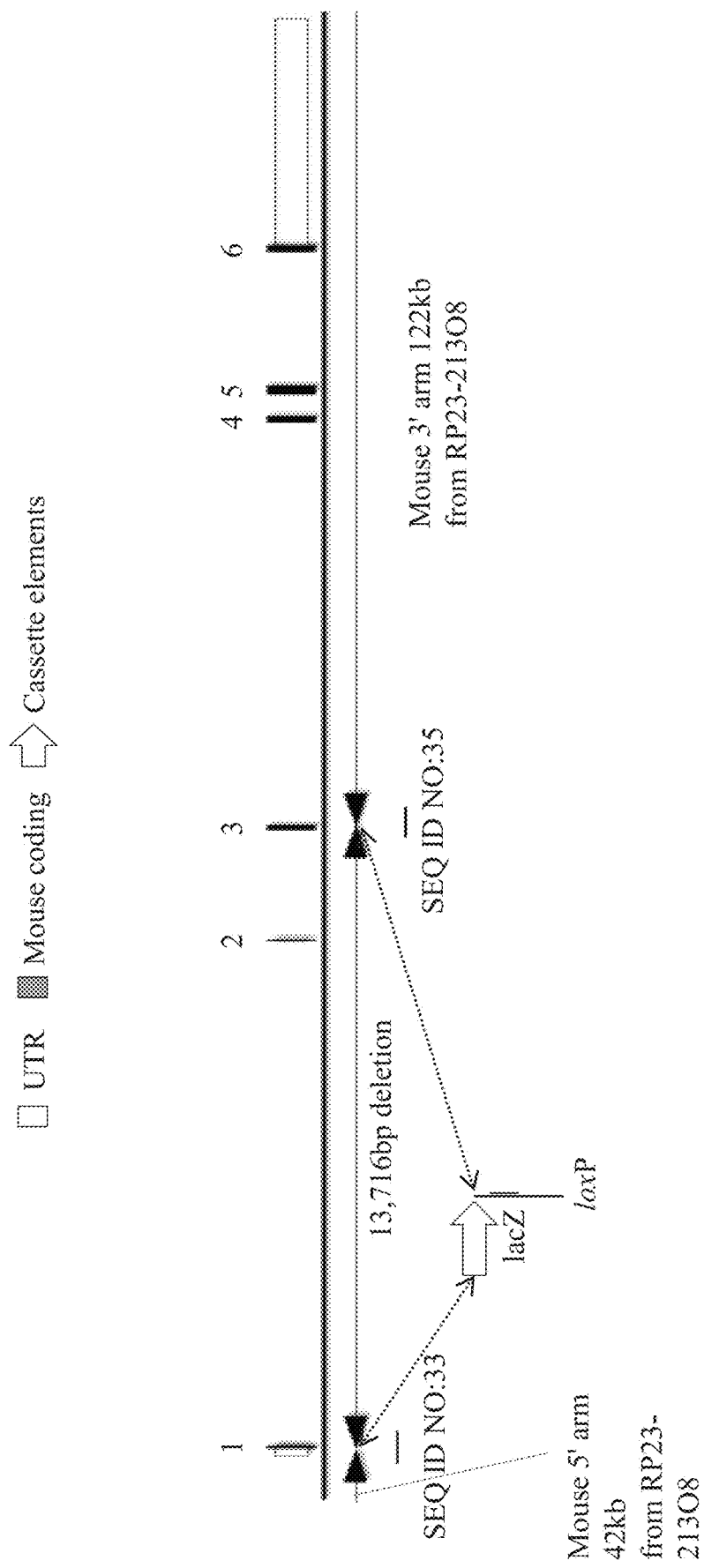
FIG. 4 shows a diagram, not to scale, of an exemplary disrupted murine Rs1 gene as described in Example 1. A deletion of exons 1-3 (13,716 bp deletion) of a mouse Rs1 locus is shown resulting from the insertion of a lacZ reporter gene operably linked to a mouse Rs1 start (ATG) codon. Exons (vertical slashes) are numbered above each exon, and untranslated regions (open box) and remaining coding sequence (striped rectangle) are also indicated. Locations of selected nucleotide junctions are marked with a line below each junction and indicated by SEQ ID NO.
Figure 5:
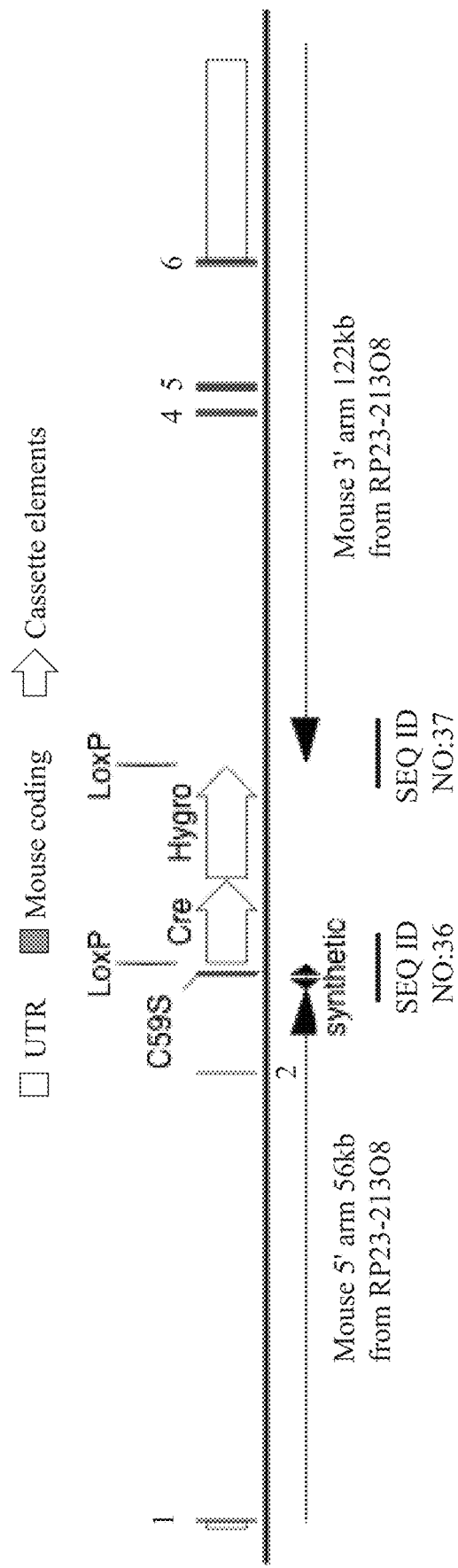
FIG. 5 shows a diagram, not to scale, of a targeting vector for creating a mutant Rs1 gene in a rodent (e.g., mouse) as described in Example 1. Consecutive exons (vertical slashes) are indicated by number above or below each exon. An exemplary point mutation in exon three (C59S; TGT to AGT) is indicated above exon three by insertion of a synthetic DNA fragment and cassette elements by homologous recombination. The Rs1C59S-SDC targeting vector contains a self-deleting drug selection cassette (e.g., a hygromycin resistance gene flanked by loxP sequences; see U.S. Pat. Nos. 8,697,851, 8,518,392 and 8,354,389, all of which are incorporated herein by reference). Upon homologous recombination, the synthetic DNA fragment contained in the targeting vector is inserted in the place of exon three of an endogenous murine Rs1 locus as shown. The drug selection cassette is removed in a development-dependent manner, i.e., progeny derived from mice whose germ line cells containing a disruption in an Rs1 locus as described above will shed the selectable marker from differentiated cells during development. Locations of selected nucleotide junctions are marked with a line below each junction and indicated by SEQ ID NO.
Figure 6:
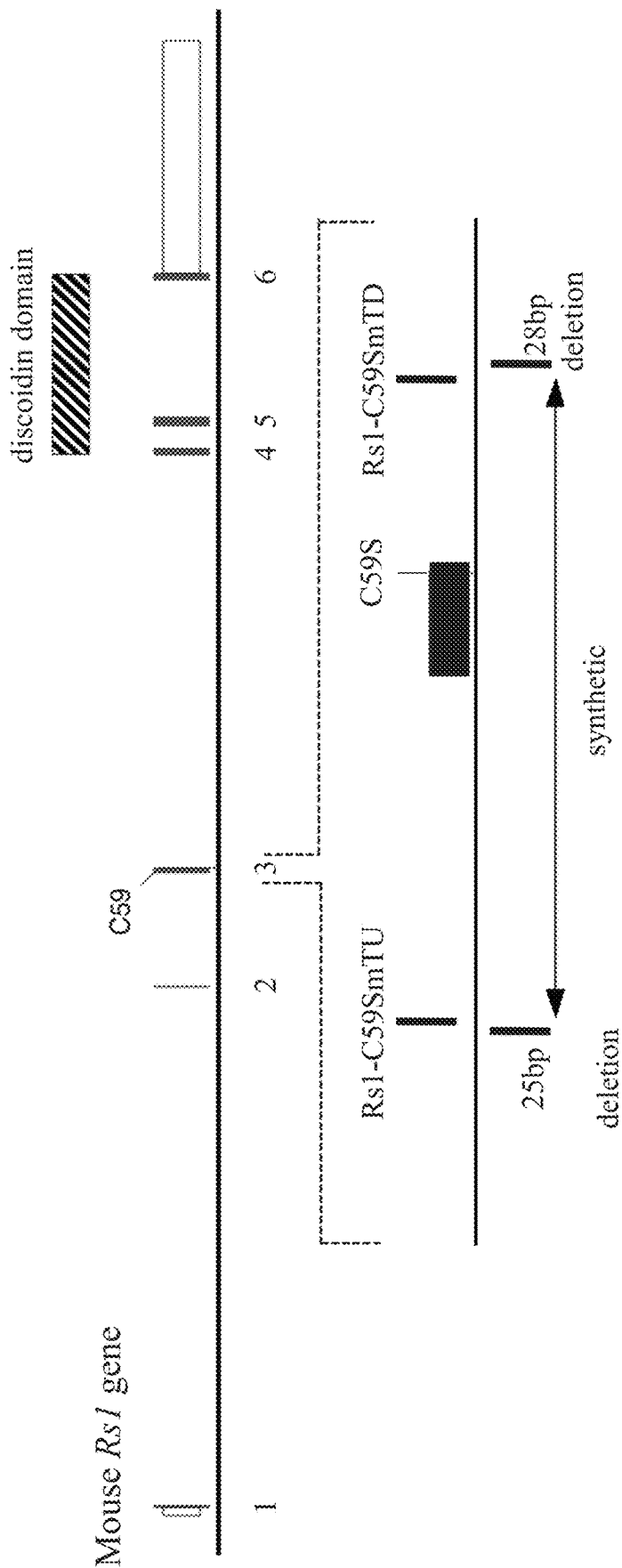
FIG. 6 shows a diagram, not to scale, of a close-up view of exon three of a mouse Rs1 gene and the design of the mutant Rs1 gene illustrated in FIG. 5 (see also Example 1). Exon three (black rectangle) with the targeted point mutation (C59S) and surrounding introns are shown along with two small deletions designed to fall over TAQMAN® assays. Integration of the targeting vector by homologous recombination results in an exon three that encodes a portion of an RS1 polypeptide having a C59S substitution and two small deletions (25 bp and 28 bp) in the surrounding introns in the mutant Rs1 gene. Approximate location of probes (i.e., Rs1-C59SmTU and Rs1-C59SmTD) employed in a screening assay described in Example 1 are indicated by thick vertical slashes.

As described above, exemplary non-human Rs1 nucleic acid and amino acid sequences for use in constructing targeting vectors for non-human animals containing a disrupted or engineered Rs1 gene are provided above. Other non-human Rs1 sequences can also be found in the GenBank database. Rs1 targeting vectors, in some embodiments, comprise DNA sequences encoding a reporter gene, a selectable marker, a recombinase gene (or combinations thereof) and non-human Rs1 sequences (i.e., flanking sequences of a target region) for insertion into the genome of a transgenic non-human animal. In one example, a deletion start point may be set of immediately downstream (3') of a start codon to allow an insert nucleic acid to be operably linked to an endogenous regulatory sequence (e.g., a promoter). FIGS. 2-4 illustrate an exemplary method and targeting vector for making a targeted deletion of a portion of the coding sequence (e.g., exons 1-3) a murine Rs1 gene, excluding the start codon, and replacement with a cassette that contains a sequence from a lacZ gene that encodes β-galactosidase and a drug selection cassette that encodes neomycin phosphotransferase (Neo) for the selection of G418-resistant embryonic stem (ES) cell colonies. The targeting vector also includes a sequence encoding a recombinase (e.g., Cre) regulated by an ES-cell specific micro RNAs (miRNAs) or a germ-cell specific promoter (e.g., protamine 1 promoter; Prot-Cre-SV40). The neomycin selection cassette and Cre recombinase-encoding sequences are flanked by loxP recombinase recognition sites that enable Cre-mediated excision of the neomycin selection cassette in a development-dependent manner, i.e., progeny derived from rodents whose germ cells contain the disrupted Rs1 gene described above will shed the selectable marker during development (see U.S. Pat. Nos. 8,697,851, 8,518,392, 8,354,389, 8,946, 505, and 8,946,504, all of which are herein incorporated by reference). This allows for, among other things, automatic excision of the neomycin selection cassette from either differentiated cells or germ cells. Thus, prior to phenotypic analysis the neomycin selection cassette is removed leaving only the lacZ reporter gene (fused to the mouse Rs1 start codon) operably linked to the murine Rs1 promoter (FIG. 4).

Methods for generating non-human animals as described herein employ the use of self-deleting selection cassette technology (see U.S. Pat. Nos. 8,697,851, 8,518,392 and 8,354,389, all of which are incorporated herein by reference). The use of this technology allows for the drawbacks from the presence of selection cassettes in the genome of non-human animals, which facilitate selection of drug-resistant clones, to be avoided. Such self-deleting selection cassette technology is characterized, in some embodiments, by the inclusion of a promoter that is operably linked to a recombinase gene within the targeting vector. The promoter is transcriptionally competent such that the promoter regulates expression of the recombinase gene in a developmentally-dependent fashion due to promoter activity restricted to undifferentiated cells (i.e., ES cells; for transcriptional competence see also, e.g., Ram, R. and E. Meshorer, 2009, Genes Dev. 23:2793-98; Xu, J. et al., 2009, Genes Dev. 23:2824-38). As a result, the recombinase polypeptide is only expressed after the ES cell beings to differentiate (i.e., develop). ES cells that have incorporated a targeting vector as described herein retain the selection cassette due to inactivity of the promoter that controls expression of (i.e., operably inked to) the recombinase gene, but promote excision of the selection cassette once the ES cells begin to differentiate as a result of commencement of recombinase expression. Thus, by design, progeny developing from an ES cell containing the targeting vector within their genome express the recombinase at an early developmental stage and the selectable marker is excised upon differentiation (i.e., development) mediated by action of the recombinase polypeptide on the site-specific recombinase recognition sites flanking the selection cassette.

Suitable promoters that are inactive in undifferentiated ES cells are provided herein. Operably linking such promoters to a recombinase gene provides for expression specifically upon differentiation. As described herein, targeting vectors are designed with site-specific recombinase recognition sites in a parallel orientation flanking a selection marker so that the recombinase polypeptide directs an excision (i.e., deletion) of the selectable marker upon expression. Site-specific recombinase recognition sites may also be placed in inverted orientation flanking a selection marker so that the recombinase polypeptide directs an inversion of the selectable marker upon expression. For some selectable markers, inversion may be sufficient for inactivation. However, complete removal of the selectable marker may also be desired. When a selection cassette is flanked by site-specific recombinase recognition sites in a parallel orientation, expression of the recombinase polypeptide in a differentiated cell will cause the cell to excise the selectable marker from the genome. If the differentiated cells are maintained in selection, they will die due to deletion of the selectable marker from the genome. In this way, undifferentiated ES cells are maintained and enriched in culture for later use as donor cells to a host embryo.

As described herein, disruption of an Rs1 gene can comprise a replacement of or an insertion/addition to the Rs1 gene or a portion thereof with an insert nucleic acid. In some embodiments, an insert nucleic acid comprises a reporter gene. In some certain embodiments, a reporter gene is positioned in operable linkage with an endogenous Rs1 promoter. Such a modification allows for the expression of a reporter gene driven by an endogenous Rs1 promoter. Alternatively, a reporter gene is not placed in operable linkage with an endogenous Rs1 promoter and is operably linked to another promoter.

A variety of reporter genes (or detectable moieties) can be used in targeting vectors described herein. Exemplary reporter genes include, for example, β-galactosidase (encoded lacZ gene), Green Fluorescent Protein (GFP), enhanced Green Fluorescent Protein (eGFP), MmGFP, blue fluorescent protein (BFP), enhanced blue fluorescent protein (eBFP), mPlum, mCherry, tdTomato, mStrawberry, J-Red, DsRed, mOrange, mKO, mCitrine, Venus, YPet, yellow fluorescent protein (YFP), enhanced yellow fluorescent protein (eYFP), Emerald, CyPet, cyan fluorescent protein (CFP), Cerulean, T-Sapphire, luciferase, alkaline phosphatase, or a combination thereof. The methods described herein demonstrate the construction of targeting vectors that employ a lacZ reporter gene that encodes β-galactosidase, however, persons of skill upon reading this disclosure will understand that non-human animals described herein can be generated in the absence of a reporter gene or with any reporter gene known in the art.

Figure 7:
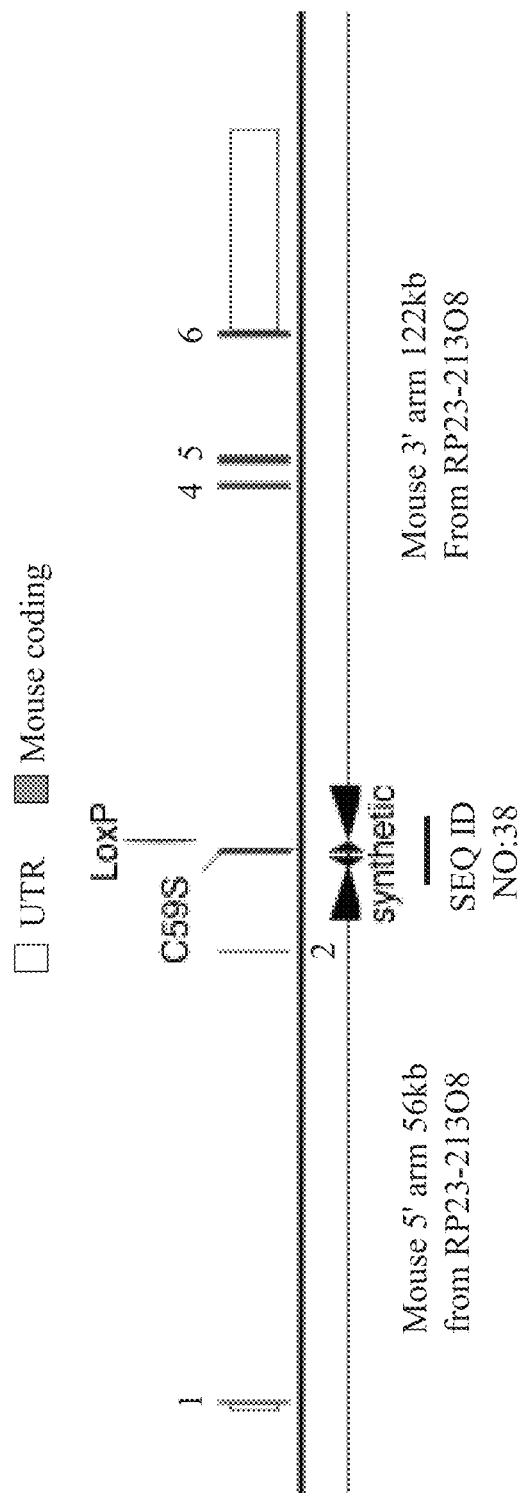
FIG. 7 shows a diagram, not to scale, of a close-up view of a mutant Rs1 gene in a rodent (e.g., mouse) created after recombinase-mediated excision of the cassette contained within the targeting vector described in Example 1. Exon three with the point mutation resulting in a C59S substitution in the Rs1 gene product is shown with a remaining loxP site. Location of the nucleotide junction that remained after recombinase-mediated excision of the cassette is marked with a line below the junction and indicated by SEQ ID NO.
Figure 9:
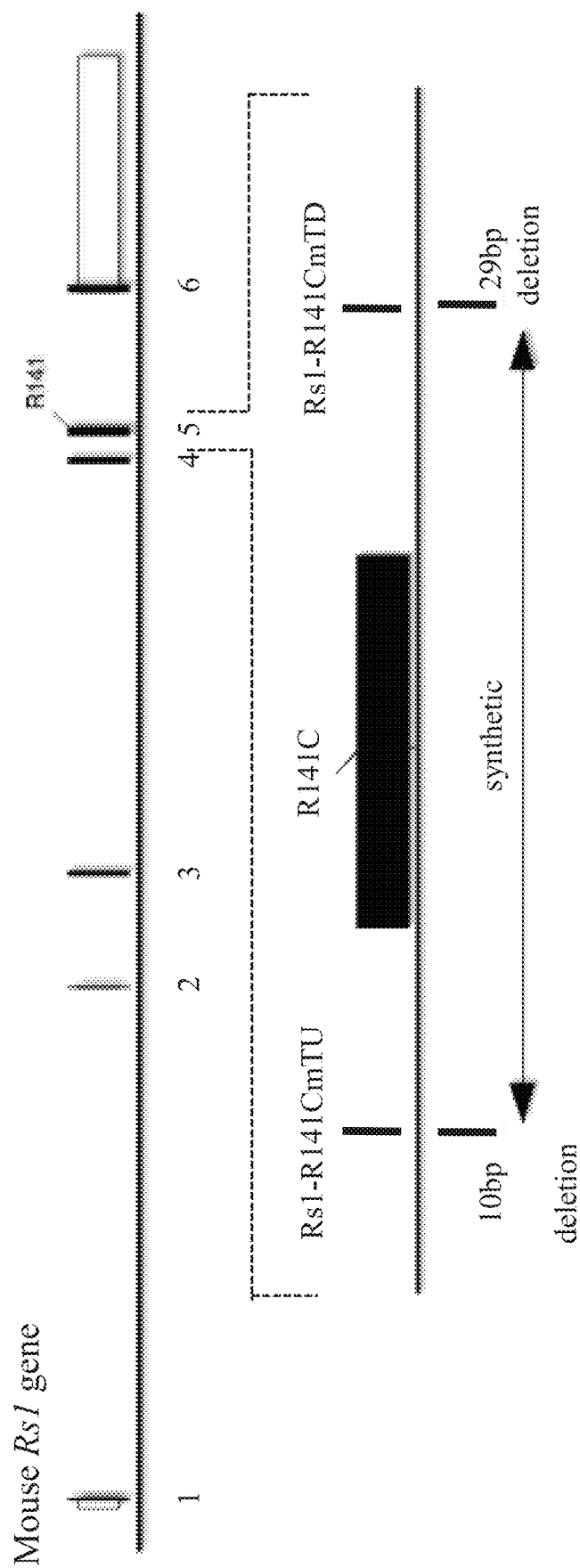
FIG. 9 shows a diagram, not to scale, of a close-up view of exon five of a mouse Rs1 gene and the design of the mutant Rs1 gene illustrated in FIG. 8 (see also Example 1). Exon five (black rectangle) with the targeted point mutation (R141C) and surrounding introns are shown along with two small deletions designed to fall over TAQMAN® assays. Integration of the targeting vector by homologous recombination results in an exon five that encodes a portion of an RS1 polypeptide having a R141C substitution and two small deletions (10 bp and 29 bp) in the surrounding introns in the mutant Rs1 gene. Approximate location of probes (i.e., Rs1-R141CmTU and Rs1-R141CmTD) employed in a screening assay described in Example 1 are indicated by thick vertical slashes.
Figure 10:
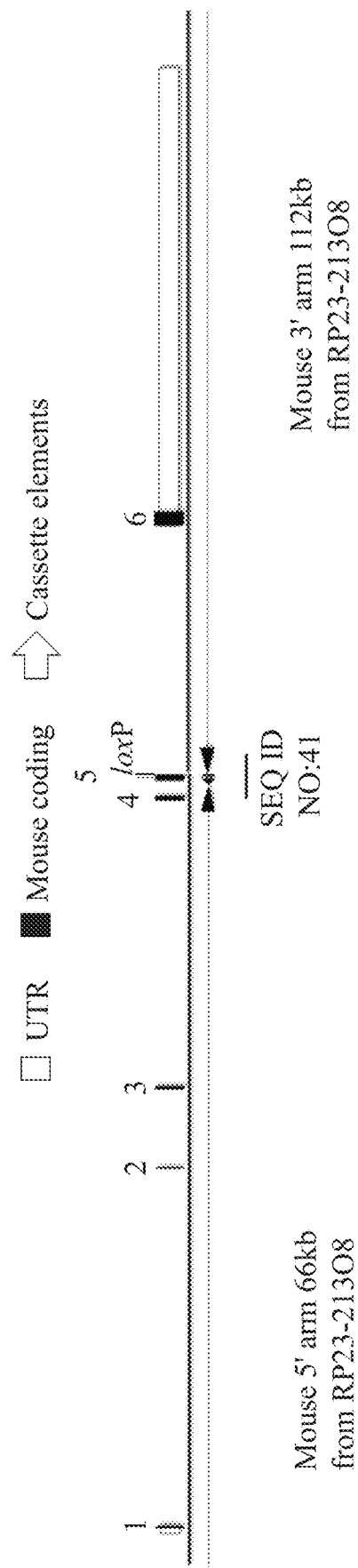
FIG. 10 shows a diagram, not to scale, of a close-up view of a mutant Rs1 gene in a rodent (e.g., mouse) created after recombinase-mediated excision of the cassette contained within the targeting vector described in Example 1. Exon five with the point mutation resulting in a R141C substitution in the Rs1 gene product is shown with a remaining loxP site. Location of the nucleotide junction that remained after recombinase-mediated excision of the cassette is marked with a line below the junction and indicated by SEQ ID NO.

Rs1 targeting vectors, in some embodiments, comprise DNA sequences encoding a mutant (or variant) Rs1 gene, a selectable marker and a recombinase, and non-human Rs1 sequences (i.e., flanking sequences of a target region) for insertion into the genome of a transgenic non-human animal. In one example, one or more point mutations may be introduced (e.g., by site-directed mutagenesis) into the coding sequence of an Rs1 gene or RS1-encoding sequence (e.g., an exon) so that a desired RS1 polypeptide (e.g., a variant RS1 polypeptide) is encoded by the mutant Rs1 gene or RS1-encoding sequence. Such a mutant Rs1 sequence may be operably linked to an endogenous regulatory sequence (e.g., a promoter) or constitutive promoter as desired. FIGS. 5-7 and 8-10 illustrate two exemplary targeting vectors for making selected point mutations in an exon (e.g., exon three and five, respectively) of a murine Rs1 gene and a small deletion in surrounding introns with a cassette that contains a drug selection marker that encodes hygromycin (Hyg) for the selection of mutant embryonic stem (ES) cell colonies. As described in the examples section, the small deletions introduced into the surrounding mouse Rs1 introns for each point mutation were designed to facilitate screening of mutant (or variant) ES cell colonies. As shown in the FIGS. 5 and 8, the targeting vectors also each included a sequence encoding a recombinase (e.g., Cre) regulated by an ES-cell specific miRNAs or a germ-cell specific promoter (e.g., protamine 1 promoter; Prot-Cre-SV40). The hygromycin selection cassette and Cre recombinase-encoding sequences are flanked by loxP recombinase recognition sites that enable Cre-mediated excision of the hygromycin selection cassette in a development-dependent manner, e.g., progeny derived from rodents whose germ cells containing the mutant (or variant) Rs1 gene described above will shed the selectable marker during development (see U.S. Pat. Nos. 8,697,851, 8,518,392, 8,354,389, 8,946, 505, and 8,946,504, all of which are herein incorporated by reference). This allows for, among other things, automatic excision of the hygromycin selection cassette from either differentiated cells or germ cells. Thus, prior to phenotypic analysis the hygromycin selection cassette is removed leaving the mutant Rs1 exons operably linked to the murine Rs1 promoter (FIGS. 7 and 10).

Rs1 targeting vectors, in some embodiments, may comprise DNA sequences corresponding to a mutant (or variant) Rs1 gene as described above, which mutant (or variant) Rs1 gene comprises a heterologous Rs1 gene or heterologous RS1-encoding sequence. Suitable heterologous Rs1 sequences are provided herein and may be substituted for sequences exemplified in the Examples section below. Such heterologous sequences may also be engineered to contain point mutations that encode amino acid substitutions as compared to a wild-type or parental heterologous RS1 polypeptide sequence.

Where appropriate, the coding region of the genetic material or polynucleotide sequence(s) encoding a reporter polypeptide (and/or a selectable marker, and/or a recombinase), in whole or in part, or a RS1 polypeptide (e.g., a variant RS1 polypeptide) may be modified to include codons that are optimized for expression in the non-human animal (e.g., see U.S. Pat. Nos. 5,670,356 and 5,874,304). Codon optimized sequences are synthetic sequences, and preferably encode the identical polypeptide (or a biologically active fragment of a full-length polypeptide which has substantially the same activity as the full-length polypeptide) encoded by the non-codon optimized parent polynucleotide. In some embodiments, the coding region of the genetic material encoding a reporter polypeptide (e.g., lacZ), in whole or in part, may include an altered sequence to optimize codon usage for a particular cell type (e.g., a rodent cell). In some embodiments, the coding region of the genetic material encoding a RS1 polypeptide as described herein (e.g., a variant RS1 polypeptide), in whole or in part, may include an altered sequence to optimize codon usage for a particular cell type (e.g., a rodent cell). To give but one example, the codons of the reporter or mutant Rs1 gene to be inserted into the genome of a non-human animal (e.g., a rodent) may be optimized for expression in a cell of the non-human animal. Such a sequence may be described as a codon-optimized sequence.

Compositions and methods for making non-human animals that comprise a disruption or mutation in an Rs1 gene as described herein are provided, including compositions and methods for making non-human animals that express a reporter gene under control of Rs1 regulatory sequences such as a Rs1 promoter, and non-human animals that express a variant RS1 polypeptide under control of Rs1 regulatory sequences such as a Rs1 promoter. In some embodiments, compositions and methods for making non-human animals that express a reporter or a variant RS1 polypeptide under control of endogenous regulatory sequences such as an endogenous promoter (e.g., an endogenous Rs1 promoter) are also provided. Methods include inserting a targeting vector, as described herein, comprising a reporter gene (e.g., lacZ; see FIGS. 2-4), into the genome of a non-human animal so that a portion of the coding sequence of an Rs1 gene is deleted, in whole or in part. In some embodiments, methods include inserting a targeting vector into the genome of a non-human animal so that exons 1-3 of an Rs1 gene are deleted.

Figures 11A, 11B, 11C:
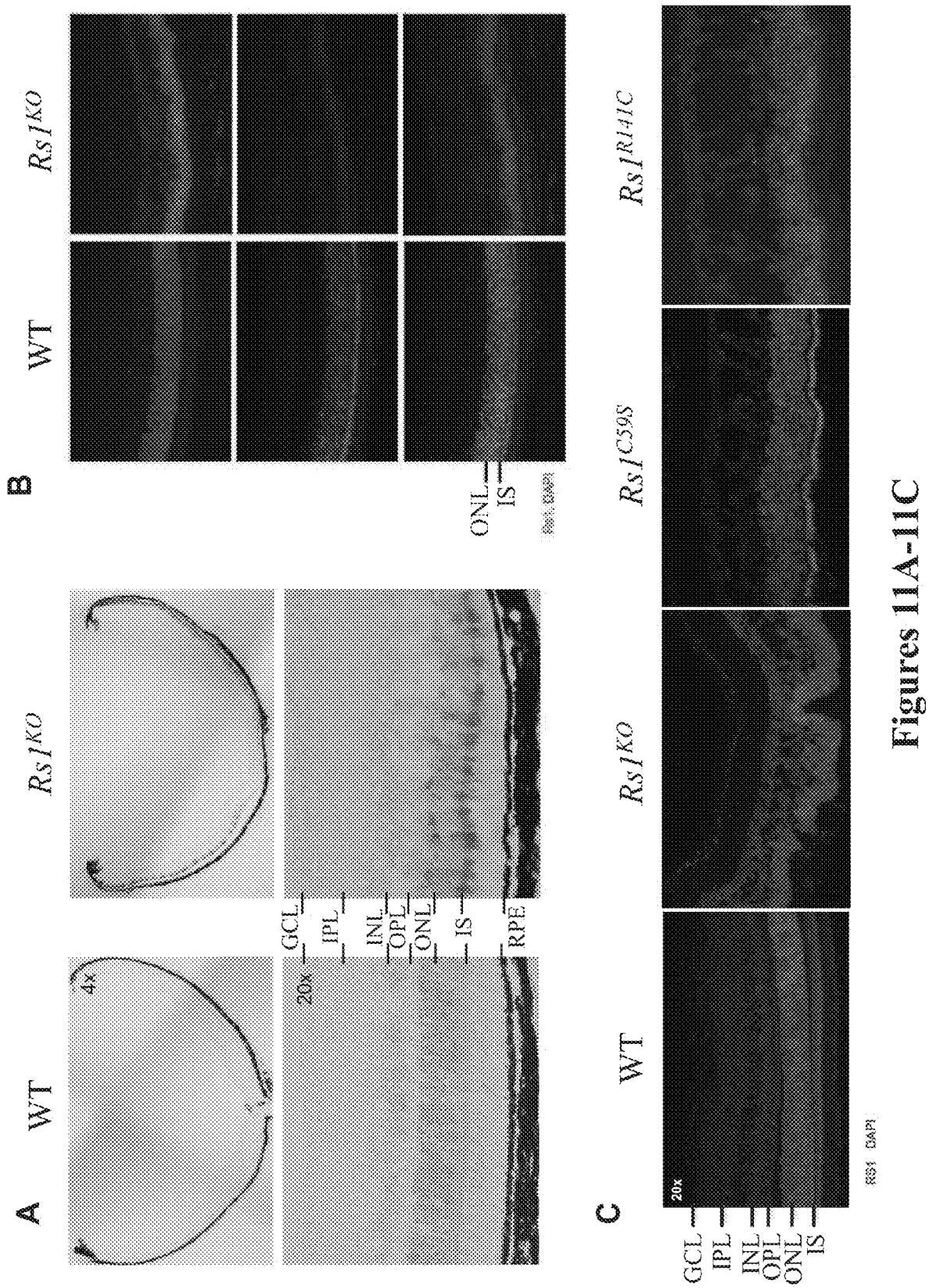
FIGS. 11A-11C show distribution of Rs1 mRNA and protein expression in retinas of Rs1 null ($Rs1^{KO}$) and Rs1 mutant ($Rs1^{C59S}$, $Rs1^{R14IC}$) animals by lacZ expression, RNASCOPE® and Immunohistochemistry (IHC). A, lacZ staining demonstrating positive X-gal signals in ONL and photoreceptor IS of $Rs1^{KO}$ animals. B. Rs1 mRNA expression via RNASCOPE® demonstrating endogenous Rs1 mRNA expression in wild-type (WT) animals. No Rs1 mRNA was detected in retinas from $Rs1^{KO}$ animals. C, IHC showing RS1 protein distribution in all retinal layers of WT animals. No RS1 protein expression was detected in $Rs1^{KO}$ animals and confined to ONL and IS of $Rs1^{C59S}$ and $Rs1^{R14IC}$ animals (GCL: ganglion cell layer; IPL: inner plexiform layer; INL: inner nuclear layer; OPL: outer plexiform layer; ONL: outer nuclear layer; IS: inner segments; RPE: retinal pigment epithelium). Rs1: red; DAPI: blue.

Insertion of a reporter gene operably linked to an Rs1 promoter (e.g., an endogenous Rs1 promoter) employs a relatively minimal modification of the genome and results in expression of reporter polypeptide in an Rs1-specific manner in the non-human animal (e.g., see FIGS. 11A-11C). In some embodiments, a non-human animal or cell as described herein comprises an Rs1 gene that comprises a targeting vector as described herein; in some certain embodiments, a targeting vector that appears in FIG. 2 or 4.

In various embodiments, a disrupted Rs1 gene as described herein includes one or more (e.g., first and second) insertion junctions resulting from insertion of a reporter gene.

In various embodiments, a disrupted Rs1 gene as described herein includes a first insertion junction that includes a sequence that is at least 80% (e.g., 80%, 85%, 90%, 91%, 92%, 93%, 94%, 95%, 96%, 97%, 98%, 99% or more) identical to SEQ ID NO:33 and a second insertion junction that includes a sequence that is at least 80% (e.g., 80%, 85%, 90%, 91%, 92%, 93%, 94%, 95%, 96%, 97%, 98%, 99% or more) identical to SEQ ID NO:34. In various embodiments, a disrupted Rs1 gene as described herein includes a first insertion junction that includes a sequence that is substantially identical or identical to SEQ ID NO:33 and a second insertion junction that includes a sequence that is substantially identical or identical to SEQ ID NO:34.

In various embodiments, a disrupted Rs1 gene as described herein includes a first insertion junction that includes a sequence that is at least 80% (e.g., 80%, 85%, 90%, 91%, 92%, 93%, 94%, 95%, 96%, 97%, 98%, 99% or more) identical to SEQ ID NO:33 and a second insertion junction that includes a sequence that is at least 80% (e.g., 80%, 85%, 90%, 91%, 92%, 93%, 94%, 95%, 96%, 97%, 98%, 99% or more) identical to SEQ ID NO:35. In various embodiments, a disrupted Rs1 gene as described herein includes a first insertion junction that includes a sequence that is substantially identical or identical to SEQ ID NO:33 and a second insertion junction that includes a sequence that is substantially identical or identical to SEQ ID NO:35.

In various embodiments, a disrupted Rs1 gene or allele as described herein includes a sequence that is at least 80% (e.g., 80%, 85%, 90%, 91%, 92%, 93%, 94%, 95%, 96%, 97%, 98%, 99% or more) identical to SEQ ID NO:23 or SEQ ID NO:25. In various embodiments, a disrupted Rs1 gene or allele as described herein includes a sequence that is substantially identical or identical to SEQ ID NO:23 or SEQ ID NO:25.

In various embodiments, a disrupted Rs1 gene or allele as described herein comprises a deletion of 13,716 bp of an endogenous Rs1 gene or allele. In various embodiments, a disrupted Rs1 gene or allele as described herein lacks a sequence that is substantially identical or identical to SEQ ID NO:24.

Methods also include inserting a targeting vector, as described herein, encoding a variant RS1 polypeptide (see FIGS. 5-7 and 8-10), in whole or in part, into the genome of a non-human animal so that a portion (e.g., an exon) of the coding sequence of a Rs1 gene is altered. In some embodiments, methods include inserting targeting vector into the genome of a non-human animal so that an exon of a Rs1 gene is mutated to encode a variant RS1 polypeptide.

Insertion of a mutant Rs1 gene operably linked to a Rs1 promoter (e.g., an endogenous Rs1 promoter) employs a relatively minimal modification of the genome and results in expression of variant RS1 polypeptide in the non-human animal that is functionally and structurally different than an RS1 polypeptide that appears in a wild-type non-human animal. In some embodiments, a non-human animal or cell described herein comprises an Rs1 gene that comprises a targeting vector as described herein; in some certain embodiments, a targeting vector that appears in FIG. 5 or 8.

In various embodiments, a mutant Rs1 gene as described herein includes one or more (e.g., first and second) insertion junctions resulting from insertion of a targeting vector as described herein.

In various embodiments, a mutant Rs1 gene as described herein includes a first insertion junction that includes a sequence that is at least 80% (e.g., 80%, 85%, 90%, 91%, 92%. 93%, 94%, 95%, 96%, 97%, 98%, 99% or more) identical to SEQ ID NO:36 and a second insertion junction that includes a sequence that is at least 80% (e.g., 80%, 85%, 90%, 91%, 92%, 93%, 94%, 95%, 96%, 97%, 98%, 99% or more) identical to SEQ ID NO:37. In various embodiments, a mutant Rs1 gene as described herein includes a first insertion junction that includes a sequence that is substantially identical or identical to SEQ ID NO:36 and a second insertion junction that includes a sequence that is substantially identical or identical to SEQ ID NO:37.

In various embodiments, a mutant Rs1 gene as described herein includes an insertion junction that includes a sequence that is at least 80% (e.g., 80%, 85%, 90%, 91%, 92%, 93%, 94%, 95%, 96%, 97%, 98%, 99% or more) identical to SEQ ID NO:38. In various embodiments, a mutant Rs1 gene as described herein includes an insertion junction that includes a sequence that is substantially identical or identical to SEQ ID NO:38.

In various embodiments, a mutant Rs1 gene as described herein comprises a third exon that includes a point mutation such that the mutant Rs1 gene encodes an RS1 polypeptide having a C59S amino acid substitution. In various embodiments, a mutant Rs1 gene as described herein comprises a third exon that includes a codon mutation of TGT to AGT such that the mutant Rs1 gene encodes an RS1 polypeptide having a C59S amino acid substitution.

In various embodiments, a mutant Rs1 gene as described herein includes a first insertion junction that includes a sequence that is at least 80% (e.g., 80%, 85%, 90%, 91%, 92%, 93%, 94%, 95%, 96%, 97%, 98%, 99% or more) identical to SEQ ID NO:39 and a second insertion junction that includes a sequence that is at least 80% (e.g., 80%, 85%, 90%, 91%, 92%, 93%, 94%, 95%, 96%, 97%, 98%, 99% or more) identical to SEQ ID NO:40. In various embodiments, a mutant Rs1 gene as described herein includes a first insertion junction that includes a sequence that is substantially identical or identical to SEQ ID NO:39 and a second insertion junction that includes a sequence that is substantially identical or identical to SEQ ID NO:40.

In various embodiments, a mutant Rs1 gene as described herein includes an insertion junction that includes a sequence that is at least 80% (e.g., 80%, 85%, 90%, 91%. 92%, 93%, 94%, 95%, 96%, 97%, 98%, 99% or more) identical to SEQ ID NO:41. In various embodiments, a mutant Rs1 gene as described herein includes an insertion junction that includes a sequence that is substantially identical or identical to SEQ ID NO:41.

In various embodiments, a mutant Rs1 gene as described herein comprises a fifth exon that includes a point mutation such that the mutant Rs1 gene encodes an RS1 polypeptide having a R141C amino acid substitution. In various embodiments, a mutant Rs1 gene as described herein comprises a fifth exon that includes a codon mutation of CGC to TGC such that the mutant Rs1 gene encodes an RS1 polypeptide having a R141C amino acid substitution.

In various embodiments, a mutant Rs1 gene or allele as described herein comprises a sequence that is at least 80% (e.g., 80%, 85%, 90%, 91%, 92%, 93%, 94%, 95%, 96%, 97%, 98%, 99% or more) identical to SEQ ID NO:27 or SEQ ID NO:29. In various embodiments, a mutant Rs1 gene or allele as described herein comprises a sequence that is substantially identical or identical to SEQ ID NO:27 or SEQ ID NO:29.

Alternatively, other Rs1 genes or RS1-encoding sequences may be employed in the methods described herein to generate non-human animals whose genomes contain a mutant Rs1 gene as described herein. For example, a heterologous Rs1 gene may be introduced into a non-human animal, which heterologous Rs1 gene encodes a variant RS1 polypeptide as described herein (i.e., comprises a mutation that establishes a Retinoschisis-like phenotype in a non-human animal). In another example, a transgenic Rs1 gene may be randomly inserted into the genome a non-human animal and an endogenous Rs1 gene rendered non-functional (e.g., via genetic modification, gene knockdown with DNA or RNA oligonucleotides, etc.). Exemplary alternative Rs1 genes or RS1-encoding sequences are provided herein. Persons of skill upon reading this disclosure will understand that such Rs1 genes or RS1-encoding sequences can be employed in the methods described herein to generate non-human animals.

Targeting vectors described herein may be introduced into ES cells and screened for ES clones harboring a disrupted or mutant Rs1 gene as described herein in Frendewey, D., et al., 2010, Methods Enzymol. 476:295-307. A variety of host embryos can be employed in the methods and compositions disclosed herein. For example, the pluripotent and/or totipotent cells having the targeted genetic modification can be introduced into a pre-morula stage embryo (e.g., an 8-cell stage embryo) from a corresponding organism. See, e.g., U.S. Pat. Nos. 7,576,259, 7,659,442, 7,294,754, and U.S. Patent Application Publication No. 2008-0078000 A1, all of which are incorporated herein by reference in their entireties. In other instances, donor ES cells may be implanted into a host embryo at the 2-cell stage, 4-cell stage, 8-cell stage, 16-cell stage, 32-cell stage, or 64-cell stage. A host embryo can also be a blastocyst or can be a pre-blastocyst embryo, a pre-morula stage embryo, a morula stage embryo, an uncompacted morula stage embryo, or a compacted morula stage embryo.

In some embodiments, the VELOCIMOUSE® method (Poueymirou, W. T. et al., 2007, Nat. Biotechnol. 25:91-99) may be applied to inject positive ES cells into an 8-cell embryo to generate fully ES cell-derived F0 generation heterozygous mice ready for lacZ expression profiling or breeding to homozygosity. Exemplary methods for generating non-human animals having a disrupted or mutant Rs1 gene are provided in the Example section.

Methods for generating transgenic non-human animals, including knockouts and knock-ins, are well known in the art (see, e.g., Kitamura, D. et al., 1991, Nature 350:423-6; Komori, T. et al., 1993, Science 261:1171-5; Shinkai, Y. et al., 1993, Science 259:822-5; Mansour, S. L. et al., 1998, Nature 336:348-52; Gene Targeting: A Practical Approach, Joyner, ed., Oxford University Press, Inc., 2000; Valenzuela, D. M. et al., 2003, Nature Biotech. 21(6):652-9; Adams, N. C. and N. W. Gale, in Mammalian and Avian Transgenesis-New Approaches, ed. Lois, S.P.a.C., Springer Verlag, Berlin Heidelberg, 2006). For example, generation of transgenic rodents may involve disruption of the genetic loci of an endogenous rodent gene and introduction of a reporter gene into the rodent genome, in some embodiments, at the same location as the endogenous rodent gene, or may involve the altering the genetic loci of an endogenous rodent gene and introduction of one or more mutations into the rodent genome, in some embodiments, at the same location as the endogenous rodent gene, resulting in the expression of a variant polypeptide.

A schematic illustration (not to scale) of the genomic organization of a mouse Rs1 gene is provided in FIG. 1. An exemplary targeting vector for deletion of a portion of the coding sequence of mouse Rs1 gene using a reporter gene is provided in FIG. 2. As illustrated, genomic DNA containing exons 1-3 (with the exception of the ATG start codon in exon 1) of a mouse Rs1 gene is deleted and replaced with a reporter gene and a self-deleting drug selection cassette flanked by site-specific recombinase recognition sites. The targeting vector includes a recombinase-encoding sequence that is operably linked to a promoter that is developmentally regulated such that the recombinase is expressed in undifferentiated cells. Upon homologous recombination, exons 1-3 of an endogenous mouse Rs1 gene are deleted (or replaced) by the sequence contained in the targeting vector as shown and engineered mice having a Rs1 gene that has the structure depicted in FIG. 4 are created via Cre-mediated excision of the neomycin cassette during development leaving the lacZ reporter gene (fused to a mouse Rs1 start codon) operably linked to the mouse Rs1 promoter.

Exemplary targeting vectors for creating mutations (e.g., substitution mutations) in mouse Rs1 gene are provided in FIGS. 5-7 and 8-10. As illustrated, a mutant mouse Rs1 gene (i.e., a mutant Rs1 gene having point mutations in exon three or five) is created with a targeting vector that includes a self-deleting drug selection cassette flanked by site-specific recombinase recognition sites placed downstream of a mutant Rs1 exon and within a Rs1 intron (see also FIG. 5 or 8). The targeting vector includes a recombinase-encoding sequence that is operably linked to a promoter that is developmentally regulated such that the recombinase is expressed in undifferentiated cells. Upon homologous recombination, a single exon (and portions of surrounding introns) of an endogenous mouse Rs1 gene is replaced by the sequence contained in the targeting vector as shown and engineered mice having a mutant Rs1 gene that has the structure depicted in FIG. 7 or 10 are created via Cre-mediated excision of the selection cassette during development leaving a mutant Rs1 gene having a point mutation in a single exon operably linked to a mouse Rs1 promoter, and small deletions (with a unique loxP site) within an adjacent intron(s). The resulting mutant Rs1 genes each encode an RS1 polypeptide that includes an amino acid substitution (e.g., C59S or R141C).

Exemplary promoters than can be included in targeting vectors described herein include a Protamine 1 (Prm1) promoter (such as the one set forth in SEQ ID NO: 30), a Blimp1 promoter 1 kb (such as the one set forth in SEQ ID NO: 31), and a Blimp/promoter 2 kb (such as the one set forth in SEQ ID NO: 32). Additional suitable promoters that can be used in targeting vectors described herein include those described in U.S. Pat. Nos. 8,697,851, 8,518,392 and 8,354,389; all of which are incorporated herein by reference).

A transgenic founder non-human animal can be identified based upon the presence of a reporter gene (or absence of Rs1) in its genome and/or expression of a reporter in tissues or cells of the non-human animal (or lack of expression of RS1), or the presence of one or more point mutations in an Rs1 coding sequence (e.g., an exon) and/or a deletion of a non-coding Rs1 sequence (e.g., an intron) in its genome and/or expression of a variant RS1 polypeptide in tissues or cells of the non-human animal (or lack of expression of wild-type RS1 polypeptide). A transgenic founder non-human animal can then be used to breed additional non-human animals carrying the reporter gene or mutant Rs1 gene thereby creating a series of non-human animals each carrying one or more copies of a disrupted or mutant Rs1 gene as described herein.

Transgenic non-human animals may also be produced to contain selected systems that allow for regulated or directed expression of a transgene or polynucleotide molecule (e.g., an insert nucleic acid). Exemplary systems include the Cre/loxP recombinase system of bacteriophage P1 (see, e.g., Lakso, M. et al., 1992, Proc. Natl. Acad. Sci. USA 89:6232-6236) and the FLP/Frt recombinase system of *S. cerevisiae* (O'Gorman, S. et al, 1991, Science 251:1351-1355). Such animals can be provided through the construction of "double" transgenic animals, e.g., by mating two transgenic animals, one containing a transgene encoding a selected polypeptide (e.g., a reporter, variant or heterologous RS1 polypeptide) and the other containing a transgene encoding a recombinase (e.g., a Cre recombinase).

Although embodiments employing a disruption or mutation in an Rs1 gene in a mouse are extensively discussed herein, other non-human animals that comprise such modifications (or alterations) in an Rs1 gene locus are also provided. In some embodiments, such non-human animals comprise a disruption in an Rs1 gene (e.g., a mouse with a deletion of a portion of an Rs1 coding sequence) characterized by insertion of a reporter operably linked to an endogenous Rs1 promoter or a mutation in an Rs1 gene (e.g., a mouse with one or more point mutations in one or more Rs1 exons) characterized by insertion of a mutant Rs1 exon or exons (e.g., an exon that contains one or more point mutations) operably linked to an endogenous Rs1 promoter. Such non-human animals include any of those which can be genetically modified to disrupt or mutate a coding sequence of a Rs1 gene as disclosed herein, including, e.g., mammals, e.g., mouse, rat, rabbit, pig, bovine (e.g., cow, bull, buffalo), deer, sheep, goat, chicken, cat, dog, ferret, primate (e.g., marmoset, rhesus monkey), etc. For those non-human animals for which suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing somatic cell nuclear transfer (SCNT) to transfer the genetically modified genome to a suitable cell, e.g., an enucleated oocyte, and gestating the modified cell (e.g., the modified oocyte) in a non-human animal under suitable conditions to form an embryo.

Briefly, methods for nuclear transfer include steps of: (1) enucleating an oocyte; (2) isolating a donor cell or nucleus to be combined with the enucleated oocyte; (3) inserting the cell or nucleus into the enucleated oocyte to form a reconstituted cell; (4) implanting the reconstituted cell into the womb of an animal to form an embryo; and (5) allowing the embryo to develop. In such methods oocytes are generally retrieved from deceased animals, although they may be isolated also from either an oviduct and/or ovary of live animals. Oocytes may be matured in a variety of medium known to persons of skill in the art prior to enucleation. Enucleation of the oocyte can be performed in a variety of ways known to persons of skill in the art. Insertion of a donor cell or nucleus into an enucleated oocyte to form a reconstituted cell is typically achieved by microinjection of a donor cell under the zona pellucida prior to fusion. Fusion may be induced by application of a DC electrical pulse across the contact/fusion plane (electrofusion), by exposure of the cells to fusion-promoting chemicals, such as polyethylene glycol, or by way of an inactivated virus, such as the Sendai virus. A reconstituted cell is typically activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, are typically cultured in medium known to persons of skill in the art and then transferred to the womb of an animal. See, e.g., U.S. Pat. No. 7,612,250; U.S. Patent Application Publication Nos. 2004-0177390 A1 and 2008-0092249 A1; and International Patent Application Publication Nos. WO 1999/005266 A2 and WO 2008/017234 A1; each of which is incorporated herein by reference.

Methods for modifying a non-human animal genome (e.g., a pig, cow, rodent, chicken, etc. genome) include, e.g., employing a zinc finger nuclease (ZFN), a transcription activator-like effector nuclease (TALEN), or a Cas protein (i.e., a CRISPR/Cas system) to modify a genome to include a disrupted or mutant Rs1 gene as described herein.

In some embodiments, a non-human animal of the present disclosure is a mammal. In some embodiments, a non-human animal as described herein is a small mammal, e.g., of the superfamily Dipodoidea or Muroidea. In some embodiments, a non-human animal as described herein is a rodent. In some embodiments, a rodent as described herein is selected from a mouse, a rat, and a hamster. In some embodiments, a rodent as described herein is selected from the superfamily Muroidea. In some embodiments, a genetically modified animal as described herein is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, white-tailed rats, *Malagasy* rats and mice), Platacanthomyidae (e.g., spiny dormice), and Spalacidae (e.g., mole rats, bamboo rats, and zokors). In some certain embodiments, a rodent as described herein is selected from a true mouse or rat (family Muridae), a gerbil, a spiny mouse, and a crested rat. In some certain embodiments, a mouse as described herein is from a member of the family Muridae. In some embodiment, a non-human animal as described herein is a rodent. In some certain embodiments, a rodent as described herein is selected from a mouse and a rat. In some embodiments, a non-human animal as described herein is a mouse.

In some embodiments, a non-human animal as described herein is a rodent that is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In some certain embodiments, a mouse as described herein is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129/SvJae, 129S6 (129/SvEvTac), 129S7, 129S8, 129T1, 129T2 (see, e.g., Festing et al., 1999, Mammalian Genome 10:836; Auerbach, W. et al., 2000, Biotechniques 29(5): 1024-1028, 1030, 1032). In some certain embodiments, a genetically modified mouse as described herein is a mix of an aforementioned 129 strain and an aforementioned C57BL/6 strain. In some certain embodiments, a mouse as described herein is a mix of aforementioned 129 strains, or a mix of aforementioned BL/6 strains. In some certain embodiments, a mouse as described herein is a mix of or derived from aforementioned BL/6 strains that does not contain (or lacks) a Crb1$^{rd8}$ mutation (i.e., comprises a wild-type Crb1). In some certain embodiments, a 129 strain of the mix as described herein is a 129S6 (129/SvEvTac) strain. In some embodiments, a mouse as described herein is a BALB strain, e.g., BALB/c strain. In some embodiments, a mouse as described herein is a mix of a BALB strain and another aforementioned strain.

In some embodiments, a non-human animal as described herein is a rat. In some certain embodiments, a rat as described herein is selected from a Wistar rat, an LEA strain, a Sprague Dawley strain, a Fischer strain, F344, F6, and Dark Agouti. In some certain embodiments, a rat strain as described herein is a mix of two or more strains selected from the group consisting of Wistar, LEA, Sprague Dawley, Fischer, F344, F6, and Dark Agouti.

A rat pluripotent and/or totipotent cell can be from any rat strain, including, for example, an ACI rat strain, a Dark Agouti (DA) rat strain, a Wistar rat strain, a LEA rat strain, a Sprague Dawley (SD) rat strain, or a Fischer rat strain such as Fisher F344 or Fisher F6. Rat pluripotent and/or totipotent cells can also be obtained from a strain derived from a mix of two or more strains recited above. For example, a rat pluripotent and/or totipotent cell can be from a DA strain or an ACI strain. An ACI rat strain is characterized as having black agouti, with white belly and feet and an RTI$^{av1}$/ haplotype. Such strains are available from a variety of sources including Harlan Laboratories. An example of a rat ES cell line from an ACI rat is an ACI.G1 rat ES cell. A Dark Agouti (DA) rat strain is characterized as having an agouti coat and an RT1$^{av1}$/haplotype. Such rats are available from a variety of sources including Charles River and Harlan Laboratories. Examples of a rat ES cell line from a DA rat are the DA.2B rat ES cell line and the DA.2C rat ES cell line. In some cases, rat pluripotent and/or totipotent cells are from an inbred rat strain. See, e.g., U.S. Patent Application Publication No. 2014-0235933 A1, incorporated herein by reference. Rat ES cells and methods of making genetically modified rats have also been described in the art. See, e.g., US 2014/0235933 A1, US 2014/0310828 A1, Tong et al. (2010) Nature 467:211-215, and Tong et al. (2011) Nat Protoc. 6(6): doi: 10.1038/nprot.2011.338 (all of which are incorporated herein by reference).

Non-human animals are provided that comprise a disruption or mutation in an Rs1 gene. In some embodiments, a disruption or mutation in an Rs1 gene results in a loss-of-function. In particular, loss-of-function mutations include mutations that result in a decrease or lack of expression of RS1 and/or a decrease or lack of activity/function of RS1. In some embodiments, loss-of-function mutations result in one or more phenotypes as compared to wild-type non-human animals. Expression of RS1 may be measured directly, e.g., by assaying the level of RS1 in a cell or tissue of a non-human animal as described herein.

Typically, expression level and/or activity of RS1 is decreased if the expression and/or activity level of RS1 is statistically lower ($p \leq 0.05$) than the level of RS1 in an appropriate control cell or non-human animal that does not comprises the same disruption (e.g., deletion). In some embodiments, concentration and/or activity of RS1 is decreased by at least 20%, 30%, 40%, 50%, 60%, 70%, 80%, 90%, 95%, 99% or more in a homozygous female or a hemizygous male animal relative to a control cell or non-human animal which lacks the same disruption (e.g., deletion).

In other embodiments, cells or organisms having a disruption or mutation in an Rs1 gene that reduces the expression level and/or activity of RS1 are selected using methods that include, but not limited to, Southern blot analysis, DNA sequencing, PCR analysis, or phenotypic analysis. Such cells or non-human animals are then employed in various methods and compositions described herein.

In some embodiments, an endogenous Rs1 gene is not deleted (i.e., intact). In some embodiments, an endogenous Rs1 gene is altered, disrupted, deleted or replaced with a heterologous sequence (e.g., a reporter gene encoding sequence). In some embodiments, all or substantially all of an endogenous Rs1 gene is replaced with an insert nucleic acid; in some certain embodiments, replacement includes replacement of a portion of the coding sequence of an endogenous Rs1 gene with a reporter gene (e.g., lacZ) so that the reporter gene is in operable linkage with an Rs1 promoter (e.g., an endogenous Rs1 promoter). In some embodiments, a portion of a reporter gene (e.g., a function fragment thereof) is inserted into an endogenous non-human Rs1 gene. In some embodiments, a reporter gene is a lacZ gene. In some embodiments, a reporter gene is inserted into one of the two copies of an endogenous Rs1 gene in a female non-human animal, giving rise to a non-human female animal that is heterozygous with respect to the reporter gene. In some embodiments, a non-human female animal is provided that is homozygous for a reporter gene.

Non-human animals are provided that comprise a mutation(s) in an Rs1 gene. In some embodiments, a mutation in an Rs1 gene results in the expression of a variant RS1 polypeptide (e.g., an RS1 polypeptide that includes one or more amino acid substitutions as compared to a wild-type RS1 polypeptide). Expression of variant RS1 may be measured directly, e.g., by assaying the level of variant RS1 in a cell or tissue of a non-human animal as described herein.

In other embodiments, cells or organisms having a mutation(s) in an Rs1 gene are selected using methods that include, but not limited to, Southern blot analysis, DNA sequencing, PCR analysis, or phenotypic analysis. Such cells or non-human animals are then employed in various methods and compositions described herein.

In some embodiments, an endogenous Rs1 gene is altered or replaced with a mutant Rs1 sequence (e.g., a mutant RS1-encoding sequence, in whole or in part). In some embodiments, all or substantially all of an endogenous Rs1 gene is replaced with an insert nucleic acid; in some certain embodiments, replacement includes replacement of an endogenous Rs1 exon (e.g., exon three or five) with a mutant Rs1 exon (e.g., a synthetic exon three or synthetic exon five) so that the mutant Rs1 exon is in operable linkage with an Rs1 promoter (e.g., an endogenous Rs1 promoter) and other endogenous Rs1 exons. In some embodiments, a mutant Rs1 exon is inserted into an endogenous Rs1 gene, which mutant Rs1 exon contains one or more point mutations; in some certain embodiments, one point mutation. In some embodiments, a mutant Rs1 exon is inserted into one of the two copies of an endogenous Rs1 gene in a female non-human animal, giving rise to a female non-human animal that is heterozygous with respect to the mutant Rs1 exon. In some embodiments, a female non-human animal is provided that is homozygous for a mutant Rs1 exon. In some embodiments, non-human animals that comprise a mutant endogenous Rs1 gene further comprise one or more Rs1 introns that include a deletion and/or a site-specific recombinase recognition site (e.g., loxP).

Non-Human Animal Model of Retinoschisis and Methods of Use

Non-human animals described herein provide improved animal models for Retinoschisis. In particular, non-human animals as described herein provide improved animal models that translate to X-linked Retinoschisis disease pathology, characterized by, for example, progressive loss of central and peripheral vision due to degeneration of the retina.

For example, a disruption or mutation in an Rs1 gene as described herein may result in various symptoms (or phenotypes) in non-human animals provided herein. In some embodiments, disruption or mutation in an Rs1 gene results in non-human animals that are grossly normal at birth, but that develop one or more symptoms upon aging, e.g., after about 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, 53 weeks, 54 weeks, 55 weeks, 56 weeks, 57 weeks, 58 weeks, 59 weeks, 60 weeks, etc. In some embodiments, disruption or mutation in an Rs1 gene results in non-human animals having abnormal structure and/or function of one or both retinas. In some embodiments, disruption or mutation in an Rs1 gene results in non-human animals demonstrating one or more symptoms (or phenotypes) associated with Retinoschisis. Such symptoms (or phenotypes) may include, for example, splitting of one or both retina into two layers, abnormal retinal and/or macular structure or architecture, spoke-like streaks in the fovea (center of the macular), presence of blisters and/or rupture blood vessels in the spaces created by the splitting of one or both retina into two layers, leakage of blood into the vitreous body of one or both retinas, vision loss and/or impairment, blindness, retinal pigmentation and/or degeneration, degeneration and separation of the vitreous body from the retina, and retinal detachment. In certain embodiments, the symptoms or phenotypes include the development of cystic structures within the inner retina, and reduced ERG b- and a-wave responses as compared to wild type non-human animals, followed by a loss of photoreceptor cells. In some embodiments, a disruption or mutation in an Rs1 locus of a non-human animal as described herein results in early-onset (for example, at or by postnatal day 15, 18, 21, 24 or 27) functional and morphological phenotypes of the retina in the non-human animal. In some embodiments, the early-onset functional defects of the retina may be reflected by (i) reduced b-wave relative to a wave (resulting in negative ERG) in dark-adapted and light-adapted ERG analyses; (ii) decreased maximum response and sensitivity values of ERG b-waves; (iii) decreased maximum response values of ERG a-waves; or (iv) a combination of (i)-(iii), as compared to wild type non-human animals. In some embodiments, early-onset morphological defects of the retina may be reflected by schisis, a broader ellipsoid zone (EZ), thinner outer retina, or a combination thereof, as compared to wild type non-human animals. In some embodiments, non-human animals described herein provide improved in vivo systems for identifying and developing candidate therapeutics for the treatment of Retinoschisis (e.g., X-linked Retinoschisis). Thus, in at least some embodiments, non-human animals described herein provide improved animal models for X-linked Retinoschisis and/or eye diseases and can be used for the development and/or identification of therapeutic agents for the treatment and/or prevention of eye-related diseases, disorders or conditions.

Non-human animals as described herein provide an improved in vivo system and source of biological materials (e.g., cells) that lack expression of RS1 or that express variant RS1 polypeptides that are useful for a variety of assays. In various embodiments, non-human animals described herein are used to develop therapeutics that treat, prevent and/or inhibit one or more symptoms associated with a lack of RS1 expression and/or activity (e.g., gene therapy/replacement). In various embodiments, non-human animals described herein are used to develop therapeutics that treat, prevent and/or inhibit one or more symptoms associated with expression of variant RS1 polypeptides. Due to the expression of variant RS1 polypeptides, non-human animals described herein are useful for use in various assays to determine the functional consequences on retinal structure and development. In some embodiments, non-human animals described herein provide an animal model for screening molecules that are involved in RS1 structure and/or function.

Non-human animals described herein also provide an in vivo system for identifying a therapeutic agent for treating, preventing and/or inhibiting progressive vision loss resulting from degeneration of the structure and/or function of one or both retinas. In some embodiments, an effect of a therapeutic agent is determined in vivo, by administering said therapeutic agent to a non-human animal whose genome comprises an Rs1 gene as described herein.

Non-human animals described herein also provide improved animal models for eye-related diseases, disorders or conditions. In particular, non-human animals as described herein provide improved animal models that translate to conditions characterized by a breakdown of cell-to-cell adhesion in the neurosensory layers of one or both retinas.

Non-human animals may be administered a therapeutic agent to be tested by any convenient route, for example, by intravenous, intraperitoneal or intravitreal injection. Such animals may be included in an immunological study, so as to determine the effect of the therapeutic agent on vision (e.g., effect on neurosensory function of the retina) of the non-human animals as compared to appropriate control non-human animals that did not receive the therapeutic agent. A biopsy or anatomical evaluation of animal tissue (e.g., eye tissue) may also be performed, and/or a sample of blood may be collected.

In various embodiments, non-human animals described herein are used to identify, screen and/or develop candidate therapeutics (e.g., antibodies) that rescue photoreceptor function in one or both retinas. In various embodiments, non-human animals described herein are used to determine the efficacy of Rs1 gene delivery to photoreceptors. In some embodiments, non-human animals described herein are used to determine and/or optimize vector design of one or more candidate retinal gene therapies that encode an RS1 polypeptide.

In various embodiments, non-human animals described herein are used to determine the pharmacokinetic profiles of a candidate drug, e.g., an Rs1 gene therapy drug. In various embodiments, one or more non-human animals described herein and one or more control or reference non-human animals are each exposed to one or more candidate drugs, e.g., Rs1 gene therapy drugs, at various doses (e.g., 0.1 mg/kg, 0.2 mg/kg, 0.3 mg/kg, 0.4 mg/kg, 0.5 mg/kg, 1 mg/kg, 2 mg/kg, 3 mg/kg, 4 mg/kg, 5 mg/mg, 7.5 mg/kg, 10 mg/kg, 15 mg/kg, 20 mg/kg, 25 mg/kg, 30 mg/kg, 40 mg/kg, or 50 mg/kg or more). Candidate drugs, e.g., Rs1 gene therapy drugs, may be dosed via any desired route of administration including parenteral and non-parenteral routes of administration for evaluation in non-human animals described herein. Parenteral routes include, e.g., intravenous, intraarterial, intraportal, intramuscular, subcutaneous, intraperitoneal, intraspinal, intrathecal, intracerebroventricular, intracranial, intrapleural or other routes of injection. Non-parenteral routes include, e.g., oral, nasal, transdermal, pulmonary, rectal, buccal, vaginal, ocular. Administration may also be by continuous infusion, local administration, sustained release from implants (gels, membranes or the like), and/or intravenous injection. Blood is isolated from non-human animals at various time points (e.g., 0 hour, 6 hours, 1 day, 2 days, 3 days, 4 days, 5 days, 6 days, 7 days, 8 days, 9 days, 10 days, 11 days, or up to 30 or more days). Various assays may be performed to determine the pharmacokinetic profiles of administered drugs using samples obtained from non-human animals described herein including, but not limited to, total IgG, anti-drug response, agglutination, etc.

In various embodiments, non-human animals described herein are used to determine the therapeutic efficacy of one or more candidate drugs, e.g., Rs1 gene therapy drugs. In various embodiments, one or more non-human animals described herein and one or more control or reference non-human animals are each exposed to one or more candidate drugs, e.g., Rs1 gene therapy drugs, at various doses (e.g., 0.1 mg/µL, 0.2 mg/µL. 0.3 mg/µL, 0.4 mg/µL, 0.5 mg/µL, 0.6 mg/µL, 0.7 mg/µL, 0.8 mg/µL, 0.9 mg/µL, 1.0 mg/µL. 1.1 mg/µL, 1.2 mg/µL. 1.3 mg/µL, 1.4 mg/µL, 1.5 mg/µL, 1.6 mg/µL, 1.7 mg/µL, 1.8 mg/µL, 1.9 mg/µL, 2.0 mg/µL, 2.1 mg/µL, 2.2 mg/µL, 2.3 mg/µL, 2.4 mg/µL, 2.5 mg/µL. 2.6 mg/µL. 2.7 mg/µL, 2.8 mg/µL, 2.9 mg/µL, 3.0 mg/µL. 3.1 mg/µL, 3.2 mg/µL, 3.3 mg/µL, 3.4 mg/µL. 3.5 mg/µL, 3.6 mg/µL. 3.7 mg/µL, 3.8 mg/µL, 3.9 mg/µL, 4.0 mg/µL, 4.1 mg/µL. 4.2 mg/µL, 4.3 mg/µL, 4.4 mg/µL, 4.5 mg/µL, 4.6 mg/µL, 4.7 mg/µL, 4.8 mg/µL, 4.9 mg/µL or 5.0 mg/µL or more). In some embodiments, candidate drugs, e.g., Rs1 gene therapy drugs, are given to a non-human animal described herein at birth or shortly after birth, e.g., within 18, 15, 12, 10, 9, 8, 7, 6, 5, 4, 3, 2, or 1 day after birth. Candidate drugs, e.g., Rs1 gene therapy drugs, are preferentially dosed via an intravitreal route, however, any desired route of administration including parenteral and non-parenteral routes of administration (see above) may be evaluated in non-human animals described herein. In various embodiments, one or more candidate drugs, e.g., Rs1 gene therapy drugs, are injected via an intravitreal route at various volumes (e.g., 1 µL, 2 µL. 3 µL, 4 µL. 5 µL, 6 µL, 7 µL, 8 µL, 9 µL, 10 µL, 11 µL, 12 µL. 13 µL, 14 µL, 15 µL, 16UL, 17 µL, 18 µL, 19 µL. 20 µL, 21 µL, 22 µL, 23 µL, 24 µL, 25 µL, 26 µL, 27 µL, 28 µL, 29 µL, 30 µL. 31 µL. 32 µL, 33 µL, 34 µL, 35 µL, 36 µL, 37 µL, 38 µL, 39 µL, 40 µL, 41 µL, 42 µL, 43 µL, 44 µL, 45 µL, 46 µL, 47 µL, 48 µL, 49 µL or 50 µL or more). Injections may be continuous or follow a specific time course (e.g., weekly, biweekly, monthly, etc.). Retinal function and/or visual acuity is determined using assays known in the art and/or described herein at various time points (e.g., 0 hour, 6 hours, 1 day, 2 days, 3 days, 4 days, 5 days, 6 days, 7 days, 8 days, 9 days, 10 days, 11 days, 15, 18, 21, 24, or up to 30 or more days). Various functional and/or morphological analyses may be performed on retinas and/or eyecups harvested from non-human animals described herein and one or more control or reference non-human animals after administration of one or more candidate drugs, e.g., Rs1 gene therapy drugs, to determine the effect on RS1 function and/or RS1-dependent processes.

In various embodiments, non-human animals as described herein are used to measure the therapeutic effect of restoring Rs1 activity and the effect on retinal structure and/or function as a result of cellular changes in the eye. In various embodiments, a non-human animal as described herein or cells isolated therefrom are exposed to a candidate drug, e.g., an Rs1 gene therapy drug, and, after a subsequent period of time, analyzed for effects on Rs1-dependent processes (or interactions).

Cells (e.g., retinal cells) from non-human animals as described herein can be isolated and used on an ad hoc basis, or can be maintained in culture for many generations. In various embodiments, cells from a non-human animal described herein are immortalized (e.g., via use of a virus, cell fusion, etc.) and maintained in culture indefinitely (e.g., in serial cultures).

Non-human animals described herein provide an in vivo system for the analysis and testing of a drug or vaccine. In various embodiments, a candidate drug or vaccine may be delivered to one or more non-human animals described herein, followed by monitoring of the non-human animals to determine one or more of the immune response to the drug or vaccine, the safety profile of the drug or vaccine, or the effect on a disease or condition and/or one or more symptoms of a disease or condition. Exemplary methods used to determine the safety profile include measurements of toxicity, optimal dose concentration, efficacy of the drug or vaccine, and possible risk factors. Such drugs or vaccines may be improved and/or developed in such non-human animals.

Vaccine efficacy may be determined in a number of ways. Briefly, non-human animals described herein are vaccinated using methods known in the art and then challenged with a vaccine, or a vaccine is administered to already-infected non-human animals. The response of a non-human animal(s) to a vaccine may be measured by monitoring of, and/or performing one or more assays on, the non-human animal(s) (or cells isolated therefrom) to determine the efficacy of the vaccine. The response of a non-human animal(s) to the vaccine is then compared with control animals, using one or more measures known in the art and/or described herein.

Vaccine efficacy may further be determined by viral neutralization assays. Briefly, non-human animals described herein are immunized and serum is collected on various days post-immunization. Serial dilutions of serum are pre-incubated with a virus during which time antibodies in the serum that are specific for the virus will bind to it. The virus/serum mixture is then added to permissive cells to determine infectivity by a plaque assay or microneutralization assay. If antibodies in the serum neutralize the virus, there are fewer plaques or lower relative luciferase units compared to a control group.

Non-human animals described herein provide an in vivo system for assessing the pharmacokinetic properties and/or efficacy of a drug (e.g., an Rs1 gene delivery drug). In various embodiments, a drug may be delivered or administered to one or more non-human animals described herein, followed by monitoring of, or performing one or more assays on, the non-human animals (or cells isolated therefrom) to determine the effect of the drug on the non-human animal. Pharmacokinetic properties include, but are not limited to, how a non-human animal processes the drug into various metabolites (or detection of the presence or absence of one or more drug metabolites, including, but not limited to, toxic metabolites), drug half-life, circulating levels of drug after administration (e.g., serum concentration of drug), anti-drug response (e.g., anti-drug antibodies), drug absorption and distribution, route of administration, routes of excretion and/or clearance of the drug. In some embodiments, pharmacokinetic and pharmacodynamic properties of drugs are monitored in or through the use of non-human animals described herein.

In some embodiments, performing an assay includes determining the effect on the phenotype and/or genotype of the non-human animal to which the drug is administered. In some embodiments, performing an assay includes determining lot-to-lot variability for a drug. In some embodiments, performing an assay includes determining the differences between the effects of a drug administered to a non-human animal described herein and a reference non-human animal. In various embodiments, reference non-human animals may have a modification described herein, a modification that is different than described herein or no modification (i.e., a wild-type non-human animal).

Exemplary parameters that may be measured in non-human animals (or in and/or using cells isolated therefrom) for assessing the pharmacokinetic properties of a drug include, but are not limited to, agglutination, autophagy, cell division, cell death, complement-mediated hemolysis, DNA integrity, drug-specific antibody titer, drug metabolism, gene expression arrays, metabolic activity, mitochondrial activity, oxidative stress, phagocytosis, protein biosynthesis, protein degradation, protein secretion, stress response, target tissue drug concentration, non-target tissue drug concentration, transcriptional activity, and the like. In various embodiments, non-human animals described herein are used to determine a pharmaceutically effective dose of a drug.

Kits

The present disclosure further provides a pack or kit comprising one or more containers filled with at least one non-human animal, non-human cell, DNA fragment, and/or targeting vector as described herein. Kits may be used in any applicable method (e.g., a research method). Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both, or a contract that governs the transfer of materials and/or biological products (e.g., a non-human animal or a non-human cell as described herein) between two or more entities.

Other features of the disclosure will become apparent in the course of the following descriptions of exemplary embodiments, which are given for illustration and are not intended to be limiting.

EXAMPLES

The following examples are provided so as to describe to those persons of ordinary skill in the art how to make and use methods and compositions of the present disclosure, and are not intended to limit the scope of what the inventors regard as their disclosure. Unless indicated otherwise, temperature is indicated in Celsius, and pressure is at or near atmospheric.

Example 1. Generation of Engineered Restinoschisin-1 Rodent Lines

This example illustrates the construction of a series of targeting vectors for creating modifications in a Restinoschisin-1 (Rs1) locus of a rodent. In particular, this example specifically describes the construction of targeting vectors for creating a disruption in an Rs1 locus (i.e., a null allele) and introducing one or more point mutations into one or more exons of the coding sequence in an Rs1 locus resulting in the production of a mutant Rs1 gene that encodes a variant RS1 polypeptide having one or more amino acid substitutions as compared to a parent RS1 polypeptide. The mutant alleles, were constructed by using synthetic DNA fragments that included single exons containing point mutations (see below). As described below, sequencing oligonucleotides were designed for mouse homology boxes and ligation QC. A self-deleting cassette (SDC) containing a Hygromycin resistance gene was cloned to create a donor for targeting of bacterial artificial chromosome (BAC) clones. Two separate donors specific to each point mutation were confirmed by PCR and Sanger sequencing. Donors were linearized to remove backbone and used to target BAC clone DNA containing a rodent Rs1 gene to create mutant Rs1 genes. The modified BACs were confirmed by drug selection, PCR and Sanger sequencing across homology junctions, PFG electrophoresis, and Illumina analysis.

Briefly, for the null allele a deletion of exons 1-3 of the coding sequence (i.e., beginning 3' of ATG codon in exon one to the 3' end of exon three resulting in a 13,716 bp deletion) of a mouse Rs1 gene was made using a lacZ reporter construct placed in operable linkage with a mouse Rs1 promoter (i.e., in frame with ATG codon of exon one). The Rs1-lacZ-SDC targeting vector for creating a disruption in an endogenous mouse Rs1 locus was constructed as previously described (see, e.g., U.S. Pat. No. 6,586,251; Valenzuela et al., 2003, Nature Biotech. 21(6):652-659; and Adams, N. C. and N. W. Gale, in Mammalian and Avian Transgenesis-New Approaches, ed. Lois, S.P.a.C., Springer Verlag, Berlin Heidelberg, 2006). An exemplary targeting vector (or DNA construct) for creation of a Rs1 null allele is set forth in FIG. 2.

Briefly, the Rs1-lacZ-SDC targeting vector was generated using mouse bacterial artificial chromosome (BAC) clone RP23-21308 (Invitrogen) and a self-deleting neomycin selection cassette (lacZ-pA-ICeuI-loxP-mPrm1-Crei-SV40 pA-hUb1-em7-Neo-PGKpA-loxP) as previously described (see, U.S. Pat. Nos. 8,697,851, 8,518,392 and 8,354,389; all of which are incorporated herein by reference). The Rs1-lacZ-SDC targeting vector included a Cre recombinase-encoding sequence that is operably linked to a mouse protamine 1 promoter that is developmentally regulated such that the recombinase is expressed in undifferentiated cells. Upon homologous recombination, a deletion including nucleotides 3' of the ATG codon in exon one to the last six nucleotides before the 3' end of exon three (13,716 bp) of an endogenous murine Rs1 gene is replaced by the sequence contained in the targeting vector (~8,202 bp). The drug selection cassette is removed in a development-dependent manner, i.e., progeny derived from mice whose germ line cells containing a disrupted Rs1 gene described above will shed the selectable marker from differentiated cells during development (see U.S. Pat. Nos. 8,697,851, 8,518,392 and 8,354,389, all of which are incorporated herein by reference).

For a first mutant allele, mouse bacterial artificial chromosome (BAC) clone RP23-21308 was modified to introduce a point mutation in exon three (TGT to AGT) of an endogenous Rs1 gene so that an RS1 polypeptide having a C59S amino acid substitution would be encoded by the resulting mutant Rs1 gene (FIG. 5). Additional deletions were made in introns two (25 bp) and three (28 bp) to facilitate screening of positive clones (FIG. 6). The point mutation and the deletions were introduced using a synthetic fragment made by de novo DNA synthesis (GeneScript, Piscataway, NJ). The synthesized fragment, which included the mutant exon three and surrounding intronic sequence (5' and 3'), was contained in a plasmid backbone and propagated in bacteria under selection with ampicillin. A hygromycin resistance gene was ligated to the synthetic fragment and appended with homology arms using restriction enzymes to create the targeting vector for homologous recombination with the RP23-21308 BAC (FIG. 5). The resulting modified RP23-21308 BAC clone was then electroporated into ES cells (see below). The Rs1C59S-SDC targeting vector included a Cre recombinase-encoding sequence that is operably linked to mouse protamine 1 promoter that is developmentally regulated such that the recombinase is expressed in undifferentiated cells (FIG. 5; sec also, U.S. Pat. Nos. 8,697,851, 8,518,392 and 8,354,389; all of which are incorporated herein by reference). Upon homologous recombination, the synthetic mutated Rs1 exon three is inserted in the place of exon three of an endogenous murine Rs1 locus and the small deletions in the surrounding introns (i.e., introns two and three) are made by the sequence contained in the targeting vector. The drug selection cassette is removed in a development-dependent manner, i.e., progeny derived from mice whose germ line cells containing a mutated Rs1 gene described above will shed the selectable marker from differentiated cells during development (FIG. 7; see also U.S. Pat. Nos. 8,697,851, 8,518,392 and 8,354, 389, all of which are incorporated herein by reference). Endogenous DNA containing surrounding exons, introns and untranslated regions (UTRs) were unaltered by the mutagenesis and selection cassette. Sequence analysis of the targeting vector confirmed all exons, introns, splicing signals and the open reading frame of the mutant Rs1 gene.

Figure 8:
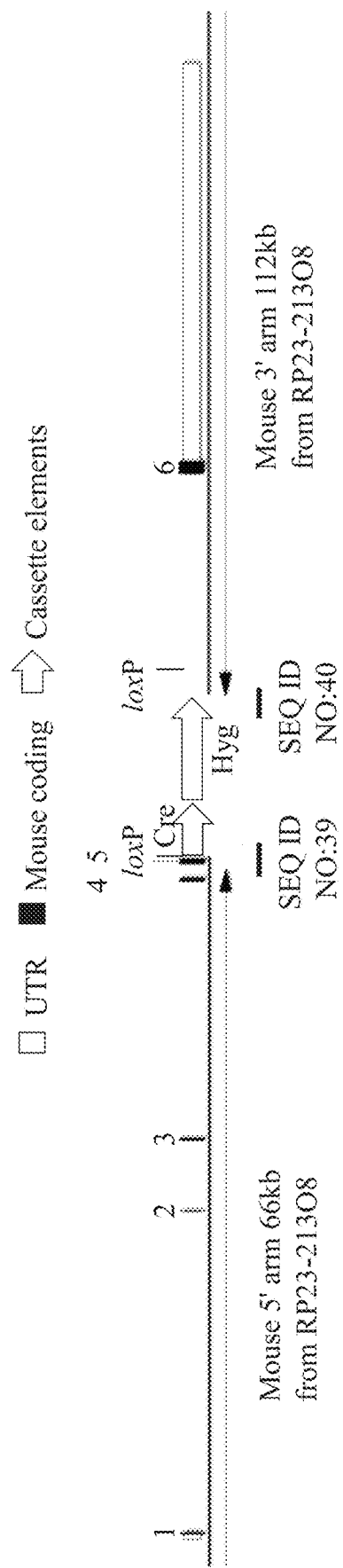
FIG. 8 shows a diagram, not to scale, of a targeting vector for creating a mutant Rs1 gene in a rodent (e.g., mouse) as described in Example 1. Consecutive exons (vertical slashes) are indicated by number above or below each exon. An exemplary point mutation in exon five (R141C; CGC to TGC) is indicated above exon five by insertion of a synthetic DNA fragment and cassette elements by homologous recombination. The Rs1R141C-SDC targeting vector contains a self-deleting drug selection cassette (e.g., a hygromycin resistance gene flanked by loxP sequences; see U.S. Pat. Nos. 8,697,851, 8,518,392 and 8,354,389, all of which are incorporated herein by reference). Upon homologous recombination, the synthetic DNA fragment contained in the targeting vector is inserted in the place of exon five of an endogenous murine Rs1 locus as shown. The drug selection cassette is removed in a development-dependent manner, i.e., progeny derived from mice whose germ line cells containing a disruption in an Rs1 locus as described above will shed the selectable marker from differentiated cells during development. Locations of selected nucleotide junctions are marked with a line below each junction and indicated by SEQ ID NO.

For a second mutant allele, mouse bacterial artificial chromosome (BAC) clone RP23-21308 was modified to introduce a point mutation in exon five (CGC to TGC) of an endogenous Rs1 gene so that an RS1 polypeptide having a R141C amino acid substitution would be produced by the resulting mutant Rs1 gene (FIG. 8). In particular, a synthetic exon five containing the R141C point mutation described above was inserted in place of the wild-type exon five along with additional deletions in intron four (10 bp) and five (29 bp), which were included to facilitate screening of positive clones (FIG. 9). The synthetic fragment made by de novo DNA synthesis (GeneScript, Piscataway, NJ). The synthesized fragment, which included the mutant exon five and surrounding intronic sequence (5' and 3'), was contained in a plasmid backbone and propagated in bacteria under selection with ampicillin. A cassette that included a hygromycin resistance gene (using a loxP-mPrm1-Crei-pA-hUb1-em7-Hygro-pA-loxP, 5,032 bp) was ligated to the synthetic fragment and appended with homology arms using restriction enzymes to create the targeting vector for homologous recombination with the RP23-21308 BAC (FIG. 8). The resulting modified RP23-21308 BAC clone was then electroporated into ES cells (sec below). The Rs1R141C-SDC targeting vector included a Cre recombinase-encoding sequence that is operably linked to mouse protamine 1 promoter that is developmentally regulated such that the recombinase is expressed in undifferentiated cells (FIG. 8; see also, U.S. Pat. Nos. 8,697,851, 8,518,392 and 8,354,389; all of which are incorporated herein by reference). Upon homologous recombination, the synthetic mutated Rs1 exon five is inserted in the place of exon five of an endogenous murine Rs1 locus and the small deletions in the surrounding introns (i.e., introns four and five) are made by the sequence contained in the targeting vector. The drug selection cassette is removed in a development-dependent manner, i.e., progeny derived from mice whose germ line cells containing a mutated Rs1 gene described above will shed the selectable marker from differentiated cells during development (FIG. 10; see also U.S. Pat. Nos. 8,697,851, 8,518,392 and 8,354,389, all of which are incorporated herein by reference). Endogenous DNA containing surrounding exons, introns and untranslated regions (UTRs) were unaltered by the mutagenesis and selection cassette. Sequence analysis of the targeting vector confirmed all exons, introns, splicing signals and the open reading frame of the mutant Rs1 gene.

Construction of each of the targeting vectors were confirmed by polymerase chain reaction and sequence analysis, and then used to electroporate mouse embryonic stem (ES) cells to create modified ES cells comprising the null and mutant Rs1 genes. The mouse ES cells used for electroporation were from a hybrid background (50% 129/S6/SvEv/Tac. 50% C57BL/6NTac; Auerbach, W. et al. (2000) Biotechniques 29(5):1024-8, 1030, 1032). The Drug-resistant clones were picked 10 days after electroporation and screened by TAQMAN® and karyotyping for correct targeting as previously described (Valenzuela et al., supra; Frendewey, D. et al., 2010, Methods Enzymol. 476:295-307) using primer/probe sets that detected proper introduction of the lacZ reporter gene or point mutations into an endogenous Rs1 gene (Table 1 and FIGS. 3, 6 and 9). Positive ES cell clones were confirmed by sequencing.

Positive ES cell clones were then used to implant female mice using the VELOCIMOUSE® method (see, e.g., U.S. Pat. No. 7,294,754; DeChiara, T. M. et al., 2010, Methods Enzymol. 476:285-94; DeChiara, T. M., 2009, Methods Mol. Biol. 530:311-24; Poueymirou et al., 2007, Nat. Biotechnol. 25:91-9), in which targeted ES cells were injected into uncompacted 8-cell stage Swiss Webster embryos, to produce healthy fully ES cell-derived F0 generation mice heterozygous for the null or mutant Rs1 genes. C57BL/6N mouse lines have been reported to contain a mutation (Crb1"48) that complicates their use in the formation animal models of retinal degeneration (see, e.g., Mattapallil, M. J. et al., 2012, Immunol. Microbiol. 53(6):2921-7; Mehalow, A. K. et al., 2003, Hum. Mol. Genet. 12:2179-89). This mutation was corrected by crossing F0 generation heterozygous males with C57B16/NTac Crbs1 females to avoid any possible complications from this mutation. Resulting F1 heterozygotes from these breedings were then intercrossed to produce F2 generation homozygotes and wild-type mice for phenotypic analyses.

The generation of the engineered Rs1 mouse lines described above resulted in the creation of unique nucleotide junctions in each engineered Rs1 locus. For the null allele, the nucleotide sequence across the upstream junction point included the following, which indicates endogenous mouse Rs1 5' sequence and a mouse Rs1 ATG codon (in uppercase font contained within the parentheses with the ATG codon indicated by brackets) contiguous with lacZ coding sequence (lowercase font):

(SEQ ID NO: 33)
(GCTCTCCACT TCACTTAGAT CTTGCTGTGA CCAAGGACAA

GGAGAAA[ATG]) ggtaccgatt taaatgatcc agtggtcctg cagaggagag attgggagaa.

The nucleotide sequence across the downstream junction point included the following, which indicates cassette sequence (lowercase font with an NheI site indicates by brackets) contiguous with the last six nucleotides of exon three and the beginning of intron four of a mouse Rs1 gene (contained within the parentheses in uppercase font): cagcccctag ataacttcgt ataatgtatg ctatacgaag ttat[gctagc]

(SEQ ID NO: 34)
(TTCCAGGTGA GTGGCTCAAC GCCCTAGCAT TCCTCCTTCC

AACTCTTAAT).

The nucleotide sequence across the downstream junction point after recombinase-mediated excision of the selection cassette included the following, which indicates remaining lacZ sequence (lowercase font with ICeu-I, loxP and NheI sites indicated by brackets) contiguous with mouse Rs1 sequence (contained within the parentheses in uppercase font): atccccccggc tagagtttaa acactagaac tagtggatcc ccgggctcga [taactataac ggtcctaagg tagcga]ctcgac [ataacttcg tataatgtat gctatacgaa gttat gctagc]

(SEQ ID NO: 35)
(TTCCAGGTGA GTGGCTCAAC GCCCTAGCAT TCCTCCTTCC

AACTCTTAAT).

For the C59S allele, the nucleotide sequence across the upstream junction point included the following, which indicates endogenous mouse Rs1 exon three and surrounding intron sequence (uppercase font contained within the parentheses below with exon three indicated by brackets and the mutated codon in bold font) contiguous with cassette sequence (lowercase font with a XhoI site in brackets and a loxP site in bold font) at the insertion point:

(SEQ ID NO: 36)
(CTGGAGT ACCTTTGTTG ATAGAACACT TGTTTAGGAT

TCGTGAAGGT AAACTGGGCA CCCATCTAGA AGCCCAGCAC

TCAGAGGTGG AGACAGGAGG TCAGGAGTTC AACAAGGTCA

TTCTCTGCTA CACAGTGAGT TTAAAATCGG CCTGGGATAC

ACGAGAGAGA CCCTGTGTAA GAGCAGTAGC AGCAGCAAGA

ACTCAAGCTG AAAAGGAACA TGCAGTGTAA GACAAAGGGC

CACTGTGTGC ATAGAGCCAG CAACCTCACA CTGTAATGAA

CGGGTCTGAC CTTTGCAAGT AAGCTTCTTG TGATGCTCTG

GTTGAGCCTT TGACTACGAC TTTTGTGACT TGTGCTCCTC

TGGATGCTTG CAG[GATGAGG GTGAGGACCC CTGGTACCAG

AAAGCATGCA AGTGTGATTG CCAGGTAGGA GCCAATGCTC

TGTGGTCTGC TGGAGCTACC TCCTTAGACA GTATTCCAG]G

TGAGTGGCTC AACGCCCTAG CATTCCTCCT TCCAACTCTT

AATCCCTCTG CTTTCTCTCA AGTTGGCTTG TGAGCTTCAC

ATCTCACCGT GGCCACTGCT CCAACATTCT GTTCATTATC

AAGTGCCAGG CTCTCTCCCT CCCTGGCTTG CCTGAGATGG

TCAGGTAAGA CCC) [ctcgag] ataacttcg tataatgtat gctatacgaa gttatatgca tgccagtagc agcaccc.

The nucleotide sequence across the downstream junction point included the following, which indicates cassette sequence (lowercase font with I-CeuI and NheI sites both in brackets, and a loxP site in bold font) contiguous with mouse Rs1 intron three sequence (uppercase font contained within the parentheses below) downstream of the insertion point: ttccatcaga cctcgacctg cagccctag ataacttcgt ataatgtatg ctatacgaag ttatgctagg [taactataac ggtcctaagg tagcga gctagc] (AGCGTGAGGG AAGTCCCTTC CTCTTAGGTA) (SEQ ID NO:37). The nucleotide sequence across the insertion point after recombinase-mediated excision of the selection cassette included the following, which indicates mouse Rs1 exon 3 sequence and remaining intron three sequence (uppercase font with exon 3 indicated by brackets) juxtaposed with remaining cassette sequence (lowercase font contained within the parentheses below with a XhoI, I-CeuI and NheI sites in brackets and a loxP site in bold font):

(SEQ ID NO: 38)
CTGGAGTGT ACCTTGTTG ATAGAACACT TGTTTTAGGAT

TCGTGAAGGT AAACTCGGGCA CCCATCTAGA AGCCCAGCAC

TCAGAGGTGG AGACAGGAGG TCAGGAGTTC AACAAGGTCA

TTCTCTGCTA CACAGTGAGT TTAAAATCGG CCTGGGATAC

ACGAGAGAGA CCCTGTGTAA GAGCAGTAGC AGCAGCAAGA

ACTCAAGCTG AAAAGGAACA TGCAGTGTAA GACAAAGGGC

CACTGTGTGC ATAGAGCCAG CAACCTCACA CTGTAATGAA

CGGGTCTGAC CTTTGCAAGT AAGCTTCTTG TGATGCTCTG

GTTGAGCCTT TGACTACGAC TTTTGTGACT TGTGCTCCTC

TGGATGCTTG CAG[GATGAGG GTGAGGACCC CTGGTACCAG

AAAGCATGCA AGTGTGATTG CCAGGTAGGA GCCAATGCTC

TGTGGTCTGC TGGAGCTACC TCCTTAGACA GTATTCCAG]G

TGAGTGGCTC AACGCCCTAG CATTCCTCCT TCCAACTCTT

AATCCCTCTG CTTTCTCTCA AGTTGGCTTG TGAGCTTCAC

ATCTCACCGT GGCCACTGCT CCAACATTCT GTTCATTATC

AAGTGCCAGG CTCTCTCCCT CCCTGGCTTG CCTGAGATGG

TCAGGTAAGA CCC ([ctcgag] ataacttcg tataatgtat gctatacgaa gttat gctagg//[taactataac ggtcctaagg tagcga gctagc] agcgtgaggg aagtcccttc ctcttaggta).

For the R141C allele, the nucleotide sequence across the upstream junction point included the following, which indicates endogenous mouse Rs1 exon five and surrounding intron sequence (uppercase font contained within the parentheses below with exon five in brackets and the mutated codon in bold font) contiguous with cassette sequence (lowercase font with a XhoI site in brackets and a loxP site in bold font) at the insertion point:

(SEQ ID NO: 39)
(TCTTTCCTAA GGAAAAGAAT TAAGAGTCGG GCTATGTCTG

AAGGCCCAGA TACCTCTTGA TGCTAGGTAA CCCTTCAAAA

CTCAGCACCT GTTGGCTTTT TACAGACATA

GATAAGAGGA_TGGCTCCTGG TAATTTGGTG TGTTCCTGGC

AG[GTGTGCTT GGCTTTCCAA GTATCAGGAC AGCAGCCAGT

GGTTACAGAT AGATTTGAAG GAGATCAAGG TGATTTCGGG

GATCCTGACC CAAGGATGCT GTGACATAGA CGAGTGGGTG

ACCAAGTACA GTGTGCCAGTA TAGGACTGAT GAGCGCCTGA

ACTGGATCTA CTATAAGGAT CAGACCGGAA ACAATCGG]GT

AAGTGGGGGT CACTCCGAGT CAGCTTCAGC TCACACTGCG

GAGACACACT CCATCCCTAT GTTCCTGCTG TCCGCGTCTG

TCTGAGCATT GACCCCTCTA CATGCTGGGT CATCTG) [ctcgag]

ataacttcg tataatgtat gctatacgaa gttatatgca tgccagtagc agcaccc.

The nucleotide sequence across the downstream junction point included the following, which indicates cassette sequence (lowercase font with I-CeuI and NheI sites both in brackets, and a loxP site in bold font) contiguous with mouse Rs1 intron five sequence (uppercase font contained within the parentheses below) downstream of the insertion point: ttccatcaga cctcgacctg cagccctag ataacttcgt ataatgtatg ctatacgaag ttatgctagg [taactataac ggtcctaagg tagcga gctagc]

(SEQ ID NO: 40)
(TTTTCCAGAT GTGATCTGGG AGACTAGCAG).

The nucleotide sequence across the insertion point after recombinase-mediated excision of the selection cassette (78 bp remaining in intron five) included the following, which indicates mouse Rs1 sequence (intron four, exon five and intron five in uppercase font) with remaining cassette sequence (loxP and cloning sites [78 bp] remaining in intron five, in lowercase font contained within the parentheses; XhoI, I-CeuI and NheI sites in brackets, a loxP site in bold font):

(SEQ ID NO: 41)
TCTTTCCTAA GGAAAAGAAT TAAGAGTCGG GCTATGTCTG

AAGGCCCAGA TACCTCTTGA TGCTAGGTAA CCCTTCAAAA

CTCAGCACCCT GTTGGCTTTT TACAGACATA GATAAGACGGA

TGGCTCCTGG TAATTTGGTG TGTTCCTGGC AGGTGTGCTT

GGCTTTCCAA GTATCAGGAC AGGAGCCAGT GGTTACAGAT

AGATTTGAAG GAGATCAAGG TGATTTCGGG GATCCTGACC

CAAGGATGCT GTGACATAGA CGAGTGGGTG ACCAAGTACA

GTGTGCAGTA TAGGACTGAT GAGCGCCTGA ACTGGATCTA

CTATAAGGAT CAGACCGGAA ACAATCGGGT AAGTGGGGGT

CACTCCGAGT CAGCTTCAGC TCACACTGCG GAGACACACT

CCATCCCTAT GTTCCTGCTG TCCGCGTCTG TCTGAGCATT

GACCCCTCTA CATGCTGGGT CATCTG ([ctcgag] ataatcttcg tataatgtat gctatacgaa gttatgctagg ggtcctaagg tagcga gctagc)TTTTCCAGAT GTGATCTGGG AGACTAGCAGC.

Taken together, this example illustrates the generation of three rodents (e.g., a mouse) lines whose genomes comprise engineered Rs1 loci. Such engineered Rs1 rodent lines provide in vivo systems for the elucidation of the biology and molecular mechanisms of Retinoschisis and for the development of therapeutics to effectively treat and or ameliorate such diseases.

TABLE 2

Primer/Probe sets for TAQMAN® assays

| Name | Primer | Sequence (5'-3') |
|---|---|---|
| Rs1-KOmTU | Forward | TGGGACAAGTGTAAATGAGGAC (SEQ ID NO: 42) |
| | Reverse | AGTGGTGCTTGGCCTTATGC (SEQ ID NO: 43) |
| | Probe | TCCCAGGCAAATCAGGACAAAGGGTC (SEQ ID NO: 44) |
| Rs1-KOmTD | Forward | GAGCCAGCAACCTCACAC (SEQ ID NO: 45) |
| | Reverse | GCATCCAGAGGAGCACAAGTC (SEQ ID NO: 46) |
| | Probe | TGTAATGAACGGGTCTGACCTTTGCAA (SEQ ID NO: 47) |
| Rs1-C59SmTU | Forward | TCGTGAAGGTCTTGATTTGATCCT (SEQ ID NO: 48) |
| | Reverse | ACCTCCTGTCTCCACCTCTG (SEQ ID NO: 49) |
| | Probe | AAGCACCATGTAAACTGGGCACCC (SEQ ID NO: 50) |
| Rs1-C59SmTD | Forward | CCCTGGCTTGCCTGAGATG (SEQ ID NO: 51) |
| | Reverse | GGACTTCCCTCACGCTGAGTT (SEQ ID NO52) |
| | Probe | TCAGGTAAGACCCAATTGTCAATGCA (SEQ ID NO: 53) |
| Rs1-R141CmTU | Forward | GAGTCGGGCTATGTCTGAAGG (SEQ ID NO:54) |
| | Reverse | GCCAACAGGTGCTGAGTTT (SEQ ID NO: 55) |
| | Probe | CCAGATTTGGGATGATACCTCTTGATGC (SEQ ID NO: 56) |
| Rs1-R141CmTD | Forward | CCTCTACATGCTGGGTCATCTG (SEQ ID NO: 57) |
| | Reverse | GGACTTCCCTCACGCTGAGTT (SEQ ID NO: 58) |
| | Probe | GACCCACATTCATTTACAAACTGC (SEQ ID NO: 59) |

Example 2. Characterization of Engineered Rs1 Rodent Lines

This example describes the characterization of engineered Rs1 rodent lines made according to Example 1. In particular, this example demonstrates the localization and distribution of RS1 protein in the retina of these engineered mice. Retinal architecture is also described for all engineered Rs1 lines.

LacZ Expression Profiling. Mice were euthanized by $CO_2$ inhalation. Eyes were enucleated and fixed with 4% paraformaldehyde in PBS (Electron Microscopy Sciences) for 3 hr at 4° C. After three washings with 1×PBS (ThermoFisher Sci.), eyes were dissected under a dissecting microscope. The anterior portion and lens were removed; the rest of the eye (eyecup) was stained with HistoMark X-Gal Substrate Set (KPL) for 2-days at 37° C. with gentle rotating. After staining, eyecups were rinsed with 1×PBS thoroughly, then were transferred to 30% sucrose overnight. The eyecups were embedded in Tissue-Tek® O.C.T. Compound (VWR) and frozen on dry ice. Twenty-micron cryostat sections were prepared on Superfrost® Plus Micro Slides. Sections were dried for 30 minutes at room temperature, then washed three times with 1×PBS to remove O.C.T. Compound, and coverslipped with ProLong Gold Antifade Mountant with DAPI (ThermoFisher Sci.) Representative results from male mice are set forth in FIG. 11A.

Rs1 mRNA expression. The expression pattern of Rs1 mRNA in the engineered Rs1 mouse lines described in Example 1 was determined by in situ hybridization using RNASCOPE® according to manufacturer's specifications (Advanced Cell Diagnostics). Briefly, formalin or 4% paraformaldehyde (PFA)-fixed and paraffin or O.C.T. embedded mouse eye cups were cut into 5 to 10 µm sections and mounted on SUPERFROST® Plus glass slides. The procedure began with 10 minute Pretreat 1 (ACD, 320037) at room temperature, followed by 20-minute boiling in Pretreat 2 (ACD, 320043) with Oster Steamer (IHC World, LLC, Model 5709) and pretreatment 3 (ACD, 320037) for 30 minutes at 40° C. in a HybEZ Oven (ACD, 310010). An additional DNase treatment step was included to reduce potential background from probe hybridization with chromosomal DNA. After pretreatment 3, slides were washes three times with water, and a solution of DNase I (50 u/ml in 1×DNase I buffer, AM2224, Ambion) was added to the eye tissue for a 30-minute incubation at 40° C. Slides were then washed five times with water, hybridized with RNA-SCOPE® probes for two hours at 40° C. and the remainder of the manufacturer's assay protocol was implemented (ACD, 322360) from Amplified 1 to Amplified 6. The slides were washed twice (two minutes each at room temperature) each step by RNASCOPE® wash buffer (ACD, 310091). After Amplified steps, signal was detected by incubation Red working solution (1:60 ratio of Red B to Red A) at room temperature for 10 minutes in the absence of light, followed by washing the slides in water several times and viewing under microscope. In some experiments, IHC technique was followed, fluorescent signals were visualized and captured using an open-field Nikon Eclipse Ti-E microscope. Representative results from male mice are set forth in FIG. 11B.

Figures 12A, 12B, 12C, 12D:
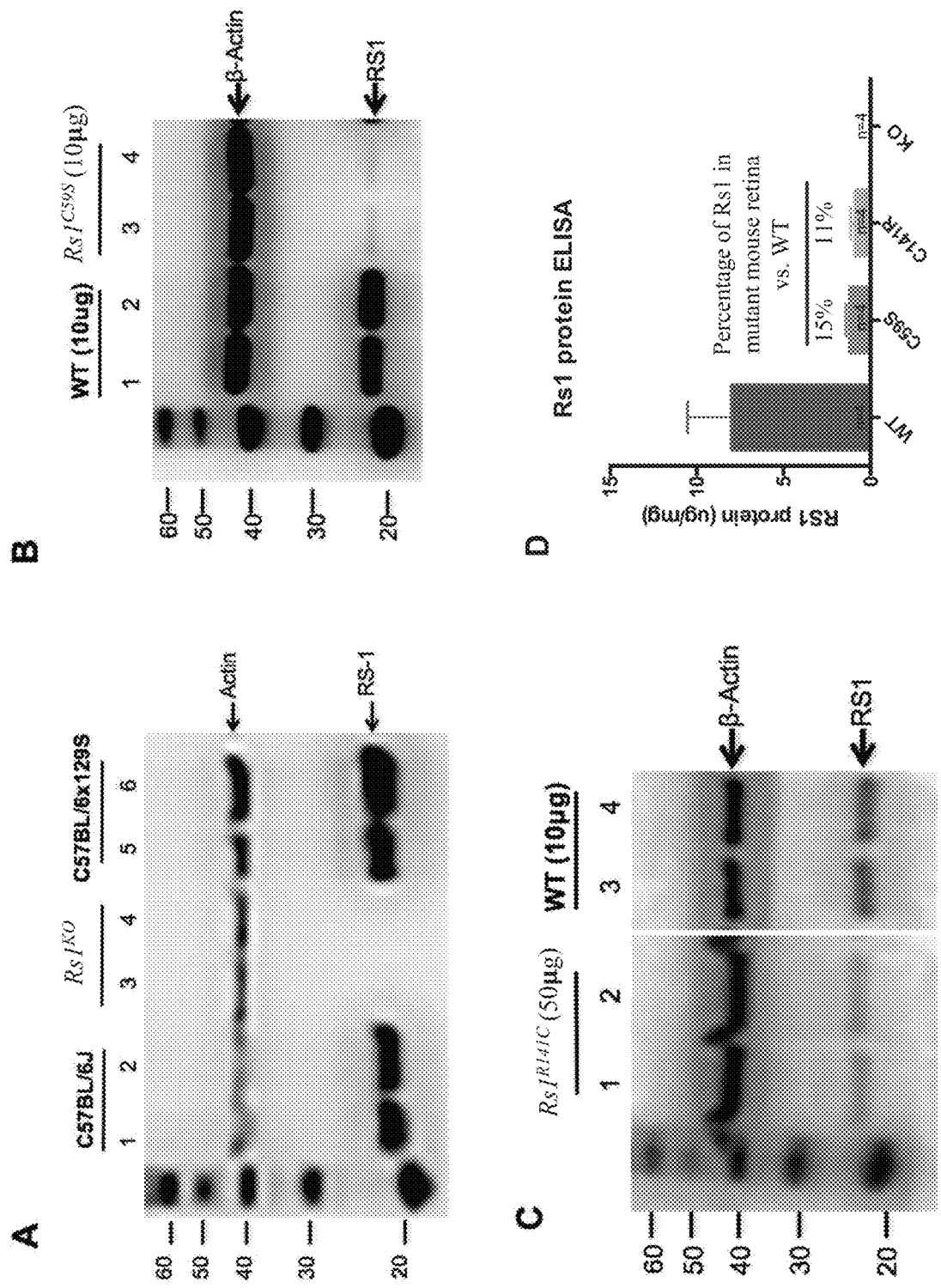
FIGS. 12A-12E show RS1 protein expression in retinas of Rs1 null ($Rs1^{KO}$) and Rs1 mutant ($Rs1^{C59S}$, $Rs1^{R14IC}$) animals by Western blot and ELISA assays. A. Western blot of SDS-PAGE gel under reducing condition showing RS1 expression in $Rs1^{KO}$ and C57BL/6-derived male strains. B, Western blot of SDS-PAGE gel under reducing condition showing RS1 expression in wild-type (WT) and $Rs1^{C59S}$ male animals. C. Western blot of SDS-PAGE gel under reducing condition showing RS1 expression in wild-type (WT) and $Rs1^{R14IC}$ male animals. D. ELISA assay showing the level of RS1 protein in wild-type (WT), $Rs1^{KO}$, $Rs1^{C59S}$ and $Rs1^{R14IC}$ male animals. Percent of RS1 protein expressed in Rs1 mutant animals as compared to wild-type littermates is indicated above each bar. E, RS1 protein expression in retinas of Rs1 knock-out female animals in Western blot and ELISA assay. KO: homozygous Rs1 knock-out ($Rs1^{-/-}$); HET: heterozygous Rs1 knock-out ($Rs1^{-/+}$). RS1 HET female animals had similar amount of RS1 protein as wild type ("WT") male and female animals.
Figure 12E:
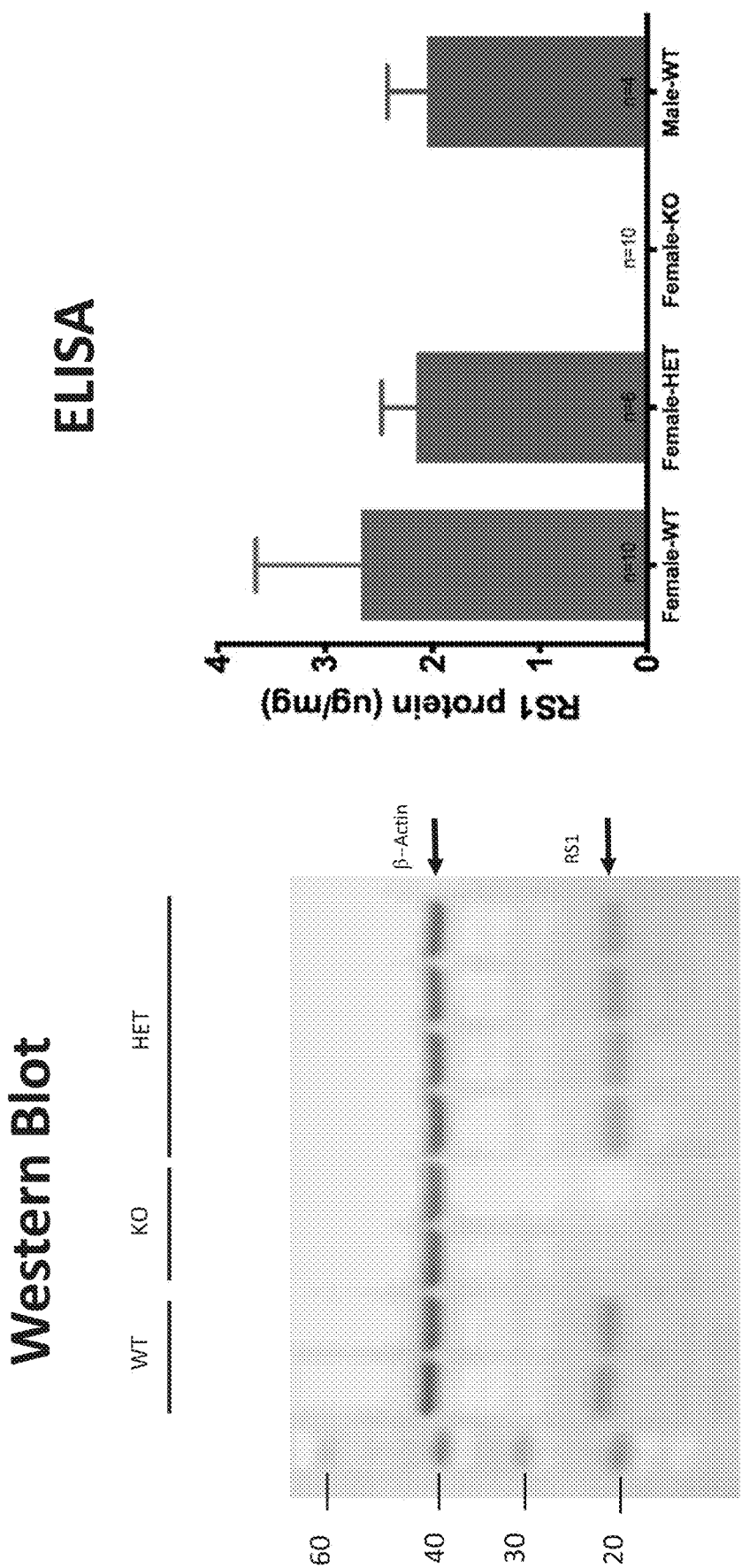

RS1 protein expression. The protein expression level in various layers of the retina of wild-type and engineered Rs1 rodents was determined by Immunohistochemistry (IHC), Western blot and an ELISA assay. Representative results from male mice are set forth in FIG. 11C and FIGS. 12A-12D; and representative results from female homozygous KO (Rs1$^{-/-}$) and Rs1 heterozygous KO (Rs1$^{-/+}$) lines are set forth in FIG. 12E.

Immunohistochemistry (IHC). Briefly, animals were euthanized by $CO_2$ inhalation. Eyes were enucleated and fixed with 4% PFA (Electron Microscopy Sciences) in 1×PBS (ThermoFisher Sci.) for three hours at 4° C. After three washes with 1×PBS, eyes were dissected under a dissecting microscope. The anterior segment and lens were removed, and the rest of the eye (eyecup) was incubated in 30% sucrose at 4° C. overnight. Eyecups were then embedded in TISSUE-TEK® O.C.T. Compound (VWR) and snap frozen on dry ice. Ten-micron cryostat sections were prepared on SUPERFROST® Plus Micro Slide used for immunofluorescent staining. Sections on slides were encircled with Liquid Blocker Super Pap Pen (Electron Microscopy Sciences) and air dried 30 minutes at room temperature. Blocking solution was prepared as 5% normal goat serum (VectorLabs), 1% Bovine Serum Albumin (Sigma-Aldrich) and 0.3% Triton-X 100 (Sigma-Aldrich) in 1×PBS. Wash solution was prepared as 0.1% Tween 20 (Amresco) in 1×PBS. Slides were placed in a staining container with black lid, washed three times with 1×PBS to remove O.C.T. Compound. Blocking solution was added to slides and remained for one hour at room temperature. After removal of blocking solution, primary antibodies were diluted in blocking solution and applied to sections overnight at 4° C. On the second day, slides were washed three times with Wash solution. Fluorophore-conjugated secondary antibodies were diluted at 1:1000 in 1×PBS and applied on sections for one hour at room temperature (in the dark to avoid photobleaching). Slides were washed three times with 1×PBS and coverslipped with ProLong Gold Antifade Mountant with DAPI (ThermoFisher Sci.).

ELISA. Briefly, mouse retina was isolated under dissection microscope and homogenized in 100 µl RIPA buffer per retina with cocktail protease inhibitors in metal bead tube with Omini Homogenizer. Protein concentration was determined with BCA kit and then stored at −80° C. until use (ELISA, Western blot). ELISA plates (NUNC) were coated with RS1 standard protein (Novus Biologicals, 0-40 ng/ml) and total retinal protein sample (1:2000 dilution in PBS) in triplicate at 4° C. overnight. After three washes with T-TBS solution (T-TBS buffer, 0.05% Tween20 in TBS solution), plates were blocked with blocking buffer (1% BSA, 5% goat serum in TBS) for one hour at room temperature. After 3 washes, anti-RS1 polyclonal antibody (Novus Biologicals USA, 1:4000 in blocking buffer) was added to the plates and incubated for two hours at room temperature followed by addition of biotin-conjugated goat anti-mouse antibody (Jackson Lab, 1:5000) and Strepavidin-HRP (Thermo, 1:200), and, finally the substrate working solution (R&D systems) in the absence of light. The reaction was stopped by 2N HCl. Optical density (OD) was recorded with Spectra-Max Plus system (Molecular Devices).

Western blot. 10-20 µg total retinal protein was loaded onto 4-12% Bis-Tris gels in sample buffer (Nupage LDS sample buffer, Thermo) containing 4% SDS for protein separation and then transferred to nitrocellulose membrane (0.45 µm pore size, Invitrogen) followed by blocking with SuperBlock T20 (TBS, Thermo) for one hour at room temperature. Blots were incubated with anti-RS1 antibody (Novus Biologicals USA, 1:4000) for two hours at room temperature or overnight at 4° C. After incubation with anti-RS1 antibody, HRP conjugated anti-mouse polyclonal antibody (Cell Signaling) was added at 1:5000 for one hour at room temperature. Protein bands were visualized and imaged using SuperSignal West Pico chemiluminescence (Thermo) by C-Dogit Blot Scanner (Li-Cor).

Figures 13A, 13B, 13C:
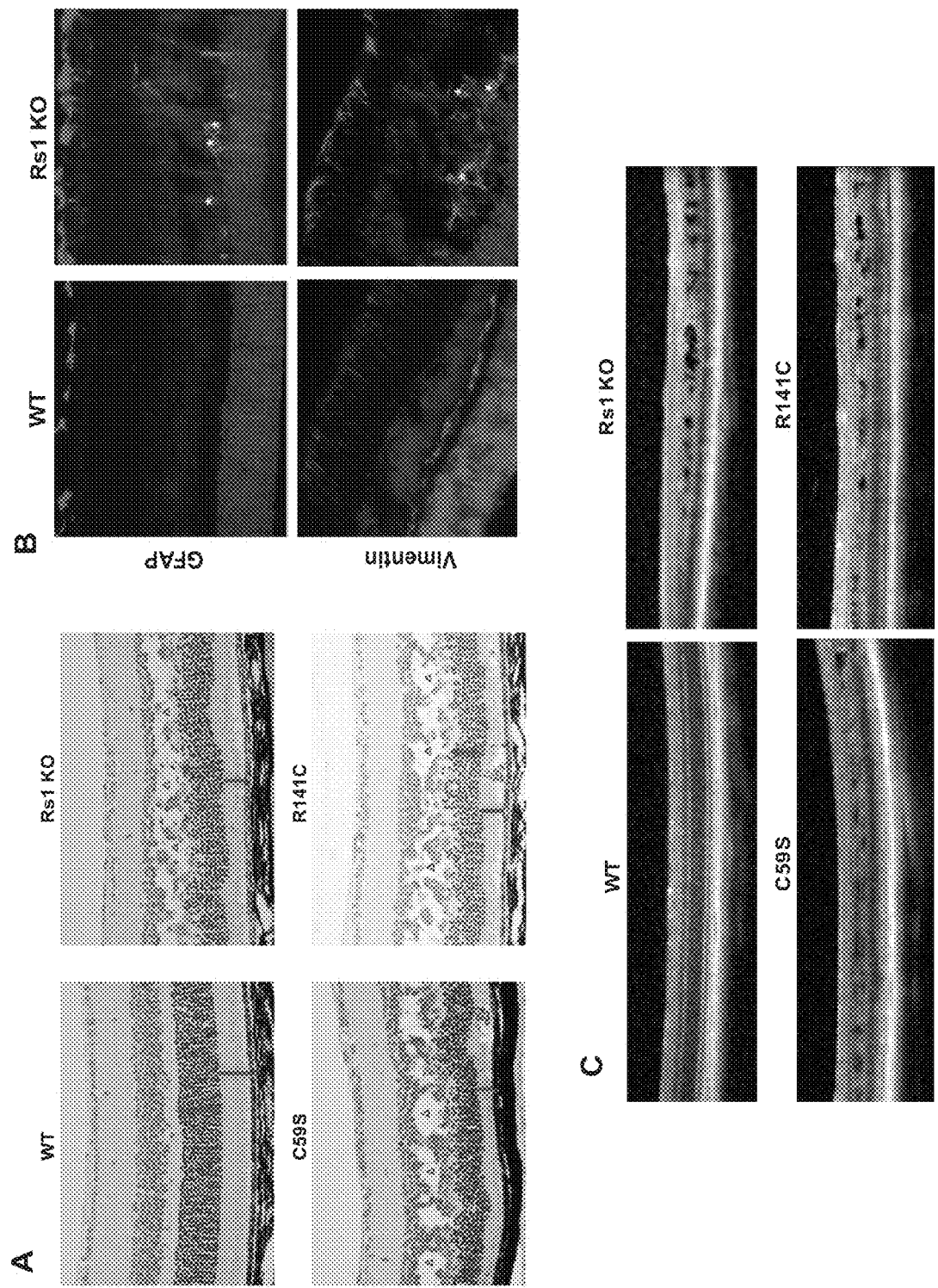
FIGS. 13A-13D show the pathological changes in retinas of Rs1 null ($Rs1^{KO}$) and Rs1 mutant ($Rs1^{C59S}$, $Rs1^{R14IC}$) animals by histological, IHC and optical coherence tomography (OCT) analysis. A, histological examination of showed cavities and splitting in the INL (red triangles) and overall disorganization of the INL and OPL, degeneration of photoreceptors with thinning of the ONL (vertical red double headed arrow) and inner/outer segments (vertical red line) in $Rs1^{KO}$, $Rs1^{C59S}$ and $Rs1^{R14IC}$ male animals. B. IHC with retina-specific cell markers (GFAP-glial fibrillary acidic protein and vimentin) revealed gliosis of the INL (* indicated activated Müller cells) in $Rs1^{KO}$ male animals. C. Retinoschisis and photoreceptor degeneration were observed in $Rs1^{KO}$, $Rs1^{C59S}$ and $Rs1^{R14IC}$ male animals by in vivo imaging using Spectralis Heidelberg Optical Coherence Tomography (OCT). D. Schisis was not observed in heterozygous RS1 knock-out female (Rs1-1+) ("Het"), while homozygous RS1 knock-out female ($Rs1^{-/-}$) ("KO") had a phenotype that matched hemi KO male.

Histology. Briefly, animals were euthanized by $CO_2$ inhalation. Eyes were enucleated and fixed with Davidson's fixative (Electron Microscopy Sciences) for one hour at room temperature, transferred to Tissue Processing Embedding Cassettes (Electron Microscopy Sciences), and washed with tap water for five minutes at room temperature. Cassettes were fixed with 10% Neutral Buffered Formalin in Phosphate Buffer (Electron Microscopy Sciences). Eyes were processed through serial dilutions of ethanol, three changes of xylene and two changes of paraffin for embedding. Five-micron paraffin sections were prepared on SUPERFROST® Plus Micro Slide (VWR) and stained with hematoxylin and eosin according to manufacturer's specifications (Hematoxylin and Eosin (H&E) Staining (Regressive) Ricca Chemical Company). Representative results from male mice are set forth in FIGS. 13A-13B.

Taken together, this example demonstrates that the pathological features typical of the disease phenotype associated with X-linked Retinoschisis was recapitulated in the engineered Rs1 rodent lines made in accordance with Example 1. Thus, such engineered rodent lines are useful for the evaluation and development of therapeutics (e.g., experimental gene therapy).

Example 3. Functional and Morphological Analysis of Engineered Rs1 Rodent Lines

Figure 13D:
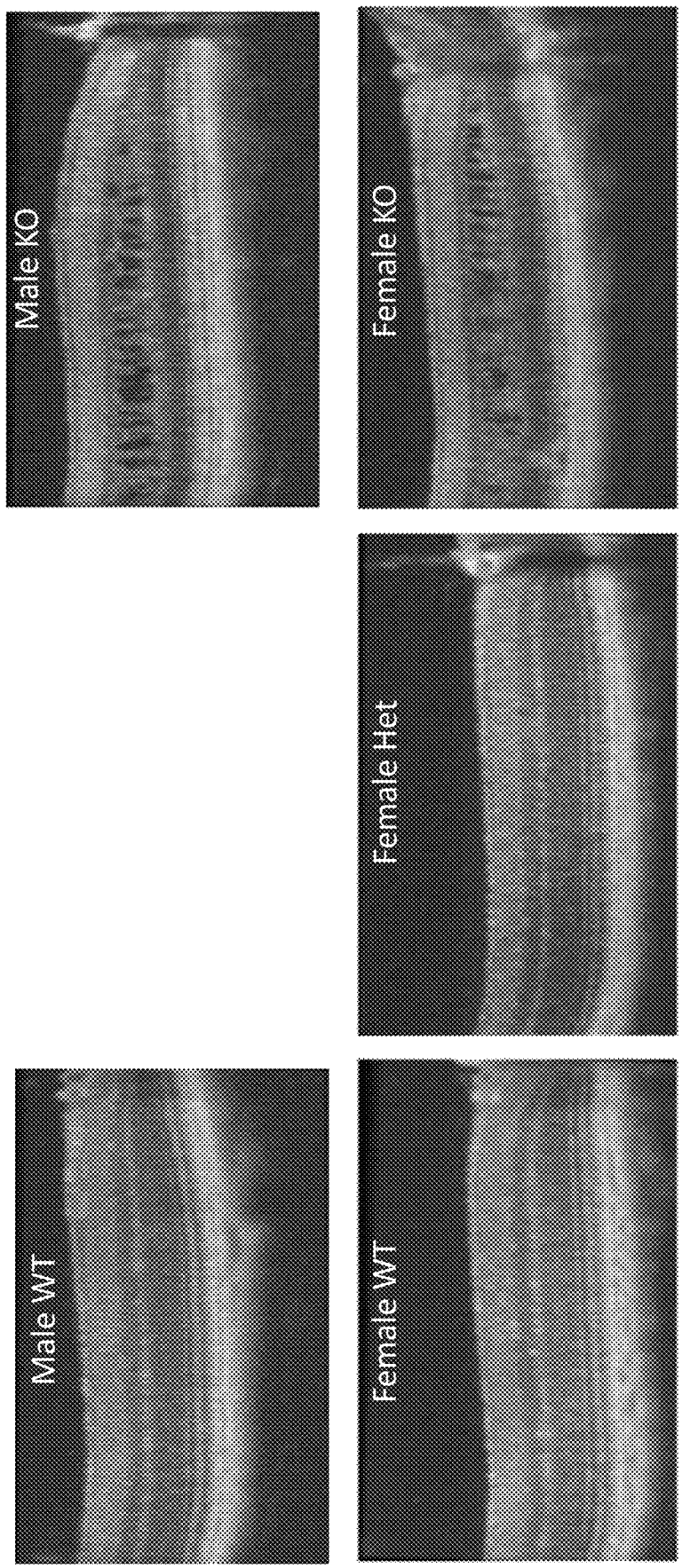
Figures 14A, 14B, 14C:
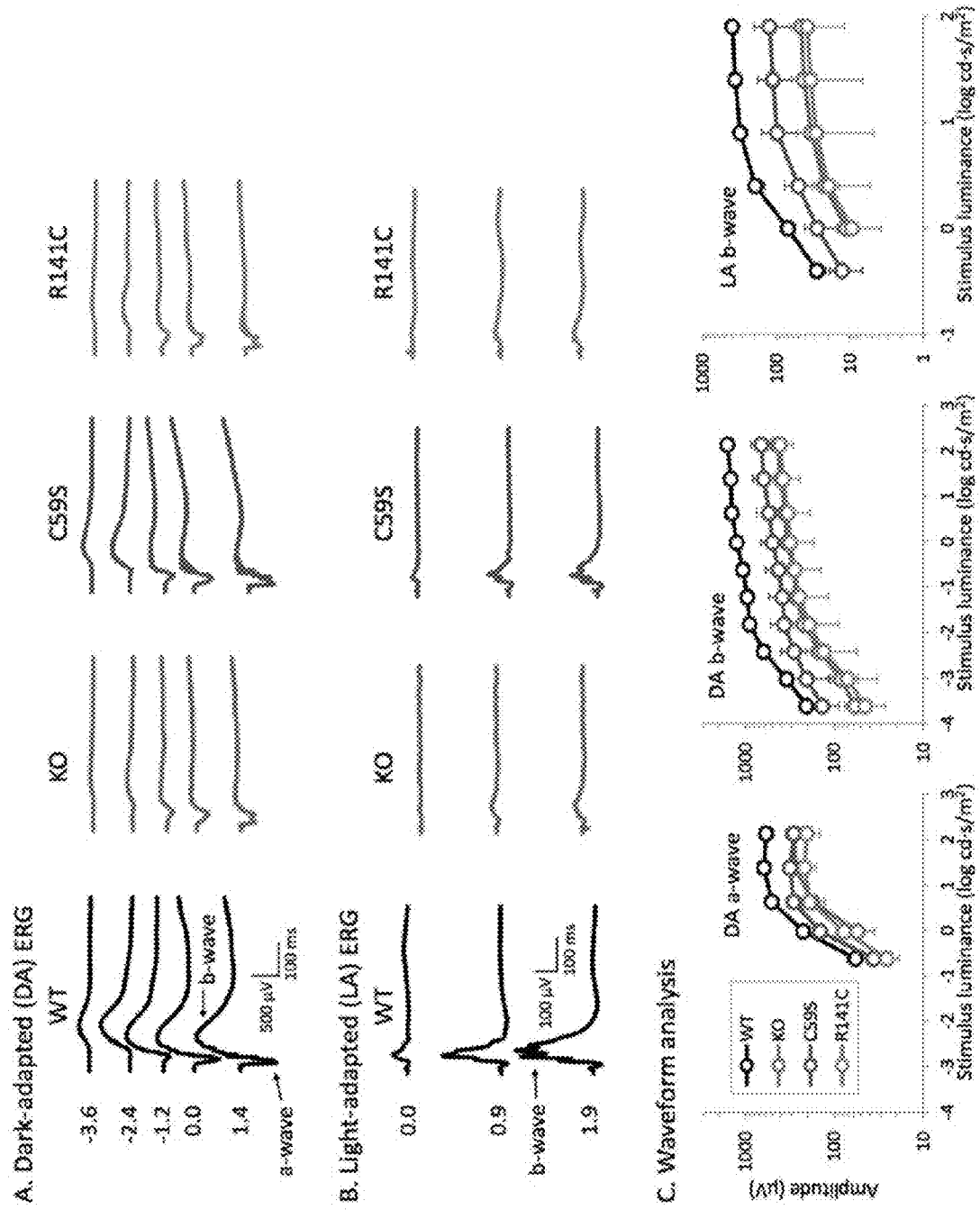
FIGS. 14A-D show the analysis of outer retinal function by dark-adapted (DA-) and light-adapted (LA-) full-field electroretinograms (ERGs) in 20-week old animals. A, representative ERGs obtained under dark-adapted conditions from a wild-type (WT), $Rs1^{KO}$ (KO), $Rs1^{C59S}$ (C59S) and $Rs1^{R14IC}$ (R141C) male animals. B, representative ERGs obtained under light-adapted conditions from a wild-type (WT), $Rs1^{KO}$ (KO), $Rs1^{C59S}$ (C59S) and $Rs1^{R14IC}$ (R141C) male animals. C, representative amplitude of the major components of the dark- and light-adapted ERG plotted as a function of stimulus luminance. Data points indicate average (±SD) for six male animals. In comparison to wild-type, both the a- and b-waves of $Rs1^{KO}$, $Rs1^{C59S}$ and $Rs1^{R14IC}$ (R141C) male animals were reduced in amplitude. Stimulus luminance (A and B) are noted to the left of the left most waveform graph. D, representative ERGs obtained under dark-adapted and light-adapted conditions from a wild-type ($Rs1^{+/+}$), homozygous knock-out ($Rs1^{-/-}$) and heterozygous knock-out (Rs1-4+) female animals. ERGs of carrier (heterozygous) females matched those of WT controls under all conditions. In comparison, the ERG phenotype of homozygous knock-out females was comparable to that of hemizygous knock-out males, with a negative waveform and a reduced amplitude a-wave.
Figure 14D:
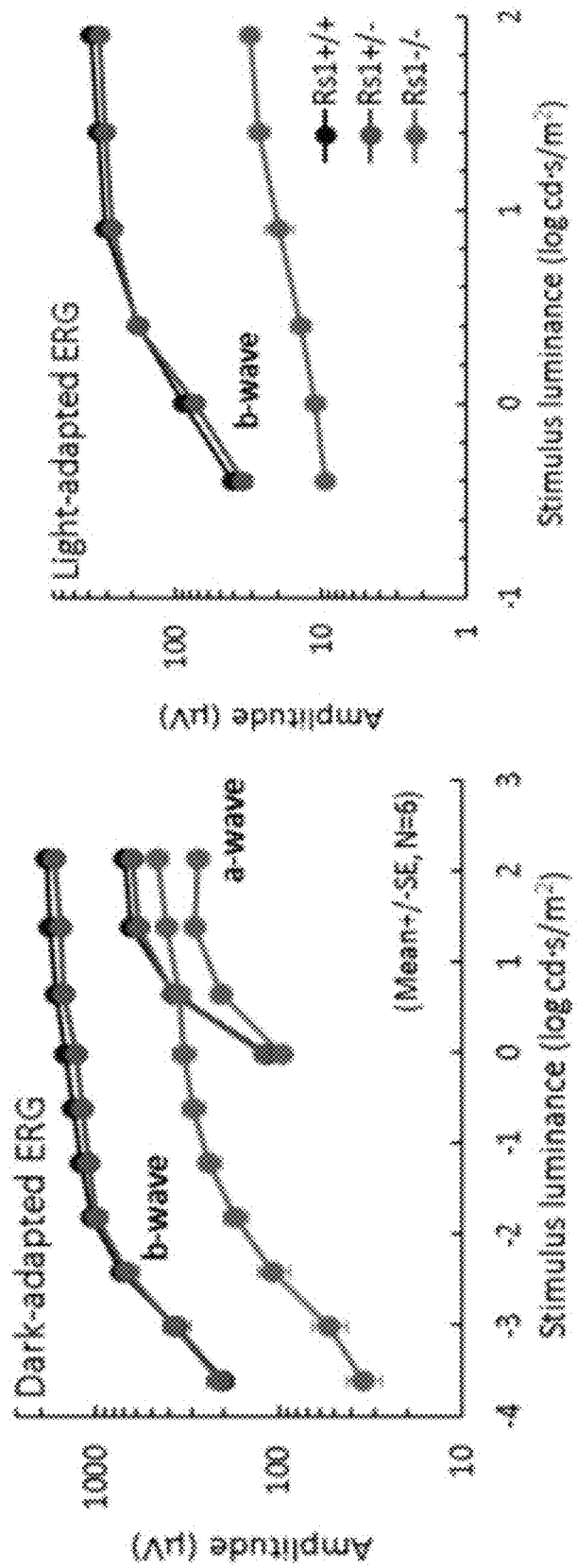

This example describes the characterization of the retina phenotype of the engineered Rs1 rodent lines made according to Example 1. In particular, outer retinal function in null and mutant Rs1 rodent lines made in Example 1 was evaluated by dark-adapted (DA-) and light-adapted (LA-) full-field electroretinograms (ERGs). Retinal architecture was also assessed by optical coherence tomography (OCT). Representative results from male mice are set forth in FIGS. 13C and 14A-14C; and representative results from female homozygous KO (Rs1$^{-/-}$) and heterozygous KO (Rs1$^{-/+}$) lines are set forth in FIGS. 13D and 14D.

Optical Coherence Tomography (OCT). Briefly, in-life ophthalmic examinations were carried out on designated time points with Heidelberg Spectralis HRA+OCT system (Heidelberg Engineering, Franklin, MA, USA). Animals were anesthetized with ketamine (120 mg/kg) and xylazine (5 mg/kg) intraperitoneally. Pupils were dilated using a 0.5% Tropicamide ophthalmic solution (Bausch & Lomb, Rochester, NY). Infrared fundus images were taken from center and selected quadrant (normally nasal-superior and temporal-superior) followed by obtaining a series of 61 lateral optical scans for retinal morphological evaluation.

Electroretinography (ERG). Briefly, animals were dark-adapted overnight and anesthetized (ketamine: 80 mg/kg; xylazine: 16 mg/kg), after which eye drops were used for pupil dilation (1% tropicamide; 2.5% phenylephrine HCl) and to anesthetize the corneal surface (1% proparacaine HCl). Needle electrodes served as reference (check) and ground (tail), and ERGs were recorded using a stainless steel electrode wetted with 1% carboxymethylcellulose. Strobe flash stimuli were presented to the dark-adapted eye and superimposed on a steady adapting field (20 cd/m$^2$) after at least five minutes of light adaptation. Stimuli ranged from −3.6 to 2.1 log cd s/m$^2$. Responses were amplified (0.03-1000 Hz) and stored using an LKC (Gaithersburg, MD) UTAS E-3000 signal averaging system. The amplitude of the a-wave was measured at 8 ms after flash onset from the pre-stimulus baseline while b-wave amplitude was measured from the a-wave trough to the b-wave peak.

Taken together, this example demonstrates that the phenotype displayed in the engineered Rs1 rodent lines described herein replicates that observed in patients with X-linked Retinoschisis. Further, variability in this phenotype correlates with the nature of the genetic mutation. The present specification specifically demonstrates the creation of non-human animal models of Retinoschisis. The pathological and functional features typically associated with X-linked Retinoschisis including the development of cystic structures within the inner retina and the characteristic reduced ERG b- and a-wave responses followed by a loss of photoreceptor cells were recapitulated in all three engineered Rs1 rodent lines described herein. Such engineered lines are useful for further understanding into the molecular mechanisms underlying the cellular disorganization of the retinal structure, and provide suitable in vivo systems for the development of gene therapies for the treatment of X-linked juvenile Retinoschisis.

Example 4. Early-Onset Phenotypes of the Retina in Rs1$^{KO}$ Mice

This Example describes experiments conducted to investigate early-onset functional and morphological phenotype of the retina in Rs1 knockout (KO) mice described in Example 1.

Figure 15:
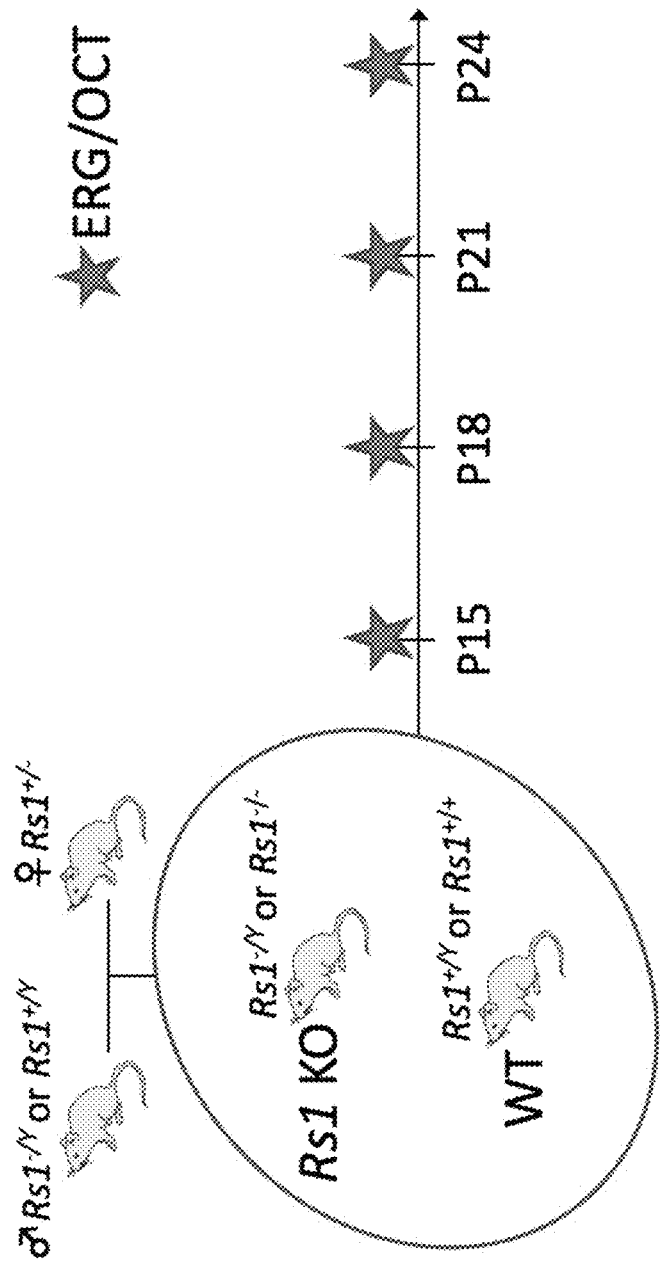
FIG. 15 shows the experimental design for a study described in Example 4 to investigate early onset phenotype of the retina in $Rs1^{KO}$ mice. ♂Rs1 (−/Y) or Rs1 (+/Y) and ♀Rs1 (+/−) mice were bred to obtain $Rs1^{KO}$ mice: Rs1 (−/Y) or Rs1 (−/−), and Rs1 WT mice: Rs1 (+/Y) or Rs1 (+/+). ERG was conducted at P15, 18, 21 and 24, and each mouse underwent twice or less ERG or OCT at an interval of 6 days.
Figure 17A:
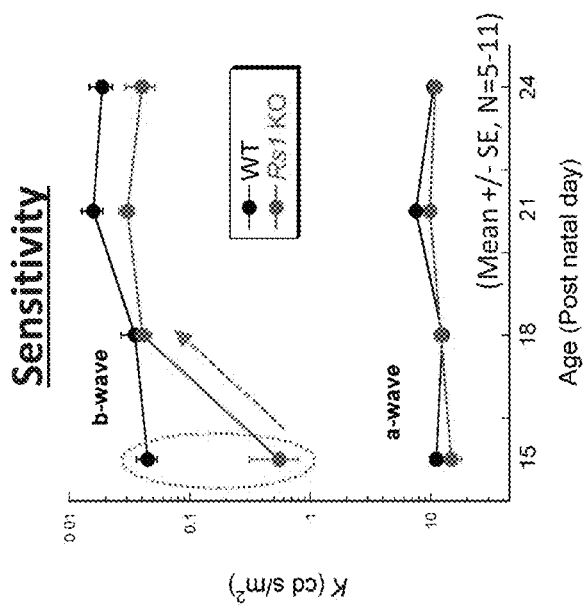
FIGS. 17A-17B show changes in ERG parameters over time of $Rs1^{KO}$ mice and wild type (WT) mice (Naka-Rushton analysis). In comparison to WT control, the Rmax values of both a-wave and b-wave at P15 were lower in $Rs1^{KO}$ mice; both the Rmax and Sensitivity values of the DA-ERG and LA-ERG b-waves were greatly reduced in $Rs1^{KO}$ mice at P15. At the older ages, the reduced Rmax values persisted, but Sensitivity values were comparable in $Rs1^{KO}$ and WT mice.
Figure 17A:
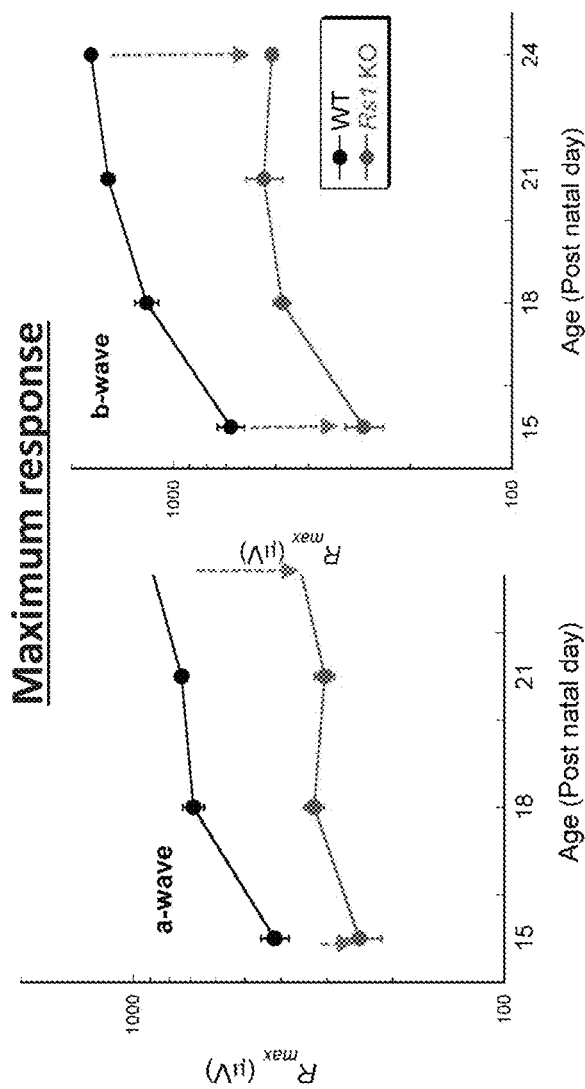
Figure 17B:
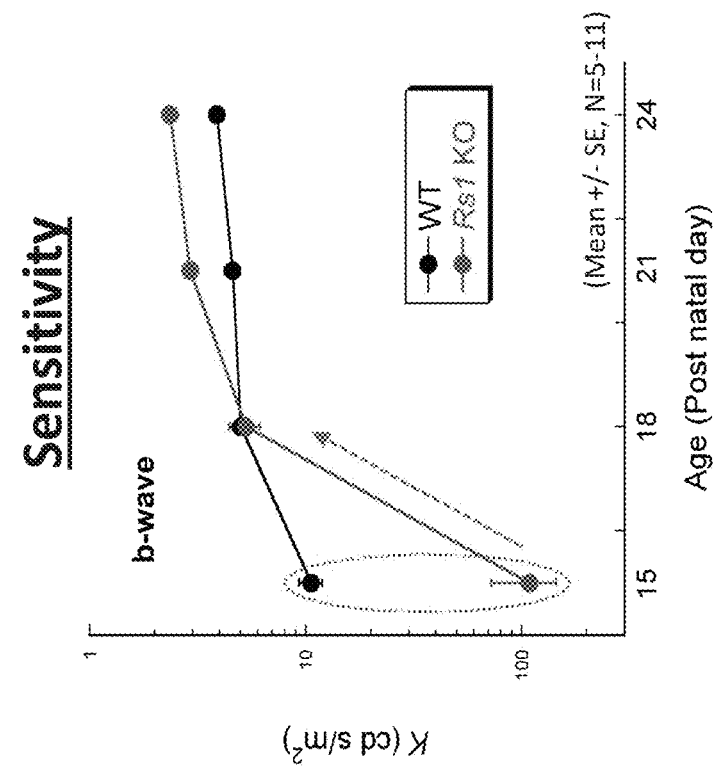
Figure 17B:
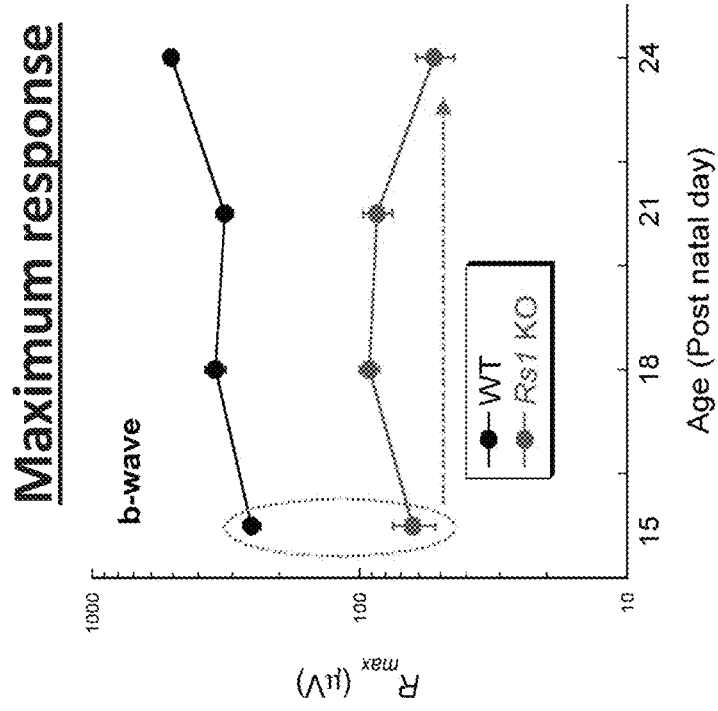
Figure 18:
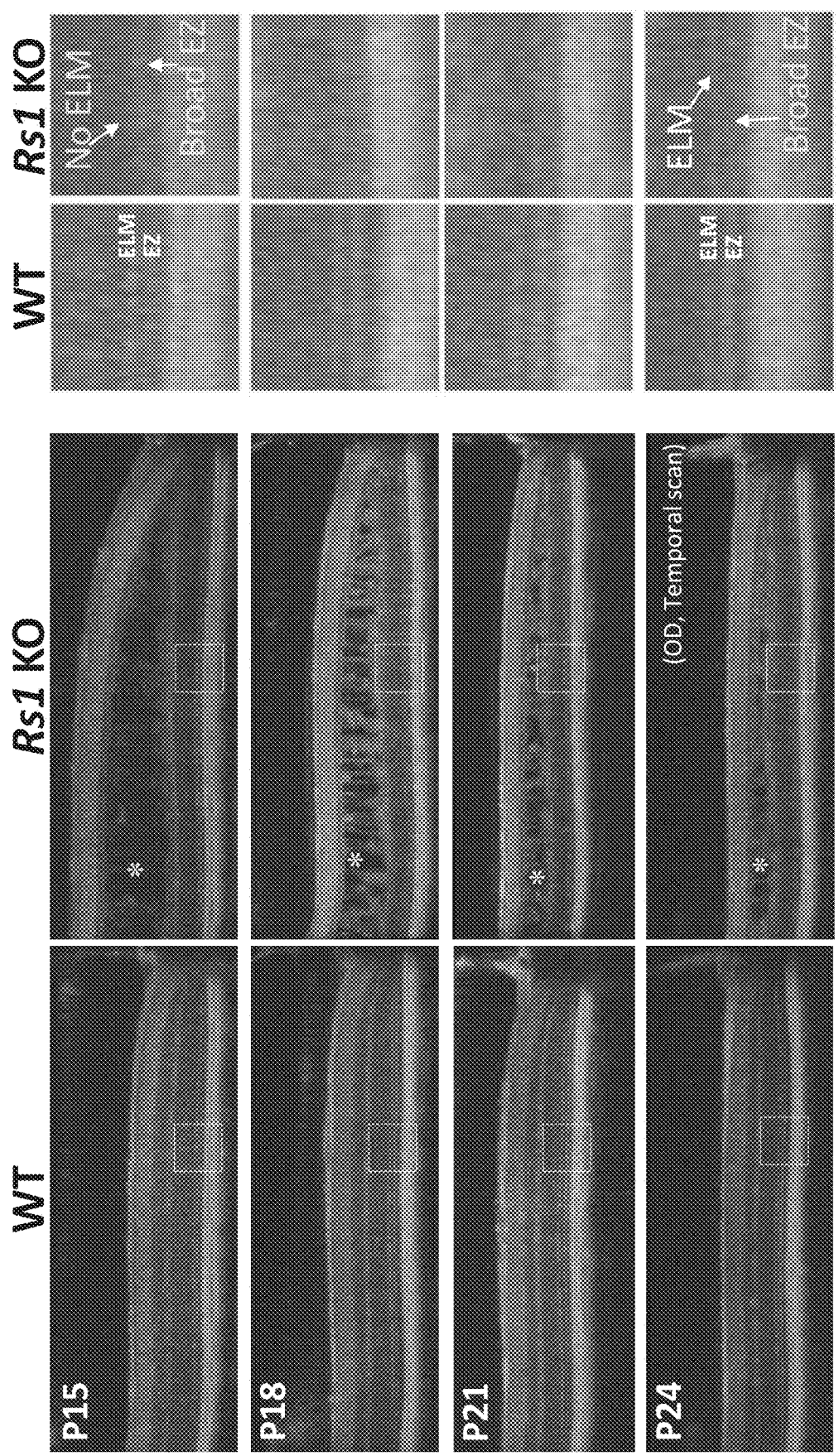
FIG. 18 shows changes in OCT images over time. Prominent schisis in INL and OPL (asterisk) and no evidence of ELM was observed at P15, which tended to moderate at later time points. The ellipsoid zone (EZ) in Rs1$^{KO}$ retina was broader than WT throughout the period.
Figures 19A, 19B, 19C:
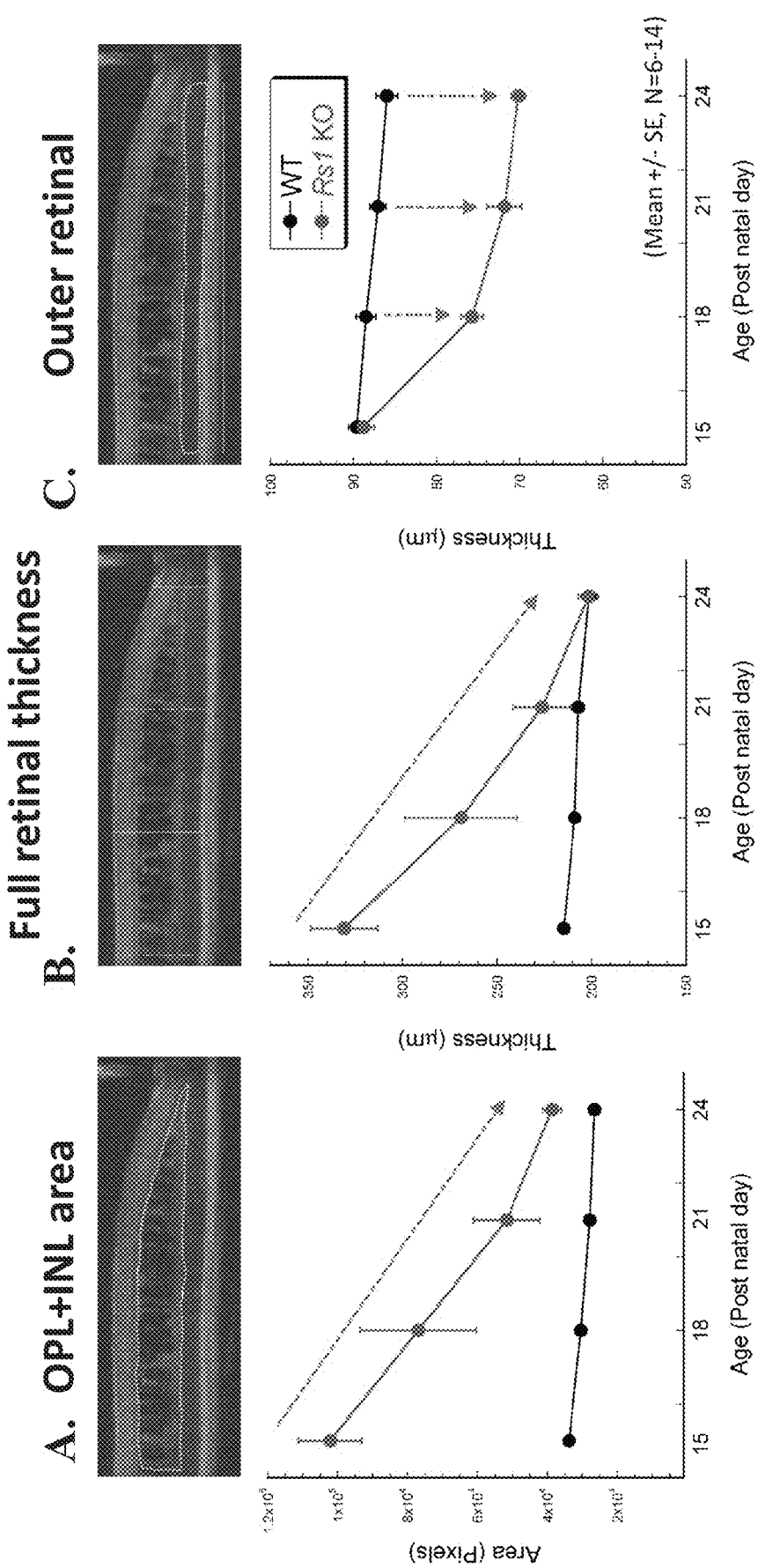
FIGS. 19A-19C show the results from a quantitative OCT analysis. Retina (including outer retina) in WT mice was slightly thinned during the developmental period (C). The retina (A and B) in Rs1$^{KO}$ mice became thinner, mainly related to moderated schisis, and outer retina in Rs1$^{KO}$ retina was thinner than WT during the period (C).

The retinas of Rs1$^{KO}$ mice and wild-type (WT) littermates were examined every three days between postnatal day 15 to 24 (P15, P18, P21 and P24) (FIG. 15). Outer retinal function was evaluated by dark-adapted (DA-) and light-adapted (LA-) full-field ERGs. ERG a-wave and b-wave amplitudes were analyzed with Naka-Rushton equation, yielding maximum response (Rmax) and sensitivity (K) parameters. Retinal architecture was assessed by optical coherence tomography (OCT).

The results from male mice are shown in FIGS. 16A-19C. The outer retinal function evaluated by dark-adapted and light-adapted ERGs indicated reduced b-wave relative to a-wave in all time points and retinoschisis phenotype was present throughout the observation time course (P15-P24). The Rs1$^{KO}$ retinas also exhibited early photoreceptor defects, specifically, decreased a-wave amplitude, broader EZ, and thinner outer retina (ONL+PRL). In Rs1$^{KO}$ retinas, the b-wave involvement was greater than a-wave for both amplitude and sensitivity, indicating early impact of Rs1 deletion on the synapse.

These observations indicate that retinoschisin plays important roles during early retinal development.

What is claimed is:

1. An isolated cell or tissue of a rodent,
   wherein the genome of the rodent comprises a mutation in exon 3 or exon 5 of an endogenous rodent Rs1 gene, wherein the mutation in exon 3 or exon 5 encodes a C59S or R141C amino acid substitution in the endogenous rodent Rs1 polypeptide, respectively;
   wherein the rodent is a mouse or a rat;
   wherein the rodent expresses the rodent Rs1 gene comprising the mutation, and displays one or more symptoms of Retinoschisis when the rodent is a female rodent homozygous for the rodent Rs1 gene comprising the mutation, or when the rodent is a male rodent hemizygous for the rodent Rs1 gene comprising the mutation; and
   wherein the genome of the isolated cell or tissue comprises the mutation.

2. An immortalized cell made from the isolated rodent cell of claim 1.

3. A rodent embryonic stem (ES) cell whose genome comprises a mutation in exon 3 or exon 5 of an endogenous rodent Rs1 gene, wherein the mutation in exon 3 or exon 5 encodes a C59S or R141C amino acid substitution in the endogenous rodent Rs1 polypeptide, respectively;
   wherein the rodent ES cell is a mouse ES cell or a rat ES cell;
   wherein a rodent generated using the rodent ES cell and comprising the mutation in the rodent genome (i) expresses the rodent Rs1 gene comprising the mutation, and (ii) displays one or more symptoms of Retinoschisis when the rodent is a female rodent homozygous for the rodent Rs1 gene comprising the mutation, or when the rodent is a male rodent hemizygous for the rodent Rs1 gene comprising the mutation.

4. A rodent embryo generated from comprising the embryonic stem cell of claim 3.

5. The isolated cell or tissue of claim 1, wherein the mutation is in exon 3 of the endogenous rodent Rs1 gene, and the rodent Rs1 gene comprising the mutation encodes an Rs1 polypeptide comprising the C59S substitution.

6. The isolated cell or tissue of claim 1, wherein the mutation is in exon 5 of the endogenous rodent Rs1 gene, and the rodent Rs1 gene comprising the mutation encodes an Rs1 polypeptide comprising the R141C substitution.

7. The isolated cell or tissue of claim 1, wherein the rodent is a male rodent.

8. The isolated cell or tissue of claim 1, wherein the rodent is a female rodent.

9. The isolated cell or tissue of claim 1, wherein the rodent is homozygous for the rodent Rs1 gene comprising the mutation.

10. The isolated cell or tissue of claim 1, wherein the rodent is heterozygous for the rodent Rs1 gene comprising the mutation.

11. The isolated cell or tissue of claim 1, wherein the rodent is a mouse.

12. The isolated cell or tissue of claim 1, wherein the rodent is a rat.

13. The rodent ES cell of claim 3, wherein the mutation is in exon 3 of the endogenous rodent Rs1 gene, and the rodent Rs1 gene comprising the mutation encodes an Rs1 polypeptide comprising the C59S substitution.

14. The rodent ES cell of claim 3, wherein the mutation is in exon 5 of the endogenous rodent Rs1 gene, and the rodent Rs1 gene comprising the mutation encodes an Rs1 polypeptide comprising the R141C substitution.

15. The rodent ES cell of claim 3, wherein the rodent ES cell is homozygous for the rodent Rs1 gene comprising the mutation.

16. The rodent ES cell of claim 3, wherein the rodent ES cell is heterozygous for the rodent Rs1 gene comprising the mutation.

17. The rodent ES cell of claim 3, wherein the rodent ES cell is a mouse ES cell.

18. The rodent ES cell of claim 3, wherein the rodent ES cell is a rat ES cell.

19. The rodent embryo of claim 4, wherein the mutation is in exon 3 of the endogenous rodent Rs1 gene, and the rodent Rs1 gene comprising the mutation encodes an Rs1 polypeptide comprising the C59S substitution.

20. The rodent embryo of claim 4, wherein the mutation is in exon 5 of the endogenous rodent Rs1 gene, and the rodent Rs1 gene comprising the mutation encodes an Rs1 polypeptide comprising the R141C substitution.

21. The rodent embryo of claim 4, wherein the rodent embryo is a male embryo.

22. The rodent embryo of claim 4, wherein the rodent embryo is a female embryo.

23. The rodent embryo of claim 4, wherein the rodent embryo is homozygous for the rodent Rs1 gene comprising the mutation.

24. The rodent embryo of claim 4, wherein the rodent embryo is heterozygous for the rodent Rs1 gene comprising the mutation.

25. The rodent embryo of claim 4, wherein the rodent embryo is a mouse embryo.

26. The rodent embryo of claim 4, wherein the rodent embryo is a rat embryo.

\* \* \* \* \*

UNITED STATES PATENT AND TRADEMARK OFFICE
CERTIFICATE OF CORRECTION

| | |
|---|---|
| PATENT NO. | : 12,082,565 B2 |
| APPLICATION NO. | : 17/348907 |
| DATED | : September 10, 2024 |
| INVENTOR(S) | : Susannah Brydges |

It is certified that error appears in the above-identified patent and that said Letters Patent is hereby corrected as shown below:

In the Claims

Column 139, Claim 4, Line 66, should read:
A rodent embryo comprising the

Signed and Sealed this
Third Day of December, 2024

Katherine Kelly Vidal
*Director of the United States Patent and Trademark Office*